(12) United States Patent
Takebe et al.

(10) Patent No.: US 12,421,500 B2
(45) Date of Patent: Sep. 23, 2025

(54) HEPATO-BILIARY-PANCREATIC TISSUES AND METHODS OF MAKING SAME

(71) Applicant: CHILDREN'S HOSPITAL MEDICAL CENTER, Cincinnati, OH (US)

(72) Inventors: Takanori Takebe, Cincinnati, OH (US); Hiroyuki Koike, Tokyo (JP)

(73) Assignee: Children's Hospital Medical Center, Cincinnati, OH (US)

( * ) Notice: Subject to any disclaimer, the term of this patent is extended or adjusted under 35 U.S.C. 154(b) by 939 days.

(21) Appl. No.: 17/263,124

(22) PCT Filed: Jul. 16, 2019

(86) PCT No.: PCT/US2019/041985
§ 371 (c)(1),
(2) Date: Jan. 25, 2021

(87) PCT Pub. No.: WO2020/023245
PCT Pub. Date: Jan. 30, 2020

(65) Prior Publication Data
US 2021/0180026 A1    Jun. 17, 2021

Related U.S. Application Data

(60) Provisional application No. 62/703,559, filed on Jul. 26, 2018.

(51) Int. Cl.
*C12N 5/00* (2006.01)
*A61K 35/28* (2015.01)
(Continued)

(52) U.S. Cl.
CPC ............ *C12N 5/0677* (2013.01); *A61K 35/28* (2013.01); *A61K 35/39* (2013.01); *A61K 35/407* (2013.01);
(Continued)

(58) Field of Classification Search
CPC ....... C12N 5/0677; A61K 35/28; A61K 35/39
See application file for complete search history.

(56) References Cited

U.S. PATENT DOCUMENTS 5,912,227 A    6/1999    Croom, Jr. et al.
5,942,435 A    8/1999    Wheeler
(Continued)

FOREIGN PATENT DOCUMENTS

CA    2968065 A1    6/2016
CN    1299408 A     6/2001
(Continued)

OTHER PUBLICATIONS

Scavuzzo et al. Organotypic pancreatoids with native mesenchyme develop Insulin producing endocrine cells. Scientific Reports 7: 1-12. (Year: 2017).*

(Continued)

*Primary Examiner* — James D Schultz
*Assistant Examiner* — Keenan A Bates
(74) *Attorney, Agent, or Firm* — Norton Rose Fulbright US LLP

(57) ABSTRACT

Disclosed herein are hepato-biliary-pancreatic organoid ("HBPO" or "HBP organoid") compositions, and methods of making and using hepato-biliary-pancreatic organoid compositions. The disclosed compositions may have two or more functions selected from hepatic tissue function, biliary tissue function, exocrine pancreatic function, and endocrine pancreatic tissue function. Methods of treating individuals using the hepato-biliary-pancreatic organoid compositions is also disclosed.

17 Claims, 41 Drawing Sheets
Specification includes a Sequence Listing.

(51) Int. Cl.
*A61K 35/39* (2015.01)
*A61K 35/407* (2015.01)
*A61K 35/413* (2015.01)
*A61K 35/44* (2015.01)
*A61K 35/545* (2015.01)
*C12N 5/071* (2010.01)

(52) U.S. Cl.
CPC ............ *A61K 35/413* (2013.01); *A61K 35/44* (2013.01); *A61K 35/545* (2013.01); *C12N 5/0671* (2013.01); *C12N 5/0697* (2013.01); *C12N 2501/115* (2013.01); *C12N 2501/155* (2013.01); *C12N 2501/415* (2013.01); *C12N 2501/727* (2013.01); *C12N 2502/14* (2013.01); *C12N 2502/22* (2013.01); *C12N 2506/45* (2013.01); *C12N 2513/00* (2013.01); *C12N 2533/90* (2013.01)

(56) References Cited

U.S. PATENT DOCUMENTS

| | | |
|---|---|---|
| 6,607,501 B2 | 8/2003 | Gorsuch |
| 7,160,719 B2 | 1/2007 | Nyberg |
| 7,291,626 B1 | 11/2007 | Beachy et al. |
| 7,326,572 B2 | 2/2008 | Fisk et al. |
| 7,510,876 B2 | 3/2009 | D'Amour et al. |
| 7,514,185 B2 | 4/2009 | Fukushima et al. |
| 7,541,185 B2 | 6/2009 | D'Amour et al. |
| 7,625,753 B2 | 12/2009 | Kelly et al. |
| 7,695,958 B2 | 4/2010 | Funatsu et al. |
| 7,704,738 B2 | 4/2010 | D'Amour et al. |
| 7,727,998 B2 | 6/2010 | Moriya et al. |
| 7,776,592 B2 | 8/2010 | Wandinger-Ness et al. |
| 7,927,869 B2 | 4/2011 | Rosero |
| 7,985,585 B2 | 7/2011 | D'Amour et al. |
| 7,993,916 B2 | 8/2011 | Agulnick et al. |
| 8,187,878 B2 | 5/2012 | Dalton et al. |
| 8,216,826 B2 | 7/2012 | Lee et al. |
| 8,216,836 B2 | 7/2012 | D'Amour et al. |
| 8,298,822 B2 | 10/2012 | Kruse et al. |
| 8,318,492 B2 | 11/2012 | Choo et al. |
| 8,501,476 B2 | 8/2013 | Morgan et al. |
| 8,586,357 B2 | 11/2013 | D'Amour et al. |
| 8,603,809 B2 | 12/2013 | Kruse |
| 8,609,406 B2 | 12/2013 | Subramanian et al. |
| 8,609,413 B2 | 12/2013 | Suter et al. |
| 8,623,645 B2 | 1/2014 | D'Amour et al. |
| 8,632,645 B2 | 1/2014 | Daitou et al. |
| 8,633,024 B2 | 1/2014 | D'Amour et al. |
| 8,642,339 B2 | 2/2014 | Sato et al. |
| 8,647,873 B2 | 2/2014 | D'Amour et al. |
| 8,658,151 B2 | 2/2014 | Kelly et al. |
| 8,685,386 B2 | 4/2014 | West et al. |
| 8,685,730 B2 | 4/2014 | Odorico et al. |
| 8,758,323 B2 | 6/2014 | Michaud et al. |
| 9,127,254 B2 | 9/2015 | Cohen et al. |
| 9,133,439 B2 | 9/2015 | Davis et al. |
| 9,181,301 B2 | 11/2015 | Carlson et al. |
| 9,200,258 B2 | 12/2015 | Mezghanni et al. |
| 9,206,393 B2 | 12/2015 | Kruse |
| 9,234,170 B2 | 1/2016 | Snoeck et al. |
| 9,334,479 B2 | 5/2016 | Herrera Sanchez et al. |
| 9,375,514 B2 | 6/2016 | Kruse et al. |
| 9,381,181 B2 | 7/2016 | Roberts et al. |
| 9,394,522 B2 | 7/2016 | Brolen et al. |
| 9,446,076 B2 | 9/2016 | Gaussin et al. |
| 9,447,380 B2 | 9/2016 | Subramanian et al. |
| 9,476,030 B2 | 10/2016 | Gadue et al. |
| 9,499,795 B2 | 11/2016 | D'Amour et al. |
| 9,605,243 B2 | 3/2017 | D'Amour et al. |
| 9,616,039 B2 | 4/2017 | Roberts et al. |
| 9,618,500 B2 | 4/2017 | Giselbrecht et al. |
| 9,650,609 B2 | 5/2017 | Nyberg |
| 9,675,646 B2 | 6/2017 | Bitar |
| 9,677,085 B2 | 6/2017 | Guye et al. |
| 9,719,067 B2 | 8/2017 | Snoeck et al. |
| 9,719,068 B2 | 8/2017 | Wells et al. |
| 9,732,116 B2 | 8/2017 | Steiner et al. |
| 9,752,124 B2 | 9/2017 | Sato et al. |
| 9,763,964 B2 | 9/2017 | Pellicciari et al. |
| 9,765,301 B2 | 9/2017 | Huch Ortega et al. |
| 9,771,562 B2 | 9/2017 | Shen et al. |
| 9,790,470 B2 | 10/2017 | Vallier et al. |
| 9,828,583 B2 | 11/2017 | Rajagopal et al. |
| 9,849,104 B2 | 12/2017 | Bisgaier et al. |
| 9,850,461 B2 | 12/2017 | Rizzi et al. |
| 9,856,458 B2 | 1/2018 | Rosowski et al. |
| 9,878,005 B2 | 1/2018 | Johns et al. |
| 9,914,920 B2 | 3/2018 | Goodwin et al. |
| 9,926,532 B2 | 3/2018 | Esteban et al. |
| 9,938,499 B2 | 4/2018 | Slukvin et al. |
| 10,000,740 B2 | 6/2018 | Vallier et al. |
| 10,023,922 B2 | 7/2018 | Stelzer et al. |
| 10,045,977 B2 | 8/2018 | Wu et al. |
| 10,047,341 B2 | 8/2018 | Yu et al. |
| 10,052,337 B2 | 8/2018 | Lancaster et al. |
| 10,087,416 B2 | 10/2018 | Chan et al. |
| 10,087,417 B2 | 10/2018 | Freed et al. |
| 10,100,279 B2 | 10/2018 | Nicholas et al. |
| 10,130,748 B2 | 11/2018 | Nyberg et al. |
| 10,172,889 B2 | 1/2019 | Sokal et al. |
| 10,174,289 B2 | 1/2019 | Wells et al. |
| 10,179,176 B2 | 1/2019 | Kay et al. |
| 10,220,386 B2 | 3/2019 | Williamson et al. |
| 10,222,370 B2 | 3/2019 | Keshavarzian et al. |
| 10,260,039 B2 | 4/2019 | Bhatia et al. |
| 10,265,153 B2 | 4/2019 | La Francesca et al. |
| 10,265,453 B2 | 4/2019 | Flieg et al. |
| 10,301,303 B2 | 5/2019 | Liu |
| 10,350,147 B2 | 7/2019 | Kyrkanides et al. |
| 10,369,254 B2 | 8/2019 | Yanagawa et al. |
| 10,407,664 B2 | 9/2019 | Knoblich et al. |
| 10,426,757 B2 | 10/2019 | Sabatini et al. |
| 10,449,221 B2 | 10/2019 | Kotton et al. |
| 10,472,612 B2 | 11/2019 | Ingber et al. |
| 10,479,977 B2 | 11/2019 | Wang et al. |
| 10,487,314 B2 | 11/2019 | Accili et al. |
| 10,532,111 B2 | 1/2020 | Kay et al. |
| 10,538,741 B2 | 1/2020 | Sokal et al. |
| 10,545,133 B2 | 1/2020 | Ewald et al. |
| 10,555,929 B2 | 2/2020 | Mantzoros |
| 10,668,108 B2 | 6/2020 | Takebe et al. |
| 10,781,425 B2 | 9/2020 | Wells et al. |
| 11,053,477 B2 | 7/2021 | Wells et al. |
| 11,066,650 B2 | 7/2021 | Wells et al. |
| 2003/0129751 A1 | 7/2003 | Grikscheit et al. |
| 2003/0228685 A1 | 12/2003 | Nyberg |
| 2005/0266554 A1 | 12/2005 | D'Amour et al. |
| 2006/0110369 A1 | 5/2006 | Funatsu et al. |
| 2006/0236415 A1 | 10/2006 | Silversides et al. |
| 2007/0238169 A1 | 10/2007 | Abilez et al. |
| 2007/0239083 A1 | 10/2007 | Voss |
| 2008/0193421 A1 | 8/2008 | Kruse et al. |
| 2008/0195224 A1 | 8/2008 | Teitelbaum et al. |
| 2008/0286366 A1 | 11/2008 | Fischer et al. |
| 2009/0011502 A1 | 1/2009 | D'Amour et al. |
| 2009/0042287 A1 | 2/2009 | D'Amour et al. |
| 2009/0220959 A1 | 9/2009 | D'Amour et al. |
| 2009/0253202 A1 | 10/2009 | D'Amour et al. |
| 2009/0263357 A1 | 10/2009 | Sayre et al. |
| 2009/0311765 A1 | 12/2009 | Maguire et al. |
| 2010/0016410 A1 | 1/2010 | Wagner et al. |
| 2010/0041150 A1 | 2/2010 | Kelly et al. |
| 2010/0048871 A1 | 2/2010 | Cho et al. |
| 2010/0075295 A1 | 3/2010 | Dryden et al. |
| 2010/0151568 A1 | 6/2010 | D'Amour et al. |
| 2011/0125286 A1 | 5/2011 | Selden et al. |
| 2011/0151564 A1 | 6/2011 | Menu et al. |
| 2011/0218512 A1 | 9/2011 | Tullis et al. |
| 2011/0231942 A1 | 9/2011 | He et al. |
| 2011/0294735 A1 | 12/2011 | Marsh et al. |
| 2011/0300543 A1 | 12/2011 | Wang |
| 2012/0009086 A1 | 1/2012 | Nyberg et al. |

(56) References Cited

U.S. PATENT DOCUMENTS

| | | |
|---|---|---|
| 2012/0009618 A1 | 1/2012 | Yu et al. |
| 2012/0070419 A1 | 3/2012 | Christiansen-Weber |
| 2012/0071451 A1 | 3/2012 | Spenard et al. |
| 2012/0135519 A1 | 5/2012 | Ameri et al. |
| 2012/0149630 A1 | 6/2012 | Zugates et al. |
| 2012/0196275 A1 | 8/2012 | Mezghanni et al. |
| 2012/0196312 A1 | 8/2012 | Sato et al. |
| 2012/0201890 A1 | 8/2012 | Williams et al. |
| 2012/0264209 A1 | 10/2012 | Odorico et al. |
| 2012/0270295 A1 | 10/2012 | Choo et al. |
| 2012/0291096 A1 | 11/2012 | Boldyrev et al. |
| 2013/0031645 A1 | 1/2013 | Touboul et al. |
| 2013/0095567 A1 | 4/2013 | Brolen et al. |
| 2013/0115673 A1 | 5/2013 | West et al. |
| 2013/0137130 A1 | 5/2013 | Wells et al. |
| 2013/0189327 A1 | 7/2013 | Ortega et al. |
| 2013/0217005 A1 | 8/2013 | Snoeck et al. |
| 2013/0281374 A1 | 10/2013 | Levy et al. |
| 2013/0316442 A1 | 11/2013 | Meurville et al. |
| 2013/0330823 A1 | 12/2013 | Rezania |
| 2014/0038279 A1 | 2/2014 | Ingber et al. |
| 2014/0044713 A1 | 2/2014 | De Lau et al. |
| 2014/0141509 A1 | 5/2014 | Gadue et al. |
| 2014/0193905 A1 | 7/2014 | Kelly et al. |
| 2014/0212910 A1 | 7/2014 | Bhatia et al. |
| 2014/0234953 A1 | 8/2014 | Vacanti et al. |
| 2014/0242693 A1 | 8/2014 | Fryer et al. |
| 2014/0243227 A1 | 8/2014 | Clevers et al. |
| 2014/0273210 A1 | 9/2014 | Baker et al. |
| 2014/0302491 A1 | 10/2014 | Nadauld et al. |
| 2014/0308695 A1 | 10/2014 | Bruce et al. |
| 2014/0328808 A1 | 11/2014 | Watanabe et al. |
| 2014/0336282 A1 | 11/2014 | Ewald et al. |
| 2014/0369973 A1 | 12/2014 | Bernstein et al. |
| 2015/0017140 A1 | 1/2015 | Bhatia et al. |
| 2015/0151297 A1 | 6/2015 | Williamson et al. |
| 2015/0153326 A1 | 6/2015 | Kogel et al. |
| 2015/0185714 A1 | 7/2015 | Geveci |
| 2015/0197802 A1 | 7/2015 | Zink et al. |
| 2015/0201588 A1 | 7/2015 | Kamb et al. |
| 2015/0238656 A1 | 8/2015 | Orlando et al. |
| 2015/0247124 A1 | 9/2015 | Snoeck et al. |
| 2015/0273071 A1 | 10/2015 | Green et al. |
| 2015/0273127 A1 | 10/2015 | Flieg et al. |
| 2015/0290154 A1 | 10/2015 | Roberts et al. |
| 2015/0330970 A1 | 11/2015 | Knoblich et al. |
| 2015/0343018 A1 | 12/2015 | Sansonetti et al. |
| 2015/0359849 A1 | 12/2015 | Greenberg et al. |
| 2015/0361393 A1 | 12/2015 | Nicholas et al. |
| 2016/0002602 A1 | 1/2016 | Almeida-Porada et al. |
| 2016/0022873 A1 | 1/2016 | Besner et al. |
| 2016/0046905 A1 | 2/2016 | Inoue et al. |
| 2016/0060707 A1 | 3/2016 | Goldenberg et al. |
| 2016/0068805 A1 | 3/2016 | Martin et al. |
| 2016/0101133 A1 | 4/2016 | Basu et al. |
| 2016/0102289 A1 | 4/2016 | Yu et al. |
| 2016/0121023 A1 | 5/2016 | Edelman et al. |
| 2016/0122722 A1 | 5/2016 | Ejiri et al. |
| 2016/0143949 A1 | 5/2016 | Ingber et al. |
| 2016/0177270 A1 | 6/2016 | Takebe et al. |
| 2016/0184387 A1 | 6/2016 | Charmot et al. |
| 2016/0186140 A1 | 6/2016 | Dalton et al. |
| 2016/0206664 A1 | 7/2016 | Sokal et al. |
| 2016/0215014 A1 | 7/2016 | Steiner et al. |
| 2016/0237400 A1 | 8/2016 | Xian |
| 2016/0237401 A1 | 8/2016 | Vallier et al. |
| 2016/0237409 A1 | 8/2016 | Little et al. |
| 2016/0244724 A1 | 8/2016 | Ferro |
| 2016/0245653 A1 | 8/2016 | Park et al. |
| 2016/0256672 A1 | 9/2016 | Arumugaswami et al. |
| 2016/0257937 A1 | 9/2016 | Wauthier et al. |
| 2016/0263098 A1 | 9/2016 | Mantzoros |
| 2016/0289635 A1 | 10/2016 | Sasai et al. |
| 2016/0296599 A1 | 10/2016 | Dinh et al. |
| 2016/0298087 A1 | 10/2016 | Qu et al. |
| 2016/0312181 A1 | 10/2016 | Freed et al. |
| 2016/0312190 A1 | 10/2016 | Ghaedi et al. |
| 2016/0312191 A1 | 10/2016 | Spence et al. |
| 2016/0319240 A1 | 11/2016 | Chan et al. |
| 2016/0340645 A1 | 11/2016 | D'Amour et al. |
| 2016/0340749 A1 | 11/2016 | Stelzer et al. |
| 2016/0354408 A1 | 12/2016 | Hariri et al. |
| 2016/0361466 A1 | 12/2016 | Yanagawa et al. |
| 2016/0376557 A1 | 12/2016 | Dubart Kupperschmitt et al. |
| 2017/0002330 A1 | 1/2017 | Vunjak-Novakovic et al. |
| 2017/0027994 A1 | 2/2017 | Kotton et al. |
| 2017/0035661 A1 | 2/2017 | Kyrkanides et al. |
| 2017/0035784 A1 | 2/2017 | Lancaster et al. |
| 2017/0037043 A1 | 2/2017 | Liu |
| 2017/0067014 A1 | 3/2017 | Takebe et al. |
| 2017/0101628 A1 | 4/2017 | Ingber et al. |
| 2017/0107469 A1 | 4/2017 | Costa et al. |
| 2017/0107483 A1 | 4/2017 | Pendergraft et al. |
| 2017/0107498 A1 | 4/2017 | Sareen et al. |
| 2017/0128625 A1 | 5/2017 | Bhatia et al. |
| 2017/0151049 A1 | 6/2017 | La Francesca et al. |
| 2017/0152486 A1 | 6/2017 | Shen et al. |
| 2017/0152528 A1 | 6/2017 | Zhang |
| 2017/0184569 A1 | 6/2017 | Keshavarzian et al. |
| 2017/0191030 A1 | 7/2017 | Huch Ortega et al. |
| 2017/0198261 A1 | 7/2017 | Sabaawy et al. |
| 2017/0202885 A1 | 7/2017 | Agulnick |
| 2017/0204375 A1 | 7/2017 | Accili et al. |
| 2017/0205396 A1 | 7/2017 | Izpisua Belmonte et al. |
| 2017/0205398 A1 | 7/2017 | Bruce et al. |
| 2017/0239262 A1 | 8/2017 | Lefebvre |
| 2017/0240863 A1 | 8/2017 | Sokal et al. |
| 2017/0240866 A1 | 8/2017 | Wells et al. |
| 2017/0240964 A1 | 8/2017 | Leung et al. |
| 2017/0242035 A1 | 8/2017 | Kiehntopf et al. |
| 2017/0258772 A1 | 9/2017 | Sabatini et al. |
| 2017/0260501 A1 | 9/2017 | Semechkin et al. |
| 2017/0260509 A1 | 9/2017 | Hung et al. |
| 2017/0266145 A1 | 9/2017 | Nahmias et al. |
| 2017/0267970 A1 | 9/2017 | Gupta et al. |
| 2017/0267977 A1 | 9/2017 | Huang et al. |
| 2017/0275592 A1 | 9/2017 | Sachs et al. |
| 2017/0285002 A1 | 10/2017 | Taniguchi et al. |
| 2017/0292116 A1 | 10/2017 | Wells et al. |
| 2017/0296621 A1 | 10/2017 | Sansonetti et al. |
| 2017/0304294 A1 | 10/2017 | Wu et al. |
| 2017/0304369 A1 | 10/2017 | Ang et al. |
| 2017/0319548 A1 | 11/2017 | Lefebvre |
| 2017/0321188 A1 | 11/2017 | Viczian et al. |
| 2017/0321191 A1 | 11/2017 | Kojima |
| 2017/0335283 A1 | 11/2017 | Wang et al. |
| 2017/0342385 A1 | 11/2017 | Sachs et al. |
| 2017/0348433 A1 | 12/2017 | Kay et al. |
| 2017/0349659 A1 | 12/2017 | Garcia et al. |
| 2017/0349884 A1 | 12/2017 | Karp et al. |
| 2017/0360962 A1 | 12/2017 | Kay et al. |
| 2017/0362573 A1 | 12/2017 | Wells et al. |
| 2017/0362574 A1 | 12/2017 | Sareen et al. |
| 2018/0021341 A1 | 1/2018 | Harriman et al. |
| 2018/0030409 A1 | 2/2018 | Lewis et al. |
| 2018/0042970 A1 | 2/2018 | Rossen et al. |
| 2018/0043357 A1 | 2/2018 | Bocchi et al. |
| 2018/0059119 A1 | 3/2018 | Takáts et al. |
| 2018/0112187 A1 | 4/2018 | Smith et al. |
| 2018/0142206 A1 | 5/2018 | Kime et al. |
| 2018/0171302 A1 | 6/2018 | Accili |
| 2018/0179496 A1 | 6/2018 | Rajesh et al. |
| 2018/0193421 A1 | 7/2018 | Soula |
| 2018/0250410 A1 | 9/2018 | Borros Gomez et al. |
| 2018/0258400 A1 | 9/2018 | Ng et al. |
| 2018/0344901 A1 | 12/2018 | Spence et al. |
| 2019/0031992 A1 | 1/2019 | Kerns et al. |
| 2019/0078055 A1 | 3/2019 | Wells et al. |
| 2019/0093076 A1 | 3/2019 | Schulz |
| 2019/0153395 A1 | 5/2019 | Barrett et al. |
| 2019/0153397 A1 | 5/2019 | Wells et al. |
| 2019/0298775 A1 | 10/2019 | Takebe et al. |
| 2019/0300849 A1 | 10/2019 | Carpino et al. |
| 2019/0314387 A1 | 10/2019 | Takebe et al. |

(56) References Cited

U.S. PATENT DOCUMENTS

| | | |
|---|---|---|
| 2019/0367882 A1 | 12/2019 | Wells et al. |
| 2020/0040309 A1 | 2/2020 | Takebe et al. |
| 2020/0056157 A1 | 2/2020 | Takebe et al. |
| 2020/0102543 A1 | 4/2020 | Okazaki et al. |
| 2020/0149004 A1 | 5/2020 | Spence et al. |
| 2020/0190478 A1 | 6/2020 | Wells et al. |
| 2020/0199537 A1 | 6/2020 | Takebe et al. |
| 2020/0199538 A1 | 6/2020 | Ng et al. |
| 2021/0008123 A1 | 1/2021 | Takebe et al. |
| 2021/0030811 A1 | 2/2021 | Kim et al. |
| 2021/0096126 A1 | 4/2021 | Takebe et al. |
| 2021/0115366 A1 | 4/2021 | Mahe et al. |
| 2021/0180026 A1 | 6/2021 | Takebe et al. |
| 2021/0189349 A1 | 6/2021 | Wells et al. |
| 2021/0292714 A1 | 9/2021 | Takebe et al. |
| 2021/0324334 A1 | 10/2021 | Takebe et al. |
| 2021/0363490 A1 | 11/2021 | Yoshihara et al. |
| 2021/0371815 A1 | 12/2021 | Holloway et al. |
| 2021/0395695 A1 | 12/2021 | Kim et al. |
| 2022/0041684 A1 | 2/2022 | Patterson |
| 2022/0056420 A1 | 2/2022 | Wells et al. |
| 2022/0090011 A1 | 3/2022 | Ngan et al. |
| 2022/0275345 A1 | 9/2022 | Mayhew et al. |
| 2023/0251275 A1 | 8/2023 | Al Gharaibeh et al. |

FOREIGN PATENT DOCUMENTS

| | | |
|---|---|---|
| CN | 101600461 A | 12/2009 |
| CN | 101855554 A | 10/2010 |
| CN | 102307990 A | 1/2012 |
| CN | 102439135 A | 5/2012 |
| CN | 102459574 A | 5/2012 |
| CN | 102740888 A | 10/2012 |
| CN | 103068970 A | 4/2013 |
| CN | 103154237 A | 6/2013 |
| CN | 103561751 A | 2/2014 |
| CN | 104387451 A | 3/2015 |
| CN | 105209605 A | 12/2015 |
| CN | 105985395 A | 10/2016 |
| CN | 109415685 A | 3/2019 |
| CN | 110371967 A | 10/2019 |
| CN | 110381967 A | 10/2019 |
| CN | 110582564 A | 12/2019 |
| EP | 1063289 A1 | 12/2000 |
| EP | 2393917 A2 | 12/2011 |
| EP | 2393917 B1 | 4/2016 |
| EP | 3228306 A1 | 10/2017 |
| JP | 2003521673 A | 7/2003 |
| JP | 2004166717 A | 6/2004 |
| JP | 2008503203 A | 2/2008 |
| JP | 2008505638 A | 2/2008 |
| JP | 2012516685 A | 7/2012 |
| JP | 2012254081 A | 12/2012 |
| JP | 2013066414 A | 4/2013 |
| JP | 2013511969 A | 4/2013 |
| JP | 2013521810 A | 6/2013 |
| JP | 2013528397 A | 7/2013 |
| JP | 2013535201 A | 9/2013 |
| JP | 2014514918 A | 6/2014 |
| JP | 2014516562 A | 7/2014 |
| JP | 2014233281 A | 12/2014 |
| JP | 2019000014 A | 1/2019 |
| JP | 2020516247 A | 6/2020 |
| JP | 2020523000 A | 8/2020 |
| JP | 7068305 B2 | 5/2022 |
| JP | 7148552 B2 | 10/2022 |
| KR | 20060114355 A | 11/2006 |
| WO | WO-9207615 A1 | 5/1992 |
| WO | WO-9821312 A1 | 5/1998 |
| WO | 9945100 A1 | 9/1999 |
| WO | WO-9949807 A2 | 10/1999 |
| WO | 03046141 A2 | 6/2003 |
| WO | WO-2003082201 A2 | 10/2003 |
| WO | WO-2004020614 A1 | 3/2004 |
| WO | WO-2005001072 A1 | 1/2005 |
| WO | 2005063971 A2 | 7/2005 |
| WO | WO-2005081970 A2 | 9/2005 |
| WO | WO-2005097974 A2 | 10/2005 |
| WO | WO-2005113747 A2 | 12/2005 |
| WO | WO-2006126236 A1 | 11/2006 |
| WO | 2008073352 A1 | 6/2008 |
| WO | WO-2008075339 A2 | 6/2008 |
| WO | WO-2009022907 A2 | 2/2009 |
| WO | WO-2009086596 A1 | 7/2009 |
| WO | WO-2009146911 A2 | 12/2009 |
| WO | WO-2010008905 A2 | 1/2010 |
| WO | WO-2010090513 A2 | 8/2010 |
| WO | WO-2010094694 A1 | 8/2010 |
| WO | WO-2010127399 A1 | 11/2010 |
| WO | 2010136583 A2 | 12/2010 |
| WO | WO-2010143747 A1 | 12/2010 |
| WO | WO-2011050672 A1 | 5/2011 |
| WO | 2011064309 A1 | 6/2011 |
| WO | WO-2011116930 A1 | 9/2011 |
| WO | WO-2011139628 A1 | 11/2011 |
| WO | WO-2011140441 A2 | 11/2011 |
| WO | WO-2012014076 A2 | 2/2012 |
| WO | WO-2012027474 A1 | 3/2012 |
| WO | WO-2012089669 A1 | 7/2012 |
| WO | 2012126013 A2 | 9/2012 |
| WO | WO-2012118799 A2 | 9/2012 |
| WO | WO-2012154834 A1 | 11/2012 |
| WO | WO-2012155110 A1 | 11/2012 |
| WO | WO-2012166903 A1 | 12/2012 |
| WO | WO-2012168930 A2 | 12/2012 |
| WO | WO-2012178215 A1 | 12/2012 |
| WO | WO-2013040087 A2 | 3/2013 |
| WO | WO-2013067498 A1 | 5/2013 |
| WO | WO-2013086486 A1 | 6/2013 |
| WO | WO-2013086502 A1 | 6/2013 |
| WO | WO-2013093812 A2 | 6/2013 |
| WO | WO-2013096741 A2 | 6/2013 |
| WO | WO-2013127921 A1 | 9/2013 |
| WO | WO-2013155060 A1 | 10/2013 |
| WO | WO-2013174794 A1 | 11/2013 |
| WO | WO-2013176772 A1 | 11/2013 |
| WO | WO-2013192290 A1 | 12/2013 |
| WO | WO-2014013334 A2 | 1/2014 |
| WO | WO-2014018691 A1 | 1/2014 |
| WO | WO-2014048637 A1 | 4/2014 |
| WO | WO-2014053596 A1 | 4/2014 |
| WO | WO-2014062138 A1 | 4/2014 |
| WO | WO-2014082096 A1 | 5/2014 |
| WO | WO-2014083132 A1 | 6/2014 |
| WO | WO-2014090993 A1 | 6/2014 |
| WO | WO-2014093595 A1 | 6/2014 |
| WO | WO-2014093622 A2 | 6/2014 |
| WO | WO-2014093655 A1 | 6/2014 |
| WO | WO-2014093661 A2 | 6/2014 |
| WO | WO-2014093712 A1 | 6/2014 |
| WO | WO-2014127170 A1 | 8/2014 |
| WO | 2014148646 A1 | 9/2014 |
| WO | WO-2014151921 A1 | 9/2014 |
| WO | WO-2014153230 A1 | 9/2014 |
| WO | WO-2014153294 A1 | 9/2014 |
| WO | WO-2014159356 A1 | 10/2014 |
| WO | WO-2014173907 A1 | 10/2014 |
| WO | WO-2014182885 A2 | 11/2014 |
| WO | WO-2014197934 A1 | 12/2014 |
| WO | WO-2014199622 A1 | 12/2014 |
| WO | WO-2014204728 A1 | 12/2014 |
| WO | WO-2014204729 A1 | 12/2014 |
| WO | WO-2015021358 A2 | 2/2015 |
| WO | WO-2015060790 A1 | 4/2015 |
| WO | WO-2015071474 A2 | 5/2015 |
| WO | WO-2015075175 A1 | 5/2015 |
| WO | WO-2015076388 A1 | 5/2015 |
| WO | WO-2015108893 A1 | 7/2015 |
| WO | WO-2015123183 A1 | 8/2015 |
| WO | WO-2015129822 A1 | 9/2015 |
| WO | WO-2015130919 A1 | 9/2015 |
| WO | WO-2015135893 A1 | 9/2015 |
| WO | WO-2015138032 A2 | 9/2015 |
| WO | WO-2015152954 A1 | 10/2015 |

(56) References Cited

FOREIGN PATENT DOCUMENTS

| | | |
|---|---|---|
| WO | WO-2015156929 A1 | 10/2015 |
| WO | WO-2015157163 A1 | 10/2015 |
| WO | WO-2015168022 A1 | 11/2015 |
| WO | WO-2015173425 A1 | 11/2015 |
| WO | 2015189320 A1 | 12/2015 |
| WO | WO-2015183920 A2 | 12/2015 |
| WO | WO-2015184273 A1 | 12/2015 |
| WO | WO-2015184375 A2 | 12/2015 |
| WO | WO-2015185714 A1 | 12/2015 |
| WO | WO-2015196012 A1 | 12/2015 |
| WO | WO-2015200901 A1 | 12/2015 |
| WO | WO-2016011377 A1 | 1/2016 |
| WO | WO-2016015158 A1 | 2/2016 |
| WO | WO-2016030525 A1 | 3/2016 |
| WO | WO-2016033163 A1 | 3/2016 |
| WO | WO-2016056999 A1 | 4/2016 |
| WO | WO-2016057571 A1 | 4/2016 |
| WO | WO-2016061464 A1 | 4/2016 |
| WO | WO-2016073989 A2 | 5/2016 |
| WO | WO-2016083612 A1 | 6/2016 |
| WO | WO-2016083613 A2 | 6/2016 |
| WO | WO-2016085765 A1 | 6/2016 |
| WO | WO-2016094948 A1 | 6/2016 |
| WO | WO-2016103002 A1 | 6/2016 |
| WO | WO-2016103269 A1 | 6/2016 |
| WO | WO-2016115326 A1 | 7/2016 |
| WO | WO-2016121512 A1 | 8/2016 |
| WO | 2016141131 A1 | 9/2016 |
| WO | 2016148253 A1 | 9/2016 |
| WO | WO-2016140716 A1 | 9/2016 |
| WO | WO-2016141084 A1 | 9/2016 |
| WO | WO-2016141137 A1 | 9/2016 |
| WO | WO-2016141224 A1 | 9/2016 |
| WO | WO-2016144769 A1 | 9/2016 |
| WO | WO-2016164413 A1 | 10/2016 |
| WO | WO-2016168950 A1 | 10/2016 |
| WO | WO-2016174604 A1 | 11/2016 |
| WO | WO-2016176208 A1 | 11/2016 |
| WO | WO-2016183143 A1 | 11/2016 |
| WO | 2016204809 A1 | 12/2016 |
| WO | WO-2016193441 A2 | 12/2016 |
| WO | WO-2016207621 A1 | 12/2016 |
| WO | WO-2016210313 A1 | 12/2016 |
| WO | WO-2016210416 A2 | 12/2016 |
| WO | WO-2017009263 A1 | 1/2017 |
| WO | WO-2017023803 A1 | 2/2017 |
| WO | WO-2017036533 A1 | 3/2017 |
| WO | WO-2017037295 A1 | 3/2017 |
| WO | WO-2017041041 A1 | 3/2017 |
| WO | WO-2017048193 A1 | 3/2017 |
| WO | WO-2017048322 A1 | 3/2017 |
| WO | WO-2017049243 A1 | 3/2017 |
| WO | WO-2017059171 A1 | 4/2017 |
| WO | WO-2017060884 A1 | 4/2017 |
| WO | WO-2017066507 A1 | 4/2017 |
| WO | WO-2017066659 A1 | 4/2017 |
| WO | WO-2017070007 A2 | 4/2017 |
| WO | WO-2017070224 A1 | 4/2017 |
| WO | WO-2017070337 A1 | 4/2017 |
| WO | WO-2017070471 A1 | 4/2017 |
| WO | WO-2017070506 A1 | 4/2017 |
| WO | WO-2017070633 A2 | 4/2017 |
| WO | 2017083696 A1 | 5/2017 |
| WO | WO-2017075389 A1 | 5/2017 |
| WO | WO-2017077535 A1 | 5/2017 |
| WO | WO-2017079632 A1 | 5/2017 |
| WO | WO-2017083705 A1 | 5/2017 |
| WO | WO-2017083838 A1 | 5/2017 |
| WO | WO-2017096192 A1 | 6/2017 |
| WO | WO-2017096282 A1 | 6/2017 |
| WO | WO-2017112901 A1 | 6/2017 |
| WO | WO-2017115982 A1 | 7/2017 |
| WO | WO-2017117333 A1 | 7/2017 |
| WO | WO-2017117547 A1 | 7/2017 |
| WO | WO-2017117571 A1 | 7/2017 |
| WO | WO-2017120543 A1 | 7/2017 |
| WO | WO-2017121754 A1 | 7/2017 |
| WO | WO-2017123791 A1 | 7/2017 |
| WO | WO-2017136462 A2 | 8/2017 |
| WO | WO-2017136479 A1 | 8/2017 |
| WO | WO-2017139455 A1 | 8/2017 |
| WO | WO-2017139638 A1 | 8/2017 |
| WO | WO-2017142069 A1 | 8/2017 |
| WO | WO-2017143100 A1 | 8/2017 |
| WO | WO-2017149025 A1 | 9/2017 |
| WO | WO-2017153992 A1 | 9/2017 |
| WO | WO-2017160234 A1 | 9/2017 |
| WO | WO-2017160671 A1 | 9/2017 |
| WO | WO-2017172638 A1 | 10/2017 |
| WO | WO-2017174609 A1 | 10/2017 |
| WO | WO-2017175876 A1 | 10/2017 |
| WO | WO-2017176810 A1 | 10/2017 |
| WO | WO-2017184586 A1 | 10/2017 |
| WO | WO-2017192997 A1 | 11/2017 |
| WO | WO-2017205511 A1 | 11/2017 |
| WO | WO-2017218287 A1 | 12/2017 |
| WO | WO-2017220586 A1 | 12/2017 |
| WO | WO-2018011558 A1 | 1/2018 |
| WO | WO-2018019704 A1 | 2/2018 |
| WO | WO-2018026947 A1 | 2/2018 |
| WO | WO-2018027023 A1 | 2/2018 |
| WO | WO-2018027112 A1 | 2/2018 |
| WO | WO-2018035574 A1 | 3/2018 |
| WO | WO-2018038042 A1 | 3/2018 |
| WO | WO-2018044685 A1 | 3/2018 |
| WO | WO-2018044885 A1 | 3/2018 |
| WO | WO-2018044937 A2 | 3/2018 |
| WO | WO-2018044940 A1 | 3/2018 |
| WO | WO-2018085615 A1 | 5/2018 |
| WO | WO-2018085622 A1 | 5/2018 |
| WO | WO-2018085623 A1 | 5/2018 |
| WO | WO-2018091677 A1 | 5/2018 |
| WO | WO-2018094522 A1 | 5/2018 |
| WO | WO-2018106628 A1 | 6/2018 |
| WO | WO-2018115852 A1 | 6/2018 |
| WO | 2018170280 A1 | 9/2018 |
| WO | WO-2018191673 A1 | 10/2018 |
| WO | WO-2018197544 A1 | 11/2018 |
| WO | WO-2018200481 A1 | 11/2018 |
| WO | WO-2018226267 A1 | 12/2018 |
| WO | WO-2018229251 A1 | 12/2018 |
| WO | WO-2019060336 A1 | 3/2019 |
| WO | WO-2019074793 A1 | 4/2019 |
| WO | WO-2019126626 A1 | 6/2019 |
| WO | 2019140151 A1 | 7/2019 |
| WO | WO-2020023245 A1 | 1/2020 |
| WO | WO-2020056158 A1 | 3/2020 |
| WO | WO-2020069285 A1 | 4/2020 |
| WO | WO-2020100481 A1 | 5/2020 |
| WO | WO-2020154374 A1 | 7/2020 |
| WO | WO-2020160371 A1 | 8/2020 |
| WO | WO-2020227711 A1 | 11/2020 |
| WO | WO-2020243633 A1 | 12/2020 |
| WO | WO-2020247528 A1 | 12/2020 |
| WO | WO-2021030373 A1 | 2/2021 |
| WO | WO-2021041443 A2 | 3/2021 |
| WO | 2021087508 A1 | 5/2021 |
| WO | WO-2021262676 A1 | 12/2021 |
| WO | 2022261471 A2 | 12/2022 |
| WO | 2023023180 A1 | 2/2023 |
| WO | WO-2023030158 A1 | 3/2023 |

OTHER PUBLICATIONS

McCracken et al. Modelling human development and disease in pluripotent stem-cell-derived gastric organoids. Nature 516: 400-404. (Year: 2014).*

Sebrell et al. Live imaging analysis of human gastric epithelial spheroids reveals spontaneous rupture, rotation and fusion events. Cell Tissue Res. 371: 293-307. Published 2017 (Year: 2018).*

Buske et al. On the biomechanics of stem cell niche formation in the gut—modelling growing organoids. FEBS Journal 279: 3475-3487. (Year: 2012).*

(56) References Cited

OTHER PUBLICATIONS

Xiang et al. Fusion of Regionally Specified hPSC-Derived Organoids Models Human Brain Development and Interneuron Migration. Cell Stem Cell 21: 383-398. (Year: 2017).*

Abe T., et al., "Reporter Mouse Lines for Fluorescence Imaging," Development, Growth & Differentiation, May 2013, vol. 55, No. 4, pp. 390-405.

Adam M., et al., Psychrophilic Proteases Dramatically Reduce Single-Cell RNA-Seq Artifacts: a Molecular Atlas of Kidney Development, Development, Oct. 1, 2017, vol. 144, No. 19, pp. 3625-3632.

Anderson C.M.H., et al., "Inhibition of Intestinal Dipeptide Transport by the Neuropeptide VIP is an Anti-absorptive Effect via the VPAC1 Receptor in a Human Enterocyte-like Cell Line (Caco-2)," British Journal of Pharmacology, 2003, vol. 138, No. 4, pp. 564-573.

Ang L.T., et al., "A Roadmap for Human Liver Differentiation from Pluripotent Stem Cells," Cell Reports, Feb. 20, 2018, vol. 22, pp. 2190-2205.

Arora R., et al., Multiple Roles and Interactions of Tbx4 and Tbx5 in Development of the Respiratory System, PLoS Genetics, Aug. 2, 2012, vol. 8, No. 8, e1002866, 14 pages.

Asahina K., et al., Septum Transversum-Derived Mesothelium gives rise to Hepatic Stellate Cells and Perivascular Mesenchymal Cells in Developing Mouse Liver, Hepatology, Mar. 2011, vol. 53, No. 3, pp. 983-995.

Baker C., et al., "Hypoganglionosis in the Gastric Antrum Causes Delayed Gastric Emptying," Neurogastroenterology and Motility, May 2020, vol. 32(5): e13766, 18 pages.

Balbinot C., et al., "Fine-tuning and Autoregulation of the Intestinal Determinant and Tumor Suppressor Homeobox Gene CDX2 by Alternative Splicing," Call Death and Differentiation, 2017, vol. 24, No. 12, pp. 2173-2186.

Baptista P.M., et al., "Transplantable Liver Organoids, Too Many Cell Types to Choose: a Need for Scientific Self-Organization," Current Transplantation Reports, Feb. 15, 2020, vol. 7, pp. 18-23.

Barber K., et al., "Derivation of Enteric Neuron Lineages from Human Pluripotent Stem Cells," Nature Protocols, Apr. 2019, vol. 14, No. 4, pp. 1261-1279.

Barnes R.M., et al., "Analysis of the Hand1 Cell Lineage Reveals Novel Contributions to Cardiovascular, Neural Crest, Extra-Embryonic, and Lateral Mesoderm Derivatives," Developmental Dynamics, vol. 239, 2010, pp. 3086-3097.

Baron M., et al., A Single-Cell Transcriptomic Map of the Human and Mouse Pancreas Reveals Inter- and Intra-cell Population Structure, Cell Systems, Oct. 26, 2016, vol. 3, No. 4, pp. 346-360.

Batterham R.L., et al., "Gut Hormone PYY3-36 Physiologically Inhibits Food Intake," Nature, Aug. 8, 2002, vol. 418, pp. 650-654.

Bauwens C.L., et al., "Control of Human Embryonic Stem Cell Colony and Aggregate Size Heterogeneity Influences Differentiation Trajectories," Stem Cells, vol. 26, No. 9, Sep. 2008, pp. 2300-2310.

Beckett E.A.H., et al., "Inhibitory Responses Mediated by Vagal Nerve Stimulation are Diminished in Stomachs of Mice with Reduced Intramuscular Interstitial Cells of Cajal," Mar. 20, 2017, Scientific Reports, vol. 7, No. 44759, 11 pages.

Blanchard J.W., et al., "Reconstruction of the Human Blood-Brain Barrier in vitro reveals a Pathogenic Mechanism of APOE4 in Pericytes," Nature Medicine, Jun. 2020, vol. 26, No. 6, pp. 952-963.

Bohorquez D.V., et al., "Neuroepithelial Circuit Formed by Innervation of Sensory Enteroendocrine Cells," The Journal of Clinical Investigation, 2015, vol. 125, No. 2, pp. 782-786.

Bolte C., et al., "FOXF1 Transcription Factor Promotes Lung Regeneration After Partial Pneumonectomy," Scientific Reports, Sep. 6, 2017, vol. 7(1 ):10690, 14 pages.

Brandenberg N., et al., "High-Throughput Automated Organoid Culture via Stem-Cell Aggregation in Microcavity Arrays," Nature Biomedical Engineering, 2020, vol. 4, pp. 863-874.

Breit S., et al., "Vagus Nerve as Modulator of the Brain-Gut Axis in Psychiatric and Inflammatory Disorders," Frontiers in Psychiatry, Mar. 13, 2018, vol. 9, Article. 44, 15 pages.

Briggs J.A., et al., The Dynamics of Gene Expression in Vertebrate Embryogenesis at SingleCell Resolution, Science, Jun. 1, 2018, vol. 360, No. 6392, eaar5780, 23 pages.

Brooks S.J.H., et al., "Extrinsic Primary Afferent Signaling in the Gut," Nature Reviews Gastroenterology and Hepatology, 2013, vol. 10, No. 5, pp. 286-296.

Brosch M., et al., "Epigenomic Map of Human Liver Reveals Principles of Zonated Morphogenic and Metabolic Control," Nature Communications, 2018, vol. 9, Article. 4150, 13 pages.

Bult C.J., et al., Mouse Genome Database (MGD) 2019, Nucleic Acids Research, Jan. 8, 2019, vol. 47, No. D1, pp. D801-D806.

Buning J.W., etaL, "Higher Hydrocortisone Dose Increases Bilirubin in Hypopituitary Patients—results from an RCT," European Journal of Clinical Investigation, 2016, vol. 46, No. 5, pp. 475-480.

Burleigh D.E., et al., "Stimulation of Intestinal Secretion by Vasoactive Intestinal Peptide and Cholera Toxin," Autonomic Neuroscience: Basic and Clinical, 2007, vol. 133, pp. 64-75.

Bykov V.L., "Paneth Cells: History of Discovery, Structural and Functional Characteristics and the Role in the Maintenance of Homeostasis in the Small Intestine," Morfologiia, 2014, vol. 145, No. 1, pp. 67-80.

Cakir B., et al., "Development of Human Brain Organoids with Functional Vascular-like System," Nature Methods, Nov. 2019, vol. 16, No. 11,21 pages.

Calder, L.E., Retinoic Acid-mediated Regulation of GLI3 Enables High Yield Motoneuron Derivation from Human Embryonic Stem Cells Independent of Extrinsic Activation of SHH Signaling, Dissertation, Jan. 2015, 24 pages.

Cao J., et al., "A Human Cell Atlas of Fetal Gene Expression," Science, Nov. 13, 2020, vol. 370(6518), 42 pages.

Cao J., et al., The Single-Cell Transcriptional Landscape of Mammalian Organogenesis, Nature, Feb. 2019, vol. 566, No. 7745, pp. 496-502.

Cardoso W.V., et al., "Regulation of Early Lung Morphogenesis: Questions, Facts and Controversies," Development, 2006, vol. 133, pp. 1611-1624.

Carpenedo R.L., et al., "Homogeneous and Organized Differentiation Within Embryoid Bodies Induced by Microsphere-mediated Delivery of Small Molecules," Biomaterials, May 2009, vol. 30, No. 13, pp. 2507-2515.

Carpenedo R.L., et al., "Rotary Suspension Culture Enhances the Efficiency, Yield, and Homogeneity of Embryoid Body Differentiation," Stem Cells, 2007, vol. 25, pp. 2224-2234.

Carpenedo R.L., "Microsphere-Mediated Control of Embryoid Body Microenvironments," May 2010, 24 pages.

Chambers M. S., et al., Highly Efficient Neural Conversion of Human ES and IPS Cells by Dual Inhibition of SMAD Signaling, Nature Biotechnol., Mar. 2009, vol. 27(3), pp. 275-280.

Chandrasekaran A., et al., "Astrocyte Differentiation of Human Pluripotent Stem Cells: New Tools for Neurological Disorder Research," Frontiers in Cellular Neuroscience, Sep. 26, 2016, vol. 10, Article. 215, 27 pages.

Chen M., et al., "Gene Ablation for PEPTI in Mice Abolishes the Effects of Dipeptides on Small Intestinal Fluid Absorption, Short Circuit Current and Intracellular pH," American Journal of Physiology—Gastrointestinal and Liver Physiology, Apr. 29, 2010, 33 pages.

Chen Y., et al., "Robust Bioengineered 3D Functional Human Intestinal Epithelium," Scientific Reports, vol. 5 (13708), Sep. 16, 2015, XP055454950, DOI: 10.1038/srep13708, 11 pages.

Chua C.C., et al., "Single Luminal Epithelial Progenitors Can Generate Prostate Organoids in Culture," Nature Cell Biology, Oct. 2014, vol. 16(10), 26 pages.

Cohen M., et al., Lung Single-Cell Signaling Interaction Map Reveals Basophil Role in Macrophage Imprinting, Cell, Nov. 1, 2018, vol. 175, No. 4, pp. 1031-1044.

Conley B.J., et al., "Derivation, Propagation and Differentiation of Human Embryonic Stem Cells," The International Journal of Biochemistry & Cell Biology, 2004, vol. 36, pp. 555-567.

(56) References Cited

OTHER PUBLICATIONS

Cox H.M., et aL, "Peptide YY Is Critical for Acylethanolamine Receptor Gpr119-Induced Activation of Gastrointestinal Mucosal Responses," Cell Metabolism, Jun. 9, 2010, vol. 11, pp. 532-542.
Cox H.M., "Neuroendocrine Peptide Mechanisms Controlling Intestinal Epithelial Function," Current Opinion in Pharmacology, 2016, vol. 31, pp. 50-56.
Creeden J.F., et al., "Bilirubin as a Metabolic Hormone: the Physiological Relevance of Low Levels," American Journal of Physiology—Endocrinology and Metabolism, 2021, vol. 320, No. 2, 59 pages.
Daviaud N., et al., "Vascularization and Engraftment of Transplanted Human Cerebral Organoids in Mouse Cortex," Disorders of the Nervous System, Nov./Dec. 2018, vol. 5, No. 6, 18 pages.
De Carvalho A.L.R.T et al., "The in Vitro Multi-Lineage Differentiation and Maturation of Lung and Airway Cells From Human Pluripotent Stem Cell-derived Lung Progenitors in 3D," Nature Protocols, Apr. 2021, 16(4), pp. 1802-1829.
De Soysa T.Y., et al., Single-cell Analysis of Cardiogenesis Reveals Basis for Organ-level Developmental Defects, Nature, Aug. 2019, vol. 572, No. 7767, pp. 120-124.
Dolle L., et al., "EpCAM and the Biology of Hepatic Stem/Progenitor Cells," American Journal of physiology gastrointestinal liver physiology, 2015, vol. 308, pp. G233-G250.
Duh G., et al., "EGF Regulates Early Embryonic Mouse Gut Development in Chemically Defined Organ Culture," International Pediatric Research Foundation, 2000, vol. 48, No. 6, pp. 794-802.
Dye B.R., et al., "Take a Deep Breath and Digest the Material: Organoids and Biomaterials of the Respiratory and Digestive Systems," Materials Research Society, Sep. 2017, vol. 7, No. 3, pp. 502-514.
Egerod K.L., et al., "A Major Lineage of Enteroendocrine Cells Coexpress CCK, Secretin, GIP, GLP-1, PYY, and Neurotensin but Not Somatostatin," Endocrinology, Dec. 1, 2012, vol. 153, No. 12, pp. 5782-5795.
Egerod K.L., et al., "Profiling of G Protein-coupled Receptors in Vagal Afferents Reveals Novel Gut-to-brain Sensing Mechanisms," Molecular Metabolism, 2018, vol. 12, pp. 62-75.
El Sebae G.K., et al., "Single-Cell Murine Genetic Fate Mapping Reveals Bipotential Hepatoblasts and Novel Multi-organ Endoderm Progenitors," Development, Oct. 1, 2018, vol. 145, No. 19, dev168658, 7 pages.
Erkan M., et al., Organ-, Inflammation- and Cancer Specific Transcriptional Fingerprints of Pancreatic and Hepatic Stellate Cells,. Molecular Cancer, Dec. 2010, vol. 9, No. 1, pp. 1-15.
Farrell J.A., et al., Single-Cell Reconstruction of Developmental Trajectories During Zebrafish Embryogenesis, Science, Jun. 1, 2018, vol. 360, No. 6392, eaar3131, 18 pages.
Fattahi F., et al., Deriving Human ENS Lineages for Cell Therapy and Drug Discovery in Hirschsprung Disease, Nature, Feb. 2016, vol. 531 (7592), pp. 105-109.
Faure S., et al., "Enteric Neural Crest Cells Regulate Vertebrate Stomach Patterning and Differentiation," Development, 2015, vol. 142, pp. 331-342.
Ferretti E., et al., Mesoderm Specification and Diversification: From Single Cells to Emergent Tissues,. Current Opinion in Cell Biology, Dec. 2019, vol. 61, pp. 110-116.
Fomin M.E., et al., "Human Fetal Liver Cultures Support Multiple Cell Lineages That Can Engraft Immunodeficient Mice," Open Biology, 2017, 16 pages.
Forster R., et al., "Human Intestinal Tissue with Adult Stem Cell Properties Derived from Pluripotent Stem Cells," Stem Cell Reports, Jun. 3, 2014, vol. 2, No. 6, pp. 838-852.
Foulke-Abel J., et al., Human Enteroids as a Model of Upper Small Intestinal Ion Transport Physiology and Pathophysiology, Gastroenterology, Mar. 2016, vol. 150, No. 3, pp. 638-649.
Francou A., et al., Second Heart Field Cardiac Progenitor Cells in the Early Mouse Embryo, Biochimica et Biophysica Acta, Apr. 1, 2013, vol. 1833, No. 4, pp. 795-798.

Franklin V., et al., Regionalisation of the Endoderm Progenitors and Morphogenesis of the Gut Portals of the Mouse Embryo,. Mechanisms of Development, Jul. 1, 2008, vol. 125, No. 7, pp. 587-600.
Freddo A.M., et al., "Coordination of Signaling and Tissue Mechanics During Morphogenesis of Murine Intestinal Villi: A Role for Mitotic Cell Rounding," Integrative Biology, 2016, 33 pages.
Fukuda M., et al., "Small Intestinal Stem Cell Identity Is Maintained with Functional Paneth Cells in Heterotopically Grafted Epithelium Onto the Colon," Genes & Development, 2014, vol. 28, No. 16, pp. 1752-1757.
Furness J.B., et al., "The Identification of Neuronal Control Pathways Supplying Effector Tissues in the Stomach," Cell and Tissue Research, Dec. 2020, vol. 382, No. 3, pp. 433-445.
Gage B.K., et al., "Generation of Functional Liver Sinusoidal Endothelial Cells from Human Pluripotent Stem-Cell Derived Venous Angioblasts," Cell Stem Cell, Aug. 6, 2020, vol. 27, pp. 254-269.
Galand G., "Brush Border Membrane Sucrase-Isomaltase, Maltase-Glucoamylase and Trehalase in Mammals. Comparative Development, Effects of Glucocorticoids, Molecular Mechanisms, and Phylogenetic Implications," Comparative Biochemistry & Physiology, 1989, vol. 94B, No. 1, 11 pages.
Gao S., et al., "Fetal Liver: An Ideal Niche for Hematopoietic Stem Cell Expansion," Science China, Life Sciences, Review, Aug. 2018, vol. 61 (8), pp. 885-892.
Gerdes H-H., et al., "Intercellular Transfer Mediated by Tunneling Nanotubes," Current Opinion in Cell Biology, 2008, vol. 20, pp. 470-475.
Gilbert M.A., et al., "Protein-Elongating Mutations in MYH11 Are Implicated in a Dominantly Inherited Smooth Muscle Dysmotility Syndrome With Severe Esophageal, Gastric, and Intestinal Disease," Human Mutation, 2020, vol. 41, pp. 973-982.
Gillich A., et al., "Capillary Cell Type Specialization in the Alveolus," Nature, Oct. 2020, 586(7831), pp. 785-789.
Gissen P., et al., "Structural and Functional Hepatocyte Polarity and Liver Disease," Journal of Hepatology, 2015, vol. 63, pp. 1023-1037.
Godoy P., et al., "Recent Advances in 2D and 3D in vitro Systems Using Primary Hepatocytes, Alternative Hepatocyte Sources and Non-parenchymal Liver Cells and their use in Investigating Mechanisms of Hepatotoxicity Cell Signaling and ADME," Arch Toxicol, Aug. 2013, vol. 87, 216 pages.
Gonzales L.W., et al., "Differentiation of Human Pulmonary Type II Cells in Vitro by Glucocorticoid Plus Cyclic Amp," AJP—Lung Articles in Press, 2002, 45 pages.
Goodwin K., et al., "Smooth Muscle Differentiation Shapes Domain Branches During Mouse Lung Development," Development, 2019, 146, 37 pages.
Graffmann N., et al., "Modeling Nonalcoholic Fatty Liver Disease With Human Pluripotent Stem Cell-Derived Immature Hepatocyte-Like Cells Reveals Activation of PLIN2 and Confirms Regulatory Functions of Peroxisome Proliferator-Activated Receptor Alpha," Stem Cells and Development, vol. 25 (15), 2016, pp. 1119-1133.
Grand R. J., et al., "Development of the Human Gastrointestinal Tract—A Review," Gastroenterology, May 1976, vol. 70, No. 5, pp. 790-810.
Grapin-Botton A., Antero-posterior Patterning of the Vertebrate Digestive Tract: 40 Years After Nicole Le Douarin's PhD Thesis, The International Journal of Developmental Biology, Jan. 1, 2005, vol. 49, Nos. 2-3, pp. 335-347.
Gribble F.M., et al., "Function and Mechanisms of Enteroendocrine Cells and Gut Hormones in Metabolism," Reviews, Apr. 2019, vol. 15, pp. 226-237.
Griffin O.D., et al., "Human B1 Cells in Umbilical Cord and Adult Peripheral Blood Express the Novel Phenotype CD20+CD27+CD43+CD70-," Journal of Experimental Medicine, 2011, vol. 208(1), pp. 67-80.
Guye P., et al., "Genetically Engineering Self-organization of Human Pluripotent Stem Cells into a Liver Bud-like Tissue Using Gata6," Nature Communications, Jan. 6, 2016, 12 pages.
Ham O., et al., "Blood Vessel Formation in Cerebral Organoids Formed From Human Embryonic Stem Cells," Biochemical and Biophysical Research Communications, 2020, vol. 521, pp. 84-90.

(56) References Cited

OTHER PUBLICATIONS

Han L., et al., Single Cell Transcriptomics Identifies a Signaling Network Coordinating Endoderm and Mesoderm Diversification during Foregut Organogenesis, Nature Communications, Aug. 2020, vol. 11, No. 4158, pp. 1-16.

Harrison S.P., et al., "Liver Organoids: Recent Developments, Limitations and Potential," Frontiers in Medicine, May 2021, vol. 8, 18 pages.

Hawkins F., et al., "Prospective Isolation of NKX2-1-Expressing Human Lung Progenitors Derived From Pluripotent Stem Cells," The Journal of Clinical Investigation, 2017, 127(6), pp. 2277-2294.

Hill D R., et al., "Bacterial Colonization Stimulates a Complex Physiological Response in the Immature Human Intestinal Epithelium," Developmental Biology, Microbiology and Infectious Disease, Tools and Resources, Nov. 7, 2017, XP055822977, retrieved from the Internet: https://elifesciences.org/articles/29132,35 pages.

Hoffmann A.D., et al., Sonic Hedgehog Is required in Pulmonary Endoderm for Atrial Septation, Development, 2009, vol. 136, pp. 1761 1770.

Holloway E.M., et al., "Differentiation of Human Intestinal Organoids with Endogenous Vascular Endothelial Cells," Developmental Cell, 2020, vol. 54, pp. 516-528.

Homan K.A., et al., "Flow-Enhanced Vascularization and Maturation of Kidney Organoids in Vitro," Nature Methods, 2019, 16(3), pp. 255-262.

Horie M., et al., TBX4 is involved in the Super-Enhancer-Driven Transcriptional Programs Underlying Features Specific to Lung Fibroblasts,. The American Journal of Physiology—Lung Cellular and Molecular Physiology, Jan. 1, 2018, vol. 314, No. 1, pp. L177-L191.

Huang W-K., et al., "Generation of Hypothalamic Arcuate Organoids From Human Induced Pluripotent Stem Cells," Cell Stem Cell, 2021, pp. 1657-1670.

Huss J. M., et al., "Constitutive Activities of Estrogen-Related Receptors: Transcriptional Regulation of Metabolism by the ERR Pathways in Health and Disease," Biochimica et Biophysica Acta, 2015, vol. 1852, 2015, pp. 1912-1927.

Huycke T.R., et al., "Genetic and Mechanical Regulation of Intestinal Smooth Muscle Development," 2019, Cell, vol. 179, pp. 90-105.

Huynh N., et al., "61.06 Feasibility and Scalability of Spring Parameters in Distraction Enterogenesis in a Murine Model," 2017, 3 pages, Retrieved from Internet: URL:https://www.asc-abstracts.org/abs2017/61-06-feasibility-and-scalability-of-spring-parameters-in- distraction-enterogenesis-in-a-murine-model/, Retrieved on Jun. 4, 2022.

Hyland N.P., et al., "Functional Consequences of Neuropeptide Y Y2 Receptor Knockout and Y2 Antagonism in Mouse and Human Colonic Tissues," British Journal of Pharmacology, 2003, vol. 139, pp. 863-871.

Ibarra-Soria X. et al., Defining Murine Organogenesis at Single-Cell Resolution Reveals a Role for the Leukotriene Pathway in Regulating Blood Progenitor Formation,. Nature Cell Biology, Feb. 2018, vol. 20, No. 2, pp. 127-134.

Jacob A., et al., "Derivation of Self-Renewing Lung Alveolar Epithelial Type II Cells From Human Pluripotent Stem Cells," Nature Protocols, 2019, 14(12), pp. 3303-3332.

Jacob F., et al., "Human Pluripotent Stem Cell-Derived Neural Cells and Brain Organoids Reveal SARS-CoV-2 Neurotropism Predominates in Choroid Plexus Epithelium," Cell Stem Cell, 2020, vol. 27, pp. 937-950.

Kaelberer M.M., et al., "A Gut-Brain Neural Circuit for Nutrient Sensory Transduction," Science, Sep. 21, 2018, 361 (6408), 18 pages.

Kalucka J., et al., "Single-Cell Transcriptome Atlas of Murine Endothelial Cells," Cell, 2020, vol. 180, pp. 764-779.

Khalil H.A., et al., "Intestinal Epithelial Replacement by Transplantation of Cultured Murine and Human Cells Into the Small Intestine," Plos One, May 31, 2019, vol. 14, No. 5, 13 pages.

Khan J.A., et al., "Fetal Liver Hematopoietic Stem Cell Niches Associate With Portal Vessels," Science, Jan. 8, 2016, vol. 351 (6269), pp. 176-180.

Kharchenko V. P., et al., Bayesian Approach to Single-cell Differential Expression Analysis, Nature Methods, Jul. 2014, vol. 11, No. 7, pp. 740-742.

Kim E., et al., Isl1 Regulation of Nkx2.1 in the Early Foregut Epithelium Is Required for Trachea-Esophageal Separation and Lung Lobation, Developmental Cell, Dec. 16, 2019, vol. 51, No. 6, pp. 675-683.

Kimura M., et al., "Digitalized Human Organoid for Wireless Phenotyping," iScience, cell press, XP055822469, DOI: 10.1016/j.isci.2018.05.007, retrieved from the Internet: https://www.ncbi.nlm.nih.gov/pmc/articles/PMC6147234/, Jun. 29, 2018, vol. 4, pp. 294-301.

Kinchen J., et al., "Structural Remodeling of the Human Colonic Mesenchyme in Inflammatory Bowel Disease," Cell, 2018, vol. 175, No. 2, pp. 372-388.

Kiselev Y. V., et al., SCmap—A Tool for Unsupervised Projection of Single Cell RNA-seq data, Nature Methods, May 2018, vol. 15 (5), pp. 359-362.

Kitano K., et al., "Bioengineering of Functional Human Induced Pluripotent Stem Cell-derived Intestinal Grafts," Nature Communications, 2017, vol. 8, No. 765, 13 pages.

Knox S.M., et al., "Parasympathetic Innervation Maintains Epithelial Progenitor Cells During Salivary Organogenesis," Science, Sep. 24, 2010, 329(5999), pp. 1645-1647.

Koike H., et al., "Engineering Human Hepato-Biliary-Pancreatic Organoids from Pluripotent Stem Cells," Nature Protocols, Feb. 2021, vol. 16(2), pp. 919-936.

Koike H., et al., Modeling human hepato-biliary-pancreatic organogenesis from the foregutmidgut boundary, Nature, Oct. 2019, vol. 574(7776), pp. 112-116.

Koslowski M., et al., "MS4A12 Is a Colon-Selective Store-Operated Calcium Channel Promoting Malignant Cell Processes," Cancer Research, May 1, 2008, vol. 68, No. 9, 3458-3466.

Kotobank, "Encyclopedia—Basement Membrane," Machine translated by Google, 2023, 6 pages.

Kuna L., et al., "Peptic Ulcer Disease: A Brief Review of Conventional Therapy and Herbal Treatment Options," Journal of Clinical Medicine, 2019, vol. 8, No. 2, 19 pages.

Lanas A., et al., "Peptic Ulcer Disease," vol. 390, Aug. 5, 2017, pp. 613-624.

Langfelder P., et al., WGCNA: An R package for weighted correlation network analysis, BMC Bioinformatics, Dec. 2008, vol. 9 (1), pp. 1-13.

Langmead B., et al., Fast Gapped-read Alignment with Bowtie 2, Nature Methods, Apr. 2012, vol. 9 (4), pp. 357-359.

Lasrado R., et al., "Lineage-Dependent Spatial and Functional Organization of the Mammalian Enteric Nervous System," Science, 2017, vol. 356, pp. 722-726.

Le Douarin N., et al., Role of the Mesoderm in the Induction of the Synthesis of Glycogen During Differentiation of the Hepatic Endoderm, CR Acad Hebd Seances Acad Sci D, 1967, vol. 264, pp. 1872-1874.

Le Guen L., et al., "Mesenchymal-Epithelial Interactions During Digestive Tract Development and Epithelial Stem Cell Regeneration," Cellular and Molecular Life Sciences, 2015, vol. 72, No. 20, pp. 3883-3896.

Lee G., et al., "Derivation of Neural Crest Cells From Human Pluripotent Stem Cells," Nature Protocols, Mar. 18, 2010, vol. 5(4), pp. 688-701.

Li et al., RSEM: Accurate Transcript Quantification from RNA-Seq data with or without a Reference Genome, BMC Bioinformatics Aug. 2011, vol. 12, No. 323, 16 pages.

Li L.C., et al., Single-Cell Transcriptomic Analyses Reveal Distinct Dorsal/Ventral Pancreatic Programs,. EMBO Reports, Oct. 2018, vol. 19, No. 10, e46148,14 pages.

Li Z., et al., "Essential Roles of Enteric Neuronal Serotonin in Gastrointestinal Motility and the Development/Survival of Enteric Dopaminergic Neurons," The Journal of Neuroscience, Jun. 15, 2011, vol. 31, No. 24, pp. 8998-9009.

(56) References Cited

OTHER PUBLICATIONS

Lian X., et al., "Robust Cardiomyocyte Differentiation From Human Pluripotent Stem Cells via Temporal Modulation of Canonical Wnt Signaling," PNAS, May 29, 2012, pp. E1848-E1857.

Lino S., et al., "Interstitial Cells of Cajal Are Involved in Neurotransmission in the Gastrointestinal Tract," The Japan Society of Histochemistry and Cytochemistry, 2006, 39 (6), pp. 145-153.

Lippmann E.S., et al., "Human Blood-Brain Barrier Endothelial Cells Derived from Pluripotent Stem Cells," Nature Biotechnology, Aug. 2012, 30(8), pp. 783-791.

Lis R., et al., "Conversion of Adult Endothelium to Immunocompetent Haematopoietic Stem Cells," Nature, May 2017, vol. 545 (7655), pp. 439-445.

Little D.R., et al., "Differential Chromatin Binding of the Lung Lineage Transcription Factor NKX2-1 Resolves Opposing Murine Alveolar Cell Fates in Vivo," Nature Communications, 2021, vol. 12, 18 pages.

Loh K. M., et al., Mapping the Pairwise Choices Leading From Pluripotency to Human Bone, Heart, and Other Mesoderm Cell Types, Cell, Jul. 14, 2016, vol. 166, No. 2, pp. 451-467.

Ma T.Y., et al., "IEC-18, A Nontransformed Small Intestinal Cell Line for Studying Epithelial Permeability," Journal of Laboratory and Clinical Medicine, Aug. 1992, vol. 120, No. 2, pp. 329-341.

Mahe M., et al., "Establishment of Human Epithelial Enteroids and Colonoids from Whole Tissue and Biopsy," Journal of Visualized Experiments, Mar. 6, 2015, vol. 97, 13 pages.

Manno L. G., et al., Molecular Diversity of Midbrain Development in Mouse, Human and Stem Cells, Cell, Oct. 6, 2016, vol. 167, (2), pp. 566-580.

Mansour A.A., et al., "An In Vivo Model of Functional and Vascularized Human Brain Organoids," Nature Biotechnology, Jun. 2018, 36(5), pp. 432-441.

Mashima H., et al., INSL5 may be a Unique Marker of Colorectal Endocrine Cells and Neuroendocrine Tumors, Biochemical and Biophysical Research Communications, 2013, vol. 432, pp. 586-592.

Mccann C.J., et al., "Enteric Neural Stem Cell Therapies for Enteric Neuropathies," Neurogastroenterology and Motility, vol. 30, e13369, 2018, doi: 10.1111/nmo.13369, pp. 1-9.

Mccauley H.A., "Enteroendocrine Regulation of Nutrient Absorption," The Journal of Nutrition, 2019, pp. 10-21.

Mccauley H.A., et al., "Enteroendocrine Cells Couple Nutrient Sensing to Nutrient Absorption by Regulating Ion Transport," Nature Communications, 2020, vol. 11, 10 pages.

Mccauley K.B., et al., "Efficient Derivation of Functional Human Airway Epithelium from Pluripotent Stem Cells via Temporal Regulation of Wnt Signaling," Cell Stem Cell, 2017, vol. 20, pp. 844-857.

Mccauley K.B., et al., "Single-Cell Transcriptomic Profiling of Pluripotent Stem Cell-Derived SCGB3A2+ Airway Epithelium," Stem Cell Reports, 2018, vol. 10, pp. 1579-1595.

McGrath P.S., et al., The Basic Helix-Loop-Helix Transcription Factor NEUROG3 Is Required for Development of the Human Endocrine Pancreas, Diabetes, Jul. 2015, vol. 64, pp. 2497-2505.

McIntyre B., et al., "Gli3-mediated hedgehog inhibition in human pluripotent stem cells initiates and augments developmental programming of adult hematopoiesis," The American Society of Hematology, Feb. 28, 2013, vol. 121 (9), pp. 1543-1552.

McKimpson W.M., et al., "A Fluorescent Reporter Assay of Differential Gene Expression Response to Insulin in Hepatocytes," Methods in Cell Physiology, American Journal of Physiology Cell Physiology, May 15, 2019, vol. 317, pp. C143-C151.

Mellitzer G., et al., "Loss of Enteroendocrine Cells in Mice Alters Lipid Absorption and Glucose Homeostasis and Impairs Postnatal Survival," The Journal of Clinical Investigation, vol. 120, No. 5, May 2010, pp. 1708-1721.

Menendez L., et al., Directed differentiation of human pluripotent cells to neural crest stem cells, Nature Protocols, Jan. 2013, vol. 8 (1), pp. 203-212.

Menoret S., et al., "Generation of Immunodeficient Rats With Rag1 and Il2rg Gene Deletions and Human Tissue Grafting Models," Transplantation, Aug. 2018, vol. 102, No. 8, pp. 1271-1278.

Mentlein R., et al., "Proteolytic Processing of Neuropeptide Y and Peptide YY by Dipeptidyl Peptidase IV," Regulatory Peptides, 1993, vol. 49, pp. 133-144.

Miranda J., et al., "A Novel Mutation in FOXF1 Gene Associated with Alveolar Capillary Dysplasia with Misalignment of Pulmonary Veins, Intestinal Malrotation and Annular Pancreas," Neonatology, 2013, vol. 103, pp. 241-245.

MITAKA., et al., "Characterization of Hepatic-organoid Cultures," Drug Metabolism Reviews, 2010, vol. 42, No. 3, pp. 472-481.

Mitaka T., "Reconstruction of Hepatic Organoid by Hepatic Stem Cells," Journal of Hepatobiliary Pancreatic Surgery, 2002, vol. 9 (6), pp. 697-703.

Moignard V., et al., Decoding the Regulatory Network of Early Blood Development From Single-Cell Gene Expression Measurements, Nature Biotechnology, Mar. 2015, vol. 33, No. 3, pp. 269-276.

Moniot B., et al., "SOX9 Specifies the Pyloric Sphincter Epithelium Through Mesenchymal-epithelial Signals," Development, Aug. 2004, vol. 131, No. 15, pp. 3795-3804.

Montecino-Rodriguez E., et al., "Identification of a B-1 B Cell-Specified Progenitor," Natural Immunology, Mar. 2006, vol. 7(3), pp. 293-301.

Moodaley R., et al., "Agonism of Free Fatty Acid Receptors 1 and 4 Generates Peptide YY-Mediated Inhibitory Responses in Mouse Colon," British journal of Pharmacology, 2017, vol. 174, pp. 4508-4522.

Morrisey E.E., et al., "Preparing for the First Breath: Genetic and Cellular Mechanisms in Lung Development," Developmental Cell, Jan. 19, 2010, vol. 18, pp. 8-23.

Morrison A. J., et al., Single-cell transcriptome analysis of avian neural crest migration reveals signatures of invasion and molecular transitions, eLife., Dec. 2017, vol. 6, 27 pages.

Moschidou D., et al., "Human Mid-Trimester Amniotic Fluid Stem Cells Cultured under Embryonic Stem Cell Conditions with Valproic Acid Acquire Pluripotent Characteristics," Stem Cells and Development, Feb. 1, 2013, vol. 22, No. 3, pp. 444-458.

Nagy N., et al., "Enteric Nervous System Development: a Crest Cell's Journey From Neural Tube to Colon," Seminars in Cell & Developmental Biology, 2017, vol. 66, pp. 94-106.

Nagy N., et al., "Sonic Hedgehog Controls Enteric Nervous System Development by Patterning the Extracellular Matrix," Development, 2016, 143(2), pp. 264-275.

Nakahara T., et al., "Human Papillomavirus Type 16 E1E4 Contributes to Multiple Facets of the Papillomavirus Life Cycle," Journal of Virology, Oct. 31, 2005, vol. 79, No. 20, pp. 13150-13165.

Nakamura T., et al., "Intestinal Stem Cell Transplantation," Journal of Gastroenterology, 2017, vol. 52, pp. 151-157.

Nantasanti S., et al., Disease Modeling and Gene Therapy of Copper Storage Disease in Canine Hepatic Organoids, Stem Cell Reports, 2015, vol. 5, pp. 895-907.

Nasr T., et al., Endosome-Mediated Epithelial Remodeling Downstream of Hedgehog-Gli Is Required for Tracheoesophageal Separation, Developmental Cell, Dec. 16, 2019, vol. 51, No. 6, pp. 665-674.

Naujok O., et al., Cytotoxicity and Activation of the WNT/Beta-Catenin Pathway in Mouse Embryonic Stem Cells Treated with Four GSK3 Inhibitors, BMC Research Notes, 2014, vol. 7, No. 273, pp. 1-8.

Nedvetsky P.I., et al., "Parasympathetic Innervation Regulates Tubulogenesis in the Developing Salivary Gland," Developmental Cell, 2014, vol. 30, pp. 449-462.

Ng S., et al., "Human iPSC-Derived Hepatocyte-Like Cells Support Plasmodium Liver-Stage Infection In Vitro," Stem cell reports, Mar. 10, 2015, vol. 4, pp. 348-359.

Nguyen J., et al., "The Next Generation of Endothelial Differentiation: Tissue-Specific Ecs," Cell Stem Cell, Jul. 1, 2021, vol. 28(7), pp. 1188-1204.

(56) References Cited

OTHER PUBLICATIONS

Norlen P., et al., "The Vagus Regulates Histamine Mobilization From Rat Stomach ECL Cells by Controlling Their Sensitivity to Gastrin," The Journal of Physiology, 2005, 564(Pt 3), pp. 895-905.
Nowotschin S., et al., The Emergent Landscape of the Mouse Gut Endoderm at Single-Cell Resolution, Nature, May 2019, vol. 569, No. 7756, pp. 361-367.
Oceguera-Yanez F., et al., "Engineering the AAVS1 Locus for Consistent and Scalable Transgene Expression in Human iPSCs and their Differentiated Derivatives," Methods, 2015, 13 pages.
Ogaki S., et al., A Cost-Effective System for Differentiation of Intestinal Epithelium from Human Induced Pluripotent Stem Cells, Scientific Reports, Nov. 30, 2015, 11 pages.
Ohashi S., et al., "Epidermal Growth Factor Receptor and Mutant p53 Expand an Esophageal Cellular Subpopulation Capable of Epithelial-to-Mesenchymal Transition through ZEB Transcription Factors," Tumor and Stem Cell Biology, Apr. 27, 2010, vol. 70, No. 10, pp. 4147-4184.
Paik D.T., et al., "Single-cell RNA-Seq Unveils Unique Transcriptomic Signatures of Organ-Specific Endothelial Cells," Circulation, Nov. 10, 2020, 142(19), pp. 1848-1862.
Palikuqi B., et al., "Adaptable Haemodynamic Endothelial Cells for Organogenesis and Tumorigenesis," Nature, Sep. 17, 2020, vol. 585, 33 pages.
Panaro B.L., et al., "The Melanocortin-4 Receptor Is Expressed in Enteroendocrine L Cells and Regulates the Release of Peptide YY and Glucagon-like Peptide 1 In Vivo," Cell Metabolism, Dec. 2, 2014, vol. 20, pp. 1018-1029.
Park B., et al., "Hematopoietic Stem Cell Expansion and Generation: the Ways to Make a Breakthrough," Blood Research, Dec. 2015, vol. 50, No. 4, 10 pages.
Payushina O.V., Hematopoietic Microenvironment in the Fetal Liver: Roles of Different Cell Populations, Review Article, International Scholarly Research Network Cell Biology, 2012, 8 pages.
Pedersen J.K., et al., Endodermal Expression of Nkx6 Genes depends differentially on Pdx1, Developmental Biology, Dec. 15, 2005, vol. 288, No. 2, pp. 487-501.
Peng T., et al., Coordination of Heart and Lung Co-development by a Multipotent Cardiopulmonary Progenitor, Nature, Aug. 2013, vol. 500, No. 7464, pp. 589-592.
Penkala I.J., et al., "Age-Dependent Alveolar Epithelial Plasticity Orchestrates Lung Homeostasis and Regeneration," Cell Stem Cell, Oct. 7, 2021, vol. 28, pp. 1775-1789.
Perriot S., et al., "Differentiation of Functional Astrocytes From Human-Induced Pluripotent Stem Cells in Chemically Defined Media," STAR Protocols, Dec. 17, 2021,2(4):100902, 13 pages.
Perriot S., et al., "Human Induced Pluripotent Stem Cell-Derived Astrocytes Are Differentially Activated by Multiple Sclerosis-Associated Cytokines," Stem Cell Reports, Nov. 13, 2018, vol. 11, pp. 1199-1210.
Pijuan-Sala B., et al., A Single-Cell Molecular Map of Mouse Gastrulation and Early Organogenesis, Nature, Feb. 2019, vol. 566, No. 7745, pp. 490-495.
Pradhan A., et al., "The S52F FOXF1 Mutation Inhibits STAT3 Signaling and Causes Alveolar Capillary Dysplasia," American Journal of Respiratory and Critical Care Medicine, Oct. 15, 2019, vol. 200, No. 8, pp. 1045-1056.
Qian X., et al., "Brain-Region-Specific Organoids Using Mini-bioreactors for Modeling ZIKV Exposure," Cell, 2016, vol. 165, pp. 1238-1254.
Qian X., et aL, "Generation of Human Brain Region-specific Organoids Using a Miniaturized Spinning Bioreactor," Nature Protocols, Mar. 2018, 13(3), pp. 565-580.
Qin X., "Why is Damage Limited to the Mucosa in Ulcerative Colitis but Transmural in Crohn's Disease", World Journal of Gastrointestinal Pathophysiology, Aug. 15, 2013, vol. 4, No. 3, pp. 63-64.

Que J., et al., Mesothelium Contributes to Vascular Smooth Muscle and Mesenchyme During Lung Development, Proceedings of the National Academy of Sciences USA, Oct. 28, 2008, vol. 105, No. 43, pp. 16626-16630.
Rakhilin N., et al., "Simultaneous Optical and Electrical in Vivo Analysis of the Enteric Nervous System," Nature Communications, Jun. 7, 2016, 7:11800, 7 pages.
Ran F.A., et al., "Genome Engineering using the CRISPR-Cas9 System," Nature Protocols, Nov. 2013, 8(11), pp. 2281-2308.
Rana M.S., et al., A Molecular and Genetic Outline of Cardiac Morphogenesis, Acta Physiologica (Oxf), Apr. 2013, vol. 207, No. 4, pp. 588-615.
Rice A.C., et aL, "A New Animal Model of Hemolytic Hyperbilirubinemia-Induced Bilirubin Encephalopathy (Kernicterus)," Pediatric Research, 2008, vol. 64, No. 3, pp. 265-269.
Riehl T., et al., "CD44 and TLR4 Mediate Hyaluronic Acid Regulation of Lgr5+ Stem Cell Proliferation, Crypt Fission, and Intestinal Growth in Postnatal and Adult Mice," The American Journal of Physiology—Gastrointestinal and Liver Physiology, Dec. 1, 2015, vol. 309, No. 11, pp. G874-G887.
Robert-Moreno A., et al., "Impaired Embryonic Haematopoiesis Yet Normal Arterial Development in the Absence of the Notch ligand Jagged1 ," EMBO Journal, 2008, vol. 27(13), pp. 1886-1895.
Robert-Moreno A., et al., "RBPj ?-dependent Notch Function Regulates Gata2 and is Essential for the Formation of Intra-embryonic Hematopoietic Cells," Development and disease, 2005, vol. 132(5), pp. 1117-1126.
Roberts D.J., et aL, "Epithelial-mesenchymal Signaling During the Regionalization of the Chick Gut," Development, 1998, vol. 125, No. 15, pp. 2791-2801.
Rothstein L.T., etaL, "Human B-1 cells take the stage," Annals of the New York Academy of Sciences, May 2013, vol. 1285, pp. 97-114.
Rubin L.L., et al., Targeting the Hedgehog Pathway in Cancer, Nature Reviews Drug Discovery, 2006, vol. 5, pp. 1026-1033.
Rydning A., et al., "Mast Cell Derived Histamine is Involved in Gastric Vasodilation During Acid Back Diffusion via Activation of Sensory Neurons," May 15, 2002, 36 pages.
Sanchez-Valle V., et al., "Role of Oxidative Stress and Molecular Changes in Liver Fibrosis: A Review," Current Medicinal Chemistry, 2012, vol. 19, No. 28, pp. 4850-4860.
Sander M., et al., Homeobox Gene Nkx6.1 lies Downstream of Nkx2.2 in the major Pathway of Beta-Cell formation in the Pancreas, Development, Dec. 15, 2000, vol. 127, No. 24, pp. 5533-5540.
Sathananthan A.H., et al., "Human Embryonic Stem Cells and their Spontaneous Differentiation," Italian Journal of Anatomy and Embryology, 2005, vol. 110 (Supplement 1), No. 2, pp. 151-157.
Sauka-Spengler T., et al., Snapshot: Neural Crest, Cell, Oct. 2010, vol. 143, No. 3, 486-486.e1.
Schlieve C. R., et al., Neural Crest Cell Implantation Restores Enteric Nervous System Function and Alters the Gastrointestinal Transcriptome in Human Tissue-Engineered Small Intestine, Stem Cell Reports, ISSCR, Sep. 12, 2017, vol. 9, pp. 883-896.
Scialdone A., et al., Resolving Early Mesoderm Diversification Through Single-Cell Expression Profiling, Nature, Jul. 2016, vol. 535, No. 7611, pp. 289-293.
Scott A., et al., "Repeated Mechanical Lengthening of Intestinal Segments in a Novel Model," Journal of Pediatric Surgery, Jun. 2015, vol. 50, No. 6, pp. 954-957.
Seet C.S., et al., Generation of Mature T Cells from Human Hematopoietic Stem/Progenitor Cells in Artificial Thymic Organoids, Nature Methods, May 2017, vol. 14 (5), pp. 521-530.
Semrau S., et al., Dynamics of lineage commitment revealed by single-cell transcriptomics of differentiating embryonic stem cells, Nature Communications, Oct. 2017, vol. 8 (1), pp. 1-16.
Shacham-Silverberg V., et al., "Generation of Esophageal Organoids and Organotypic Raft Cultures from Human Pluripotent Stem Cells," Methods of Cell Biology, May 13, 2020, vol. 159, pp. 1-23.
Shaylor L.A., et al., "Convergence of Inhibitory Neural Inputs Regulate Motor Activity in the Murine and Monkey Stomach," American Journal of Physiology—gastrointestinal and Liver Physiology, Sep. 15, 2016, 44 pages.

(56) References Cited

OTHER PUBLICATIONS

Shi Y., et aL, "Vascularized Human Cortical Organoids (vOrganoids) Model Cortical Development in Vivo," PloS Biology, 2020, 8(5), 29 pages.
Shin Y., et aL, "Blood-Brain Barrier Dysfunction in a 3D In Vitro Model of Alzheimer's Disease," Advanced Science, 2019, 6(20), 10 pages.
Simões F.C., et al., "The Ontogeny, Activation and Function of the Epicardium During Heart Development and Regeneration," Development, Apr. 1, 2018, vol. 145, No. 7, dev155994; 13 pages.
Simian M., et aL, "Organoids: A Historical Perspective of Thinking In Three Dimensions," Journal of Cell Biology, 2017, vol. 216, No. 1, pp. 31-40.
Singh A., et al., "Evaluation of Transplantation Sites for Human Intestinal Organoids," Plos One, Aug. 27, 2020, 15(8), 12 pages.
Singh A., et al., "Gastrointestinal Organoids: a Next-Generation Tool for Modeling Human Development," American Journal of Physiology—gastrointestinal and Liver Physiology, 2020, 319(3), pp. G375-G381.
Smith D.M., et al., "BMP Signalling Specifies the Pyloric Sphincter," Nature, Dec. 16, 1999, vol. 402, pp. 748-749.
Soldatow V. Y., et al., "In Vitro Models for Liver Toxicity Testing," Toxicology Research 2.1, 2013, vol. 2, pp. 23-39.
Song L., et al., "Assembly of Human Stem Cell Derived Cortical Spheroids and Vascular Spheroids to Model 3-D Brain-like Tissues," 2019, Scientific Reports, vol. 9, No. 5977, 16 pages.
Srinivasan B., et al., "TEER Measurement Techniques for in Vitro Barrier Model Systems," Journal of Laboratory Automation, 2015, 20 (2), 20 pages.
Stevens M.L., et al., "Genomic Integration of Wnt/-catenin and BMP/smad1 Signaling Coordinates Foregut and Hindgut Transcriptional Programs," Development, 2017, 144(7), pp. 1283-1295.
Strauss K.A., et al., "Crigler-Najjar Syndrome Type 1: Pathophysiology, Natural History, and Therapeutic Frontier," Hepatology, 2020, 71(6), pp. 1923-1939.
Sugimoto S., et al., "An Organoid-based Organ-Repurposing Approach to Treat Short Bowel Syndrome," Nature, Apr. 2021, vol. 99, 26 pages.
Sugimura R., et al., "Haemotopoietic Stem and Progenitor Cells from Human Pluripotent Stem Cells," Nature, May 25, 2017, vol. 545 (7655), pp. 432-438.
Sullins V. F., et al., "Intestinal Lengthening in an Innovative Rodent Surgical Model," Journal of Pediatric Surgery, Dec. 2014, vol. 49, No. 12, pp. 1791-1794.
Sun X-Y., et al., "Generation of Vascularized Brain Organoids to Study Neurovascular Interactions," eLife, 2022, vol. 11,28 pages.
Sung T.S., et al., "The Cells and Conductance Mediating Cholinergic Neurotransmission in the Murine Proximal Stomach," The Journal of Physiology, 2018, 596(9), pp. 1549-1574.
Sweetman D., et al., The Migration of Paraxial and Lateral Plate Mesoderm Cells Emerging From the Late Primitive Streak Is Controlled by Different Wnt Signals, BMC Developmental Biology, Dec. 2008, vol. 8, No. 1, pp. 1-15.
Tan S.H., et al., "AQP5 Enriches for Stem Cells and Cancer Origins in the Distal Stomach," Nature, 2020, 578 (7795), pp. 437-443.
Tanaka M., "Molecular and Evolutionary Basis of Limb Field Specification and Limb Initiation," Development, Growth & Differentiation, Jan. 2013, vol. 55, No. 1, pp. 149-163.
Tang X. et al. Transcriptome Regulation and Chromatin Occupancy by E2F3 and MYC in Mice, Scientific Data, Feb. 16, 2016, vol. 3, No. 1, pp. 1-8.
Tanimizu N., et al., "Generation of Functional Liver Organoids on Combining Hepatocytes and Cholangiocytes with Hepatobiliary Connections Ex Vivo," Nature Communications, Jun. 2021, 12 pages.
Tanimizu N., et al., "Tissue Structure Formation by Liver Epithelial Cells," 2012, vol. 84, No. 8, pp. 658-665.
TCW J. et al., "An Efficient Platform for Astrocyte Differentiation from Human Induced Pluripotent Stem Cells," Stem Cell Reports, vol. 9, 2017, pp. 600-614.

Teixeira V., et al., "Neonatal Vitamin C and Cysteine Deficiencies Program Adult Hepatic Glutathione and Specific Activities of Glucokinase, Phosphofructokinase, and Acetyl-CoA Carboxylase in Guinea Pigs' Livers," 2021, Antioxidants, 10, 953, 17 pages.
Testaz S., et al., Sonic hedgehog restricts adhesion and migration of neural crest cells independently of the Patched-Smoothened-Gli signaling pathway, PNAS, Oct. 23, 2001, vol. 98 (22), pp. 12521-12526.
Theodosiou N.A., et al., "Sox9 and Nkx2. 5 Determine the Pyloric Sphincter Epithelium Under the Control of BMP Signaling," Developmental Biology, 2005, 279, pp. 481-490.
Thompson C.A., et al., "GATA4 Is Sufficient to Establish Jejunal Versus Ileal Identity in the Small Intestine," Cellular and Molecular Gastroenterology and Hepatology, May 2017, 3(3), pp. 422-446.
Thwaites D.T., et al., "H+/Dipeptide Absorption Across the Human Intestinal Epithelium Is Controlled Indirectly via a Functional Na+/H+ Exchanger," Gastroenterology, 2002, vol. 122, pp. 1322-1333.
Tough I.R., et al., "Endogenous Peptide YY and Neuropeptide Y Inhibit Colonic Ion Transport, Contractility and Transit Differentially via Y1 and Y2 Receptors," British journal of Pharmacology, 2011, vol. 164, pp. 471-484.
Traber M.G., et al., "Vitamins C and E: Beneficial Effects from a Mechanistic Perspective," Free Radical Biology and Medicine, 2011,51 (5), pp. 1000-1013.
Tsai Y-H., et al., "In Vitro Patterning of Pluripotent Stem Cell-Derived Intestine Recapitulates in Vivo Human Development," Development, 2016, 144(6), 57 pages.
Ueda T., et al., "Expansion of Human NOD/SCID-repopulating Cells by Stem Cell Factor Flk2/Flt3 ligand, thrombopoietin, IL-6, and soluble IL-6 receptor," Journal of Clinical Investment, 2000, vol. 105(7), pp. 1013-1021.
Uenishi I.G., et al., "NOTCH Signaling Specifies Arterial-type Definitive Hemogenic Endothelium from Human Pluripotent Stem Cells," Nature Communication, 2018,14 pages.
Ustiyan V., et al., "FOXF1 Transcription Factor Promotes Lung Morphogenesis by Inducing Cellular Proliferation in Fetal Lung Mesenchyme," Developmental Biology, 2018, 443(1), pp. 50-63.
Vallicelli C., et al., "Small Bowel Emergency Surgery: Literature's Review," World Journal of Emergency Surgery, 2011, vol. 6, No. 1,8 pages.
Van De Steeg E., et al., "Complete OATP1B1 and OATP1B3 Deficiency Causes Human Rotor Syndrome by Interrupting Conjugated Bilirubin Reuptake Into the Liver," The Journal of Clinical Investigation, 2012, vol. 122, No. 2, pp. 519-528.
Vannucchi M.G., "The Telocytes: Ten Years after Their Introduction in the Scientific Literature. An Update on Their Morphology, Distribution, and Potential Roles in the Gut," International Journal of Molecular Sciences, 2020, vol. 21, 15 pages.
Vila Ellis L., et al., "Epithelial Vegfa Specifies a Distinct Endothelial Population in the Mouse Lung," Developmental Cell, 2020, 52, pp. 617-630.
Wagner D.E., et al., Lineage Tracing Meets Single-cell Omics: Opportunities and Challenges, Nature Reviews Genetics, Jul. 2020, vol. 21, No. 7, pp. 410-427.
Walsh K.T., et al., "The Enteric Nervous System for Epithelial Researchers: Basic Anatomy, Techniques, and Interactions With the Epithelium," Cellular and Molecular Gastroenterology and Hepatology, 2019, vol. 8, No. 3, pp. 369-378.
Wang, et al., "Spatially Monitoring Oxygen Level in 3D Microfabricated Cell Culture Systems Using Optical Oxygen Sensing Beads," Lab on a Chip, 2013, vol. 13, pp. 1586-1592.
Wang J., et al., WebGestalt 2017: A more comprehensive, powerful, flexible and interactive gene set enrichment analysis toolkit, Nucleic Acids Research, Jul. 2017, vol. 45, 8 pages.
Wang L., et al., "The Maintenance and Generation of Membrane Polarity in Hepatocytes," Hepatology, 2004, vol. 39, No. 4, pp. 892-899.
Wang Y., et al., "Loss of Lrig1 Leads to Expansion of Brunner Glands Followed by Duodenal Adenomas with Gastric Metaplasia," The American Journal of Pathology, Apr. 2015, vol. 185, No. 4, 12 pages.

(56) References Cited

OTHER PUBLICATIONS

Ward S.M., et al., "Involvement of Intramuscular Interstitial Cells of Cajal in Neuroeffector Transmission in the Gastrointestinal Tract," The Journal of Physiology, 2006, vol. 576, pp. 675-682.
Weinreb C., et al., Lineage tracing on transcriptional landscapes links state to fate during differentiation, Science, Feb. 14, 2020, vol. 367, ( 6479), 48 pages.
Weinreb C., et al., SPRING: A Kinetic Interface for Visualizing High Dimensional Single-cell Expression Data, Bioinformatics, Apr. 2018, vol. 34 ( 7), pp. 1246-1248.
Weisenberg, E. M.D., "Esophagus—General Histology"; Pathology Outlines, Copyright 2003-2023, 2023,3 Pages.
Westfal M.L., et al., "Pediatric Enteric Neuropathies: Diagnosis and Current Management," Current Opinion in Pediatrics, 2017, 29(3), pp. 347-353.
Wilkinson C. A., et al., "Long-term Ex-vivo Haematopoietic-stem-Cell Expansion Allows Nonconditioned Transplantation," Nature, 2019, vol. 571 (7763), pp. 117-121.
Wimmer R.A., et al., "Generation of Blood Vessel Organoids From Human Pluripotent Stem Cells," Nature Protocols, 2019, vol. 14, pp. 3082-3100.
Wimmer R.A., et al., "Human Blood Vessel Organoids as a Model of Diabetic Vasculopathy," Nature, 2019, 565(7740), 41 pages.
Wong G.L.H., et al., "High Incidence of Mortality and Recurrent Bleeding in Patients With Helicobacter Pylori-Negative Idiopathic Bleeding Ulcers," Gastroenterology, 2009, vol. 137, pp. 525-531.
Wright E.M., et al., "Biology of Human Sodium Glucose Transporters," Physiological Reviews, 2011, vol. 91,62 pages.
Wright E.M., et al., "Regulation of Na+/Glucose Cotransporters," The Journal of Experimental Biology, 1997, vol. 200, pp. 287-293.
Xie T., et aL, Single-Cell Deconvolution of Fibroblast Heterogeneity in Mouse Pulmonary Fibrosis, Cell Reports, Mar. 27, 2018, vol. 22, No. 13, pp. 3625-3640.
Yao S., et al., Long-Term Self-Renewal and Directed Differentiation of Human Embryonic Stem Cells in Chemically Defined Conditions, PNAS, 2006, vol. 103, No. 18, pp. 6907-6912.
Yu G., et al., ClusterProfiler: An R package for Comparing Biological Themes Among Gene Clusters, Omics: A Journal Integrative Biology, May 2012, vol. 16 (5), pp. 284-287.
Yu Q., et al., "Charting Human Development Using a Multi-Endodermal Organ Atlas and Organoid Models," Cell, 2021, vol. 184, pp. 3281-3298.
Yuelei C., et al., BMP Signaling Pathway and Colon Cancer, CNKI, Oct. 15, 2009, 1 page.
Yun C.H.C., et al., "CAMP-mediated Inhibition of the Epithelial Brush Border Na +/H+ exchanger, NHE3, requires an Associated Regulatory Protein," PNAS, 1997, vol. 94, pp. 3010-3015.
Zaret K.S., From Endoderm to Liver Bud: Paradigms of Cell Type Specification and Tissue Morphogenesis, Current Topics in Developmental Biology, Jan. 2016, vol. 117, pp. 647-669.
Zeltner N., et al., Feeder-free derivation of neural crest progenitor cells from human pluripotent stem cells, Journal of Visualized Experiments, May 2014, vol. 87, 9 pages.
Zhang C., et al., "Angiopoietin-like 5 and IGFBP2 Stimulate Ex-vivo Expansion of Human Cord Blood Hematopoietic Stem Cells as Assayed by NOD/SCID transplantation," Hematopoiesis and stem Cells, 2008, vol. 111 (7), pp. 3415-3423.
Zhang S., et al., "Vascularized Organoids on a Chip: Strategies for Engineering Organoids With Functional Vasculature," Lab Chip, 2021,21 (3), pp. 473-488.
Zhang X., et al., A Comprehensive Structure-Function Study of Neurogenin3 Disease-Causing Alleles during Human Pancreas and Intestinal Organoid Development, Developmental Cell, Aug. 5, 2019, vol. 50, pp. 367-380.
Zhao C-M., et al., "Control of Gastric Acid Secretion in Somatostatin Receptor 2 Deficient Mice: Shift from Endocrine/Paracrine to Neurocrine Pathways," Endocrinology, 2008, 149(2), pp. 498-505.
Ader M., et al., "Modeling Human Development in 3D Culture," Current Opinion in Cell Biology, Dec. 2014, vol. 31, pp. 23-28.
Adorini L., et al., "Farnesoid X Receptor Targeting to Treat Nonalcoholic Steatohepatitis," Drug Discovery Today, Sep. 2012, vol. 17 (17/18), pp. 988-997.
Agopian V.G., et al., "Intestinal Stem Cell Organoid Transplantation Generates Neomucosa in Dogs," Journal of Gastrointestinal Surgery, Jan. 23, 2009, vol. 13 (5), pp. 971-982.
Ahnfelt-Ronne J., et al., "An Improved Method for Three-Dimensional Reconstruction of Protein Expression Patterns in Intact Mouse and Chicken Embryos and Organs," Journal of Histochemistry and Cytochemistry, 2007, vol. 55 (9), pp. 925-930.
Ajmera V., et al., "Novel Plasma Biomarkers Associated with Liver Disease Severity in Adults with Nonalcoholic Fatty Liver Disease," Hepatology, Jan. 2017, vol. 65 (1), pp. 65-77.
Aleo M.D., et al., "Human Drug-Induced Liver Injury Severity is Highly Associated with Dual Inhibition of Liver Mitochondrial Function and Bile Salt Export Pump," Hepatology, 2014, vol. 60 (3), pp. 1015-1022.
Alessi D.R., et al., "LKB1-Dependent Signaling Pathways," Annual Review of Biochemistry, 2006, vol. 75, pp. 137-163.
Alkhatatbeh M.J., et al., "Low Simvastatin Concentrations Reduce Oleic Acid-Induced Steatosis in HepG2 Cells: An In Vitro Model of Non-Alcoholic Fatty Liver Disease," Experimental and Therapeutic Medicine, 2016, vol. 11 (4), pp. 1487-1492.
Allard J., et al., "Immunohistochemical Toolkit for Tracking and Quantifying Xenotransplanted Human Stem Cells," Regenerative Medicine, 2014, vol. 9(4), pp. 437-452.
Altman G. H., et al., "Cell Differentiation by Mechanical Stress," The FASEB Journal, 2001, vol. 16 (2), pp. 270-272.
Ameri J., et al., "FGF2 Specifies HESC-Derived Definitive Endoderm into Foregut/Midgut Cell Lineages in a Concentration-Dependent Manner," Stem Cells, Nov. 2010, vol. 28 (1), pp. 45-56.
Amieva M.R., et al., "Helicobacter Pylori Enter and Survive within Multivesicular Vacuoles of Epithelial cells," Cellular Microbiology, Oct. 4, 2002, vol. 4 (10), pp. 677-690.
An W.F., et al., "Discovery of Potent and Highly Selective Inhibitors of GSK3b," Molecular Libraries, Probe Report, May 2014, 115 Pages.
Anderson G., et al., "Loss of Enteric Dopaminergic Neurons and Associated Changes in Colon Motility in an MPTP Mouse Model of Parkinson's Disease," Experimental Neurology, Sep. 2007, vol. 207 (1), 16 pages.
Andrews P.W., et al., "Embryonic Stem (ES) cells and Embryonal Carcinoma (EC) Cells: Opposite Sides of the same Coin," Biochemical Society Transactions, 2005, vol. 33 (6), pp. 1526-1530.
Ang S.L., et al., "The Formation and Maintenance of the Definitive Endoderm Lineage in the Mouse: Involvement of HNF3/Forkhead Proteins," Development, Company of Biologist Limited, 1993, vol. 119, pp. 1301-1315.
Anlauf M., et al., "Chemical Coding of the Human Gastrointestinal Nervous System: Cholinergic, VIPergic, and Catecholaminergic Phenotypes," The Journal of Comparative Neurology, 2003, vol. 459, pp. 90-111.
Aronson B.E., et al., "GATA4 Represses an ileal Program of Gene Expression in the Proximal Small Intestine by Inhibiting the Acetylation of Histone H3, Lysine 27," Biochimica et Biophysica Acta, Nov. 2014, vol. 1839 (11), pp. 1273-1282.
Arora N., et al., "A Process Engineering Approach to Increase Organoid Yield," Technical and Resources, 2017, vol. 144, pp. 1128-1136.
Arroyo J.D., et al., "Argonaute2 Complexes Carry a Population of Circulating MicroRNAs Independent of Vesicles in Human Plasma," PNAS, 2011, vol. 108 (12), pp. 5003-5008.
Asai A., et al., "Paracrine Signals Regulate Human Liver Organoid Maturation from Induced Pluripotent Stem Cells," Human Development, 2017, vol. 144, pp. 1056-1064.
Aurora M., et al., "hPSC-Derived Lung and Intestinal Organoids as Models of Human Fetal Tissue," Developmental Biology, 2016, vol. 420, pp. 230-238.
Avansino J.R., et al., "Orthotopic Transplantation of Intestinal Mucosal Organoids in Rodents," Surgery, Sep. 2006, vol. 140 (3), pp. 423-434.

(56) References Cited

OTHER PUBLICATIONS

Baetge G., et al., "Transient Catecholaminergic (TC) Cells in the Vagus Nerves and Bowel of Fetal Mice: Relationship to the Development of Enteric Neurons," Developmental Biology, 1989, vol. 132, pp. 189-211.
Bain C.C., et al., "Constant Replenishment from CirculatingMonocytes Maintains the Macrophage Pool in Adult Intestine," Nat Immunol, Oct. 2014, vol. 15 (10), pp. 929-937.
Bain C.C., et al., "Resident and Pro-Inflammatory Macrophages in the Colon Represent Alternative Context-Dependent Fates of the Same Ly6Chi Monocyte Precursors," Mucosal Immunology, May 2013, vol. 6 (3), pp. 498-510.
Bain G., "Embryonic Stem Cells Express Neuronal Properties in Vitro," Developmental Biology, 1995, vol. 168, pp. 842-357.
Bajpai R., et al., "CHD7 Cooperates with PBAF to Control Multipotent Neural Crest Formation," Nature, Feb. 18, 2010, vol. 463, pp. 958-962.
Bansal D., et al., "An Ex-Vivo Human Intestinal Model to Study Entamoeba Histolytica Pathogenesis," PLoS Neglected Tropical Diseases, Nov. 17, 2009, vol. 3 (11), 11 pages.
Baptista P.M., et al., "The Use of Whole Organ Decellularization for the Generation of a Vascularized Liver Organoid," Hepatology, 2011, vol. 53 (2), pp. 604-617.
Bar-Ephraim Y.E., et al., "Modelling Cancer Immunomodulation using Epithelial Organoid Cultures," bioRxiv, Aug. 7, 2018, pp. 1-13.
Barker N., et al., "Lgr5(+ve) Stem Cells Drive Self-Renewal in the Stomach and Build Long-Lived Gastric Units In Vitro," Cell Stem Cell, Jan. 8, 2010, vol. 6, pp. 25-36.
Barker N., et al., "Tissue-Resident Adult Stem Cell Populations of Rapidly Self-Renewing Organs," Cell Stem Cell, Dec. 3, 2010, vol. 7, pp. 656-670.
Barlow A.J., et al., "Critical Nos. of Neural Crest Cells are Required in the Pathways from the Neural Tube to the Foregut to Ensure Complete Enteric Nervous System Formation," Development, 2008, vol. 135, pp. 1681-1691.
Bartfeld S., et al., "In Vitro Expansion of Human Gastric Epithelial Stem Cells and Their Responses to Bacterial Infection," Gastroenterology, Jan. 2015, vol. 148 (1), pp. 126-136.
Bartfeld S., et al., "Stem Cell-Derived Organoids and their Application for Medical Research and Patient Treatment," Journal of Molecular Medicine, 2017, vol. 95, pp. 729-738.
Barth C.A., et al., "Transcellular Transport of Fluorescein in Hepatocyte Monolayers: Evidence for Functional Polarity of Cells in Culture," Proceedings of the National Academy of Sciences USA, 1982, vol. 79, pp. 4985-4987.
Bastide P., et al., "Sox9 Regulates Cell Proliferation and is required for Paneth Cell Differentiation in the Intestinal Epithelium," JCB, 2007, vol. 178, Issue 4, pp. 635-648.
Battle M A., et al., "GATA4 is Essential for Jejunal Function in Mice," Gastroenterology, 2008, vol. 135, pp. 1676-1686.
Baumann K., "Colonic Organoids for Drug Testing and Colorectal Disease Modelling," Nature Reviews Molecular Cell Biology, Jul. 2017, vol. 18, No. 8, p. 467.
Bayha E., et al., "Retinoic Acid Signaling Organizes Endodermal Organ Specification Along the Entire Antero-Posterior Axis," PLoS one, Jun. 10, 2009, vol. 4 (6), e5845, 15 pages.
Beck F., et al., "Expression of Cdx-2 in the Mouse Embryo and Placenta: Possible Role in Patterning of the Extra-Embryonic Membranes," Dev Dyn, 1995, vol. 204, pp. 219-227.
Begriche K., et al., "Drug-induced Toxicity on Mitochondria and Lipid Metabolism: Mechanistic Diversity and Deleterious Consequences for the Liver," Journal of Hepatology, 2011, vol. 54, pp. 773-794.
Bell L.N., et al., "Epidemiology of Idiosyncratic Drug-Induced Liver Injury," Seminars in Liver Disease, 2009, vol. 29, Issue 4, pp. 337-347.
Bergeles C., et al., "From Passive Tool Holders to Microsurgeons: Safer, Smaller, Smarter Surgical Robots," IEEE Transactions on Biomedical Engineering, 2014, vol. 61, Issue 5, pp. 1565-1576.
Bergner A.J., et al., "Birthdating of Myenteric Neuron Subtypes in the Small Intestine of the Mouse," The Journal of Comparative Neurology, 2014, vol. 522, pp. 514-527.
Bernadi P., "The Permeability Transition Pore. Control Points of a Cyclosporin A-Sensitive Mitochondrial Channel Involved in Cell Death," Biochimica et Biophysica Acta, 1996, vol. 1275, pp. 5-9.
Bernstein B.E., et al., "The NIH Roadmap Epigenomics Mapping Consortium," Nature Biotechnology, 2010, vol. 28, Issue 10, pp. 1045-1048.
Beuling E., et al., "Co-Localization of Gata4 and Hnfl alpha in the Gastrointestinal Tract is Restricted to the Distal Stomach and Proximal Small Intestine," Gastroenterology, AGA Abstracts, Abstract T1933, 2007, vol. 132, p. A586.
Beuling E., et al., "Conditional Gata4 Deletion in Mice Induces Bile Acid absorption in the Proximal Small Intestine," Gut, 2010, vol. 59, Issue 7, pp. 888-895.
Beuling E., et al., "Fog Cofactors Partially Mediate Gata4 Function in the Adult Mouse Small Intestine," Gastroenterology, AGA Abstracts, Abstract W1467, 2007, vol. 132, pp. A692-A693.
Beuling E., et al., "GATA4 Mediates Gene Repression in the Mature Mouse Small Intestine through Interactions with Friend of Gata (FOG) Cofactors," Developmental Biology, 2008, vol. 322, Issue 1, pp. 179-189.
Beuling E., et al., "The Absence of GATA4 in the Distal Small Intestine Defines the Ileal Phenotype," Gastroenterology, ABA Abstract, Abstract 602, 2008, vol. 134, pp. A83-A84.
Bharadwaj S., et al., "Current Status of Intestinal and Multivisceral Transplantation," Gastroentrerol Rep (Oxf), 2017, vol. 5, Issue 1, pp. 20-28.
Bhutani N., et al., "Reprogramming towards Pluripotency Requires AID-Dependent DNA Demethylation," Nature, 2010, vol. 463, Issue 7284, pp. 1042-1047.
Bitar K.N., et al., "Intestinal Tissue Engineering: Current Concepts and Future Vision of Regenerative Medicine in the Gut," Neurogastroenterology & Motility, Jan. 2012, vol. 24, Issue 1, pp. 7-19.
Blaugrund E., et al., "Distinct Subpopulations of Enteric Neuronal Progenitors Defined by Time of Development, Sympathoadrenal Lineage Markers and Mash-1-Dependence," Development, vol. 122, 1996, pp. 309-320.
Bohan T.P., et al., "Effect of L-Carnitine Treatment for Valproate-Induced Hepatotoxicity," Neurology, 2001, vol. 56, pp. 1405-1409.
Bohorquez D.V., et al., "An Enteroendocrine Cell—Enteric Glia Connection Revealed by 3D Electron Microscopy," PLOS One, Feb. 2014, vol. 9, Issue 2, e89881, 13 pages.
Bonilla-Claudio M., et al., "Bmp Signaling Regulates a Dose-Dependent Transcriptional Program to Control Facial Skeletal Development," Development, 2012, vol. 139, pp. 709-719.
Boroviak T., et al., "Single Cell Transcriptome Analysis of Human, Marmoset and Mouse Embryos Reveals Common and Divergent Features of Preimplantation Development," Development, 2018, vol. 145, No. 21, pp. 1-18.
Bort R., et al., "Diclofenac Toxicity to Hepatocytes: A Role for Drug Metabolism in Cell Toxicity," Journal of Pharmacology and Experimental Therapeutics, 1998, vol. 288, Issue 1 , pp. 65-72.
Bort R., et al., "Hex Homeobox Gene-Dependent Tissue Positioning is Required for Organogenesis of the Ventral Pancreas," Development, Feb. 15, 2004, vol. 131 (4), pp. 797-806.
Bosse T., et al., "Gata4 and Hnfl Alpha are partially required for the Expression of Specific Intestinal Genes during Development," American Journal of Physiology: Gastrointestinal and Liver Physiology, May 2007, vol. 292, pp. G1302-G1314.
Bouchi R., et al., "FOXO1 Inhibition Yields Functional Insulin-Producing Cells in Human Gut Organoid Cultures," Nature Communications, 2014, vol. 5, Issue 4242, 24 pages.
Boullata J.I., et al., "A.S.P.E.N. Clinical Guidelines: Parental Nutrition Ordering, Order Review, Compounding, Labeling and Dispensing," The Journal of Parenteral and Enteral Nutrition, 2014, vol. 38, Issue 3, pp. 334-377.
Bragdon B., et al., "Bone Morphogenetic Proteins: A Critical Review," Cellular Signalling, 2011, vol. 23, pp. 609-620.

(56) References Cited

OTHER PUBLICATIONS

Bravo P., et al., "Efficient In Vitro Vectorial Transport of a Fluorescent Conjugated Bile Acid Analogue by Polarized Hepatic Hybrid WIF-B and WIF-B9 Cells," Hepatology, 1998, vol. 27, pp. 576-583.
Brevini T.A.L. et al., "No shortcuts to Pig Embryonic Stem Cells," Theriogenology, 2010, vol. 74, pp. 544-550.
Broda T.R., et al., "Generation of Human Antral and Fundic Gastric Organoids from Pluripotent Stem Cells," Nature Protocols, Nov. 2018. Vol. 14(1), pp. 28-50.
Browning J.D., et al., "Molecular Mediators of Hepatic Steatosis and Liver Injury," Journal of Clinical Investigation, 2004, vol. 114, Issue 2, pp. 147-152.
Bruens L., et al., "Expanding the Tissue Toolbox: Deriving Colon Tissue from Human Pluripotent Stem Cells," Cell Stem Cell, Jul. 2017, vol. 21, Issue 1, pp. 3-5.
Brugmann S.A., et al., "Building Additional Complexity to in Vitro-Derived Intestinal Tissues," Stem Cell Research & Therapy, 2013, vol. 4, Issue Suppl 1, p. S1, 5 pages.
Bujko A., et al., "Transcriptional and Functional Profiling Defines Human Small Intestinal Macrophage Subsets," Journal of Experimental Medicine, 2018, vol. 215 (2), pp. 441-458.
Bulmer J.N., et al., "Macrophage Populations in the Human Placenta and Amniochorion," Clinical Experimental Immunology, 1984, vol. 57 (2), pp. 393-403.
Burke P., et al., "Towards a Single-Chip, Implantable RFID System: is a Single-Cell Radio Possible?," Biomed Microdevices, 2010, vol. 12, pp. 589-596.
Burn S.F., et al., "Left-right Asymmetry in Gut Development: what happens next?," BioEssays, 2009, vol. 31, pp. 1026-1037.
Burnicka-Turek O., et al., "INSL5-Deficient Mice Display an Alteration in Glucose Homeostasis and an Impaired Fertility," Endocrinology, Oct. 2012, vol. 153, No. 10, pp. 4655-4665.
Burns A J., et al., "In Ovo Transplantation of Enteric Nervous System Precursors From Vagal to Sacral Neural Crest Results in Extensive Hindgut Colonisation," Development, 2002, Issue 129, pp. 2785-2796.
Burns A J., et al., "Neural Stem Cell Therapies for Enteric Nervous System Disorders," Nature Reviews/Gastroenterology & Hepatology, May 2014, Issue11, pp. 317-328.
Burns A.J., et al., "Enteric Nervous System Development: Analysis of the Selective Developmental Potentialities of Vagal and Sacral Neural Crest Cells using Quail-Chick Chimeras," The Anatomical Record, 2001, vol. 262, pp. 16-28.
Burrin D., et al., "Enteral Obeticholic Acid Prevents Hepatic Cholestasis in Total Parenteral Nutrition-Fed Neonatal Pigs," Hepatology, vol. 62, Oct. 2015, p. 307A.
Buta C., et al., "Reconsidering Pluripotency Tests: Do We Still Need Teratoma Assays?," Stem Cell Research, 2013, vol. 11, pp. 552-562.
Cabezas J., et al., "Nonalcoholic Fatty Liver Disease: A Pathological View," Chapter 8, in Liver Biopsy—Indications, Procedures Results, N. Tagaya (Ed.), InTechOpen, Nov. 21, 2012, pp. 161-188.
Camp J.G., et al., "Multilineage Communication Regulates Human Liver Bud Development from Pluripotency," Nature, 2017, vol. 546 (7659), pp. 533-538.
Campbell E.L., et al., "Transmigrating Neutrophils Shape the Mucosal Microenvironment Through Localized Oxygen Depletion to Influence Resolution of Inflammation," Immunity, 2014, vol. 40 (1), pp. 66-77.
Campbell F.C., et al., "Transplantation of Cultured Small Bowel Enterocytes," Gut, Sep. 1993, vol. 34, Issue 9, pp. 1153-1155.
Caneparo L., et al., "Intercellular Bridges in Vertebrate Gastrulation," PloS ONE, 2011, vol. 6, Issue 5, e20230, 6 pages.
Cao L., et al., "Development of Intestinal Organoids as Tissue Surrogates: Cell Composition and the Epigenetic Control of Differentiation," Molecular Carcinogenesis, 2015, vol. 54, pp. 189-202.
Capeling M.M., et al., "Nonadhesive Alginate Hydrogels Support Growth of Pluripotent Stem Cell-Derived Intestinal Organoids," Stem Cell Reports, Feb. 2019, vol. 12, Issue 2, pp. 381-394.

Chai P.R., et al., "Ingestible Biosensors for Real-Time Medical Adherence Monitoring: MyTMed," Processing Hawaii International Conference on System Sciences, Jan. 2016, pp. 3416-3423.
Chai P.R., et al., "Utilizing an Ingestible Biosensor to Assess Real-Time Medication Adherence," Journal of Medical Toxicology, 2015, vol. 11, pp. 439-444.
Chang H.M., et al., "BMP15 Suppresses Progesterone Production by Down-Regulating STAR via ALK3 in Human Granulosa Cells," Molecular Endocrinology, 2013, vol. 27, pp. 2093-2104.
Chang J.H., et al., "Evaluating the In Vitro Inhibition of UGT1A1, OATP1B1, OATP1B3, MRP2, and BSEP in Predicting Drug-Induced Hyperbilirubinemia," Molecular Pharmaceutics, 2013, vol. 10, pp. 3067-3075.
Chatterjee S., et al., "Hepatocyte-Based in Vitro Model for Assessment of Drug-Induced Cholestasis," Toxicology and Applied Pharmacology, 2014, vol. 274, pp. 124-136.
Chauhan R.K., et al., "Genetic and Functional Studies of Hirschsprung Disease," Doctoral Thesis: Department of Clinical Genetics, Erasmus University Rotterdam, the Netherlands, 2016, 202 pages.
Chen B., et al., "Dynamic Imaging of Genomic Loci in Living Human Cells by an Optimized CRISPR/Cas System," Cell, 2013, vol. 155, Issue 7, pp. 1479-1491.
Chen C., et al., "Pdx1 Inactivation Restricted to the Intestinal Epithelium in Mice alters Duodenal Gene Expression in Enterocytes and Enteroendocrine Cells," American Journal of Physiology Gastrointestinal and Liver Physiology, 2009, vol. 297, pp. G1126-G1137.
Chen L.Y., et al., "Mass Fabrication and Delivery of 3D Multilayer µTags into Living cells," Scientific Reports, 2013, vol. 3, Issue 2295, 6 pages.
Chen T.W., et al., "Ultrasensitive Fluorescent Proteins for Imaging Neuronal Activity," Nature, Jul. 18, 2013, vol. 499, pp. 295-300.
Chen Y., et al., "Retinoic Acid Signaling is Essential for Pancreas Development and Promotes Endocrine at the Expense of Exocrine Cell Differentiation in Xenopus," Developmental Biology, 2004, vol. 271, pp. 144-160.
Cheng X., et al., "Self-Renewing Endodermal Progenitor Lines Generated from Human Pluripotent Stem Cells," Cell Stem Cell, Apr. 6, 2012, vol. 10, pp. 371-384.
Choi E., et al., "Cell Lineage Distribution Atlas of the Human Stomach Reveals Heterogeneous Gland Populations in the Gastric Antrum," Gut, 2014, vol. 63, Issue 11, pp. 1711-1720.
Choi E., et al., "Expression of Activated Ras in Gastric Chief Cells of Mice Leads to the Full Spectrum of Metaplastic Lineage Transitions," Gastroenterology, Apr. 2016, vol. 150, Issue 4, pp. 918-930.
Choi K.D., et al., "Identification of the Hemogenic Endothelial Progenitor and Its Direct Precursor in Human Pluripotent Stem Cell Differentiation Cultures," Cell Reports, Sep. 27, 2012, vol. 2(3), pp. 553-567.
Christoffersson J., et al., "Developing Organ-on-a-chip Concepts Using Bio-Mechatronic Design Methodology," Biofabrication, May 26, 2017, vol. 9, Issue 2, 025023; 14 pages.
Chughlay M.F., et al., "N-Acetylcysteine for Non-Paracetamol Drug-Induced Liver Injury: a Systematic Review," British Journal of Clinical Pharmacology, 2016, vol. 81, pp. 1021-1029.
Churin Y., et al., "Helicobacter Pylori CagA Protein Targets the c-Met Receptor and Enhances the Motogenic Response," Journal of Cell Biology, 2003, vol. 161, No. 2, pp. 249-255.
Cieslar-Pobuda A., et al., "The Expression Pattern of PFKFB3 Enzyme Distinguishes Between Induced-Pluripotent Stem Cells and Cancer Stem Cells," Oncotarget, Aug. 13, 2015, vol. 6, Issue 30, pp. 29753-29770.
Cincinnati Children's Hospital Medical Center, "Scientists Grow Human Esophagus in Lab: Tiny Organoids Enable Personalized Disease Diagnosis, Regenerative Therapies," CCHMC Public Press Release, Sep. 20, 2018, 2 pages.
Clarke L.L., "A Guide to Using Chamber Studies of Mouse Intestine," American Journal of Physiology: Gastrointestinal and Liver Physiology, Jun. 2009, vol. 296, issue 6, pp. G1151-G1166.
Clevers H., "Modeling Development and Disease with Organoids," Cell, Jun. 16, 2016, vol. 165, Issue 7, pp. 1586-1597.

(56) References Cited

OTHER PUBLICATIONS

Coghlan M., et al., "Selective Small Molecule Inhibitors of Glycogen Synthase Kinase-3 Modulate Glycogen Metabolism and Gene Transcription," Chemistry & Biology, Oct. 2000, vol. 7, Issue 10, pp. 793-803.
Collier A.J., et al., "Comprehensive Cell Surface Protein Profiling Identifies Specific Markers of Human Naive and Primed Pluripotent States," Cell Stem Cell, Jun. 1, 2017, vol. 20, pp. 874-890.
Correia C., et al., "Combining Hypoxia and Bioreactor Hydrodynamics Boosts Induced Pluripotent Stem Cell Differentiation towards Cardiomyocytes," Stem Cell Reviews and Reports, Dec. 2014, vol. 10, pp. 786-801.
Cortez A R., et al., "Transplantation of Human Intestinal Organoids into the Mouse Mesentery: A More Physiological and Anatomic Engraftment Site," Surgery, 2018, vol. 164, pp. 643-650.
Costa M., et al., "A Method for Genetic Modification of Human Embryonic Stem Cells using Electroporation," Nature Protocols, Apr. 5, 2007, vol. 2, No. 4, pp. 792-796.
Couzin J., "Small RNAs Make Big Splash," Science, Dec. 20, 2002, vol. 298, pp. 2296-2297.
Covacci A., et al., "Molecular Characterization of the 128-kDa Immunodominant Antigen of Helicobacter Pylori Associated with Cytotoxicity and Duodenal Ulcer," Proceedings of the National Academy of Sciences USA, Jun. 15, 1993, vol. 90, pp. 5791-5795.
Crespo M., et al., "Colonic Organoids Derived from Human Induced Pluripotent Stem Cells for Modeling Colorectal Cancer and Drug Testing," Nature Medicine, Jun. 19, 2017, vol. 23, No. 7, pp. 878-884.
Crocenzi F.A., et al., "Ca(2+)-Dependent Protein Kinase C Isoforms are Critical to Estradiol 17beta-D-Glucuronide-Induced Cholestasis in the Rat," Hepatology, Dec. 2008, vol. 48, pp. 1885-1895.
Cumano A., et al., "Lymphoid Potential, Probed before Circulation inMouse, Is Restricted to Caudal Intraembryonic Splanchnopleura," Cell, Sep. 20, 1996, vol. 86 (6), pp. 907-916.
Cunningham T.J., et al., "Mechanisms of Retinoic Acid Signalling and its Roles in Organ and Limb Development," Nature Reviews Molecular Cell Biology, vol. 16, No. 2, Jan. 5, 2015, pp. 110-123.
Curchoe C.L., et al., "Early Acquisition of Neural Crest Competence During hESCs Neuralization," PloS One, Nov. 2010, vol. 5, pp. 1-17.
Cutrin J.C., et al., "Reperfusion Damage to the Bile Canaliculi in Transplanted Human Liver," Hematology, 1996, vol. 24, pp. 1053-1057.
Dahl A., et al., "Translational Regenerative Medicine—Hepatic Systems," Chapter 34, Clinical Aspects of Regenerative Medicine, eds. A. Atala, M.D. and J. Allickson, PhD, Elsevier, Inc., 2015, pp. 469-484.
D'Amour K A., et al., "Production of Pancreatic Hormone-Expressing Endocrine Cells from Human Embryonic Stem Cells," Nature Biotechnology, 2006, vol. 24, No. 11, pp. 1392-1401.
D'Amour K.A et al., "Efficient Differentiation of Human Embryonic Stem Cells to Definitive Endoderm," Nature Biotechnology, Dec. 2005, vol. 23, No. 12, pp. 1534-1541.
Das R., "RFID Forecasts, Players and Opportunities 2017-2027," IDTechEx, 2017, downloaded from https://www.idtechex.com/en/research-report/rfid-forecasts-players-and-opportunities-2017-2027/546, 8 pages.
Dash A., et al., "Pharmacotoxicology of Clinically-Relevant Concentrations of Obeticholic Acid in an Organotypic Human Hepatocyte System," Toxicol in Vitro, 2017, vol. 39, pp. 93-103.
Date S., et al., "Mini-Gut Organoids: Reconstitution of the Stem Cell Niche," Annual Review of Cell and Developmental Biology, Nov. 2015, vol. 31, pp. 269-289.
Davenport C., et al., "Anterior-Posterior Patterning of Definitive Endoderm Generated from Human Embryonic Stem Cells Depends on the Differential Signaling of Retinoic Acid, Wnt-, and BMP-Signaling," Stem Cells, 2016, vol. 34, pp. 2635-2647.
Davidson M.D., et al., "Long-Term Exposure to Abnormal Glucose Levels Alters Drug Metabolism Pathways and Insulin Sensitivity in Primary Human Hepatocytes," Scientific Reports, 2016, vol. 6, 28178, 11 pages.
Davies L.C., et al., "Tissue-Resident Macrophages," Nat Immunol, Oct. 2013, vol. 14 (10), pp. 986-995.
De Santa Barbara P., et al., "Bone Morphogenetic Protein Signaling Pathway Plays Multiple Roles During Gastrointestinal Tract Development," Developmental Dynamics, 2005, vol. 234, pp. 312-322.
De Santa Barbara P., et al., "Development and Differentiation of the Intestinal Epithelium," Cellular and Molecular Life Sciences, 2003, vol. 60, No. 7, pp. 1322-1332.
Dedhia P.H., et al., "Organoid Models of Human Gastrointestinal Development and Disease," Gastroenterology, Jan. 14, 2016, vol. 150, pp. 1098-1112.
Dekaney C.M., et al., "Expansion of Intestinal Stem Cells Associated with Long-Term Adaptation Following Ileocecal Resection in Mice," American Journal of Physiology: Gastrointestinal and Liver Physiology, Sep. 13, 2007, vol. 293, pp. G1013-G1022.
Dekkers J F., et al., "A Functional CFTR Assay Using Primary Cystic Fibrosis Intestinal Organoids," Nature Medicine, Jul. 2013, vol. 19, No. 7, pp. 939-945.
Dekkers R., et al., "A Bioassay Using Intestinal Organoids to Measure CFTR Modulators in Human Plasma," Journal of Cystic Fibrosis, 2015, vol. 14 (2), pp. 178-181.
Demehri F.R., et al., "Development of an Endoluminal Intestinal Attachment for Clinically Applicable Distraction Enterogenesis Device," Journal of Pediatric Surgery, Jan. 2016, vol. 51, pp. 101-106.
Demehri F.R., et al., "Development of an Endoluminal Intestinal Lengthening Device using a Geometric Intestinal Attachment Approach," Surgery, 2015, vol. 158, pp. 802-811.
Deng H., et al., "Effects of All-Trans Retinoic Acid on the Differentiation of Neural Stem Cells and the Expression of c-myc Gene," Chinese Journal of Tissue Engineering Research, Mar. 18, 2007, vol. 11, pp. 2039-2042.
Deng H., "Mechanisms of Retinoic Acid on the Induction of Differentiation of Neural Stem Cells for Newborn Rat Striatum," Chinese Doctoral and Master Dissertations Full-Text Database (Doctoral) Basic Science, Issue 4, May 20, 2005, pp. 1-91. (Translation).
Denham M., et al., "Multipotent Caudal Neural Progenitors derived from Human Pluripotent Stem Cells that give Rise to Lineages of the Central and Peripheral Nervous System," Stem Cells, Mar. 5, 2015, vol. 33, pp. 1759-1770.
DeSchepper S., et al., "Self-Maintaining Gut Macrophages Are Essential forIntestinal Homeostasis," Cell, Oct. 4, 2018, vol. 175 (2), pp. 400-415.
Dessimoz J., et al., "FGF Signaling is Necessary for Establishing Gut Tube Domains along the Anterior-Posterior Axis in Vivo," Mech Dev, 2006, vol. 123, pp. 42-55.
DeWard A.D., et al., "Cellular Heterogeneity in the Mouse Esophagus Implicates the Presence of a Nonquiescent Epithelial Stem Cell Population," Cell Reports, Oct. 23, 2014, vol. 9, No. 2, pp. 701-711.
Discher D.E., et al., "Growth Factors, Matrices, and Forces Combine and Control Stem Cells," Science, Jun. 2009, vol. 324, pp. 1673-1677.
Dobreva G., et al., "SATB2 Is a Multifunctional Determinant of Craniofacial Patterning and Osteoblast Differentiation," Cell, 2006, vol. 125, Issue 5, pp. 971-986.
Driver I., et al., "Specification of regional intestinal stem cell identity during Drosophila metamorphosis," Development, 2014, vol. 141, pp. 1848-1856.
Duluc I., et al., "Fetal Endoderm Primarily Holds the Temporal and Positional Information Required for Mammalian Intestinal Development," The Journal of Cell Biology, 1994, vol. 126, pp. 211-221.
Dumortier G., et al., "Tolérance hépatique des antipsychotiques atypiques, [Hepatic Tolerance of Atypical Antipsychotic Drugs]," L'Encephale, 2002, vol. 28, pp. 542-551.
Dunn, "Cationic Nanoparticles for the Targeting and Delivery of Nucleic Acids to the Pulmonary Endothelium," University of Cincinnati, Sep. 19, 2018, Doctoral Thesis; downloaded from https://

(56) References Cited

OTHER PUBLICATIONS etd.ohiolink.edu/apexprod/rws_olink/r/1501/10?clear=10&p10_accession_num=ucin1544098242321181; 160 pages.

Dvir-Ginzberg M., et al., "Liver Tissue Engineering within Alginate Scaffolds: Effects of Cell-Seeding Density on Hepatocyte Viability, Morphology, and Function," Tissue Engineering, 2003, vol. 9, pp. 757-766.

Eberhard J., et al., "A Cohort Study of the Prognostic and Treatment Predictive Value of SATB2 Expression in Colorectal Cancer," British Journal of Cancer, 2012, vol. 106, pp. 931-938.

Edling Y., et al., "Increased Sensitivity for Troglitazone-Induced Cytotoxicity using a Human in Vitro Co-Culture Model," Toxicol in Vitro, 2009, vol. 23, pp. 1387-1395.

Eicher A.K., et al., "Translating Developmental Principles to Generate Human Gastric Organoids," Cellular and Molecular Gastroenterology and Hepatology, 2018, vol. 5, pp. 353-363.

Ekser B., et al., "Comparable Outcomes in Intestinal Retransplantation: Single-Center Cohort Study," The Journal of Clinical and Translational Research, 2018, vol. 32, e13290, 10 pages.

El Kasmi K.C., et al., "Phytosterols Promote Liver Injury and Kupffer Cell Activation in Parenteral Nutrition-Associated Liver Disease," Science Translational Medicine, 2013, vol. 5, Issue 206 206ra137, 10 pages.

El Taghdouini A., et al., "In Vitro Reversion of Activated Primary Human Hepatic Stellate Cells," Fibrogenesis & Tissue Repair, 2015, vol. 8, No. 14, 15 pages.

Elbashir S.M., et al., "Functional Anatomy of siRNAs for Mediating Efficient RNAi in *Drosophila melanogaster* Embryo Lysate," The EMBO Journal, 2001, vol. 20, No. 23, pp. 6877-6888.

Engmann J., et al., "Fluid Mechanics of Eating, Swallowing and Digestion-Overview and Perspectives," Food & Function, 2013, vol. 4, pp. 443-447.

Evans M.J., et al., "Establishment in Culture of Pluripotential Cells from Mouse Embryos," Nature, Jul. 1981, vol. 292, pp. 154-156.

Ezashi T., et al., "Low O2 Tensions and the Prevention of Differentiation of hES Cells," PNAS, Mar. 2005, vol. 102, Issue 13, pp. 4783-4788.

Fagerberg L., et al., "Analysis of the Human Tissue-specific Expression by Genome-wide Integration of Transcriptomics and Antibody-based proteomics," Molecular & Cellular Proteomics, 2014, vol. 13, pp. 397-406.

Fahrmayr C., et al., "Phase I and II Metabolism and MRP2-Mediated Export of Bosentan in a MDCKII-OATP1B1-CYP3A4-UGT1A1-MRP2 quadruple-Transfected Cell Line," British Journal of Pharmacology, 2013, vol. 169, pp. 21-33.

Falasca L., et al., "The Effect of Retinoic Acid on the re-establishment of Differentiated Hepatocyte Phenotype in Primary Culture," Cell Tissue Res, Aug. 1998, vol. 293, pp. 337-347.

Fatehullah A., et al., "Organoids as an in Vitro Model of Human Development and Disease," Nature Cell Biology, Mar. 2016, vol. 18, Issue 3, pp. 246-254.

Feldstein A.E., et al., "Free Fatty Acids Promote Hepatic Lipotoxicity by Stimulating TNF-α Expression via a Lysosomal Pathway," Hepatology, Jul. 2004, vol. 40 (1), pp. 185-194.

Finkbeiner S.R., et al., "A Gutsy Task: Generating Intestinal Tissue from Human Pluripotent Stem Cells," Digestive Diseases and Sciences, 2013, vol. 58, pp. 1176-1184.

Finkbeiner S.R., et al., "Stem Cell-Derived Human Intestinal Organoids as an Infection Model for Rotaviruses," mBio, Jul./Aug. 2012, vol. 3, issue 4, e00159-12, 6 pages.

Finkbeiner S.R., et al., "Transcriptome-wide Analysis Reveals Hallmarks of Human Intestine Development and Maturation in Vitro and In Vivo," Stem Cell Reports, Jun. 3, 2015, vol. 4, pp. 1140-1155.

Finkenzeller K., "RFID Handbook: Fundamentals and Applications in Contactless Smart Cards, Radio Frequency Identification and Near-Field Communication," Third Edition, John Wiley & Sons, Ltd., 2010, 8 pages.

Fisher A., et al., "Entacapone-Induced Hepatotoxicity and Hepatic Dysfunction," Movement Disorders, 2002, vol. 17, pp. 1362-1365.

Fitzpatrick D R., et al., "Identification of SATB2 as the Cleft Palate Gene on 2q32-q33," Human Molecular Genetics, 2003, vol. 12, Issue 19, pp. 2491-2501.

Fon Tacer K., et al., "Research Resource: Comprehensive Expression Atlas of the Fibroblast Growth Factor System in Adult Mouse," Molecular Endocrinology, 2010, vol. 24, No. 10, pp. 2050-2064.

Fordham R.P., et al., "Transplantation of Expanded Fetal Intestinal Progenitors Contributes to Colon Regeneration after Injury," Cell Stem Cell, Dec. 5, 2013, vol. 13, pp. 734-744.

Fromenty B., "Drug-induced liver injury in obesity," Journal of Hepatology, 2013, vol. 58, pp. 824-826.

Fu M., et al., "Embryonic Development of the Ganglion Plexuses and the Concentric Layer Structure of Human Gut: a Topographical Study," Anatomy and Embryology, Feb. 27, 2004, vol. 208, pp. 33-41.

Fu M., et al., "HOXB5 expression is spatially and temporarily Regulated in Human Embryonic Gut during Neural Crest Cell Colonization and Differentiation of Enteric Neuroblasts," Developmental Dynamics, 2003, vol. 228, pp. 1-10.

Fukuda A., et al., "Ectopic Pancreas Formation in Hes1-Knockout Mice Reveals Plasticity of Endodermal Progenitors of the Gut, Bile Duct, and Pancreas," The Journal of Clinical Investigation, Jun. 2006, vol. 116 (6), pp. 1484-1493.

Furness J.B., "The Enteric Nervous System and Neurogastroenterology," Nature Reviews/Gastroenterology & Hepatology, May 2012, vol. 9, pp. 286-294.

Gafni O., et al., "Derivation of Novel Human Ground State Naive Pluripotent Stem Cells," Nature, Oct. 29, 2013, vol. 504, pp. 282-286; Supplementary Information in 14 pages.

Geerts A., et al., "Formation of Normal Desmin Intermediate Filaments in Mouse Hepatic Stellate Cells Requires Vimentin," Hepatology, Oct. 2001, vol. 33, pp. 177-188.

Genthe J.R., et al., "Ventromorphins: A New Class of Small Molecule Activators of the Canonical BMP Signaling Pathways," ACS Chemical Biology, 2017, vol. 12, Issue 9, pp. 2436-2447.

Georgas K M., et al., "An illustrated Anatomical Ontology of the Developing Mouse Lower Urogenital Tract," Development, May 15, 2015, vol. 142, pp. 1893-1908.

Gerdes H.H., et al., "Tunneling Nanotubes, an Emerging Intercellular Communication Route in Development," 2013, vol. 130, pp. 381-387.

Gessner R.C., et al., "Functional Ultrasound Imaging for Assessment of Extracellular Matrix Scaffolds used for Liver Organoid Formation," Biomaterials, 2013, vol. 34, pp. 9341-9351.

Giles D.A., et al., "Thermoneutral Housing Exacerbates Nonalcoholic Fatty Liver Disease in Mice and Allows for Sex-Independent Disease Modeling," Nature Medicine, 2017, vol. 23, Issue 7, pp. 829-838.

Ginestet C., Book Review in the Journal of the Royal Statistical Society. Series A (Statistics in Society) (2011), of ggplot2: Elegant Graphics for Data Analysis, by H. Wickham, 2009, vol. 174, Issue 1, p. 245 (2 pages).

Glocker E.O., et al., "Inflammatory Bowel Disease and Mutations Affecting the Interleukin-10 Receptor," N Engl J Med, Nov. 19, 2009, vol. 361 (21), pp. 2033-2045.

Glorioso J.M., et al., "Pivotal Preclinical Trial of the Spheroid Reservoir Bioartificial Liver," Journal of Hepatology, 2015, vol. 63, Issue 2, pp. 388-398.

Goldenring J.R., et al., "Differentiation of the Gastric Mucosa: III. Animal Models of Oxyntic Atrophy and Metaplasia," American Journal of Physiology—Gastrointestinal and Liver Physiology, 2006, vol. 291, pp. G999-G1004.

Goldenring J.R., et al., "Overexpression of Transforming Growth Factor-alpha Alters Differentiation of Gastric Cell Lineages," Digestive Diseases and Sciences, 1996, vol. 41, Issue 4, pp. 773-784.

Goldstein A.M., et al., "BMP Signaling is Necessary for Neural Crest Cell Migration and Ganglion Formation in the Enteric Nervous System," Mechanisms of Development, 2005, vol. 122, pp. 821-833.

Gomez M.C., et al., "Derivation of Cat Embryonic Stem-Like Cells from in Vitro-Produced Blastocysts on Homologous and Heterologous Feeder Cells," Theriogenology, Sep. 1, 2010, vol. 74, Issue 4, pp. 498-515.

(56) References Cited

OTHER PUBLICATIONS

Gomez-Pinilla P.J., et al., "Ano1 is a Selective Marker of Interstitial Cells of Cajal in the Human and Mouse Gastrointestinal Tract," American Journal of Physiology: Gastrointestinal and Liver Physiology, 2009, vol. 296, Issue 6, pp. G1370-G1381.

Gori M., et al., "Investigating Nonalcoholic Fatty Liver Disease in a Liver-on-a-Chip Microfluidic Device," PLOS One, Jul. 2016, vol. 11, Issue 7, e0159729, 15 pages.

Gouon-Evans V., et al., "BMP-4 is Required for Hepatic Specification of Mouse Embryonic Stem Cell-Derived Definitive Endoderm," Nature Biotechnology, Nov. 2006, vol. 24, Issue 11, pp. 1402-1411.

Gracz A.D., et al., "Brief report: CD24 and CD44 Mark Human Intestinal Epithelial Cell Populations with Characteristics of Active and Facultative Stem Cells," Stem Cells, Apr. 4, 2013, vol. 31, pp. 2024-2030.

Gracz A.D., et al., "Sox9 Expression Marks a Subset of CD24-Expressing Small Intestine Epithelial Stem Cells that Form Organoids in Vitro," American Journal of Physiology: Gastrointestinal and Liver Physiology, 2010, vol. 298, Issue 5, pp. G590-G600.

Gradwohl G., et al., "Neurogenin3 is Required for the Development of the Four Endocrine Cell Lineages of the Pancreas," Proceedings of the National Academy of Sciences USA, Feb. 15, 2000, vol. 97, No. 4, pp. 1607-1611.

Grapin-Botton A., "Three-Dimensional Pancreas Organogenesis Models," Diabetes Obesity and Metabolism, Sep. 2016, vol. 18 (Suppl 1), pp. 33-40.

Green M.D., et al., "Generation of Anterior Foregut Endoderm from Human Embryonic and Induced pluripotent Stem Cells," Nature Biotechnology, Mar. 2011, vol. 29, Issue 3, pp. 267-272.

Gregersen H., et al., "The Zero-Stress State of the Gastrointestinal Tract: Biomechanical and Functional Implications," Digestive Diseases and Sciences, Dec. 2000, vol. 45(12), pp. 2271-2281.

Gregorieff A., et al., "Wnt Signaling in the Intestinal Epithelium: from Endoderm to Cancer," Genes & Development, 2005, vol. 19, pp. 877-890.

Groneberg D.A., et al., "Intestinal Peptide Transport: Ex Vivo Uptake Studies and Localization of Peptide Carrier PEPT1," American Journal of Physiology: Gastrointestinal and Liver Physiology, Sep. 2001, vol. 281, pp. G697-G704.

Grosse A.S., et al., "Cell Dynamics in Fetal Intestinal Epithelium: Implications for Intestinal Growth and Morphogenesis," Development, 2011, vol. 138, pp. 4423-4432.

Guan Y., et al., "Human Hepatic Organoids for the Analysis of Human Genetic Diseases," JCI Insight, Sep. 7, 2017, vol. 2, Issue 17, e94954; 17 pages.

Guilak F., et al., "Control of Stem Cell Fate by Physical Interactions with the Extracellular Matrix," Cell Stem Cell, Jul. 2009, vol. 5, pp. 17-26.

Guo G., et al., "Epigenetic Resetting of Human Pluripotency," Development, 2017, vol. 144, pp. 2748-2763.

Guo Z., et al., "Injury-Induced BMP Signaling Negatively Regulates Drosophila Midgut Homeostasis," Journal of Cell Biology, 2013, vol. 201, Issue 6, pp. 945-961.

Gurdon J.B., "Adult Frogs Derived from the Nuclei of Single Somatic Cells," Developmental Biology, 1962, vol. 4, pp. 256-273.

Gurken A. "Advances in Small Bowel Transplantation," Turkish Journal of Surgery, 2017, vol. 33, Issue 3, pp. 135-141.

Gyorgy A.B., et al., "SATB2 Interacts with Chromatin-Remodeling Molecules in Differentiating Cortical Neurons," European Journal of Neuroscience, 2008, vol. 27, pp. 865-873.

Haimovich G., et al., "Intercellular mRNA Trafficking Via Membrane Nanotube-Like Extensions in Mammalian Cells," PNAS, 2017, vol. 114, Issue 46, pp. E9873-E9882.

Halpern K. B., et al., "Single-cell Spatial Reconstruction Reveals Global Division of Labor in the Mammalian Liver," Nature, 2017, vol. 542, No. 7641, pp. 352-356.

Han B., et al., "Microbiological Safety of a Novel Bio-Artificial Liver support System Based on Porcine Hepatocytes: an Experimental Study," European Journal of Medical Research, 2012, vol. 17, Issue 1, Journal 13, 8 pages.

Han M E., et al., "Gastric Stem Cells and Gastric Cancer Stem Cells," Anatomy & Cell Biology, 2013, vol. 46, Issue 1, pp. 8-18.

Hannon G.J., "RNA Interference," Nature, 2002, vol. 418, Issue 6894, pp. 244-251.

Hannon N.R.F., et al., "Generation of Multipotent Foregut Stem Cells from Human Pluripotent Stem Cells," Stem Cell Reports, Oct. 2013, vol. 1, Issue 4, pp. 293-306.

Hao M.M., et al., "Development of Enteric Neuron Diversity," Journal of Cellular and Molecular Medicine, 2009, vol. 13, Issue 7, pp. 1193-1210.

Haramis A.P.G., et al., "De Novo Crypt Formation and Juvenile Polyposis on BMP Inhibition in Mouse Intestine," Science, 2004, vol. 303, Issue 5664, pp. 1684-1686.

Hardwick J.C.H., et al., "Bone Morphogenetic Protein 2 Is Expressed by, and Acts Upon, Mature Epithelial Cells in the Colon," Gastroenterology, 2004, vol. 126, Issue 1, pp. 111-121.

Hardy T., et al., "Nonalcoholic Fatty Liver Disease: New Treatments," Current Opinion in Gastroenterology, May 2015, vol. 31, Issue 3, pp. 175-183.

Hassan W., et al., "Reduced Oxidative Stress Contributes to the Lipid Lowering Effects of Isoquercitrin in Free Fatty Acids Induced Hepatocytes," Oxidative Medicine and Cellular Longevity, 2014, vol. 2014, 313602, 18 pages.

Haveri H., et al., "Transcription Factors GATA-4 and GATA-6 in Normal and Neoplastic Human Gastrointestinal Mucosa," BMC Gastroenterology, 2008, vol. 8, Issue 9, 13 pages.

He X.C., et al., "BMP Signaling Inhibits Intestinal Stem Cell Self-Renewal through Suppression of Wnt-beta-Catenin Signaling," Nature Genetics, 2004, vol. 36, Issue 10, pp. 1117-1121.

Heidari R., et al., "Factors Affecting Drug-Induced Liver Injury: Antithyroid Drugs as Instances," Clinical and Molecular Hepatology, 2014, vol. 20, Issue 3, pp. 237-248.

Hentsch B., et al., "Hlx Homeo Box Gene is Essential for an Inductive Tissue Interaction that Drives Expansion of Embryonic Liver and Gut," Genes & Development, 1996, vol. 10 (1), pp. 70-79.

Hernandez F., et al., "Refining Indications for Intestinal Retransplantation," International Small Bowel Symposium 2013; Abstract 12.241, retrieved from https://www.tts.org/component/tts/view=presentation &id=13241, Accessed, Jun. 12, 2017, 3 pages.

Higashiyama H., et al., "Embryonic Cholecystitis and Defective Gallbladder Contraction in the Sox17-Haploinsufficient Model of Biliary Atresia," Development, 2017, vol. 144 (10), pp. 1906-1917.

Higuchi Y., et al., "Gastrointestinal Fibroblasts Have Specialized, Diverse Transcriptional Phenotypes: A Comprehensive Gene Expression Analysis of Human Fibroblasts," PLOS One, Jun. 2015, vol. 10, Issue 6, 19 pages.

Hockemeyer D., et al., "Genetic Engineering of Human ES and iPS Cells using TALE Nucleases," Nature Biotechnology, 2012, vol. 29, Issue 8, pp. 731-734.

Hoeffel G., et al., "C-Myb+ Erythro-Myeloid Progenitor-Derived FetalMonocytes Give Rise to Adult Tissue-Resident Macrophages," Immunity, Apr. 21, 2015, vol. 42 (4), pp. 665-678.

Hoffmann W., "Current Status on Stem Cells and Cancers of the Gastric Epithelium," International Journal of Molecular Sciences, 2015, vol. 16, Issue 8, pp. 19153-19169.

Holland P.W.H., et al., "Classification and Nomenclature of all Human Homeobox Genes," BMC Biology, 2007, vol. 5, Issue 47, pp. 1-28.

Hooton D., et al., "The Secretion and Action of Brush Border Enzymes in the Mammalian Small Intestine," Reviews of Physiology, Biochemistry and Pharmacology, 2015, vol. 168, pp. 59-118.

Hou P., et al., "Pluripotent Stem Cells Induced from Mouse Somatic Cells by Small-Molecule Compounds," Science, 2013, vol. 341, Issue 6146, pp. 651-654.

Howell J.C., et al., "Generating Intestinal tissue from Stem Cells: Potential for Research and Therapy," Regenerative Medicine, Nov. 2011, vol. 6, Issue 6, pp. 743-755.

Hsu F., et al., "The UCSC Known Genes," Bioinformatics, 2006, vol. 22, Issue 9, pp. 1036-1046.

Hu H., et al., "Long-Term Expansion of Functional Mouse and Human Hepatocytes as 3D Organoids," Cell, 2018, vol. 175, Issue 6, pp. 1591-1606.

(56) References Cited

OTHER PUBLICATIONS

Hu X., et al., "Micrometer-Scale Magnetic-Resonance-Coupled Radio-Frequency Identification and Transceivers for Wireless Sensors in Cells," Physical Review Applied, 2017, vol. 8, Issue 1, 13 pages.

Huang H., "Differentiation of Human Embryonic Stem Cells into Smooth Muscle Cells in Adherent Monolayer Culture," Biochemical and Biophysical Research Communications, 2006, vol. 351 pp. 321-327.

Huch M., et al., "Lgr5+ Liver Stem Cells, Hepatic Organoids and Regenerative medicine," Regenerative Medicine, 2013, vol. 8, Issue 4, pp. 385-387.

Huch M., et al., "Long-Term Culture of Genome-Stable Bipotent Stem Cells from Adult Human Liver," Cell, 2015, Issue 160, pp. 299-312.

Huch M., et al., "Modeling mouse and Human development using Organoid cultures," Development, 2015, Issue 142, pp. 3113-3125.

Huebsch N., et al., "Automated Video-Based Analysis of Contractility and Calcium Flux in Human-Induced Pluripotent Stem Cell-Derived Cardiomyocytes Cultured Over Different Spatial Scales," Tissue Engineering: Part C, 2015, vol. 21, No. 5, pp. 467-479.

Huh W.J., et al., "Ménétrier's Disease: Its Mimickers and Pathogenesis," Journal of Pathology and Translational Medicine, 2016, vol. 50, Issue 1, pp. 10-16.

Hutvagner G., et al., "A microRNA in a Multiple-Turnover RNAi Enzyme Complex," Science, Sep. 20, 2002, vol. 297, No. 5589, pp. 2056-2060.

Hynds R.E., et al., "The Relevance of Human Stem Cell-Derived Organoid Models for Epithelial Translational Medicine," Stem Cells, 2013, vol. 31, No. 3, pp. 417-422.

Iacovino M., et al., "HoxA3 is an Apical Regulator of Hemogenic Endothelium," Nat Cell Biol, Jan. 2011, vol. 13 (1), pp. 72-78.

Ijpenberg., et al., "Wt1 and Retinoic Acid Signaling are Essential for Stellate cell development and Liver Morphogenesis," Developmental Biology, Dec. 2007, vol. 312, No. 1, pp. 157-170.

Inoue H., et al., "IPS Cells: A game Changer for Future Medicine," The EMBO Journal, 2014, vol. 33, No. 5, pp. 409-417.

Ito K., et al., "Temporal Transition of Mechanical Characteristics of HUVEC/MSC Spheroids Using a Microfluidic Chip with Force Sensor Probes," Micromachines, 2016, vol. 7(221), 14 pages.

Jalan-Sakrikar N., et al., "Hedgehog Signaling Overcomes an EZH2-Dependent Epigenetic Barrier to Promote Cholangiocyte Expansion," PLoS One, 2016, vol. 11, No. 12, 19 pages.

Jean C., et al., "Pluripotent Genes in Avian Stem Cells," Develop. Growth Differ., 2013, vol. 55, pp. 41-51.

Jeejeebhoy K.N., "Short Bowel Syndrome: A Nutritional and Medical Approach," CMAJ, 2002, vol. 166, Issue 10, pp. 1297-1302.

Jenny M., et al., "Neurogenin3 is differentially Required for Endocrine Cell Fate Specification in the Intestinal and Gastric Epithelium," EMBO J, 2002, vol. 21, Issue 23, pp. 6338-6347.

Johannesson M., et al., "FGF4 and Retinoic Acid Direct Differentiation of hESCs into PDX1-Expressing Foregut Endoderm in a Time- and Concentration-Dependent Manlier," PLoS One, Mar. 2009, vol. 4, Issue 3, pp. 1-13.

Johansson K.A., et al., "Temporal Control of Neurogenin3 Activity in Pancreas Progenitors Reveals Competence Windows for the Generation of Different Endocrine Cell Types," Dev Cell, 2007, vol. 12, pp. 457-465.

Johnson L.R., et al., "Stimulation of Rat Oxyntic Gland Mucosal Growth by Epidermal Growth Factor," American Journal of Physiology, 1980, vol. 238, Issue G, pp. 45-49.

Johnston T.B., et al., "Extroversion of the Bladder, Complicated by the Presence of Intestinal Openings on the Surface of the Extroverted Area," Journal of Anatomy, 1913, vol. 48, Issue 1, pp. 89-106.

Jones P., et al., "Stromal Expression of Jagged 1 Promotes Colony Formation by Fetal Hematopoietic Progenitor Cells," Blood, Sep. 1, 1998, vol. 92, No. 5, pp. 1505-1511.

Jørgensen M.C., et al., "Neurog3-Dependent Pancreas Dysgenesis Causes Ectopic Pancreas in Hes1 Mutant Mice," Development, 2018, vol. 145 (17), 11 pages.

Jung P., et al., "Isolation and in Vitro Expansion of Human Colonic Stem Cells," Nature Medicine, Oct. 2011, vol. 17, pp. 1225-1227.

Juno R J., et al., "A serum factor(s) after Small Bowel Resection Induces Intestinal Epithelial Cell Proliferation: Effects of Timing, Site, and Extent of Resection," Journal of Pediatric Surgery, Jun. 2003, vol. 38, pp. 868-874.

Juno R.J., et al., "A Serum Factor after Intestinal Resection Stimulates Epidermal Growth Factor Receptor Signaling and Proliferation in Intestinal Epithelial Cells," Surgery, Aug. 2002, vol. 132, pp. 377-383.

Kabouridis P S., et al., "Microbiota Controls the Homeostasis of Glial Cells in the Gut Lamina Propria," Neuron, Jan. 21, 2015, vol. 85, pp. 289-295.

Kaji K., et al., "Virus Free Induction of Pluripotency and Subsequent Excision of Reprogramming Factors," Nature, Apr. 2009, vol. 458, Issue 7239, pp. 771-775.

Kanuri G., et al., "In Vitro and in Vivo Models of Non-Alcoholic Fatty Liver Disease (NAFLD)," International Journal of Molecular Sciences, 2013, vol. 14, pp. 11963-11980.

Karlikow M., et al., "*Drosophila* Cells Use Nanotube-like Structures to Transfer dsRNA and RNAi Machinery Between Cells," Scientific Reports, 2016, vol. 6, Issue 27085, 9 pages.

Katoh M., "WNT Signaling in Stem Cell Biology and Regenerative Medicine," Current Drug Targets, 2008, vol. 9, Issue 7, pp. 565-570.

Kawaguchi J., et al., "Isolation and propagation of enteric neural crest progenitor cells from mouse embryonic stem cells and embryos," Development, 2010, vol. 137, pp. 693-704.

Kawaguchi Y., et al., "The Role of the Transcriptional Regulator Ptf1a in Converting Intestinal to Pancreatic Progenitors," Nature Genetics, 2002, vol. 32, pp. 128-134.

Keeley T.M., et al., "Cytodifferentiation of the postnatal mouse stomach in normal and Huntingtin-interacting protein 1-related-deficient mice," American Journal of Physiology: Gastrointestinal and Liver Physiology, 2010, vol. 299, pp. G1241-G1251.

Keitel V., et al., "De Novo Bile Salt Transporter Antibodies as a Possible Cause of Recurrent Graft Failure after Liver Transplantation: A Novel Mechanism of Cholestasis," Hepatology, 2009, vol. 50, pp. 510-517.

Kelly G.M., et al., "Retinoic Acid and the Development of the Endoderm," Journal Developmental Biology, 2015, vol. 3, pp. 25-56.

Kennedy M., et al., "T Lymphocyte Potential Marks the Emergence of Definitive Hematopoietic Progenitors in Human Pluripotent Stem Cell Differentiation Cultures," Cell Reports, Dec. 27, 2012, vol. 2 (6), pp. 1722-1735.

Keung A.J., et al., "Presentation Counts: Microenvironmental Regulation of Stem Cells by Biophysical and Material Cues," Annual Review of Cell and Developmental Biology, 2010, vol. 26, pp. 533-556.

Khan F.A., et al., "Overview of Intestinal and Multivisceral Transplantation," UpToDate, Sep. 2018 retrieved from https://www.uptodate.com/contents/overview-of-intestinal-and-multiviscera-l-transplantation/print], 32 pages.

Kilens S., et al., "Parallel Derivation of Isogenic Human Primed and Naive Induced Pluripotent Stem Cells," Nature Communications, 2018, vol. 9, Issue 360, 13 pages.

Kilpinen H., et al., "Common Genetic Variation Drives Molecular Heterogeneity in Human iPSCs," Nature, 2017, vol. 546, Issue 7658, pp. 370-375.

Kim B.M., et al., "Regulation of Mouse Stomach Development and Barx1 Expression by specific microRNAs," Development, 2011, vol. 138, pp. 1081-1086.

Kim B.M., et al., "The Stomach Mesenchymal Transcription Factor Barx1 Specifies Gastric Epithelial Identity through Inhibition of Transient Wnt Signaling," Developmental Cell, 2005, vol. 8, pp. 611-622.

Kim D., et al., "HISAT: a Fast Spliced Aligner with Low Memory Requirements," Nature Methods, 2015, vol. 12, Issue 4, pp. 357-360.

(56) References Cited

OTHER PUBLICATIONS

Kim T.H., et al., "Stomach Development, Stem Cells and Disease," Development, 2016, vol. 143, pp. 554-565.
Klimanskaya I., et al., "Human Embryonic Stem Cells Derived without Feeder Cells," Lancet, 2005, vol. 365, Issue 9471, pp. 1636-1641.
Kock K., et al., "A Perspective on Efflux Transport Proteins in the Liver," Clinical Pharmacology & Therapeutics, 2012, vol. 92, Issue 5, pp. 599-612.
Koehler E.M., et al., "Presence of Diabetes Mellitus and Steatosis Is Associated with Liver Stiffness in a General Population: The Rotterdam Study," Hepatology, 2016, vol. 63, pp. 138-147.
Kohlnhofer B.M., et al., "GATA4 Regulates Epithelial Cell Proliferation to Control Intestinal Growth and Development in Mice," Cellular and Molecular Gastroenterology and Hepatology, 2016, vol. 2(2), pp. 189-209.
Koike M., et al., "Effects of mechanical strain on proliferation and differentiation of bone marrow stromal cell line ST2," Journal of Bone and Mineral Metabolism, 2005, vol. 23, pp. 219-225.
Kolahchi A.R., et al., "Microfluidic-Based Multi-Organ Platforms for Drug Discovery," Micromachines, 2016, vol. 7, Issue 162, pp. 1-33.
Kolodny G.M., "Evidence for Transfer of Macromolecular RNA Between Mammalian Cells in Culture," Experimental Cell Research, 1971, vol. 65, pp. 313-324.
Koo B-K., et al., "Controlled Gene Expression in Primary Lgr5 Organoid Cultures," Nature Methods, Jan. 1, 2012, vol. 9, No. 1, Jan. 1, 2012, pp. 81-83.
Kordes C., et al., "Hepatic Stellate Cells Contribute to Progenitor Cells and Liver Regeneration," Journal of Clinical Investigation, 2014, vol. 124, Issue 12, pp. 5503-5515.
Kosinski C., et al., "Indian Hedgehog Regulates Intestinal Stem Cell Fate through Epithelial-Mesenchymal Interactions during Development," Gastroenterology, Sep. 2010, vol. 139, pp. 893-903.
Kostrzewski T., et al., "Three-dimensional Perfused Human in Vitro Model of Non-Alcoholic Fatty Liver Disease," World Journal of Gastroenterology, 2017, vol. 23, Issue 2, pp. 204-215.
Kovalenko P.L., et al., "The Correlation between the Expression of Differentiation Markers in rat Small Intestinal Mucosa and the Transcript Levels of Schlafen 3," JAMA Surgery, Sep. 4, 2013, vol. 148, pp. 1013-1019.
Krahenbuhl S., et al., "Toxicity of Bile Acids on the Electron Transport Chain of Isolated Rat Liver Mitochondria," Hepatology, 1994, vol. 19, pp. 471-479.
Kraus M.R.C., et al., "Patterning and Shaping the Endoderm in Vivo and in Culture," Current Opinion Genetics & Development, 2012, vol. 22, pp. 347-353.
Krausova M., et al., "Wnt Signaling in Adult Intestinal Stem Cells and Cancer," Cellular Signalling, 2014, vol. 26, pp. 570-579.
Kretzschmar K., et al., "Organoids: Modeling Development and the Stem Cell Niche in a Dish," Developmental Cell, Sep. 2016, vol. 38, pp. 590-600.
Kroon E., et al., "Pancreatic Endoderm Derived From Human Embryonic Stem Cells Generates Glucose-Responsive Insulin Secreting Cells In Vivo," Nature Biotechnology, 2008, vol. 26, Issue 4, pp. 443-452.
Kruitwagen H.S., et al., "SCH-O-5 Long-Term Adult Feline Liver Organoid Cultures for Disease Modelling of Hepatic Lipidosis," Research Communications of the 26th ECVIM-CA Congress, Sep. 2016, ECVIM Abstracts pp. 203-204.
Kruitwagen H.S., et al., "Long-Term Adult Feline Liver Organoid Cultures for Disease Modeling of Hepatic Steatosis," Stem Cell Reports, Apr. 2017, vol. 8(4), pp. 822-830.
Kubal C.A., et al., "Challenges with Intestine and Multivisceral Re-Transplantation: Importance of Timing of Re-Transplantation and Optimal Immunosuppression," Ann Transplant, 2018, vol. 23, pp. 98-104.
Kubo A., et al., "Development of Definitive Endoderm from Embryonic Stem Cells in Culture," Development, 2004, vol. 131, Issue 7, pp. 1651-1662.

Kuci Z., et al., "Mesenchymal Stromal Cells from Pooled Mononuclear Cells of Multiple Bone Marrow Donors as Rescue Therapy in Pediatric Severe Steroid-Refractory Graft-Versus-Host Disease: A Multicenter Survey," Haematologica, 2016, vol. 101 (8), pp. 985-994.
Kudoh T., et al., "Distinct Roles for Fgf, Wnt and Retinoic Acid in Posteriorizing the Neural Ectoderm," Development, 2002, vol. 129, pp. 4335-4346.
Kullak-Ublick G.A., et al., "Drug-Induced Liver Injury: Recent Advantages in Diagnosis and Risk Assessment," Gut, 2017, vol. 66, pp. 1154-1164.
Kumar J.A., et al., "Controversies in the Mechanism of Total Parenteral Nutrition Induced Pathology," Children, 2015, vol. 2, Issue 3, pp. 358-370.
Kumar M., et al., "Signals from Lateral Plate Mesoderm Instruct Endoderm toward a Pancreatic Fate," Dev Biol, 2003, vol. 259, Issue 1, pp. 109-122.
Kuratnik A., et al., "Intestinal Organoids as Tissue Surrogates for Toxicological and Pharmacological Studies," Biochemical Pharmacology, 2013, vol. 85, Issue 12, pp. 1721-1726.
Kurpios N.A., et al., "The Direction of Gut Looping is Established by Changes in the Extracellular Matrix and in Cell: Cell Adhesion," PNAS, 2008, vol. 105, Issue 25, pp. 8499-8506.
Lachmann N., et al., "Large-Scale Hematopoietic Differentiation of Human Induced Pluripotent Stem Cells Provides Granulocytes or Macrophages for Cell Replacement Therapies," Stem Cell Report, Feb. 10, 2015, vol. 4, pp. 282-296.
Lahar N., et al., "Intestinal Subepithelial Myofibroblasts Support in Vitro and in Vivo Growth of Human Small Intestinal Epithelium," PLoS One, Nov. 2011, vol. 6(11), e26898, 9 pages.
Lai F.P-L., et al., "Correction of Hirschsprung-Associated Mutations in Human Induced Pluripotent Stem Cells via Clustered Regularly Interspaced Short Palindromic Repeats/Cas9, Restores Neural Crest Cell Function," Gastroenterology, 2017, vol. 153, No. 1, pp. 139-153.
Lambert P.F., et al., "Using an Immortalized Cell Line to Study the HPV Life Cycle in Organotypic "Raft" Cultures," Methods Molecular Medicine, 2005, vol. 119, pp. 141-155.
Lambrecht N.W.G., et al., "Identification of the K Efflux Channel Coupled to the Gastric H-K-Atpase During Acid Secretion," Physiological Genomics, 2005, vol. 21, Issue 1, pp. 81-91.
Lameris A.L., et al., "Expression Profiling of Claudins in the Human Gastrointestinal Tract in Health and During Inflammatory Bowel Disease," Scandinavian Journal of Gastroenterology, 2013, vol. 48, Issue 1, pp. 58-69.
Lancaster M.A., et al., "Organogenesis in a Dish: Modeling Development and Disease Using Organoid Technologies," Science, 2014, vol. 345, Issue 6194, 1247125, 9 pages.
Lanctot P.M., et al., "The Glycans of Stem Cells," Curr Opin Chem Biol, Aug. 2007, vol. 11(4), pp. 373-380.
Langmead G., et al., "Ultrafast and Memory-Efficient Alignment of Short DNA Sequences to the Human Genome," Genome Biology, 2009, vol. 10, 10 pages.
Lavial F., et al., "Chicken Embryonic Stem Cells as a Non-Mammalian Embryonic Stem Cell Model," Development, Growth & Differentiation, 2010, vol. 52, pp. 101-114.
Le Douarin N.M., et al., "Neural Crest Cell Plasticity and its Limits," Development 131, 2004, pp. 4637-4650.
Le S., et al., "FactoMineR: An R Package for Multivariate Analysis," Journal of Statistical Software, 2008, vol. 25, Issue 1, pp. 1-18.
Le Vee M., et al., "Polarized Expression of Drug Transporters in Differentiated Human Hepatoma HepaRG Cells," Toxicology in Vitro, 2013, vol. 27, pp. 1979-1986.
Lechner C., et al., "Development of a Fluorescence-Based Assay for Drug Interactions with Human Multidrug Resistance Related Protein (MRP2; ABCC2) in MDCKII-MRP2 Membrane Vesicles," European Journal of Pharmaceutics and Biopharmaceutics, 2010, vol. 75, pp. 284-290.
Lee C.S., et al., "Neurogenin 3 Is Essential for the Proper Specification of Gastric Enteroendocrine Cells and the Maintenance of Gastric Epithelial Cell Identity," Genes Dev, 2002, vol. 16, pp. 1488-1497.

(56) References Cited

OTHER PUBLICATIONS

Lee G., et al., "Isolation and Directed Differentiation of Neural Crest Stem Cells Derived from Human Embryonic Stem Cells," Nature Biotechnology, Dec. 2007, vol. 25, pp. 1468-1475.

Lee W.M., et al., "Intravenous N-Acetylcysteine Improves Transplant-Free Survival in Early Stage Non-Acetaminophen Acute Liver Failure," Gastroenterology, 2009, vol. 137, Issue 3, pp. 856-864.

Lennerz J.K.M., et al., "The Transcription Factor MIST1 Is a Novel Human Gastric Chief Cell Marker Whose Expression Is Lost in Metaplasia, Dysplasia, and Carcinoma," The American Journal of Pathology, 2010, vol. 177, Issue 3, pp. 1514-1533.

Leslie E.M., et al., "Differential Inhibition of Rat and Human Na+-Dependent Taurocholate Cotransporting Polypeptide (NTCP/SLC10A1) by Bosentan: A Mechanism for Species Differences in Hepatotoxicity," Journal of Pharmacology and Experimental Therapeutics, 2007, vol. 321, Issue 3, pp. 1170-1178.

Leung A.A., et al., "Tolerance Testing of Passive Radio Frequency Identification Tags for Solvent, Temperature, and Pressure Conditions Encountered in an Anatomic Pathology or Biorepository Setting," Journal of Pathology Informatics, 2010, vol. 1, 6 pages.

Levin D.E., et al., "Human Tissue-Engineered Small Intestine Forms from Postnatal Progenitor Cells," Journal of Pediatric Surgery, 2013, vol. 48, pp. 129-137.

Li H., et al., "Treefam: A Curated Database of Phylogenetic Trees of Animal Gene Families," Nucleic Acids Research, 2006, vol. 34, pp. D572-D580.

Li L., "Bmp Signaling Inhibits Intestinal Stem Cell Self-Renewal through Antagonizing Wnt Signaling," Gastroenterology, AASLD Abstracts, Abstract S1223, 2005, vol. 128, p. A702.

Li N., et al., "A Systematic Assessment of Mitochondrial Function Identified Novel Signatures for Drug-Induced Mitochondrial Disruption in Cells," Toxicological Sciences, 2014, vol. 142, Issue 1, pp. 261-273.

Li Y., et al., "In Vitro Organogenesis from Pluripotent Stem Cells," Organogenesis, Jun. 2014, vol. 10, Issue 2, pp. 159-163.

Li Z., et al., "SATB2 is a Sensitive Marker for Lower Gastrointestinal Well-Differentiated Neuroendocrine Tumors," International Journal of Clinical and Experimental Pathology, vol. 8, No. 6, Jan. 2015, pp. 7072-7082.

Lim D.A., et al., "Noggin Antagonizes BMP Signaling to Create a Niche for Adult Neurogenesis," Neuron, Dec. 2000, vol. 28, pp. 713-726.

Lin C., et al., "The Application of Engineered Liver Tissues for Novel Drug Discovery," Expert Opinion on Drug Discovery, 2015, vol. 10, Issue 5, pp. 519-540.

Lin Y., et al., "Differentiation, Evaluation, and Application of Human Induced Pluripotent Stem Cell-Derived Endothelial Cells," Arteriosclerosis, Thrombosis, and Vascular Biology, 2017, vol. 37, pp. 2014-2025.

Lindley R.M., et al., "Human and Mouse Enteric Nervous System Neurosphere Transplants Regulate the Function of Aganglionic Embryonic Distal Colon," Gastroenterology, Jul. 2008, vol. 135, No. 1, pp. 205-216.

Liu J., et al., "A Small-Molecule Agonist of the Wnt Signaling Pathway," Angewandte Chemie International Edition Engl., 2005, vol. 44, issue 13, pp. 1987-1990.

Liu J.A-J., et al., "Identification of GLI Mutations in Patients with Hirschsprung Disease that Disrupt Enteric Nervous System Development in Mice," Gastroenterology, 2015, vol. 149, No. 7, pp. 1837-1848.

Liu L., et al., "A Review of Locomotion Systems for Capsule Endoscopy," IEEE Reviews in Biomedical Engineering, 2015, vol. 8, pp. 138-151.

Logan C.Y., et al., "The Wnt Signaling Pathway in Development and Disease," Annual Review of Cell and Developmental Biology, 2004, vol. 20, pp. 781-810.

Loike J.D., et al., "Opinion: Develop Organoids, Not Chimeras, for Transplantation," The Scientist Magazine, Aug. 2019, (online: http://www.the-scientist.com/news-opinion/opinion--develop-Organoids--not--chimeras--for-transplantation-66339), 3 pages.

Longmire T.A., et al., "Efficient Derivation of Purified Lung and Thyroid Progenitors from Embryonic Stem Cells," Stem Cell, 2012, vol. 10, pp. 398-411.

Lopez-Diaz L., et al., "Intestinal Neurogenin 3 Directs Differentiation of a Bipotential Secretory Progenitor to Endocrine Cell Rather than Goblet Cell Fate," Developmental Biology, 2007, vol. 309, pp. 298-305.

Love M.I., et al., "Moderated Estimation of Fold Change and Dispersion for RNA-seq Data with DESeq2," Genome Biology, 2014, vol. 15, No. 12, pp. 1-21.

Low L.A., et al., "Organs-on-Chips: Progress, Challenges, and Future Directions," Experimental Biology and Medicine, 2017, vol. 242, pp. 1573-1578.

Lu Y., et al., "A Novel 3D Liver Organoid System for Elucidation of Hepatic Glucose Metabolism," Biotechnology and Bioengineering, Feb. 2012, vol. 109, Issue 2, pp. 595-604.

Ludwig T.E., et al., "Derivation of Human Embryonic Stem Cells in Defined Conditions," Nature Biotechnology, Feb. 2006, vol. 24, pp. 185-187.

Ludwig T.E., et al., "Feeder-Independent Culture of Human Embryonic Stem Cells," Nat Methods, Aug. 2006, vol. 3, pp. 637-646.

Lui V.C.H., et al., "Perturbation of Hoxb5 Signaling in Vagal Neural Crests Down-regulates Ret Leading to Intestinal Hypoganglionosis in Mice," Gastroenterology, Apr. 2008, vol. 134, pp. 1104-1115.

Luntz J., et al., "Mechanical Extension Implants for Short-Bowel Syndrome," Smart Structures and Materials 2006: Smart Structures and Integrated Systems, Proceedings of SPIE, 2006, vol. 6173, pp. 617309-1-617309-11.

Luo X., et al., "Generation of Endoderm Lineages from Pluripotent Stem Cells," Regenerative Medicine, 2017, vol. 12, Issue 1, pp. 77-89.

Macparland S.A., et al., "Single Cell RNA Sequencing of Human Liver Reveals Distinct Intrahepatic Macrophage Populations," Nature Communications, Oct. 2018, vol. 9, Issue 4383, 21 pages.

Maeno M., et al., "The Role of BMP-4 and GATA-2 in the Induction and Differentiation of Hematopoietic Mesoderm in Xenopus Laevis," Blood, Sep. 15, 1996, vol. 88 (6), pp. 1965-1972.

Mahe M.M., et al., "Establishment of Gastrointestinal Epithelial Organoids," Current Protocols in Mouse Biology, 2013, vol. 3, No. 4, 31 pages.

Mahe M.M., et al., "In Vivo Model of Small Intestine," Methods in Molecular Biology, 2017, vol. 1597, pp. 229-245.

Maheshwari A., et al., "TGF-β2 Suppresses Macrophage Cytokine Production and Mucosal Inflammatory Responses in the Developing Intestine," Gastroenterology, 2011, vol. 140 (1), pp. 242-253.

Majumdar A.P., "Postnatal Undernutrition: Effect of Epidermal Growth Factor on Growth and Function of the Gastrointestinal Tract in Rats," Journal of Pediatric Gastroenterology and Nutrition, 1984, vol. 3, pp. 618-625.

Makin A.J., et al., "A 7-Year Experience of Severe Acetaminophen-Induced Hepatotoxicity (1987-1993)," Gastroenterology, Dec. 1995, vol. 109, Issue. 6, pp. 1907-1916.

Malinen M.M., et al., "Differentiation of Liver Progenitor Cell Line to Functional Organotypic Cultures in 3D Nanofibrillar Cellulose and Hyaluronan-gelatin Hydrogels," Biomaterials, Jun. 2014, vol. 35, pp. 5110-5121.

Mammoto A., et al., "Mechanosensitive Mechanisms in Transcriptional Regulation," Journal of Cell Science, 2012, vol. 125, pp. 3061-3073.

Man A.L., et al., "CX3CR1+ Cell-Mediated Salmonella Exclusion Protects the Intestinal Mucosa during the Initial Stage of Infection," The Journal Immunology, 2017, vol. 198 (1), pp. 335-343.

Marcum Z.A., et al., "Medication Adherence to Multi-Drug Regimens," Clinics in Geriatric Medicine, May 2012, vol. 28, Issue 2, pp. 287-300.

Marini F., et al., "pcaExplorer: an R/Bioconductor Package for Interacting with RNA-seq Principal Components," BMC Bioinformatics, Jun. 2019, vol. 20, Issue 1, pp. 1-8.

Marini F., "pcaExplorer: Interactive Visualization of RNA-seq Data Using a Principal Components Approach," Bioconductor.org, R package version 2.3.0, 2017, 7 pages.

(56) References Cited

OTHER PUBLICATIONS

Markova S.M., et al., "Association of CYP2C9*2 with Bosentan-Induced Liver Injury," Clinical Pharmacology & Therapeutics, Dec. 2013, vol. 94, Issue 6, pp. 678-686.
Marsh M.N., et al., "A Study of the Small Intestinal Mucosa Using the Scanning Electron Microscope," Gut, 1969, vol. 10, pp. 940-949.
Martin G.R., "Teratocarcinomas and Mammalian Embryogenesis," Science, Aug. 1980, vol. 209, Issue 4458, pp. 768-776.
Martin M., et al., "Dorsal Pancreas Agenesis in Retinoic Acid-Deficient Raldh2 Mutant Mice," Developmental Biology, Aug. 2005, vol. 284, pp. 399-411.
Martin M.J., et al., "Human Embryonic Stem Cells Express an Immunogenic Nonhuman Sialic Acid," Nature Medicine, Feb. 2005, vol. 11(2), pp. 228-232.
McCauley H.A., et al., "Pluripotent Stem Cell-derived Organoids: Using Principles of Developmental Biology to Grow Human Tissues in a Dish," Development, Mar. 2017, vol. 144, pp. 958-962.
McCracken K.W., et al., "Erratum: Wnt/β-catenin promotes gastric fundus specification in mice and humans," Nature, 2017, vol. 543, Issue 136, 1 page.
McCracken K.W., et al., "Generating Human Intestinal Tissue from Pluripotent Stem Cells in Vitro," Nature Protocols, Nov. 2011, vol. 6, Issue 12, pp. 1920-1928.
McCracken K.W., et al., "Mechanism of Embryonic Stomach Development," Seminars in Cell & Development Biology, 2017, vol. 66, pp. 36-42.
McCracken K.W., et al., "Modelling Human Development and Disease in Pluripotent Stem-Cell-Derived Gastric Organoids," Nature, Oct. 2014, vol. 516, Issue 7531, pp. 400-404.
McCracken K.W., et al., "Wnt/β-Catenin Promotes Gastric Fundus Specification in Mice and Humans," Nature, Jan. 2017, vol. 541, No. 7636, 31 pages.
McCracken K.W., "Mechanisms of Endoderm Patterning and Directed Differentiation of Human Stem Cells into Foregut Tissues," Dissertation, Graduate School of the University of Cincinnati, Jun. 19, 2014, 185 pages.
McGovern D.P.B., et al., "Genome-Wide Association Identifies Multiple Ulcerative Colitis Susceptibility Loci," Nature Genetics, Apr. 2010, vol. 42, Issue 4, pp. 332-337.
McKenzie T.J., et al., "Artificial and Bioartificial Liver Support," Seminars in Liver Disease, May 2008, vol. 28, Issue 2, pp. 210-217.
McKeown S.J., et al., "Hirschsprung Disease: A Developmental Disorder of the Enteric Nervous System," Wiley Interdisciplinary Reviews Developmental Biology, Jan.-Feb. 2013, vol. 2, pp. 113-129.
McLin V.A., et al., "Repression of Wnt/β-Catenin Signaling in the Anterior Endoderm is Essential for Liver and Pancreas Development," Development, Jun. 2007, vol. 134, pp. 2207-2217.
McLin V.A., et al., "The Role of the Visceral Mesoderm in the Development of the Gastrointestinal Tract," Gastroenterology, Jun. 2009, vol. 136, pp. 2074-2091.
McMahon J.A., et al., "Noggin-Mediated Antagonism of BMP Signaling is required for Growth and Patterning of the Neural Tube and Somite," Genes & Development, May 1998, vol. 12, pp. 1438-1452.
McManus M.T., et al., "Gene Silencing in Mammals by Small Interfering RNAs," Nature Reviews Genetics, Oct. 2002, vol. 3, pp. 737-747.
Meerbrey K.L., et al., "The pINDUCER Lentiviral Toolkit for Inducible RNA Interference in Vitro and in Vivo," Proceedings of the National Academy of Sciences USA, Mar. 2011, vol. 108, pp. 3665-3670.
Mercaldi C.J., et al., "Methods to Identify and Compare Parenteral Nutrition Administered from Hospital-Compounded and Premixed Multichamber Bags in a Retrospective Hospital Claims Database," Journal of Parenteral and Enteral Nutrition, May 2012, vol. 36, Issue 3, pp. 330-336.
Merker S.R., et al., "Gastrointestinal Organoids: How they Gut it out," Developmental Biology, Dec. 2016, vol. 420, pp. 239-250.
Mica Y., et al., "Modeling Neural Crest Induction, Melanocyte Specification and Disease-Related Pigmentation Defects in hESCs and Patient-Specific iPSCs," Cell Reports, Apr. 25, 2013, vol. 3, pp. 1140-1152.
Micallef S.J., et al., "Endocrine Cells Develop within Pancreatic Bud-like Structures Derived from Mouse ES Cells Differentiated in Response to BMP4 and Retinoic Acid," Stem Cell Research, Oct. 2007, vol. 1, pp. 25-36.
Michaut A., et al., "A Cellular Model to Study Drug-Induced Liver Injury in Nonalcoholic Fatty Liver Disease: Application of Acetaminophen," Toxicology and Applied Pharmacology, Feb. 2016, vol. 292, pp. 40-55.
Miki T., et al., "Hepatic Differentiation of Human Embryonic Stem Cells Is Promoted by Three-Dimensional Dynamic Perfusion Culture Conditions," Tissue Engineering: Part C Methods, May 2011, vol. 17, Issue 5, pp. 557-568.
Miller., A.J., et al. "Generation of Lung Organoids from Human Pluripotent Stem Cells in Vitro," Nature, Feb. 28, 2019, vol. 14, No. 2, pp. 518-540.
Mills J C., et al., "Gastric Epithelial Stem Cells," Gastroenterology, Feb. 2011, vol. 140, pp. 412-424.
Miyabayashi T., et al., "Wnt/beta-Catenin/CBP Signaling Maintains Long-Term Murine Embryonic Stem Cell Pluripotency," Proceedings of the National Academy of Sciences USA, Mar. 2007, vol. 104, issue 13, pp. 5668-5673.
Múnera J.O., et al., "Differentiation of Human Pluripotent Stem Cells into Colonic Organoids via Transient Activation of BMP Signaling," Cell Stem Cell, Jul. 6, 2017, vol. 21, No. 1, pp. 51-64.
Molodecky N.A., et al., "Increasing Incidence and Prevalence of the Inflammatory Bowel Diseases With Time, Based on Systematic Review," Gastroenterology, Jan. 2012, vol. 142, pp. 46-54.
Molotkov A., et al., "Retinoic Acid Generated by Raldh2 in Mesoderm is required for Mouse Dorsal Endodermal Pancreas Development," Developmental Dynamics, Apr. 2005, vol. 232, pp. 950-957.
Montalbano G., et al., "Synthesis of Bioinspired Collagen/Alginate/Fibrin Based Hydrogels for Soft Tissue Engineering," Material Science & Engineering, C 91, 2018, pp. 236-246.
Mori R., et al., "Micropatterned Organoid Culture of Rat Hepatocytes and HepG2 Cells," Journal of Bioscience and Bioengineering, Sep. 2008, vol. 106(3), pp. 237-242.
Mork L.M., et al., "Comparison Culture Media for Bile Acid Transport Studies in Primary Human Hepatocytes," Journal of Clinical and Experimental Hepatology, 2012, vol. 2, pp. 315-322.
Moser A.R., et al., "A Dominant Mutation that Predisposes to Multiple Intestinal Neoplasia in the Mouse," Science, Jan. 1990, vol. 247, Issue 4940, pp. 322-324.
Mosher J T., et al., "Intrinsic Differences among Spatially Distinct Neural Crest Stem Cells in Terms of Migratory Properties, Fate-Determination, and Ability to Colonize the Enteric Nervous System," Developmental Biology, Mar. 2007, vol. 303, issue 1, pp. 1-15.
Mou H., et al., "Generation of Multipotent Lung and Airway Progenitors from Mouse ESCs and Patient-Specific Cystic Fibrosis iPSCs," Stem Cell, Apr. 2012, vol. 10, pp. 385-397.
Mudaliar S., et al., "Efficacy and Safety of the Farnesoid X Receptor Agonist Obeticholic Acid in Patients with Type 2 Diabetes and Nonalcoholic Fatty Liver Disease," Gastroenterology, Sep. 2013, vol. 145, pp. 574-582.
Mullin E., "Tiny Human Esophagus Grown in the Lab-Here's Why: Miniature Version of the Organ that Guides Food to the Stomach could Help Scientists Treat a Variety of Medical Ailments," National Geographic, Sep. 20, 2018, downloaded from https://www.nationalgeographic.com/science/2018/news-human-esophagus-grown-lab-stem-cells-cancer-health.html, 5 pages.
Munera J.O., et al., "Generation of Gastrointestinal Organoids from Human Pluripotent Stem Cells, Organ Regeneration," In: Tsuji T., (eds), Organ Regeneration, Methods in Molecular Biology, Humana Press, New York, NY, 2017, vol. 1597, pp. 167-177.
Munoz M., et al., "Conventional Pluripotency Markers are Unspecific for Bovine Embryonic-Derived Cell-Lines," Theriogenology, 2008, vol. 69, pp. 1159-1164.

(56) References Cited

OTHER PUBLICATIONS

Nakamura T., et al., "Advancing Intestinal Organoid Technology toward Regenerative Medicine," Cellular and Molecular Gastroenterology and Hepatology, 2018, vol. 5, pp. 51-60.
Nandivada P., et al., "Treatment of Parenteral Nutrition-Associated Liver Disease: The Role of Lipid Emulsions," Advances in Nutrition, Nov. 2013, vol. 4, No. 6, pp. 711-717.
Nantasanti S., et al., "Concise Review: Organoids are a Powerful Tool for the Study of Liver Disease and Personalized Treatment Design in Humans and Animals: Organoids for Disease Modeling and Therapy," Stem Cells Translational Medicine, Jan. 21, 2016, vol. 5(3), pp. 325-330.
Navarro V J., et al., "Drug-Related Hepatotoxicity," New England Journal of Medicine, 2006, vol. 354, pp. 731-739.
Negishi T., et al., "Retinoic Acid Signaling Positively Regulates Liver Specification by Inducing wnt2bb Gene Expression in Medaka," Hepatology, 2010, vol. 51, pp. 1037-1045.
Neiiendam J L., et al., "An NCAM-derived FGF-receptor Agonist, the FGL-peptide, Induces Neurite Outgrowth and Neuronal Survival in Primary Rat Neurons," Journal of Neurochemistry, 2004, vol. 91, issue 4, pp. 920-935.
Nelson B J., et al., "Microrobots for Minimally Invasive Medicine," Annual Review of Biomedical Engineering, 2010, vol. 15, issue 12, pp. 55-85.
Nelson C M., "On Buckling Morphogenesis," Journal of Biomechanical Engineering, 2016, vol. 138, pp. 021005-1-021005-6.
Neuschwander-Tetri B.A., et al., "Farnesoid X Nuclear Receptor Ligand Obeticholic Acid for Non-Cirrhotic, Non-Alcoholic Steatohepatitis (FLINT): A Multicentre, Randomised, Placebo-Controlled Trial," Lancet, 2015, vol. 385, No. 9972, 23 pages.
Ni X., et al. "Functional Human Induced Hepatocytes (hiHeps) with Bile Acid Synthesis and Transport Capacities: A Novel in Vitro Cholestatic Model," Scientific Reports, 2016, vol. 6, Issue 38694, 16 pages.
Nielsen C., et al., "Gizzard Formation and the Role of Bapx1," Developmental Biology, 2001, vol. 231, Issue 1, pp. 164-174.
Nishida T., et al., "Rat Liver Canalicular Membrane Vesicles Contain an ATP-Dependent Bile Acid Transport System," Proceedings of the National Academy of Sciences USA, Aug. 1991, vol. 88, Issue 15, pp. 6590-6594.
Nissim S., et al., "Iterative Use of Nuclear Receptor Nr5a2 Regulates Multiple Stages of Liver and Pancreas Development," Development Biology, Jul. 26, 2016, vol. 418 (1), pp. 108-123.
Noguchi T-A.K., et al., "Generation of Stomach Tissue from Mouse Embryonic Stem Cells," Nature Cell Biology, 2015, vol. 17, Issue 8, pp. 984-993.
Nomura S., et al., "Evidence for Repatterning of the Gastric Fundic Epithelium Associated With Menetrier's Disease and TGFα Overexpression," Gastroenterology, May 2005, vol. 128, Issue 5, pp. 1292-1305.
Obermayr F., et al., "Development and Developmental Disorders of the Enteric Nervous System," Nature Reviews/Gastroenterology & Hepatology, Jan. 2013, vol. 10, Issue 1, pp. 43-57.
Ogaki S., et al., "Wnt and Notch Signals Guide Embryonic Stem Cell Differentiation into the Intestinal Lineages," Stem Cells, Jun. 2013, vol. 31, Issue 6, pp. 1086-1096.
Okada Y., et al., "Retinoic-Acid-Concentration-Dependent Acquisition of Neural Cell Identity during in Vitro Differentiation of Mouse Embryonic Stem Cells," Developmental Biology, 2004, vol. 275, Issue 1, pp. 124-142.
Okita K., et al., "An Efficient Nonviral Method to Generate Integration-Free Human-Induced Pluripotent Stem Cells from Cord Blood and Peripheral Blood Cells," Stem Cells, Mar. 2013, vol. 31, Issue 3, pp. 458-466.
Okita K., et al., "Generation of Mouse Induced Pluripotent Stem Cells without Viral Vectors," Science, Nov. 7, 2008, vol. 322, Issue 5903, pp. 949-953.

Olbe L., et al., "A Mechanism by which Helicobacter Pylori Infection of the Antrum Contributes to the Development of Duodenal Ulcer," Gastroenterology, 1996, vol. 110, Issue 5, pp. 1386-1394.
Oorts M., et al., "Drug-induced cholestasis risk assessment in sandwich-cultured human hepatocytes," Toxicol in Vitro, 2016, vol. 34, pp. 179-186.
Ootani A., et al., "Sustained in Vitro Intestinal Epithelial Culture within a Wnt-Dependent Stem Cell Niche," Nature Medicine, 2009, vol. 15, Issue 6, pp. 701-706.
Ornitz D.M., et al., "FGF Signaling Pathways in Endochondral and Intramembranous Bone Development and Human Genetic Disease," Genes & Development, 2002, vol. 16, Issue 12, pp. 1446-1465.
Ornitz D.M., et al., "The Fibroblast Growth Factor Signaling Pathway," Wiley Interdisciplinary Reviews Developmental Biology, 2015, vol. 4, Issue 3, pp. 215-266.
Orso G., et al., "Pediatric Parenteral Nutrition-Associated Liver Disease and Cholestasis: Novel Advances in Pathomechanisms-based Prevention and Treatment," Dig Liver Dis, 2016, vol. 48, Issue 3, pp. 215-222.
Ouchi R., et al., "Modeling Steatohepatitis in Humans with Pluripotent Stem Cell-Derived Organoids," Cell Metabolism, Aug. 6, 2019, vol. 30, Issue 2, pp. 374-384.
Paddison P.J., et al., "Short Hairpin Activated Gene Silencing in Mammalian Cells," Methods in Molecular Biology, 2004, vol. 265, pp. 85-100.
Paddison P.J., et al., "RNA interference: the new somatic cell genetics?," Cancer Cell, 2002, vol. 2, Issue 1, pp. 17-23.
Pai R., et al., "Deoxycholic acid activates beta-catenin Signaling Pathway and Increases Colon Cell Cancer Growth and Invasiveness," Molecular Biology of the Cell, 2004, vol. 15, Issue 5, pp. 2156-2163.
Palaria A., et al., "Patterning of the Hepato-Pancreatobiliary Boundary by BMP Reveals Heterogeneity Within the Murine Liver Bud," Hepatology, Jul. 2018, vol. 68 (1), pp. 274-288.
Pan Q., "University of Science and Technology of China Press," Physiology, Jan. 31, 2014, pp. 149-150.
Pardal M.L., et al., "Towards the Internet of Things: An Introduction to RFID Technology," RFID Technology—Concepts, Applications, Challenges, Proceedings of the 4th International Workshop, IWRT 2010, In conjunction with ICEIS, 2010, pp. 69-78.
Paris D.B.B.P., et al., "Equine Embryos and Embryonic Stem Cells: Defining Reliable Markers of Pluripotency," Theriogenology, 2010, vol. 74, Issue 4, pp. 516-524.
Park H.R., et al., "Lipotoxicity of Palmitic Acid on Neural Progenitor Cells and Hippocampal Neurogenesis," Toxicological Research, Jun. 2011, vol. 27, Issue 2, pp. 103-110.
Park J.S., et al., "Differential Effects of Equiaxial and Uniaxial Strain on Mesenchymal Stem Cells," Biotechnology and Bioengineering, 2004, vol. 88, Issue 3, pp. 359-368.
Park J.S., et al., "The effect of Matrix Stiffness on the Differentiation of Mesenchymal Stem Cells in Response to TGF-β," Biomaterials, 2011, vol. 32, Issue 16, pp. 3921-3930.
Park K.I., et al., "Acute Injury Directs the Migration, Proliferation, and Differentiation of Solid Organ Stem Cells: Evidence for the Effect of Hypoxia-Ischemia in the CNS on Clonal "reporter" Neural Stem Cells," Experimental Neurology, 2006, vol. 199, Issue 1, pp. 156-178.
Park Y.H., et al., "Review of Atrophic Gastritis and Intestinal Metaplasia as a Premalignant Lesion of Gastric Cancer," Journal of Cancer Prevention, 2015, vol. 20, Issue 1, pp. 25-40.
Parkin D.M., "The Global Health Burden of Infection-Associated Cancers in the Year 2002," International Journal of Cancer, 2006, vol. 118, Issue 12, pp. 3030-3044.
Pastor W.A., et al., "TFAP2C Regulates Transcription in Human Naive Pluripotency by Opening Enhancers," Nature Cell Biology, 2018, vol. 20, Issue 5, pp. 553-564.
Pastula A., et al., "Three-Dimensional Gastrointestinal Organoid Culture in Combination with Nerves or Fibroblasts: A Method to Characterize the Gastrointestinal Stem Cell Niche," Stem Cells International, 2016, 16 pages.

(56) References Cited

OTHER PUBLICATIONS

Patankar J.V., et al., "Intestinal Deficiency of Gata4 Protects from Diet-Induced Hepatic Steatosis by Suppressing De Novo Lipogenesis and Gluconeogenesis in Mice," Journal of Hepatology, Posters, Abstract 1253, 2012, vol. 56, p. S496.

Patankar J.V., et al., "Intestinal GATA4 Deficiency Protects from Diet-Induced Hepatic Steatosis," Journal of Hepatology, 2012, vol. 57, Issue 5, pp. 1061-1068.

Peek Jr., R.M., et al., "Helicobacter pylori cagA+ Strains and Dissociation of Gastric Epithelial Cell Proliferation from Apoptosis," Journal of the National Cancer, 1997, vol. 89, Issue 12, pp. 863-868.

Peek Jr., R.M., "Helicobacter Pylori Infection and Disease: from Humans to Animal Models," Disease Models & Mechanisms, 2008, vol. 1, Issue 1, pp. 50-55.

Pennisi C.P., et al., "Uniaxial Cyclic Strain Drives Assembly and Differentiation of Skeletal Myocytes," Tissue Engineering: Part A, 2011, vol. 17, pp. 2543-2550.

Perdiguero E.G., et al., "Development and Maintenance of Resident Macrophages," Nature Immunology, Jan. 2016, vol. 17 (1), pp. 2-8.

Perdiguero E.G., et al., "Tissue-Resident Macrophages Originate from Yolk-Sac-Derived Erythro-Myeloid Progenitors," Nature, Feb. 26, 2015, vol. 518 (7540), pp. 547-551.

Pereira C.F., et al., "Heterokaryon-Based Reprogramming of Human B Lymphocytes for Pluripotency Requires Oct4 but Not Sox2," PLoS Genet, 2008, vol. 4, Issue 9, e1000170, 14 pages.

Pessayre D., et al., "Central Role of Mitochondria in Drug-Induced Liver Injury," Drug Metabolism Reviews, 2012, vol. 44, Issue 1, pp. 34-87.

Pessayre D., et al., "Mitochondrial involvement in Drug-Induced Liver Injury," in Adverse Drug Reaction, J. Uetrecht (ed.). Handbook of Experimental Pharmacology, 2010, pp. 311-365.

Petitte J.N., et al., "Avian Pluripotent Stem Cells," Mechanisms of Development, 2004, vol. 121, Issue 9, pp. 1159-1168.

Poling H.M., et al., "Mechanically Induced Development and Maturation of Human Intestinal Organoids in Vivo," Nature Biomedical Engineering, 2018, vol. 2, Issue 6, pp. 429-442.

Polson J., et al., "AASLD Position Paper: The Management of Acute Liver Failure," Hepatology, 2005, vol. 41, Issue 5, pp. 1179-1197.

Pompaiah M., et al., "Gastric Organoids: An Emerging Model System to Study Helicobacter pylori Pathogenesis," Current Topics in Microbiology and Immunology, 2017, vol. 400, pp. 149-168.

Prakash R., "Regulation of WNT Genes in Stem Cells Development and Organogenesis," IJP, Jun. 2014, vol. 1, Issue 6, pp. 366-372.

Pulikkot S., "Establishment of a 3D Culture Model of Gastric Stem Cells Supporting Their Differentiation into Mucous Cells Using Microfibrous Polycaprolactone Scaffold," Dissertation, United Arab Emirates University, College of Medicine and Health Sciences, May 2015, 187 pages.

Purton L E., et al., "All-Trans Retinoic Acid Enhances the Long-Term Repopulating Activity of Cultured Hematopoietic Stem Cells," Blood, 2000, vol. 95, Issue 2, pp. 470-477.

Qi M-C., et al., "Mechanical Strain induces Osteogenic Differentiation: Cbfa1 and Ets-1 Expression in Stretched Rat Mesenchymal Stem Cells," International Journal of Oral and Maxillofacial Surgery, 2008, vol. 37, pp. 453-458.

Que J., et al., "Morphogenesis of the Trachea and Esophagus: Current Players and New Roles for Noggin and Bmps," Differentiation, 2006, vol. 74, pp. 422-437.

Rachek Li., et al., "Troglitazone, but not Rosiglitazone, Damages Mitochondrial DNA and induces Mitochondrial Dysfunction and Cell Death in Human Hepatocytes," Toxicology and Applied Pharmacology, 2009, vol. 240, Issue 3, pp. 348-354.

Raju R., et al., "A Network Map of FGF-1/FGFR Signaling System," Journal of Signal Transduction, Apr. 2014, Article ID 962962, 16 pages.

Ramachandran S.D., et al., "In Vitro Generation of Functional Liver Organoid-Like Structures Using Adult Human Cells," PLoS One, Oct. 21, 2015, vol. 10, No. 10, pp. 1-14.

Ramalingam S., et al., "Distinct Levels of Sox9 Expression Mark Colon Epithelial Stem Cells that form Colonoids in Culture," The American Journal of Physiology: Gastrointestinal and Liver Physiology, 2012, vol. 302, Issue 1, pp. G10-G20.

Ramirez-Weber F.A., et al., "Cytonemes: Cellular Processes that Project to the Principal Signaling Center in *Drosophila* Imaginal Discs," Cell, May 28, 1999, vol. 97, pp. 599-607.

Ramsey V.G., et al., "The Maturation of Mucus-Secreting Gastric Epithelial Progenitors: into Digestive-Enzyme Secreting Zymogenic Cells Requires Mist1," Development, 2007, vol. 134, Issue 1, pp. 211-222.

Rane A., et al., "Drug Metabolism in the Human Fetus and Newborn Infant," Pediatric Clinics of North America, 1972, vol. 19, Issue 1, pp. 37-49.

Rankin S.A., et al., "A Molecular Atlas of Xenopus Respiratory System Development," Developmental Dynamics, 2015, vol. 244, pp. 69-85.

Rankin S.A., et al., "A Retinoic Acid-Hedgehog Cascade CoordinatesMesoderm-Inducing Signals and Endoderm Competence During Lung Specification," Cell Reports, Jun. 28, 2016, vol. 16 (1), pp. 66-78.

Rankin S.A., et al., Timing is everything: Reiterative Wnt, BMP and RA Signaling Regulate Developmental Competence during Endoderm Organogenesis, Developmental Biology, Feb. 1, 2018, vol. 434, Issue 1, pp. 121-132.

Rankin S.A., et al., "Suppression of Bmp4 Signaling by the Zinc-Finger Repressors Osr1 and Osr2 is required for Wnt/beta-Catenin-Mediated Lung Specification in Xenopus," Development, 2012, vol. 139, Issue 16, pp. 3010-3020.

Rao R.R., et al., "Gene Expression Profiling of Embryonic Stem Cells Leads to Greater Understanding of Pluripotency and Early Developmental Events," Biology of Reproduction, 2004, vol. 71, pp. 1772-1778.

Ratineau C., et al., "Endoderm- and Mesenchyme-Dependent Commitment of the Differentiated Epithelial Cell Types in the Developing Intestine of Rat," Differentiation, 2003, vol. 71, pp. 163-169.

Ray K., "Engineering Human Intestinal Organoids with a Functional ENS," Nature Reviews Gastroenterology & Hematology, Nov. 2016, 1 page.

Rector, R.S., et al., "Mitochondrial Dysfunction Precedes Insulin Resistance and Hepatic Steatosis and Contributes to the Natural History of Non-Alcoholic Fatty Liver Disease in an Obese Rodent Model," Journal of Hepatology, 2010, vol. 52, Issue 5, pp. 727-736.

Reilly G C., et al., "Intrinsic Extracellular Matrix Properties Regulate Stem Cell Differentiation," Journal of Biomechanics, Jan. 2010, vol. 43, Issue 1, pp. 55-62.

Rennert K., et al., "A Microfluidically Perfused Three Dimensional Human Liver Model," Biomaterials, 2015, vol. 71, pp. 119-131.

Reuben A., et al., "Drug-Induced Acute Liver Failure: Results of a U.S. Multicenter, Prospective Study," Hepatology, 2010, vol. 52, pp. 2065-2076.

Ricchi M., et al., "Differential Effect of Oleic and Palmitic Acid on Lipid Accumulation and Apoptosis in Cultured Hepatocytes," Journal of Gastroenterology and Hepatology, May 2009, vol. 24, Issue 5, pp. 830-840.

Richards M. et al., "The Transcriptome Profile of Human Embryonic Stem Cells as Defined by SAGE," Stem Cells, 2004, vol. 22, pp. 51-64.

Riedinger, et al., "Reversible Shutdown of Replicon Initiation by Transient Hypoxia in Ehrlich ascites Cells: Dependence of Initiation on Short-Lived Protein," European Journal of Biochemistry, Dec. 1992, vol. 210, Issue 2, pp. 389-398.

Roberts A., et al., "Identification of Novel Transcripts in Annotated Genomes using RNA-Seq," Bioinformatics, 2011, vol. 27, Issue 17, pp. 2325-2329.

Roberts A., et al., "Improving RNA-Seq Expression Estimates by Correcting for Fragment Bias," Genome Biology, 2011, vol. 12, 14 pages.

Roberts D.J., et al., "Sonic Hedgehog is an Endodermal Signal inducing Bmp-4 and Hox genes during Induction and Regionalization of the Chick hindgut," Development, 1995, vol. 121, pp. 3163-3174.

(56) References Cited

OTHER PUBLICATIONS

Rodriguez, P., et al., "BMP Signaling in the Development of the Mouse Esophagus and Forestomach," Development, 2010, vol. 137, Issue 24, pp. 4171-4176.

Rodriguez-Pineiro A.M., et al., "Studies of Mucus in Mouse Stomach, Small Intestine, and Colon. II. Gastrointestinal Mucus Proteome Reveals Muc2 and Muc5ac Accompanied by a set of Core Proteins," American Journal of Physiology: Gastrointestinal and Liver Physiology, 2013, vol. 305, pp. G348-G356.

Rohrschneider, M.R., et al., "Polarity and Cell Fate Specification in the Control of C. Elegans Gastrulation," Developmental Dynamics, 2009, vol. 238, Issue 4, pp. 789-796.

Ronn R.E., et al., "Retinoic Acid Regulates Hematopoietic Development from Human Pluripotent Stem Cells," Stem Cell Reports. 2015, vol. 4, pp. 269-281.

Roth, R.B., et al., "Gene Expression Analyses Reveal Molecular Relationships among 20 Regions of the Human CNS," Neurogenetics, 2006, vol. 7, pp. 67-80.

Rouch J.D., et al., "Scalability of an Endoluminal Spring for Distraction Enterogenesis," Journal of Pediatric Surgery, 2016, vol. 51, pp. 1988-1992.

Roy S., et al., "Cytoneme-Mediated Contact-Dependent Transport of the *Drosophila* Decapentaplegic Signaling Protein," Science, 2014, vol. 343, pp. 1244624-1 to 1244624-10.

Russo M. W., et al., "Liver Transplantation for Acute Liver Failure From Drug Induced Liver Injury in the United States," Liver Transplantation, 2004, vol. 10, Issue 8, pp. 1018-1023.

Sachs N., et al., "A Living Biobank of Breast Cancer Organoids Captures Disease Heterogeneity," Cell, 2018, vol. 172, pp. 373-386.

Saenz J.B., et al., "Stomach Growth in a Dish," Nature, Jan. 2017, vol. 541, No. 7636, pp. 160-161.

Saffrey M J., "Cellular Changes in the Enteric Nervous System During Ageing," Developmental Biology, 2013, vol. 382, pp. 344-355.

Saha S., et al., "Inhibition of Human Embryonic Stem Cell Differentiation by Medical Strain," Journal of Cellular Physiology, 2006, vol. 206, pp. 126-137.

Saini A., "Cystic Fibrosis Patients Benefit from Mini Guts," Cell Stem Cell, 2016, vol. 19, pp. 425-427.

Saito M., et al., "Reconstruction of Liver Organoid using a Bioreactor," World Journal of Gastroenterology, Mar. 2006, vol. 12, Issue 12, pp. 1881-1888.

Salas-Vidal E., et al., "Imaging Filopodia Dynamics in the Mouse Blastocyst," Developmental Biology, 2004, vol. 265, pp. 75-89.

Sampaziotis F., et al., "Potential of Human Induced Pluripotent Stem Cells in Studies of Liver Disease," Hepatology, 2015, vol. 62, Issue 1, pp. 303-311.

San Roman A.K., et al., "Boundaries, Junctions and Transitions in the Gastrointestinal Tract," Exp CellRes, Nov. 15, 2011, vol. 317 (19), pp. 2711-2718.

Sancho E., et al., "Signaling Pathways in Intestinal Development and Cancer," Annual Review of Cell and Developmental Biology, 2004, vol. 20, pp. 695-723.

Sandoiu A., "Scientists Create Human Esophagus in Stem Cell First," Medical News Today, Downloaded from https://www.medicalnewstoday.com/articles/323118.phpSep. 21, 2018, 4 pages.

Sartori-Rupp A., et al., "Correlative Cryo-Electron Microscopy Reveals the Structure of TNTs in Neuronal Cells," Nature Communications, 2019, vol. 10, 16 pages.

Sasai Y., "Cytosystems Dynamics in Self-Organization of Tissue Architecture," Nature, 2013, vol. 493, pp. 318-326.

Sasai Y., "Next-Generation Regenerative Medicine: Organogenesis from Stem Cells in 3D Culture," Cell Stem Cell, May 2013, vol. 12, pp. 520-530.

Sasselli V., et al., "The Enteric Nervous System," Developmental Biology, Jan. 2012, vol. 366, pp. 64-73.

Sato T., et al., "Single Lgr5 Stem Cells Build Crypt-Villus Structures in Vitro without a Mesenchymal Niche," Nature, 2009, vol. 459, pp. 262-265.

Sato T., et al., "Long-term Expansion of Epithelial Organoids from Human Colon, Adenoma, Adenocarcinoma, and Barrett's Epithelium," Gastroenterology, Nov. 1, 2011, vol. 141, pp. 1762-1772.

Sato T., et al., "Snapshot: Growing Organoids from Stem Cells," Cell, 2015, vol. 161, pp. 1700-1700e1.

Savidge T.C., et al., "Human Intestinal Development in a Severe-Combined Immunodeficient Xenograft model," Differentiation, 1995, vol. 58, pp. 361-371.

Savin T., et al., "On the Growth and Form of the Gut," Nature, Aug. 3, 2011, vol. 476, pp. 57-62.

Schlieve C.R., et al., "Created of Warm Blood and Nerves: Restoring an Enteric Nervous System in Organoids," Cell Stem Cell, Jan. 2017, vol. 20, pp. 5-7.

Schmelter M., et al., "Embryonic Stem Cells Utilize Reactive Oxygen Species as Transducers of Mechanical Strain-induced Cardiovascular Differentiation," The FASEB Journal, Jun. 2006, vol. 20, Issue 8, pp. 1182-1184.

Schonhoff S E., et al., "Neurogenin 3-Expressing Progenitor Cells in the Gastrointestinal Tract Differentiate into both Endocrine and Non-Endocrine Cell Types," Developmental Biology, Jun. 2004, vol. 270, No. 2, pp. 443-454.

Schumacher M A., et al., "Gastric Sonic Hedgehog Acts as a Macrophage Chemoattractant during the Immune Response to Helicobacter pylori," Gastroenterology, May 2012, vol. 142, Issue 5, pp. 1150-1159.

Schumacher M.A., et al., "The Use of Murine-derived Fundic Organoids in Studies of Gastric Physiology," J. Physiol., Apr. 15, 2015, vol. 593, Issue 8, pp. 1809-1827.

Schuppan D., et al., "Non-alcoholic Steatohepatitis: Pathogenesis and Novel Therapeutic Approaches," Journal of Gastroenterology and Hepatology, Aug. 2013, vol. 28, Suppl. 1, pp. 68-76.

Serviddio G., et al., "Ursodeoxycholic Acid Protects Against Secondary Biliary Cirrhosis in Rats by Preventing Mitochondrial Oxidative Stress," Hepatology, 2004, vol. 39, pp. 711-720.

Shah S.B., et al., "Cellular Self-assembly and Biomaterials-based Organoid Models of Development and Diseases," Acta Biomaterialia, Apr. 15, 2017, vol. 53, pp. 29-45.

Shahbazi M N., et al., "Self-organization of the human embryo in the absence of maternal tissues," Nature Cell Biology, May 4, 2016, vol. 18, Issue 6, pp. 700-708.

Shan J., et al., "Identification of a Specific Inhibitor of the Dishevelled PDZ Domain," Biochemistry, 2005, vol. 44, No. 47, pp. 15495-15503.

Shaw T.N., et al., "Tissue-Resident Macrophages in the Intestine are LongLived and Defined by Tim-4 and CD4 Expression," Journal of Experimental Medicine, 2018, vol. 215 (6), pp. 1507-1518.

Sheehan-Rooney K., et al., "Bmp and Shh Signaling Mediate the Expression of satb2 in the Pharyngeal Arches," PLoS One, Mar. 21, 2013, vol. 8, No. 3, e59533, 10 pages.

Shekherdimian S., et al., "The Feasibility of using an Endoluminal Device for Intestinal Lengthening," Journal of Pediatric Surgery, Aug. 2010, vol. 45, Issue 8, pp. 1575-1580.

Sheng J., et al., "Most Tissue-Resident Macrophages Except Microglia Are Derived from Fetal Hematopoietic Stem Cells," Immunity, Aug. 18, 2015, vol. 43 (2), pp. 382-393.

Sherwood R I., et al., "Transcriptional Dynamics of Endodermal Organ Formation," Developmental Dynamics, Jan. 2009, vol. 238, Issue 1, pp. 29-42.

Sherwood R I., et al., "Wnt Signaling Specifies and Patterns Intestinal Endoderm," Mechanisms of Development, Sep. 2011, vol. 128, pp. 387-400.

Shi X L., et al., "Evaluation of a Novel Hybrid Bioartificial Liver Based on a Multi-Layer Flat-Plate Bioreactor," World Journal of Gastroenterology, Jul. 28, 2012, vol. 18, Issue 28, pp. 3752-3760.

Shi X-L., et al., "Effects of Membrane Molecular Weight Cut-off on Performance of a Novel Bioartificial Liver," Artificial Organs, Mar. 2011, vol. 35, Issue, 3, pp. E40-E46.

Shibata Y., et al., "Prediction of Hepatic Clearance and Availability by Cryopreserved Human Hepatocytes: An Application of Serum Incubation Method," Drug Metabolism and Disposition, 2002, vol. 30(8), pp. 892-896.

(56) References Cited

OTHER PUBLICATIONS

Shih H.P., et al., "A Gene Regulatory Network Cooperatively Controlled by Pdx1 and Sox9 Governs Lineage Allocation of Foregut Progenitor Cells," Cell Reports, Oct. 13, 2015, vol. 13 (2), 326-336.
Shimizu N., et al., "Cyclic Strain Induces Mouse Embryonic Stem Cell Differentiation into Vascular Smooth Muscle Cells by Activating PDGF Receptor Beta," Journal of Applied Physiology, Mar. 2008, vol. 104, pp. 766-772.
Shyer A.E., et al., "Bending Gradients: How the Intestinal Stem Cell Gets Its Home," Cell, Apr. 23, 2015, vol. 161, Issue 3, pp. 569-580.
Shyer A.E., et al., "Villification: How the Gut Gets its Villi," Science, Oct. 11, 2013, vol. 342, pp. 212-218.
Siegel R., et al., "Colorectal Cancer Statistics, 2014," CA Cancer Journal for Clinicians, Apr. 2014, vol. 64, Issue 2, pp. 104-117.
Sigalet D L., "The Role of the Enteric Neuronal System in Controlling Intestinal Function," Clinical Surgery Society Magazine, 2003, vol. 64, p. 214.
Siller R., et al., "Small-Molecule-Driven Hepatocyte Differentiation of Human Pluripotent Stem Cells," Stem Cell Reports, May 2015, vol. 4, No. 5, pp. 939-952.
Sim Y.J., et al., "2i Maintains a Naive Ground State in ESCs through Two Distinct Epigenetic Mechanisms," Stem Cell Reports, May 9, 2017, vol. 8, Issues. 5, pp. 1312-1328.
Simkin J.E., et al., "Retinoic Acid Upregulates Ret and Induces Chain Migration and Population Expansion in Vagal Neural Crest Cells to Colonise the Embryonic Gut," PLoS ONE, May 2013, vol. 8(5), e64077, pp. 1-12.
Simon-Assmann P., et al., "In Vitro Models of Intestinal Epithelial Cell Differentiation," Cell Biology and Toxicology, Jul. 2007, vol. 23, No. 4, pp. 241-256.
Sinagoga K.L., et al., "Generating Human Intestinal Tissues from Pluripotent Stem Cells to Study Development and Disease," The EMBO Journal, May 5, 2015, vol. 34, Issue 9, pp. 1149-1163.
Singh S., et al., "Comparative Effectiveness of Pharmacological Interventions for Nonalcoholic Steatohepatitis: A Systematic Review and Network Meta-analysis," Hepatology, Nov. 2015, vol. 62, Issue 5, pp. 1417-1432.
Si-Tayeb K., et al., "Highly Efficient Generation of Human Hepatocyte-Like Cell from Induced Pluripotent Stem Cells," Hepatology, Jan. 2010, vol. 51, Issue 1, pp. 297-305.
Sitti M., et al., "Biomedical Applications of Untethered Mobile Milli/Microrobots," The Proceedings of the IEEE Institution of Electrical Engineers, Feb. 2015, vol. 103, Issue 2, pp. 205-224.
Skardal A., et al., "Organoid-on-a-Chip and Body-on-a-Chip Systems for Drug Screening and Disease Modeling," Drug Discovery Today, Sep. 2016, vol. 21, Issue 9, pp. 1399-1411.
Slaymaker I M., et al., "Rationally Engineered Cas9 Nucleases with Improved Specificity," Science, Jan. 1, 2016, vol. 351, issue 6268, pp. 84-88.
Sloan C.A., et al., "ENCODE Data at the ENCODE Portal," Nucleic Acids Research, Jan. 4, 2016, vol. 44, Issue. D1, pp. D726-D732.
Smith D.M., et al., "Roles of BMP Signaling and Nkx2.5 in Patterning at the Chick Midgut-Foregut Boundary," Development, 2000, vol. 127 (17), pp. 3671-3681.
Smith P.D., et al., "Intestinal Macrophages Lack CD14 and CD89 and Consequently are Down-Regulated for LPS- and IgA-Mediated Activities," The Journal of Immunology, 2001, vol. 167 (5), pp. 2651-2656.
Sneddon I.N., "The Relation between Load and Penetration in the Axisymmetric Boussinesq Problem for a Punch of Arbitrary Profile," International Journal of Engineering Science, May 1965, vol. 3, Issue 1, pp. 47-57.
Snoeck H W., "Generation of Anterior Foregut Derivatives from Pluripotent Stem Cells," Stem Cells Handbook, S. Sell (ed.), Jul. 3, 2013, pp. 161-175.
Snykers S., et al., "In Vitro Differentiation of Embryonic and Adult Stem Cells into Hepatocytes: State of the Art," Stem Cells, Mar. 2009, vol. 27, No. 3, pp. 577-605.

Soffers J H M., et al., "The Growth Pattern of the Human Intestine and its Mesentery," BMC Developmental Biology, Aug. 22, 2015, vol. 15, Issue 31, 16 pages.
Song W., et al., "Engraftment of Human Induced Pluripotent Stem cell-Derived Hepatocytes in Immunocompetent Mice via 3D Co-aggregation and Encapsulation," Scientific Reports, 2015, vol. 5, Issue 16884, 13 pages.
Song Z., et al., "Efficient Generation of Hepatocyte-like cells from Human Induced Pluripotent Stem Cells," Cell Res, Nov. 2009, vol. 19, Issue 11, pp. 1233-1241.
Sonntag F., et al., "Design and Prototyping of a Chip-based Multi-micro-Organoid Culture System for Substance Testing, Predictive to Human (substance) Exposure," Journal of Biotechnology, Jul. 1, 2010, vol. 148, Issue 1, pp. 70-75.
Soto-Gutierrez A., et al., "Engineering of an Hepatic Organoid to Develop Liver Assist Devices," Cell Transplant, 2010, vol. 19, No. 6, 12 pages.
Spear P.C., et al., "Interkinetic Nuclear Migration: A Mysterious Process in Search of a Function," Develop. Growth Differ, Apr. 2012, vol. 54, Issue 3, pp. 306-316.
Speer A L., et al., "Fibroblast Growth Factor 10-Fibroblast Growth Factor Receptor 2b Mediated Signaling is not Required for Adult Glandular Stomach Homeostasis," PLoS ONE, Nov. 2012, vol. 7, Issue 11, e49127, 12 pages.
Speer A L., et al., "Murine Tissue-Engineered Stomach Demonstrates Epithelial Differentiation," Journal of Surgical Research, Mar. 22, 2011, vol. 171, Issue 1, pp. 6-14.
Spence J R., et al., "Translational Embryology: Using Embryonic Principles to Generate Pancreatic Endocrine cells from Embryonic Stem Cells," Developmental Dynamics, Dec. 2007, vol. 236, issue 12, pp. 3218-3227.
Spence J R., et al., "Vertebrate Intestinal Endoderm Development," Developmental Dynamics, Mar. 2011, vol. 240, Issue 3, pp. 501-520.
Spence J.R., et al., "Directed Differentiation of Human Pluripotent Stem Cells into Intestinal Tissue in Vitro," Nature (London), Feb. 3, 2011, vol. 470, Issue 7332, pp. 105-109.
Spence J.R., et al., "Sox17 Regulates Organ Lineage Segregation of Ventral Foregut Progenitor Cells," Dev Cell, Jul. 2009, vol. 17 (1), pp. 62-74.
Stadtfeld M., et al., "Induced Pluripotent Stem Cells Generated without Viral Integration," Science, Nov. 7, 2008, vol. 322, issue 5903, pp. 945-949.
Stafford D., et al., "A Conserved Role for Retinoid Signaling in Vertebrate Pancreas Development," Development Genes and Evolution, Sep. 2004, vol. 214, Issue 9, pp. 432-441.
Stange D E., et al., "Differentiated Troy+ Chief Cells act as 'Reserve' Stem cells to Generate all Lineages of the Stomach Epithelium," Cell, Oct. 10, 2013, vol. 155, Issue 2, pp. 357-368.
Stark R., et al., "Development of an Endoluminal Intestinal Lengthening Capsule," Journal of Pediatric Surgery, Jan. 2012, vol. 47, Issue 1, pp. 136-141.
Stender S., et al., "Adiposity Amplifies the Genetic Risk of Fatty Liver Disease Conferred by Multiple Loci," Nat Genet, Jun. 2017, vol. 49, Issue 6, pp. 842-847.
Stevens J L., et al., "The Future of Drug Safety Testing: Expanding the View and Narrowing the Focus," Drug Discovery Today, Feb. 2009, vol. 14, Issue 3-4, pp. 162-167.
Stresser D.M., et al., "Validation of Pooled Cryopreserved Human Hepatocytes as a Model for Metabolism Studies," BD Biosciences, Jan. 1, 2004, Retrieved from https://www.researchgate.net/profile/David-Stresser/publication/268359224_Validation_of_Pooled_Cryopreserved_Human_Hepatocytes_as_a_Model_for_Metabolism_Studies/links/54ed49710cf2465f5330eddc/Validation-of-Pooled-Cryopreserved-Human-Hepatocytes-as-a-Model-for-Metabolism-Studies.pdf on Jan. 15, 2021, 2 pages.
Stuart T., et al., "Comprehensive Integration of Single-Cell Data," Cell, Jun. 13, 2019, vol. 177, pp. 1888-1902.
Sturgeon C.M., et al., "Wnt SignalingControls the Specification of Definitive and Primitive Hematopoiesis from HumanPluripotent Stem Cells," Natural Biotechnology, Jun. 2014, vol. 32 (6), pp. 554-561.

(56) References Cited

OTHER PUBLICATIONS

Su N., et al., "Role of FGF/FGFR Signaling in Skeletal Development and Homeostasis: Learning from Mouse Models," Bone Research, Apr. 29, 2014, vol. 2, No. 1, 24 pages.
Sugawara T., et al., "Organoids Recapitulate Organs?," Stem Cell Investigation, Jan. 2018, vol. 5(3), 4 pages.
Sugimoto S., et al., "Reconstruction of the Human Colon Epithelium in Vivo," Cell Stem Cell, 2018, vol. 22, pp. 171-176, e1-e5.
Sui L., et al., "Signaling Pathways During Maintenance and Definitive Endoderm Differentiation of Embryonic Stem Cells," The International Journal of Developmental Biology, 2013, vol. 57(1), pp. 1-12.
Sumazaki R., et al., "Conversion of Biliary System to Pancreatic Tissue in Hes1-Deficient Mice," Nature Genetics, Jan. 2004, vol. 36 (1), pp. 83-87.
Sun Y., et al., "Genome Engineering of Stem Cell Organoids for Disease Modeling," Protein Cell, May 2017, vol. 8(5), pp. 315-327.
Suzuki A., et al., "Clonal Identification and Characterization of Self-renewing Pluripotent Stem Cells in the Developing Liver," The Journal of Cell Biology, Jan. 7, 2002, vol. 156(1), pp. 173-184.
Tada M., et al., "Embryonic Germ Cells Induce Epigenetic Reprogramming of Somatic Nucleus in Hybrid Cells," EMBO Journal, 1997, vol. 16(21), pp. 6510-6520.
Taipale J., et al., "The Hedgehog and Wnt signalling pathways in cancer," Nature, May 17, 2001, vol. 411, pp. 349-354.
Tait I.S., et al., "Colonic Mucosal Replacement by Syngeneic Small Intestinal Stem Cell Transplantation," The American Journal of Surgery, Jan. 1994, vol. 167(1), pp. 67-72.
Tait I.S., et al., "Generation of Neomucosa in Vivo by Transplantation of Dissociated Rat Postnatal Small Intestinal Epithelium," Differentiation, Apr. 1994 Vol. 56,(1-2), pp. 91-100.
Takahashi K., et al., "Induction of Pluripotent Stem Cells from Adult Human Fibroblasts by Defined Factors," Cell, Nov. 30, 2007, vol. 131(5), pp. 861-872.
Takahashi K., et al., "Induction of Pluripotent Stem Cells from Mouse Embryonic and Adult Fibroblast Cultures by Defined Factors," Cell, Aug. 25, 2006, vol. 126(4), pp. 663-676.
Takahashi S., et al., "Epigenetic Differences between Naive and Primed Pluripotent Stem Cells," Cellular and Molecular Life Sciences, Apr. 2018, vol. 75(7), pp. 1191-1203.
Takaki M., et al., "In Vitro Formation of Enteric Neural Network Structure in a Gut-Like Organ Differentiated from Mouse Embryonic Stem Cells," Stem Cells, Jun. 9, 2006, vol. 24(6), pp. 1414-1422.
Takashima Y., et al., "Resetting Transcription Factor Control Circuitry toward Ground-State Pluripotency in Human," Cell, Sep. 11, 2014, vol. 158(6), pp. 1254-1269.
Takata K., et al., "Induced-Pluripotent-Stem-Cell-Derived Primitive Macrophages Provide a Platform for Modeling Tissue-Resident Macrophage Differentiation and Function," Immunity, Jul. 18, 2017, vol. 47 (1), pp. 183-198.
Takebe T., et al., "Generation of a Vascularized and Functional Human Liver from an iPSC-derived Organ Bud Transplant," Nature Protocols, Feb. 2014, vol. 9(2), pp. 396-409.
Takebe T., et al., "Human iPSC-Derived Miniature Organs: A Tool for Drug Studies," Clinical Pharmacology & Therapeutics, Sep. 2014, vol. 96(3), pp. 310-313.
Takebe T., et al., "Massive and Reproducible Production of Liver Buds Entirely from Human Pluripotent Stem Cells," Cell Reports, Dec. 5, 2017, vol. 21(10), pp. 2661-2670.
Takebe T., et al., "Vascularized and Complex Organ Buds from Diverse Tissues via Mesenchymal Cell-Driven Condensation," Cell Stem Cell, May 7, 2015, vol. 16(5), pp. 556-565.
Takebe T., et al., "Vascularized and Functional Human Liver from an iPSC-derived Organ bud Transplant," Nature, Jul. 25, 2013, vol. 499(7459), pp. 481-484.
Tamm C., et al., "A Comparative Study of Protocols for Mouse Embryonic Stem Cell Culturing," PLoS ONE, Dec. 10, 2013, vol. 8(12), e81156, 10 pages.

Tamminen K., et al., "Intestinal Commitment and Maturation of Human Pluripotent Stem Cells Is Independent for Exogenous FGF4 and R-spondin1," PLOS One, Jul. 31, 2015, vol. 10(7), e0134551, 19 pages.
Tang W., et al., "Faithful Expression of Multiple Proteins via 2A-Peptide Self-processing: a Versatile and Reliable method for Manipulating Brain Circuits," The Journal of Neuroscience, Jul. 8, 2009, vol. 29(27), pp. 8621-8629.
Teo A K.K., et al., "Activin and BMP4 Synergistically Promote Formation of Definitive Endoderm in Human Embryonic Stem Cells," Stem Cells, Apr. 2012, vol. 30(4), pp. 631-642.
Tepass U., et al., "Epithelium Formation in the Drosophila Midgut Depends on the Interaction of Endoderm and Mesoderm," Development, 1994, vol. 120 (3), pp. 579-590.
Terry B.S., et al., "Preliminary Mechanical Characterization of the Small Bowel for In Vivo Robotic Mobility," Journal of Biomechanical Engineering, Sep. 2011, vol. 133(9), 091010-1-09101-7.
Thamm K., et al., "Notch Signaling During Larval and Juvenile Development in the Polychaete Annelid *Capitella* sp. I," Developmental Biology, 2008, vol. 320 (1), pp. 304-318.
Thanasupawat T., et al., "INSL5 is a Novel Marker for Human Enteroendocrine Cells of the Large Intestine and Neuroendocrine Tumours," Oncology Reports, 2013, vol. 29, No. 1, pp. 149-154.
The ENCODE Project Consortium, "An Integrated Encyclopedia of DNA Elements in the Human Genome," Nature, Sep. 5, 2012, vol. 489, pp. 57-74.
The United States Pharmacopeia: The National Formulary (USP 24 NF 19), United States Pharmacopoeial Convention, Inc., Rockville, MD, 1999, 4 pages.
The WNT Homepage, "Small molecules in Wnt signaling," Nusse Lab, Jan. 2019, 2 pages.
Theunissen T.W., et al., "Systematic Identification of Culture Conditions for Induction and Maintenance of Naive Human Pluripotency," Cell Stem Cell, Oct. 2, 2014, vol. 15(4), pp. 471-487.
Thomson J.A., et al., "Embryonic Stem Cell Lines Derived from Human Blastocysts," Science, Nov. 6, 1998, vol. 282, No. 5391, pp. 1145-1147.
Tian X., et al., "Modulation of Multidrug Resistance-Associated Protein 2 (Mrp2) and Mrp3 Expression and Function with Small Interfering RNA in Sandwich-Cultured Rat Hepatocytes," Molecular Pharmacology, Oct. 2004, vol. 66(4), pp. 1004-1010.
Tiso N., et al., "BMP Signalling Regulates Anteroposterior Endoderm Patterning in Zebrafish," Mech Dev, Oct. 2002, vol. 118, pp. 29-37.
Toivonen S., et al., "Activin A and Wnt-dependent Specification of Human Definitive Endoderm Cells," Experimental Cell Research, Aug. 2013, vol. 319(17), pp. 2535-2544.
Tran K., et al., "Evaluation of Regional and Whole Gut Motility using the Wireless Motility Capsule: Relevance in Clinical Practice," Therapeutic Advances in Gastroenterology, Jul. 2012, vol. 5(4), pp. 249-260.
Trapnell C., et al., "Differential gene and Transcript Expression Analysis of RNA-seq Experiments with TopHat and Cufflinks," Nature Protocols, 2013, vol. 7(3), pp. 562-578.
Trapnell C., et al., "Transcript Assembly and Quantification by RNA-Seq reveals Unannotated Transcripts and Isoform Switching during Cell Differentiation," Nature Biotechnology, May 2, 2010, vol. 28(5), pp. 511-515.
Trisno S.L., et al., "Esophageal Organoids from Human Pluripotent Stem Cells Delineate Sox2 Functions during Esophageal Specification," Cell Stem Cell, Oct. 4, 2018, vol. 23(4), pp. 501-515.
Troy D.B., et al., "Remington: The Science and Practice of Pharmacy," 21st Edition, Lippincott Williams & Wilkens, 2006, Table of Contents, 6 pages.
Tsakmaki A., et al., "3D Intestinal Organoids in Metabolic Research: Virtual Reality in a Dish," Current Opinion in Pharmacology, 2017, vol. 37, pp. 51-58.
Tsedensodnom O., et al., "ROS: Redux and Paradox in Fatty Liver Disease," Hepatology, Oct. 2013, vol. 58, No. 4, pp. 1210-1212.
Tsukada N., et al., "The Structure and Organization of the Bile Canalicular Cytoskeleton with Special Reference to Actin and Actin-Binding Proteins," Hepatology, 1995, vol. 21, No. 4, pp. 1106-1113.

(56) References Cited

OTHER PUBLICATIONS

Tugizov S.M., et al., "Differential Transmission of HIV Traversing Fetal Oral/Intestinal Epithelia and Adult Oral Epithelia," Journal of Virology, 2012, vol. 86 (5), pp. 2556-2570.
Tuschl T et al., "Targeted mRNA degradation by Double-Stranded RNA in vitro," Genes & Development., 1999, vol. 13, pp. 3191-3197.
Tyml K., et al., "Lipopolysaccharide Reduces Intercellular Coupling in Vitro and Arteriolar Conducted Response in Vivo," American Journal of Physiology—Heart and Circulatory Physiology, 2001, vol. 281, pp. H1397-H1406.
Udager A., et al., "Dividing the Tubular Gut: Generation of Organ Boundaries at the Pylorus," Progress in Molecular Biology and Translational Science, 2010, vol. 96, pp. 35-62.
Uhlén M., et al., "A Human Protein Atlas for Normal and Cancer Tissues Based on Antibody Proteomics," Molecular & and Cellular Proteomics, Aug. 27, 2005, vol. 4 (12), pp. 1920-1932.
Uppal K., et al., "Meckel's Diverticulum: A Review," Clinical Anatomy, 2011, vol. 24, pp. 416-422.
Valadi H., et al., "Exosome-Mediated Transfer of mRNAs and MicroRNAs is a Novel mechanism of Genetic Exchange between Cells," Nature Cell Biology, 2007, vol. 9, No. 6, pp. 654-659.
Van Breemen R.B., et al., "Caco-2 Cell Permeability Assays to Measure Drug Absorption," Expert Opinion on Drug Metabolism & Toxicology, Aug. 2005, vol. 1, No. 2, pp. 175-185.
Van De Garde M.D., et al., "Liver Monocytes and Kupffer Cells Remain Transcriptionally Distinct during Chronic Viral Infection," PLoS One, Nov. 3, 2016, vol. 11, No. 11, 16 pages.
Van Dop W.A., et al., "Depletion of the Colonic Epithelial Precursor Cell Compartment upon Conditional Activation of the Hedgehog Pathway," Gastroenterology, 2009, vol. 136, No. 7, pp. 2195-2203.
Van Klinken B.J.W., et al., "MUC5B is the Prominent Mucin in Human Gallbladder and is also Expressed in a Subset of Colonic Goblet Cells," The American Journal of Physiology, 1998, vol. 274, pp. G871-G878.
Venick, R.S., et al., "Unique Technical and Patient Characteristics of Retransplantation: A Detailed Single-Center Analysis of Intestinal Transplantation," International Small Bowel Symposium 2013; Abstract 5.203, retrieved from https://www.tts.org/component/ts/?view=presentation&id=13190, accessed Jun. 12, 2017, 4 pages.
Verma S., et al., "Diagnosis, Management and Prevention of Drug-Induced Liver Injury," Gut, 2009, vol. 58, pp. 1555-1564.
Verzi M.P., et al., "Role of the Homeodomain Transcription Factor Bapx1 in Mouse Distal Stomach Development," Gastroenterology, 2009, vol. 136, No. 5, pp. 1701-1710.
Vosough M., et al. "Generation of Functional Hepatocyte-Like Cells from Human Pluripotent Stem Cells in a Scalable Suspension Culture," Stem Cells and Development, 2013, vol. 22, No. 20, pp. 2693-2705.
Vu J., et al., "Regulation of Appetite, Body Composition and Metabolic Hormones by Vasoactive Intestinal Polypeptide (VIP)," Journal of Molecular Neuroscience, Apr. 23, 2015, vol. 56, No. 2, pp. 377-387.
Wakayama T., et al., "Full-term Development of Mice from Enucleated Oocytes Injected with Cumulus Cell Nuclei," Nature, Jul. 23, 1998, vol. 394, pp. 369-374.
Walker E.M., et al., "GATA4 and GATA6 Regulate Intestinal Epithelial Cytodifferentiation during Development," Developmental Biology, 2014, vol. 392, pp. 283-294.
Wallace a S., et al., "Development of the Enteric Nervous System, Smooth Muscle and Interstitial cells of Cajal in the Human Gastrointestinal Tract," Cell and Tissue Research, Jan. 26, 2005, vol. 319, pp. 367-382.
Walton K.D., et al., "Epithelial Hedgehog Signals Direct Mesenchymal Villus Patterning through BMP," Abstracts / Developmental Biology, 2009, vol. 331, Abstract #354, p. 489.
Walton K.D., et al., "Hedgehog-Responsive Mesenchymal Clusters Direct Patterning and Emergence of Intestinal Villi," PNAS, Sep. 25, 2012, vol. 109, No. 39, pp. 15817-15822.
Walton K.D., et al., "Villification in the Mouse: Bmp Signals Control Intestinal Villus Patterning," Development, 2016, vol. 143, pp. 427-436.
Wan W., et al., "The Role of wnt Signaling in the Development of Alzheimer's disease: A Potential Therapeutic Target?," BioMed Research International, 2014, vol. 2014, pp. 1-9.
Wang A., et al., "Generating Cells of the Gastrointestinal system: Current Approaches and Applications for the Differentiation of Human Pluripotent Stem Cells," Journal of Molecular Medicine, Jun. 20, 2012, vol. 90, pp. 763-771.
Wang F., et al., "Isolation and Characterization of Intestinal Stem Cells based on Surface Marker Combinations and Colony-Formation Assay," Gastroenterology, 2013, vol. 145, No. 2, pp. 383-395.
Wang J., et al., "Mutant Neurogenin-3 in Congenital Malabsorptive Diarrhea," New England Journal of Medicine, Jul. 20, 2006, vol. 355, pp. 270-280.
Wang S., (Ed.), "The role of Homologous Genes in the Development of Appendages," in Basis of Developmental Biology, Press of East China University of Science and Technology, 2014, pp. 184-185.
Wang X., et al., "Cloning and Variation of Ground State Intestinal Stem Cells," Nature, Jun. 11, 2015, vol. 522, 18 pages.
Wang Y., et al., "Hepatic Stellate Cells, Liver Innate Immunity, and Hepatitis C Virus," Journal of Gastroenterology and Hepatology, 2013, vol. 28(1), pp. 112-115.
Wang Z., et al., "Retinoic Acid Regulates Morphogenesis and Patterning of Posterior Foregut Derivatives," Developmental Biology, May 23, 2006, vol. 297, pp. 433-445.
Want R., "An Introduction to RFID Technology," IEEE Pervasive Computing, 2006, vol. 5, pp. 25-33.
Ward D.F Jr., et al., "Mechanical Strain Enhances Extracellular Matrix-Induced Gene Focusing and Promotes Osteogenic Differentiation of Human Mesenchymal Stem Cells Through an Extracellular-Related Kinase-Dependent Pathway," Stem Cells and Development, 2007, vol. 16, pp. 467-479.
Ware C.B., "Concise Review: Lessons from Naive Human Pluripotent Cells," Stem Cells, 2017, vol. 35, pp. 35-41.
Warlich E., et al., "Lentiviral Vector Design and Imaging Approaches to Visualize the Early Stages of Cellular Reprogramming," Molecular Therapy, Apr. 2011, vol. 19, No. 4, pp. 782-789.
Warren C.R., et al., "Induced Pluripotent Stem Cell Differentiation Enables Functional Validation of GWAS Variants in Metabolic Disease," Cell Stem Cell, Apr. 6, 2017, vol. 20, pp. 547-557.
Warren C.R., et al., "The NextGen Genetic Association Studies Consortium: A Foray into In Vitro Population Genetics," Cell Stem Cell, 2017, vol. 20, pp. 431-433.
Watson C.L., et al., "An In Vivo Model of Human Small Intestine Using Pluripotent Stem Cells," Nature Medicine, Oct. 19, 2014, vol. 20, No. 11, 16 pages.
Wehkamp J., et al., "Paneth Cell Antimicrobial Peptides: Topographical Distribution and Quantification in Human Gastrointestinal Tissues," FEBS Letters, 2006, vol. 580, pp. 5344-5350.
Weis V.G., et al., "Current Understanding of SPEM and its Standing in the Preneoplastic Process," Gastric Cancer, 2009, vol. 12, pp. 189-197.
Wells J.M., et al., "Early Mouse Endoderm is Patterned by Soluble Factors from Adjacent Germ Layers," Development, Mar. 21, 2000, vol. 127, pp. 1563-1572.
Wells J.M., et al., "How to Make and Intestine," Development, vol. 141, No. 4, Feb. 15, 2014, pp. 752-760.
Wen S., et al., "Helicobacter Pylori Virulence Factors in Gastric Carcinogenesis," Cancer Letters, 2009, vol. 282, pp. 1-8.
Wernig M., et al., "In Vitro Reprogramming of Fibroblasts into a Pluripotent ES-cell-like State," Nature, 2007, vol. 448, pp. 318-324.
Whissell G., et al., "The Transcription Factor GATA6 Enables Self-Renewal of Colon Adenoma Stem Cells by Repressing BMP Gene Expression," Nature Cell Biology, 2014, vol. 16, No. 7, pp. 695-707.
Wieck M.M., et al., "Prolonged Absence of Mechanoluminal Stimulation in Human Intestine Alters the Transcriptome and Intestinal Stem Cell Niche," Cell Mol Gastroenterol Hepatol, 2017, vol. 3, No. 3, pp. 367-388.

(56) References Cited

OTHER PUBLICATIONS

Wiley L.A., et al., "cGMP Production of Patient-Specific iPSCs and Photoreceptor Precursor Cells to Treat Retinal Degenerative Blindness," Scientific Reports, 2016, vol. 6(30742), 16 pages.

Willet S.G., et al., "Stomach Organ and Cell Lineage Differentiation: From Embryogenesis to Adult Homeostasis," Cellular and Molecular Gastroenterology and Hepatology, Sep. 2016, vol. 2, pp. 546-559.

Williamson R.C.N., et al., "Humoral Stimulation of Cell Proliferation in Small Bowel after Transection and Resection in Rats," Gastroenterology, 1978, vol. 75, No. 2, pp. 249-254.

Wills A., et al., "Bmp Signaling is necessary and sufficient for Ventrolateral Endoderm Specification in Xenopus," Developmental Dynamics, 2008, vol. 237(8), pp. 2177-2186.

Wilmut I., et al., "Viable Offspring Derived from Fetal and Adult Mammalian Cells," Nature, Feb. 27, 1997, vol. 385, pp. 810-813.

Woltjen K., et al., "piggyBac transposition reprograms fibroblasts to induced pluripotent stem cells," Nature, Apr. 9, 2009, vol. 458, pp. 766-770.

Workman M.J., et al., "Engineered Human Pluripotent-Stem-Cell-derived Intestinal tissues with a functional Enteric Nervous System," Nature Medicine, Jan. 2017, vol. 23(1), pp. 49-59.

Workman M.J., "Generating 3D Human Intestinal Organoids with an Enteric Nervous System," Thesis, Graduate School of the University of Cincinnati, 2014, 61 pages.

Xia H.H.X., et al., "Antral-Type Mucosa in the Gastric Incisura, Body, and Fundus (Antralization): A Link Between Helicobacter pylori Infection and Intestinal Metaplasia?," American Journal of Gastroenterology, 2000, vol. 95, No. 1, pp. 114-121.

Xinaris C., et al., "Organoid Models and Applications in Biomedical Research," Nephron Jun. 25, 2015, Issue 130, pp. 191-199.

Xu R., et al., "Association between Patatin-Like Phospholipase Domain Containing 3 Gene (PNPLA3) Polymorphisms and Nonalcoholic Fatty Liver Disease: A HuGE Review and Meta-Analysis," Scientific Reports, Mar. 20, 2015, vol. 5(9284), 11 pages.

Xu R., et al. (Eds), "Retinoic Acid Receptor" in Basis and Clinic of Receptor, Shanghai Science and Technology Press, 1992, pp. 129-131.

Xue X., et al., "Endothelial PAS Domain Protein 1 Activates the Inflammatory Response in the Intestinal Epithelium to Promote Colitis in Mice," Gastroenterology, 2013, vol. 145, No. 4, pp. 831-841.

Yahagi N., et al., "Position-Specific Expression of Hox Genes along the Gastrointestinal Tract," Congenital Anomalies, 2004, vol. 44, pp. 18-26.

Yamada S., et al. "Differentiation of Immature Enterocytes into Enteroendocrine Cells by Pdx1 Overexpression," American Journal of Physiology: Gastrointestinal and Liver Physiology, 2001, vol. 281, No. 1, pp. G229-G236.

Yamaguchi Y., et al., "Purified Interleukin 5 Supports the Terminal Differentiation and Proliferation of Murine Eosinophilic Precursors," Journal of Experimental Medicine, Jan. 1988, vol. 167, No. 1, pp. 43-56.

Yanagimachi M.D., et al., "Robust and Highly-Efficient Differentiation of Functional Monocytic Cells from Human Pluripotent Stem Cells Under Serum- and Feeder Cell-Free Conditions," PLoS One, 2013, vol. 8(4), e59243, 9 pages.

Yanagita M., "Modulator of Bone Morphogenetic Protein Activity in the Progression of Kidney Diseases," Kidney International, 2006, vol. 70, pp. 989-993.

Yang K., et al., "Systems Pharmacology Modeling Predicts Delayed Presentation and Species Differences in Bile Acid-Mediated Troglitazone Hepatotoxicity," Clinical Pharmacology & Therapeutics, 2014, vol. 96(5), pp. 589-598.

Yeung E.N.W., et al., "Fibrinogen Production is Enhanced in an In-Vitro Model of Non-Alcoholic Fatty Liver Disease: An Isolated Risk Factor for Cardiovascular Events?," Lipids in Health and Disease, 2015, vol. 14 (86), 8 pages.

Yin C., et al., "Hepatic Stellate Cells in Liver Development, Regeneration, and Cancer," The Journal of Clinical Investigation, May 2013, vol. 123, No. 5, pp. 1902-1910.

Yoneda M., et al., "Noninvasive Assessment of Liver Fibrosis by Measurement of Stiffness in Patients with Nonalcoholic Fatty Liver Disease (NAFLD)," Dig Liver Dis, 2008, vol. 40, pp. 371-378.

Young H.M., et al., "Expression of Ret-, p75(NTR)-, Phox2a-, Phox2b-, and Tyrosine Hydroxylase-Immunoreactivity by Undifferentiated Neural Crest-Derived Cells and Different Classes of Enteric Neurons in the Embryonic Mouse Gut," Developmental Dynamics, 1999, vol. 216, pp. 137-152.

Young H.M., et al., "GDNF is a Chemoattractant for Enteric Neural Cells," Developmental biology, Dec. 19, 2000, vol. 229, pp. 503-516.

Yu H., et al., "The Contributions of Human Mini-Intestines to the Study of Intestinal Physiology and Pathophysiology," Annual Review of Physiology, Feb. 10, 2017, vol. 79, pp. 291-312.

Yuan Y., et al., "Peptic ulcer disease today," Nature Clinical Practice Gastroenterology & Hepatology, Feb. 2006, vol. 3, No. 2, pp. 80-89.

Yui S., et al., "Functional Engraftment of Colon Epithelium Expanded in Vitro from a Single Adult Lgr5(+) stem cell," Nature Medicine, Mar. 11, 2012, vol. 18, No. 4, pp. 618-623.

Zachos N.C., et al., "Human Enteroids/Colonoids and Intestinal Organoids Functionally Recapitulate Normal Intestinal Physiology and Pathophysiology," The Journal of Biological Chemistry, Feb. 19, 2016, vol. 29, No. 18, pp. 3759-3766.

Zain S.M., et al., "A Common Variant in the Glucokinase Regulatory Gene rs780094 and Risk of Nonalcoholic Fatty Liver Disease: A Meta-Analysis," Journal of Gastroenterology & Hepatology, 2015, vol. 30, pp. 21-27.

Zambrano E., et al., "Total parenteral Nutrition Induced Liver Pathology: An Autopsy Series of 24 Newborn Cases," Pediatric and Developmental Pathology, 2004, vol. 7, pp. 425-432.

Zborowski J., et al., "Induction of Swelling of Liver Mitochondria by Fatty Acids of Various Chain Length," Biochimica et Biophysica Acta, Oct. 22, 1963, vol. 70, pp. 596-598.

Zbuk K.M., et al., "Hamartomatous polyposis syndromes," Nature Clinical Practice Gastroenterology & Hepatology, 2007, vol. 4, No. 9, pp. 492-502.

Zhang D., et al., "Neural Crest Regionalisation for Enteric Nervous System Formation: Implications for Hirschsprung's Disease and Stem Cell Therapy," Developmental Biology, Mar. 15, 2010, vol. 339, pp. 280-294.

Zhang H., et al., "The Existence of Epithelial-to-Mesenchymal Cells with the Ability to Support Hematopoiesis in Human Fetal Liver," Cell Biology International, Mar. 2005, vol. 29, No. 3, pp. 213-219.

Zhang Q, et al., "Small-Molecule Synergist of the Wnt/β-catenin Signaling Pathway," PNAS, May 1, 2007, vol. 104, No. 18, pp. 7444-7448.

Zhang R.R., et al., "Human iPSC-Derived Posterior Gut Progenitors are Expandable and Capable of Forming Gut and Liver Organoids," Stem Cell Reports, Mar. 13, 2018, vol. 10, pp. 780-793.

Zhang W., et al., "Elastomeric Free-Form Blood Vessels for Interconnecting Organs on Chip Systems," Lab Chip, Apr. 26, 2016, vol. 16, No. 9, pp. 1579-1586.

Zhang Y., et al., "Palmitic and Linoleic Acids Induce ER Stress and Apoptosis in Hepatoma Cells," Lipids in Health and Disease, 2012, vol. 11 (1), 8 pages.

Zhang Y.S., et al., "Seeking the Right Context for Evaluating Nanomedicine: from Tissue Models in Petri Dishes to Microfluidic Organs-on-a-chip," Nanomedicine (Lond.), 2015, vol. 10, No. 5, pp. 685-688.

Zhang Y.S., et al., "Multisensor-Integrated Organs-on-Chips Platform for Automated and Continual in Situ Monitoring of Organoid behaviors," Proceedings of the National Academy of Sciences USA, 2017, vol. 114, pp. E2293-E2302.

Zhang Z., et al., "Syndecan4 Coordinates Wnt/JNK and BMP Signaling to Regulate Foregut Progenitor Development," Developmental Biology, 2016, vol. 416 (1), pp. 187-199.

Zhao Y., et al., "A XEN-like State Bridges Somatic Cells to Pluripotency during Chemical Reprogramming," Cell, 2015, vol. 163, pp. 1678-1691.

(56) References Cited

OTHER PUBLICATIONS

Zhong J., et al., "Continuous-Wave Laser-Assisted Injection of Single Magnetic Nanobeads into Living Cells," Sensors and Actuators B: Chemical, 2016, vol. 230, pp. 298-305.
Zhou H., et al., "Generation of Induced Pluripotent Stem Cells Using Recombinant Proteins," Cell Stem Cell, May 8, 2009, vol. 4, pp. 381-384.
Zhou J., et al., "The Potential for Gut Organoid Derived Interstitial Cells of Cajal in Replacement Therapy," International Journal of Molecular Sciences, Sep. 26, 2017, vol. 18, No. 10, p. 2059 in 17 pages.
Zhou Q., et al., "In Vivo Reprogramming of Adult Pancreatic Exocrine Cells to β-Cells," Nature, 2008, vol. 455, pp. 627-632.
Zorn A.M., et al., "Vertebrate Endoderm Development and Organ Formation," Annual Review of Cell and Developmental Biology, 2009, vol. 25, pp. 221-251.
Zhang Y., et al., "Development and Stem Cells of the Esophagus," Seminars in Cell & Developmental Biology, Dec. 19, 2016, vol. 66, pp. 25-35.
Abo., K.M., et al., Human iPSC-Derived Alveolar and Airway Epithelial Cells Can Be Cultured at Air-liquid Interface and Express SARS-COV-2 Host Factors. Biorxiv, Jun. 4, 2020, 27 pages.
Adachi S., et al., "Three Distinctive Steps in Peyer's Patch Formation of Murine Embryo," International Immunology, Apr. 1997, vol. 9(4), pp. 507-514.
Bar-Ephraim Y.E., et al., "Organoids in Immunological Research,". Nature Reviews Immunology, May 2020, vol. 20(5), pp. 279-293.
Barkauskas C. E. et al. "Lung Organoids: Current Uses and Future Promise," Development, Mar. 15; 2017, vol. 144(6), pp. 986-997.
Barkauskas C.E., et al., Type 2 alveolar Cells Are Stem Cells in Adult Lung. The Journal of Clinical Investigation, Jul. 1, 2013, vol. 123(7), pp. 3025-3036.
Barnes P.J., et al., "Chronic Lung Diseases: Prospects for Regeneration and Repair," European Respiratory Review, Mar. 31, 2021, vol. 30(159), 14 pages.
Basil, M. C., et al., "The Cellular and Physiological Basis for Lung Repair and Regeneration: Past, Present, and Future," Apr. 2, 2020, vol. 26(4, pp. 482-502.
Beers M.F., et al., "Alveolar Type 2 Epithelial Cell Quality Control Responses to Pulmonary Fibrosis Related SFTPC Mutations Are Dysfunctional and Substrate Specific," The FASEB Journal, Apr. 2020, vol. 34(S1), 1 page (Abstract Only).
Bergen V., et al., "Generalizing RNA Velocity to Transient Cell States Through Dynamical Modeling," Nature Biotechnology, Oct. 28, 2019, vol. 38(12), 26 pages.
Bharat A., et al., "Lung Transplantation for Patients with Severe COVID-19," Science Translational Medicine, Dec. 16, 2020, vol. 12(574): eabe4282, 13 pages.
Braegger C.P., et al., "Ontogenetic Aspects of the Intestinal Immune System in Man," International Journal of Clinical and Laboratory Research, 1992, vol. 22(1), pp. 1-4.
Cardenas-Diaz F. L., et al., Temporal and Spatial Staging of Lung Alveolar Regeneration Is Determined by the Grainyhead Transcription Factor Tfcp2l1, Cell Reports, May 30, 2023, vol. 42(5), 21 pages.
Chassaing B., et al., "Mammalian Gut Immunity," Biomedical Journal, Sep. 2014, vol. 37(5) p. 246 in 22 pages.
Cheng Y., et al., "Current Development Status of MEK Inhibitors," Molecules, 2017, vol. 22, pp. 1-20.
Choi J., et al., "Inflammatory Signals Induce AT2 Cell-Derived Damage-Associated Transient Progenitors that Mediate Alveolar Regeneration," Cell stem cell, Sep. 3, 2020, vol. 27(3), pp. 366-382.
Chung C., et al., "Hippo-Foxa2 Signaling Pathway Plays a Role in Peripheral Lung Maturation and Surfactant Homeostasis." Proceedings of the National Academy of Sciences of the United States of America, May 7, 2013, vol. 110(19), pp. 7732-7737.
Chung, M. I., et al., "Niche-mediated BMP/SMAD Signaling Regulates Lung Alveolar Stem Cell Proliferation and Differentiation," Development, May 1, 2018, vol. 145(9): dev 163014, 23 pages.

De Carvalho A.L.R.T., et al., "Glycogen Synthase Kinase 3 Induces Multilineage Maturation of Human Pluripotent Stem Cell-derived Lung Progenitors in 3D Culture," Development. Jan. 1, 20195, vol. 146(2): dev171652, 34 pages.
De Lau W., et al., "Peyer's Patch M Cells Derived from Lgr5+ Stem Cells Require SpiB and are Induced by RankL in Cultured Miniguts,". Molecular and Cellular Biology, Sep. 2012, vol. 32(18), pp. 3639-3647.
De Souza H.S.P., et al., "Immunopathogenesis of IBD: Current State of the Art," Nature Reviews Gastroenterology & Hepatology, Jan. 2016, vol. 13(1), pp. 13-27.
Dekkers J.F., et al., "High-resolution 3D Imaging of Fixed and Cleared Organoids," Nature protocol, Jun. 2019, vol. 14(6), pp. 1756-1771.
Duren Z., et al., "Modeling Gene Regulation from Paired Expression and Chromatin Accessibility Data," Proceedings of the National Academy of Sciences of the United States of America, Jun. 2, 2017, vol. 114(25), pp. E4914-E4923.
Eberl G., et al., "An Essential Function for the Nuclear Receptor RORgamma(t) in the Generation of Fetal Lymphoid Tissue Inducer Cells," Nature Immunology, Dec. 21, 2003, vol. 5(1), pp. 64-73.
Faure S., et al., "Endogenous Patterns of BMP Signaling During Early Chick Development," Developmental Biology, Apr. 1, 2002, vol. 244(1), pp. 44-65.
Faure S., et al., "Expression Pattern of the Homeotic Gene Bapx1 During Early Chick Gastrointestinal Tract Development," Gene Expression Patterns, Dec. 2013, vol. 13(8), 7 pages.
Finn J., et al., Dlk1-Mediated Temporal Regulation of Notch Signaling Is Required for Differentiation of Alveolar Type II to Type I Cells during Repair, Cell Reports, Mar. 12, 2019, vol. 26(11), pp. 2942-2954.
Flodby P., et al., "Cell-Specific Expression of Aquaporin-5 (Aqp5) in Alveolar Epithelium Is Directed by GATA6/Sp1 via Histone Acetylation," Scientific Reports, Jun. 14, 2017, vol. 7(1):3473, 12 pages.
Frank D. B., et al., "Emergence of a Wave of Wnt Signaling that Regulates Lung Alveologenesis by Controlling Epithelial Self-Renewal and Differentiation," Cell Reports, Nov. 22, 2016, vol. 17(9), pp. 2312-2325.
Gaskill C.F., et al., "Disruption of Lineage Specification in Adult Pulmonary Mesenchymal Progenitor Cells Promotes Microvascular Dysfunction," Journal of Clinical Investigation, Jun. 1, 2017, vol. 127(6), pp. 2262-2276.
Gibbs C.S., et al., "High-performance Single-cell Gene Regulatory Network Inference at Scale: The Inferelator 3.0," Bioinformatics, May 1, 2022, vol. 38(9), pp. 2519-2528.
Gokey J.J., et al., "Active Epithelial Hippo Signaling in Idiopathic Pulmonary Fibrosis," JCI insight, Mar. 3, 2018, vol. 3(6), 14 pages.
Gorin G., et al., "Protein Velocity and Acceleration from Single-cell Multiomics Experiments," Genome Biology, (2020)21:39, 6 pages.
Gorin G., et al., "RNA Velocity Unraveled," PLOS Computational Biology, Sep. 12, 2022, vol. 18(9): e1010492, 55 pages.
Granja J.M., et al., "ArchR is a Scalable Software Package for Integrative Single-Cell Chromatin Accessibility Analysis," Nature Genetics, Mar. 2021, vol. 53(3), pp. 403-411.
Grant R.A., et al., "Circuits Between Infected Macrophages and T cells in Sars-CoV-2 Pneumonia," Nature, Feb. 25, 2021, vol. 590(7847), pp. 635-641.
Green J., et al., "Diversity of Interstitial Lung Fibroblasts Is Regulated by Platelet-derived Growth Factor Receptor Alpha Kinase Activity," American Journal of Respiratory Cell and Molecular Biology, Apr. 2016, vol. 54(4), pp. 532-545.
Guo M., et al., "Single Cell RNA Analysis Identifies Cellular Heterogeneity and Adaptive Responses of the Lung at Birth," Nature Communications, Jan. 3, 2019; vol. 10(1):37, 16 pages.
Hamilton T.G., et al., "Evolutionary Divergence of Platelet-derived Growth Factor Alpha Receptor Signaling Mechanisms," Molecular and Cellular Biology, Jun. 1, 2003, vol. 23(11), pp. 4013-4025.
Hao Y., et al., "Integrated Analysis of Multimodal Single-cell Data," Cell, Jun. 24, 2021, ;vol. 184(13), pp. 3573-3587.
He B., et al., "Understanding Transcriptional Regulatory Networks Using Computational Models," Current Opinion in Genetics & Development, Apr. 1, 2016, vol. 37, pp. 101-108.

(56) References Cited

OTHER PUBLICATIONS

Herriges M.J., et al., "Long Noncoding RNAs are Spatially Correlated with Transcription Factors and Regulate Lung Development," Genes & Development, Jun. 15, 2014, vol. 28(12), pp. 1363-1379.
Hu S., et al., "Wnt/β-Catenin Signaling and Liver Regeneration: Circuit, Biology, and Opportunities," Gene expression, 2021, vol. 20(3), pp. 189-199.
Hu Y., et al., "Wnt/β-Catenin Signaling Is Critical for Regenerative Potential of Distal Lung Epithelial Progenitor Cells in Homeostasis and Emphysema," Stem Cells, Nov. 2020, vol. 38(11), pp. 1467-1478.
Ikegami., M et al. "Surfactant Protein D Influences Surfactant Ultrastructure and Uptake by Alveolar Type Ii Cells," American Journal of Physiology—Lung Cellular and Molecular Physiology, Mar. 2005, vol. 288(3), pp. L552-L561.
Jacob A., et al., "Differentiation of Human Pluripotent Stem Cells into Functional Lung Alveolar Epithelial Cells," Cell Stem Cell, Oct. 5, 2017, vol. 21(4), pp. 472-488.
Jain R., et al., "Plasticity of Hopx (+) Type I Alveolar Cells to Regenerate Type Ii Cells in the Lung," Nature Communications, 2015, vol. 13;6(1):6727, 20 pages.
Jin S., et al., "Inference and Analysis of Cell-cell Communication Using Cellchat," Nature Communications, Feb. 17, 2021, vol. 12(1):1088, 20 pages.
Kathiriya, J.J., et al., "Human Alveolar Type 2 Epithelium Transdifferentiates into Metaplastic KRT5+ Basal Cells," Nature Cell Biology, Jan. 2022, vol. 24(1), pp. 10-23.
Kim S., et al., "Engraftment Potential of Spheroid-Forming Hepatic Endoderm Derived from Human Embryonic Stem Cells," Stem Cells Development. Jun. 1, 20135, vol. 22(12), pp. 1818-1829.
Kobayashi Y., et al., "Persistence of a Regeneration-associated, Transitional Alveolar Epithelial Cell State in Pulmonary Fibrosis," Nature Cell Biology, Aug. 2020, vol. 22(8), pp. 934-946.
Koboziev I., et al., "Use of Humanized Mice to Study the Pathogenesis of Autoimmune and Inflammatory Diseases," Inflammatory Bowel Diseases, Jul. 1, 2015, 21 (7), pp. 1652-1673.
Kusakabe T., et al., "Thyroid-Specific Enhancer-binding Protein/NKX2.1 is Required for the Maintenance of Ordered Architecture and Function of the Differentiated Thyroid," Molecular Endocrinology, Aug. 2006, vol. 20(8), pp. 1796-1809.
Lacanna R., et al., "Yap/Taz Regulate Alveolar Regeneration and Resolution of Lung Inflammation," Journal of Clinical Investigation, May 1, 2019, vol. 129(5), pp. 2107-2122.
Lange M., et al., "CellRank for Directed Single-cell Fate Mapping," Nature Methods, Feb. 2022, vol. 19(2), pp. 159-170.
Laughney A.M., et al., "Regenerative Lineages and Immune-mediated Pruning in Lung Cancer Metastasis," Nature Medicine, Feb. 2020, vol. 26(2), pp. 259-269.
Lee J., et al., "IL-25 and CD4(+) TH2 Cells Enhance Type 2 Innate Lymphoid Cell-derived IL-13 Production, Which Promotes IgE-mediated Experimental Food Allergy," The Journal of Allergy and Clinical Immunology, Apr. 1, 2016, vol. 137(4), pp. 1216-1225.
Lee J.H et al., "Anatomically and Functionally Distinct Lung Mesenchymal Populations Marked by Lgr5 and Lgr6," Cell, Sep. 7, 2017, vol. 170(6), pp. 1149-1163.
Li N., et al., Early-Life Compartmentalization of Immune Cells in Human Fetal Tissues Revealed by High-Dimensional Mass Cytometry, Frontiers in Immunology, Aug. 14, 2019; vol. 10(1932), 13 pages.
Li N., et al., Mass cytometry reveals innate lymphoid cell differentiation pathways in the human fetal intestine. Journal of Experimental Medicine, May 7, 2018, vol. 215(5), pp. 1383-1396.
Li N., et al., "Memory CD4+ T Cells Are Generated in the Human Fetal Intestine," Nature Immunology, Mar. 2019, vol. 20(3), pp. 301-312.
Liang, W., et al., "MEF2C Alleviates Acute Lung Injury in Cecal Ligation and Puncture (CLP)-induced Sepsis Rats by Up-regulating AQP1," Allergologia et Immunopathologia, Sep. 1, 2021, vol. 49(5), pp. 117-124.

Lignitto L., et al., "Nrf2 Activation Promotes Lung Cancer Metastasis by Inhibiting the Degradation of Bach 1," Cell, Jul. 11, 2019, vol. 178(2), pp. 316-329.
Loh K.M., et al., "Efficient Endoderm Induction from Human Pluripotent Stem Cells by Logically Directing Signals Controlling Lineage Bifurcations," Cell Stem Cell, Feb. 6, 2014, vol. 14(2), pp. 237-252.
Mabbott N.A., et al., "Microfold (M) Cells: Important Immunosurveillance Posts in the Intestinal Epithelium," Mucosal Immunology, Jul. 1, 2013, vol. 6(4), pp. 666-677.
Maeda Y., et al., Kras(G12D) and Nkx2-1 Haploinsufficiency Induce Mucinous Adenocarcinoma of the Lung. Journal of Clinical Investigation, Dec. 3, 2012, vol. 122(12), pp. 4388-4400.
Manno., L.G., et al., "RNA Velocity of Single Cells," Nature, Aug. 2018, vol. 560 (7719), pp. 494-498.
Maruyama E.O., et al., "Cell-Specific Cre Strains for Genetic Manipulation in Salivary Glands," PLOS ONE, Jan. 11, 2016, vol. 11(1): e0146711, 12 pages.
Mcginnis C.S., et al., "DoubletFinder: Doublet Detection in Single-Cell RNA Sequencing Data Using Artificial Nearest Neighbors," Cell Systems, Apr. 24, 2019, vol. 8(4), pp. 329-337.
Miraldi E.R., et al., Leveraging Chromatin Accessibility for Transcriptional Regulatory Network Inference in T Helper 17 Cells. Genome Research, Mar. 1, 2019, vol. 29(3), pp. 449-463.
Mizumoto H., et al., "Hybrid Artificial Liver Using Hepatocyte Organoids," Regenerative Medicine, 2006, vol. 5 No. 3, pp. 81-86.
Mollaoglu G., et al., "The Lineage-Defining Transcription Factors SOX2 and NKX2-1 Determine Lung Cancer Cell Fate and Shape the Tumor Immune Microenvironment," Immunity, Oct. 16, 2018, vol. 49(4), pp. 764-779.
Mowat A., et al., "Regional Specialization Within the Intestinal Immune System," Nature Reviews Immunology, Oct. 2014, vol. 14(10), pp. 667-685.
Nabhan A., et al., "A Single Cell Wnt Signaling Niche Maintains Stemness of Alveolar Type 2 Cells," Science, Mar. 9, 2018; vol. 359(6380), pp. 1118-1123.
Negretti N. M., et al., "A Single-cell Atlas of Mouse Lung Development," Development Dec. 15, 2021, vol. 148(24), 30 pages.
Nochi T., et al., "Cryptopatches are essential for the development of human GALT," Cell Reports, Jun. 27, 2013, vol. 3(6), vol. 1874-1884.
Noel G., et al., "A Primary Human Macrophage-enteroid Co-culture Model to Investigate Mucosal Gut Physiology and Host-pathogen Interactions," Scientific Reports, Mar. 27, 2017, vol. 7(45270), 13 pages.
Ostrin E. J., et al., "β-Catenin Maintains Lung Epithelial Progenitors After Lung Specification," Development, Mar. 1, 2018, vol. 145(5), 32 pages.
Paris A.J., et al., "STAT3—BDNF-TrkB Signaling Promotes Alveolar Epithelial Regeneration After Lung Injury," Nature Cell Biology, Oct. 2020, vol. 22(10), pp. 1197-1210.
Ranganathan S., et al., "Evaluating *Shigella flexneri* Pathogenesis in the Human Enteroid Model," Infection and Immunity, Apr. 2019, vol. 87(4), 14 pages.
Riemondy K. A., et al., "Single Cell RNA Sequencing Identifies TGF-β as a Key Regenerative Cue Following LPS-induced Lung Injury," JCI Insight, Apr. 4, 2019, vol. 4(8), 18 pages.
Rindler T.N., et al., "Efficient Transduction of Alveolar Type 2 Cells with Adeno-associated Virus for the Study of Lung Regeneration," American Journal of Respiratory Cell and Molecular Biology, Jul. 2021, vol. 65(1), pp. 118-121.
Rodriguez-Castillo J. A., et al., "Understanding Alveolarization to Induce Lung Regeneration," Respiratory Research, Dec. 2018, vol. 19:1-1, 11 pages.
Rouch J.D., et al., "Development of Functional Microfold (M) Cells from Intestinal Stem Cells in Primary Human Enteroids," PLOS One. Jan. 28, 2016, vol. 11(1), 16 pages.
Ruppert C. et al., "Role of HGF in the healthy and injured lung," European Respiratory Journal, 2015, vol. 46, 2 pages.
Salahudeen A. A., et al., "Progenitor Identification and SARS-CoV-2 Infection in Human Distal Lung Organoids," Nature, Dec. 24, 2020, vol. 588(7839), pp. 670-675.

(56) References Cited

OTHER PUBLICATIONS

Serra M., et al., "Pluripotent Stem Cell Differentiation Reveals Distinct Developmental Pathways Regulating Lung-Versus Thyroid-lineage Specification," Development, Nov. 1, 2017, vol. 144(21), pp. 3879-3893.
Shinozawa T., et al., "High-Fidelity Drug-Induced Liver Injury Screen Using Human Pluripotent Stem Cell-Derived Organoids," Gastroenterology. Feb. 2021, vol. 160(3), pp. 831-846.
Spencer J., et al., "T Cell Subclasses in Fetal Human Ileum," Clinical and Experimental Immunology, 1986, pp. 553-558.
Spencer J., et al., "The Development of Gut Associated Lymphoid Tissue in the Terminal Ileum of Fetal Human Intestine," Clinical and Experimental Immunology, 1986, pp. 536-543.
Srinivas S., et al., "Cre Reporter Strains Produced by Targeted Insertion of EYFP and ECFP into the ROSA26 Locus," BMC Developmental Biology, Dec. 2001, vol. 1 (4), 8 pages.
Staab J.F., et al., "Co-Culture System of Human Enteroids/Colonoids with Innate Immune Cells,". Current Protocols in Immunology, Dec. 2020, vol. 131(1), 23 pages.
STRAS., et al., "Maturation of the Human Intestinal Immune System Occurs Early in Fetal Development," Developmental Cell, Nov. 4, 2019, vol. 51(3), pp. 357-373.
Street K., et al., "Slingshot: Cell Lineage and Pseudotime Inference for Single-cell Transcriptomics," BMC Genomics, Dec. 2018, vol. 19, pp. 1-16.
Strikoudis A., et al., "Modeling of Fibrotic Lung Disease Using 3D Organoids Derived from Human Pluripotent Stem Cells," Cell Reports, Jun. 18, 2019, vol. 27(12), pp. 3709-3723.
Strunz M., et al., "Alveolar Regeneration Through a Krt8+ Transitional Stem Cell State That Persists in Human Lung Fibrosis," Nature Communications, Jul. 16, 2020, vol. 11(1):3559, 20 pages.
Sucre J. M.S., et al., "Hyperoxia Injury in the Developing Lung is Mediated by Mesenchymal Expression of Wnt5A," American Journal of Respiratory and Critical Care Medicine, May 15, 2020, vol. 201(10), pp. 1249-1262.
Sun X., et al., "A Census of the Lung: CellCards from LungMAP," Developmental Cell, Jan. 10, 2022, vol. 57(1), pp. 112-145.
Tata P.R., et al., "Developmental History Provides a Roadmap for the Emergence of Tumor Plasticity," Developmental Cell, Mar. 26, 2018, vol. 44(6), pp. 679-693.
Toth A., et al., "Alveolar Epithelial Progenitor Cells Drive Lung Regeneration via Dynamic Changes in Chromatin Topology Modulated by Lineage-specific Nkx2-1 Activity," bioRxiv, 2022, 31 pages.
Toth A., et al., "Alveolar Epithelial Stem Cells in Homeostasis and Repair," Chapter 10 in Lung Stem Cells in Development, Health and Disease, European Respiratory Society, 2021, pp. 122-133.
Travaglini K.J., et al., "A Molecular Cell Atlas of the Human Lung from Single-cell RNA Sequencing," Nature, Nov. 26, 2020, vol. 587(7835), pp. 619-625.
Van Lieshout., L.P., et al., "A Novel Triple-Mutant AAV6 Capsid Induces Rapid and Potent Transgene Expression in the Muscle and Respiratory Tract of Mice," Molecular Therapy—Methods and Clinical Development, Open Access Jun. 15, 2018, vol. 9, pp. 323-329.
Verheyden J.M., et al., "A Transitional Stem Cell State in the Lung," Nature Cell Biology, Sep. 2020, vol. 22(9), pp. 1025-1026.
Weigmann B., et al., Isolation and Subsequent Analysis of Murine Lamina Propria Mononuclear Cells from Colonic Tissue, Nature Protocols, Oct. 2007, vol. 2(10), 2307-2311.
Weng A., et al., "Lung Injury Induces Alveolar Type 2 Cell Hypertrophy and Polyploidy with Implications for Repair and Regeneration," American Journal of Respiratory Cell and Molecular Biology, May 2022, vol. 66(5), pp. 564-576.
Wiel C., et al., "BACH1 Stabilization by Antioxidants Stimulates Lung Cancer Metastasis," Cell, Jul. 11, 2019, vol. 178(2), pp. 330-345.
Wunderlich M., et al., "AML Xenograft Efficiency Is Significantly Improved in NOD/SCID-IL2RG Mice Constitutively Expressing Human SCF, GM-CSF and IL-3," Leukemia, Oct. 2010, vol. 24(10) pp. 1785-1788.
Wunderlich M., et al., "Improved Multilineage Human Hematopoietic Reconstitution and Function in NSGS Mice," PLOS One, Dec. 12, 2018, vol. 13(12), 20 pages.
Yamaguchi T., et al., "NKX2-1/TTF-1: An Enigmatic Oncogene That Functions as a Double-edged Sword for Cancer Cell Survival and Progression," Cancer Cell, Jun. 10, 2013, vol. 23(6), pp. 718-723.
Yang Y., et al., "Transcription Factor C/EBP Homologous Protein in Health and Diseases," Frontiers in Immunology, Nov. 27, 2017, vol. 8:1612, 18 pages.
Yuan T., et al., "Fgf10 Signaling in Lung Development, Homeostasis, Disease, and Repair After Injury," Frontiers in Genetics, Sep. 25, 2018, vol. 9(418), 8 pages.
Zacharias W.J., et al., "Regeneration of the Lung Alveolus by an Evolutionarily Conserved Epithelial Progenitor," Nature, Mar. 8, 2018, vol. 555(7695), pp. 251-255.
Zepp J.A., et al., "Distinct Mesenchymal Lineages and Niches Promote Epithelial Self-Renewal and Myofibrogenesis in the Lung," Cell, Sep. 7, 2017, vol. 170(6), pp. 1134-1148.
Zhou B., et al., "Comprehensive Epigenomic Profiling of Human Alveolar Epithelial Differentiation Identifies Key Epigenetic States and Transcription Factor Co-Regulatory Networks for Maintenance of Distal Lung Identity," BMC Genomics, Dec. 2021, vol. 22(906), 25 pages.
Blanchard C., et al., "Coordinate Interaction between IL-13 and Epithelial Differentiation Cluster Genes in Eosinophilic Esophagitis," The Journal of Immunology 2010, 184(7), 4033-4041.
Bochkis I.M. et al., "Genome-wide location analysis reveals distinct transcriptional circuitry by paralogous regulators Foxa1 and Foxa2," PLoS genetics, 2012, 8, 6, e1002770, 10 pages.
Boj S.F., et al., "Forskolin-induced Swelling in Intestinal Organoids: An In Vitro Assay for Assessing Drug Response in Cystic Fibrosis Patients," J Vis Exp, Feb. 1, 20171, (120):55159.
Bolger A. M. et al., "Trimmomatic: a flexible trimmer for Illumina sequence data," Bioinformatics, 2014, 30, 2114-2120.
Bolte C., et al., "Nanoparticle Delivery of Proangiogenic Transcription Factors into the Neonatal Neurotrophic Factor-Mediated Alveolar Capillary Injury and Repair Circulation Inhibits Alveolar Simplification Caused by Hyperoxia," American Journal of Respiratory and Critical Care Medicine, Jul. 2020, vol. 202, No. 1, pp. 100-111. doi: 10.1164/rccm.201906-1232OC.
Boon et al., "Amino Acid Levels Determine Metabolism and CYP450 Function in Hepatocytes and Hepatoma Cell Lines," Nature Communications, 2020, vol. 11, 1393.
Bordi C et al., "Classification of gastric endocrine cells at the light and electron microscopical levels," Microsc. Res. Tech., 2000, 48, 258-271.
Bray N. L., et al., "Near-Optimal Probabilistic RNA-Seq Quantification," Nature Biotechnology, 2016, vol. 34, pp. 525-527.
Buettner et al., "Computational Analysis of Cell-to-cell Heterogeneity in Single-cell RNA-sequencing Data reveals Hidden Subpopulations of cells", Nature Biotech, 2015, vol. 33(2), pp. 155-160.
Butler, A., et al. Integrating Single-Cell Transcriptomic Data Across Different Conditions, Technologies, and Species,. Nature Biotechnology, 2018, 36(4), pp. 411-420.
Cai, W., et al., "Genetic polymorphisms associated with nonalcoholic fatty liver disease in Uyghur population: a case-control study and meta-analysis," Lipids in Health and Disease, 2019, vol. 18, 14.
Cain M.P., et al., "Quantitative Single-Cell Interactomes in Normal and Virus-Infected Mouse Lungs," Disease Models Mechanisms, May 2020, vol. 13, No. 6, doi: 10.1242/dmm.044404.
Cakir, et al., "Engineering of Human Brain Organoids with a Functional Vascular-Like System," Nature Methods, 2019, vol. 16, No. 11, 1169-1175.
Caldwell J. M., et al., "Novel Immunologic Mechanisms in Eosinophilic Esophagitis," Current Opinion in Immunology, 2017, vol. 48, pp. 114-121.

(56) References Cited

OTHER PUBLICATIONS

Candi E et al., "Differential roles of p63 isoforms in epidermal development: selective genetic complementation in p63 null mice," Cell Death Differ, 2006, 13, 1037-1047.

Capeling M. M et al., "Suspension culture promotes serosal mesothelial development in human intestingal organoids," Cell Reports, 2002, 38, 110379, 33 pages.

Carmona R., et al., "Conditional Deletion of WT1 in the Septum Transversum Mesenchyme Causes Congenital Diaphragmatic Hernia in Mice,". eLife, Sep. 19, 2016, vol. 5, No. e16009, pp. 1-17.

Chambers J. C., et al., "Genome-Wide Association Study Identifies Loci Influencing Concentrations of Liver Enzymes in Plasma," Nature Genetics, 2011, vol. 43, pp. 1131-1138.

Chance W.T., et al., "Preservation of Intestine Protein by Peptide YY During Total Parenteral Nutrition," Life Sciences 1996, vol. 58, No. 21, pp. 1785-1794.

Chandran S., et al., "Necrotising Enterocolitis in a Newborn Infant Treated with Octreotide for Chylous Effusion: Is Octreotide Safe?," BMJ Case Reports, 2020, 13, e232062. doi:10.1136/bcr-2019-232062.

Char V.C. et al., "Digestion and absorption of carbohydrates by the fetal lamb in utero," Pediatr Res, 1979, 13, 1018-1023.

Charlton, V. E., et al., "Effects of Gastric Nutritional Supplementation on Fetal Umbilical Uptake of Nutrients," Am J Physiol, 1981, vol. 241, pp. E178-185.

Chatterjee S., et al., "Tissue-Specific Gene Expression during Productive Human Papillomavirus 16 Infection of Cervical, Foreskin, and Tonsil Epithelium." Journal of Virology, 93(17), 2019, e00915-19.

Chen et al., "A Versatile Polypharmacology Platform Promotes Cryoprotection and Viability of Human Pluripotent and Differentiated Cells," Nature Methods, 2021, vol. 18, pp. 528-541.

Chen, F., et al., "Inhibition of Tgf beta signaling by endogenous retinoic acid is essential for primary lung bud induction," Development, 2007, vol. 134, pp. 2969-2979.

Chen H., et al., "Single-Cell Trajectories Reconstruction, Exploration and Mapping of Omics Data with STREAM," Nature Communications, 2019, vol. 10, Article 1903. doi: 10.1038/s41467-019-09670-4, 14 pages.

Chen H. et al., "Transcript profiling identifies dynamic gene expression patterns and an important role for Nrf2/Keap1 pathway in the developing mouse esophagus," PloS One 2012, 7(5), e36504, 10 pages.

Chen J., et al., "Improved Human Disease Candidate Gene Prioritization Using Mouse Phenotype," BMC Bioinformatics, 2007, vol. 8, p. 392.

Chen J., et al., "ToppGene Suite for Gene List Enrichment Analysis and Candidate Gene Prioritization," Nucleic Acids Research, 2009, vol. 37, pp. W305-W311.

Chen S., et al., "fastp: An Ultra-Fast All-in-One FASTQ Preprocessor," Bioinformatics, 2018, vol. 34, pp. 1884-1890.

Chen X., "Aberrant expression of Wnt and Notch signal pathways in Barrett's esophagus," Clinics and Research in Hepatology and Gastroenterology, 2012, 36(5), 473-483.

Chen Y., et al., "A Three-Dimensional Model of Human Lung Development and Disease from Pluripotent Stem Cells," Nature Cell Biology, May 2017, vol. 19, No. 5, pp. 542-557.

Chen Y. et al., "BMP Signaling pathway and colon cancer," Journal of Cell Biology 2009, 5, 6 pages (Chinese with machine translation).

Chen, Y., et al., "SOX2 expression inhibits terminal epidermal differentiation," Exp. Dermatol., 2015, vol. 24, pp. 966-982.

Chen Y., et al., "Regulation of Angiogenesis Through a MicroRNA (miR-130a) That Down-Regulates Antiangiogenic Homeobox Genes GAX and HOXA5," Blood, 2008, vol. 111, pp. 1217-1226.

Chen Y. et al., "The Molecular Mechanism Governing the Oncogenic Potential of SOX2 in Breast Cancer," Journal of Biological Chemistry 2008, 283(26), 17969-17978.

Cheung K.C.P., et al., "Preservation of Microvascular Barrier Function Requires CD31 Receptor-Induced Metabolic Reprogramming," Nature Communications, Jul. 2020, vol. 11, No. 1, doi: 10.1038/s41467-020-17329-8.

Chey, W. Y., et al., "Secretin: historical perspective and current status," Pancreas, 2014, vol. 43, pp. 162-182.

Chin, A. M., et al., "Morphogenesis and maturation of the embryonic and postnatal intestine," Seminars in Cell & Developmental Biology, 2017, vol. 66, pp. 81-93.

Cho C., et al., "Reck and Gpr124 Are Essential Receptor Cofactors for Wnt7a/Wnt7b-Specific Signaling in Mammalian CNS Angiogenesis and Blood-Brain Barrier Regulation," Neuron, 2017, vol. 95, pp. 1221-1225.

Cho C. F., et al., "Blood-Brain-Barrier Spheroids as an In Vitro Screening Platform for Brain-Penetrating Agents," Nature Communications, 2017, vol. 8, p. 15623.

Choi K., et al., "iGEAK: An Interactive Gene Expression Analysis Kit for Seamless Workflow Using the R/Shiny Platform," BMC Genomics, 2019, vol. 20, p. 177.

Choudhary S., et al., "Comparison and Evaluation of Statistical Error Models for scRNA-seq," Genome Biology, 2022, vol. 23, 27. doi: 10.1186/s13059-021-02584-9.

Claesson-Welsh L., et al., "Permeability of the Endothelial Barrier: Identifying and Reconciling Controversies," Trends in Molecular Medicine, Apr. 2021, vol. 27, No. 4, pp. 314-331.

Claeys, W., et al., "A mouse model of hepatic encephalopathy: bile duct ligation induces brain ammonia overload, glial cell activation and neuroinflammation," Scientific Reports, 2022, vol. 12, 17558.

Clemmensen, C. et al., "Emerging Hormonal-Based Combination Pharmacotherapies for the Treatment of Metabolic Diseases". Nat Rev Endocrinol, 2018, 14(10), pp. 670-684.

Collier et al., "Identifying Human Naïve Pluripotent Stem Cells—Evaluating State-Specific Reporter Lines and Cell-Surface Markers", BioEssays. May 2018, 40(5): 1700239 in 12 pages.

Concepcion J. P., et al., "Neonatal Diabetes, Gallbladder Agenesis, Duodenal Atresia, and Intestinal Malrotation Caused by a Novel Homozygous Mutation in RFX6," Pediatric Diabetes, 2014, vol. 15, pp. 67-72.

Coon S. D. et al., "Glucose-dependent insulinotropic polypeptide-mediated signaling pathways enhance apical PepT1 expression in intestinal epithelial cells," Am J Physiol Gastrointest Liver Physiol, 2015, 308, G56-62.

Cortina, G., et al., "Enteroendocrine Cell Dysgenesis and Malabsorption, a Histopathologic and Immunohistochemical Characterization," Human Pathology, 2007, vol. 38, pp. 570-580.

Mariotti, V., et al., "Animal models of biliary injury and altered bile acid metabolism," Biochimica et Biophysica Acta (BBA)—Molecular Basis of Disease, 2018, vol. 1864, pp. 1254-1261.

Martin M. "Cutadapt Removes Adapter Sequences From High-Throughput Sequencing Reads," EMBnet.journal, 2011 17, 10-12.

Martindale J.L., et al., "Ribonucleoprotein Immunoprecipitation (RIP) Analysis," Bio Protoc, 2020, vol. 10, No. 2, e3488. doi: 10.21769/BioProtoc.3488.

Matrka M. C., et al., "Overexpression of the Human DEK Oncogene Reprograms Cellular Metabolism and Promotes Glycolysis," PLoS One, 2017, vol. 12, e0177952.

Matsuda S., et al., "Brain-Derived Neurotrophic Factor Induces Migration of Endothelial Cells Through a TrkB-ERK-Integrin $\alpha V\beta 3$-FAK Cascade." Journal of Cellular Physiology, 227, 2012, pp. 2123-2129.

Matt N. et al., "Retinoic acid-induced developmental defects are mediated by RARβ3/RXR heterodimers in the pharyngeal endoderm," Development, 2003, 130(10), 2083-2093.

Mayor S., et al., "Pathways of Clathrin-independent Endocytosis," Nature Reviews, Molecular Cell Biology, 2007, vol. 8(8), pp. 603-612.

Mccarty, W. J., et al., "A Microfabricated Platform for Generating Physiologically-Relevant Hepatocyte Zonation," Scientific Reports, 2016, vol. 6, 26868, 10 Pages.

McMahon H.T., et al., "Molecular Mechanism and Physiological Functions of Clathrin-mediated Endocytosis," Nature Reviews Molecular Cell Biology, Aug. 2011, vol. 12(8), pp. 517-533.

(56) References Cited

OTHER PUBLICATIONS

Mcnaughton, L., et al., "Distribution of nitric oxide synthase in normal and cirrhotic human liver," Proceedings of the National Academy of Sciences, 2002, vol. 99, pp. 17161-17166.

Mendelsohn C. et al., "Developmental analsyis of the retinoic acid-inducible RARb2 promoter in transgenic animals," Development, 1991, 113, 723-734.

Miao Y., et al., "Enhancer-Associated Long Non-Coding RNA LEENE Regulates Endothelial Nitric Oxide Synthase and Endothelial Function," Nature Communications, Jan. 2018, vol. 9, No. 1, doi: 10.1038/s41467-017-02113-y.

Miao Y., et al., "Intrinsic Endocardial Defects in Hypoplastic Left Heart Syndrome," Cell Stem Cell, Jul. 2020. doi: 10.1016/j.stem.2020.07.015.

Miao Z., et al., "Single Cell Regulatory Landscape of the Mouse Kidney Highlights Cellular Differentiation Programs and Disease Targets," Nature Communications, 2021, vol. 12, No. 2277.

Midendorp S., et al., "Adult Stem Cells in the Small Intestine Are Intrinsically Programmed with Their Location-Specific Function," Stem Cells, 2014, vol. 32, pp. 1083-1091. DOI: 10.1002/stem.1655.

Miller J. L., et al., "Emergence of Oropharyngeal, Laryngeal and Swallowing Activity in the Developing Fetal Upper Aerodigestive Tract: An Ultrasound Evaluation." Early Human Development, 71, 2003, pp. 61-87.

Minoo P et al., "Defects in tracheoesophageal and lung morphogenesis in Nkx2.1 (-/-) mouse embryos," Dev. Biol., 1999, 209, 60-71.

Mitani, S., et al., "Human ESC/iPSC-Derived Hepatocyte-like Cells Achieve Zone-Specific Hepatic Properties by Modulation of WNT Signaling," Mol Ther, 2017, vol. 25, pp. 1420-1433.

Miyoshi H., et al., "In Vitro Expansion and Genetic Modification of Gastrointestinal Stem Cells in Spheroid Culture," Nature Protocols, 2013, vol. 8(12), pp. 2471-2482.

Moffett, J.R., et al., "Acetate Revisited: A Key Biomolecule at the Nexus of Metabolism, Epigenetics and Oncogenesis—Part 1: Acetyl-CoA, Acetogenesis and Acyl-CoA Short-Chain Synthetases," Frontiers in Physiology, 2020, vol. 11.

Moon C. et al., "Development of a primary mouse intestinal epithelial cell monolayer culture system to evaluate factors that modulate IgA transcytosis," Mucosal Immunol, 2014, 7, 818-828.

Moorefield E.C., et al., "Generation of renewable mouse intestinal epithelial cell monolayers and organoids for functional analyses," BMC Cell Biol, Aug. 1, 20185, vol. 19(1):15.

Mootha V.K. et al., "PGC-1alpha-responsive genes involved in oxidative phosphorylation are coordinately downregulated in human diabetes," Nat Genet 34, 267-273 (2003).

Morizane R., et al., "Differentiation of Murine Embryonic Stem and Induced Pluripotent Stem Cells to Renal Lineage In Vitro." Biochemical and Biophysical Research Communications, 390, 2009, pp. 1334-1339.

Morizane R., et al., "Generation of Nephron Progenitor Cells and Kidney Organoids from Human Pluripotent Stem Cells," Nature Protocols, 2017, vol. 12, pp. 195-207.

Morizane R., et al., "Kidney Organoids: A Translational Journey," Trends in Molecular Medicine, 2017, vol. 23, pp. 246-263.

Morizane R., et al., "Nephron Organoids Derived from Human Pluripotent Stem Cells Model Kidney Development and Injury." Nature Biotechnology, 33(11), 2015, pp. 1193-1200. https://doi.org/10.1038/nbt.3392.

Morris M. E., et al., "SLC and ABC Transporters: Expression, Localization, and Species Differences at the Blood-Brain and the Blood-Cerebrospinal Fluid Barriers," AAPS Journal, 2017, vol. 19, pp. 1317-1331.

Mounier F., et al., "Ontogenesis of Angiotensin-I Converting Enzyme in Human Kidney," Kidney International, 1987, vol. 32, pp. 684-690.

Murphy C. L., et al., "HIF-Mediated Articular Chondrocyte Function: Prospects for Cartilage Repair," Arthritis Research & Therapy, 2009, vol. 11, p. 213. DOI: 10.1186/ar2574.

Murphy P.A., et al., "Alternative RNA Splicing in the Endothelium Mediated in Part by Rbfox2 Regulates the Arterial Response to Low Flow," eLife, Jan. 2018, vol. 7, e29494. doi: 10.7554/eLife.29494.

Navin N., et al., "Tumor Evolution Inferred by Single-cell Sequencing," Nature, Apr. 7, 2011, vol. 472(7341), pp. 90-94.

Neal E.H., et al., "A Simplified, Fully Defined Differentiation Scheme for Producing Blood-Brain Barrier Endothelial Cells from Human iPSCs," Stem Cell Reports, 2019, vol. 12, pp. 1380-1388.

Nebert D. W., et al., "Letter to the Editor for 'Update of the Human and Mouse Fanconi Anemia Genes,'" Human Genomics, 2016, vol. 10, No. 1, 25 pages.

Nejak-Bowen, K., et al., "Beta-catenin regulates vitamin C biosynthesis and cell survival in murine liver," J Biol Chem, 2009, vol. 284, pp. 28115-28127.

Nelson L.J., et al., "Low-Shear Modelled Microgravity Environment Maintains Morphology and Differentiated Functionality of Primary Porcine Hepatocyte Cultures," Cells Tissues Organs, 2010, vol. 192, pp. 125-140.

Niederreither K. "Embryonic retinoic acid synthesis is essential for early mouse post-implantation development," Nature Genetics, 1999, 21(4), 444-448.

Niethamer T.K., et al., "Defining the Role of Pulmonary Endothelial Cell Heterogeneity in the Response to Acute Lung Injury," eLife, Feb. 2020, vol. 9, No. e53072. doi: 10.7554/eLife.53072.

Nishinakamura R., "Human Kidney Organoids: Progress and Remaining Challenges," Nature Reviews Nephrology, 2019, vol. 15, pp. 613-624.

Nonn, O., et al., "Maternal Angiotensin Increases Placental Leptin in Early Gestation via an Alternative Renin-Angiotensin System Pathway: Suggesting a Link to Preeclampsia," Hypertension, 2021, vol. 77, pp. 1723-1736.

Nozaki, Y., et al., "Metabolic Control Analysis of Hepatic Glycogen Synthesis In Vivo," Proceedings of the National Academy of Sciences of the United States of America, 2020, vol. 117, pp. 8166-8176.

Nyeng P. et al., FGF10 signaling controls stomach morphogenesis. Developmental Biology, 2007, 303, 295-310.

Oberg, K. C., et al., "Renal Tubular Dysgenesis in Twin-Twin Transfusion Syndrome." Pediatric Developmental Pathology, vol. 2, No. 1, 1999, pp. 25-32.

Offield M.F. et al., "PDX-1 is required for pancreatic outgrowth and differentiation of the rostral duodenum," Development, 1996, 122(3), 983-995.

Ohashi T., "Enzyme replacement therapy for lysosomal storage diseases," Pediatr Endocrinol Rev. Oct. 1, 2012;10(supp 1):26 34.

Ohmori T et al. "Efficient expression of a transgene in platelets using simian immunodeficiency virus based vector harboring glycoprotein Iba promoter: in vivo model for platelet targeting gene therapy," FASEB J. (2006);20(9):1522 4.

Ohsie S. et al., "A paucity of colonic enteroendocrine and/or enterochromaffin cells characterizes a subset of patients with chronic unexplained diarrhea/malabsorption," Hum Pathol , 2009, 40(7), 1006-1014.

Ohta et al., "Hemogenic endothelium differentiation from human pluripotent stem cells in a feeder and xeno free defined condition," Journal of Visualized Experiments. Jun. 16, 2019;148:e59823 in 6 pages.

Oliverio M. I., et al., "Reduced Growth, Abnormal Kidney Structure, and Type 2 (AT2) Angiotensin Receptor-Mediated Blood Pressure Regulation in Mice Lacking Both AT1A and AT1B Receptors for Angiotensin II," Proceedings of the National Academy of Sciences USA, 1998, vol. 95, pp. 15496-15501.

Omer, D., et al., "Human Kidney Spheroids and Monolayers Provide Insights into SARS-CoV-2 Renal Interactions," Journal of the American Society of Nephrology, 2021, vol. 32, pp. 2242-2254.

Wang D.H. et al., "Aberrant Epithelial-Mesenchymal Hedgehog Signaling Characterizes Barrett's Metaplasia," Gastroenterology 2010, 138(5),1810-1822.e2.

Wang H., et al., "Recent Progress in microRNA Delivery for Cancer Therapy by Non-Viral Synthetic Vectors," Advanced Drug Delivery Reviews, 2015, vol. 81, pp. 142-160.

(56) References Cited

OTHER PUBLICATIONS

Wang K., et al., "ANNOVAR: Functional Annotation of Genetic Variants from High-Throughput Sequencing Data," Nucleic Acids Research, 2010, vol. 38, e164.
Wang Q. et al., "Regulatable in vivo biotinylation expression system in mouse embryonic stem cells," PloS One, 2013, 8, 5, e63532, 7 pages.
Wang S., "Fundamentals of developmental biology", edited by , East China University of 25 Technology Press, Feb. 2014, 1st edition, pp. 184-185 "Role of homologous genes in development of appendages", published on Feb. 28, 2014).
Wang T. et al."Polypeptide Growth Factor and Spinal Cord Injury". Xinjiang Science and Technology Press, Yunnan Science and Technology Press, "Biological Effects of EGF", pp. 88-89, published on Apr. 30, 2003).
Wang X., et al., "A Tropomyosin Receptor Kinase Family Protein, NTRK2, is a Potential Predictive Biomarker for Lung Adenocarcinoma," PeerJ, Jun. 2019, vol. 7, doi: 10.7717/peerj.7125.
Wang, Y., et al., "Metformin Improves Mitochondrial Respiratory Activity through Activation of AMPK," Cell Reports, 2019, vol. 29, pp. 1511-1523 e1515.
Wang, Y., et al., "Transcriptional regulation of hepatic lipogenesis," Nat Rev Mol Cell Biol, 2015, vol. 16, pp. 678-689.
Watanabe H., et al., "SOX2 and p63 colocalize at genetic loci in squamous cell carcinomas," Journal of Clinical Investigation, 2014, 124(4), 1636-1645.
Watanabe M., et al., "Feasibility Study of NMR-Based Serum Metabolomic Profiling to Animal Health Monitoring: A Case Study on Iron Storage Disease in Captive Sumatran Rhinoceros (*Dicerorhinus sumatrensis*)," PLoS One, 2016, vol. 11, e0156318.
Weber R.J., et al., "Efficient Targeting of Fatty-acid modified Oligonucleotides to live Cell Membranes through Stepwise Assembly," Biomacromolecules, 2014, vol. 15(12), pp. 4621-4626.
Wei Y., et al., "Liver Homeostasis is Maintained by Midlobular Zone 2 Hepatocytes," Science, Feb. 2021, vol. 371, No. eabb1625.
Weirauch M. T. et al., "Determination and inference of eukaryotic transcription factor sequence specificity," Cell, 2014, 158, 1431-1443.
Wells J.M. et al., "Wnt/beta-catenin signaling is required for development of the exocrine pancreas," BMC Dev Biol, 2007, 7, 4, 18 pages.
Wesley, B. T., et al., "Single-Cell Atlas of Human Liver Development Reveals Pathways Directing Hepatic Cell Fates," Nature Cell Biology, 2022, vol. 24, No. 10, pp. 1487-1498.
Wessel J., et al., "Do Genes Determine Our Health? Implications for Designing Lifestyle Interventions and Drug Trials," Circulation: Cardiovascular Genetics, 2016, vol. 9, pp. 2-3.
Wesson, D., et al., "The effect of intrauterine esophageal ligation on growth of fetal rabbits," J Pediatr Surg, 1984, vol. 19, pp. 398-399.
Whitehead K. J., et al., "The Cerebral Cavernous Malformation Signaling Pathway Promotes Vascular Integrity via Rho GTPases," Nature Medicine, 2009, vol. 15, pp. 177-184.
Wieland H.A., et al., "Subtype selectivity of the novel nonpeptide neuropeptide YY1 receptor antagonist BIBO3304 and its effect on feeding in rodents," Br J Pharmacol, Oct. 1998, vol. 125(3), pp. 549-555.
Williamson K. A., et al., "Mutations in SOX2 Cause Anophthalmia-Esophageal-Genital (AEG) Syndrome," Human Molecular Genetics, 2006, 15(9), pp. 1413-1422.
Woo J. et al., "Band-mediated inhibition of Wnt signaling in the mouse thoracic foregut controls tracheo-esophageal septation and epithelial differentiation," PloS One, 2011, 6(7), e22493, 8 pages.
Wu H., et al., "Advantages of Single-Nucleus over Single-Cell RNA Sequencing of Adult Kidney: Rare Cell Types and Novel Cell States Revealed in Fibrosis," Journal of the American Society of Nephrology, Jan. 2019, vol. 30, No. 1, pp. 23-32.
Wu H., et al., "Comparative Analysis and Refinement of Human PSC-Derived Kidney Organoid Differentiation with Single-Cell Transcriptomics," Cell Stem Cell, 2018, vol. 23, pp. 869-881.e868.

Wu X., et al., "Modeling Drug-induced Liver Injury and Screening for Anti-hepatofibrotic Compounds Using Human PSC-derived Organoids,", Cell Regeneration, Biomed Central, vol. 12, No. 1, Mar. 3, 2023, pp. 1-13.
Xia, M.F., et al., "NAFLD and Diabetes: Two Sides of the Same Coin? Rationale for Gene-Based Personalized NAFLD Treatment," Frontiers in Pharmacology, 2019, vol. 10, 877.
Xia Y., et al., "Angiotensin Receptors, Autoimmunity, and Preeclampsia," Journal of Immunology, 2007, vol. 179, pp. 3391-3395.
Xiao C. et al., "Gut peptides are novel regulators of intestinal lipoprotein secretion: experimental and pharmacological manipulation of lipoprotein metabolism," Diabetes, 2015, 64, 2310-2318.
Xiao S., et al., "Gastric Stem Cells: Physiological and Pathological Perspectives," Frontiers in Cell and Developmental Biology, 2020, vol. 8, pp. 1-13.
Xu, C.-R., et al., "Chromatin 'Prepattern' and Histone Modifiers in a Fate Choice for Liver and Pancreas," Science, 2011, vol. 332, pp. 963-966.
Xu R., "Basis and Clinical Applications of Receptors", edited by et al. Shanghai Science and Technology Press, 1st edition, Feb. 1992, Section of "Retinoic Acid Receptors" on pp. 129-131, published on Feb. 29, 1992.
Xu, W., et al., "Hypoxia activates Wnt/β-catenin signaling by regulating the expression of BCL9 in human hepatocellular carcinoma," Scientific Reports, 2017, vol. 7, 40446, 13 pages.
Xu, Y., et al., "Ascorbate protects liver from metabolic disorder through inhibition of lipogenesis and suppressor of cytokine signaling 3 (SOCS3)," Nutrition & Metabolism, 2020, vol. 17, 17.
Yanan Y., et al., "Research Progress on Hedgehog Signaling Pathway and Liver Fibrosis," Chinese Journal of Anatomy, 06, Dec. 25, 2019, pp. 589-592.
Yang M., et al., "Angiogenesis-Related Genes May Be a More Important Factor than Matrix Metalloproteinases in Bronchopulmonary Dysplasia Development," Oncotarget, 2017, vol. 8, pp. 18670-18679.
Ye D.Z. et al., "Foxa1 and Foxa2 control the differentiation of goblet and enteroendocrine L- and D-cells in mice," Gastroenterology, 2009, 137, 2052-2062.
Ye F., et al., "Fibroblast Growth Factors 7 and 10 Are Expressed in the Human Embryonic Pancreatic Mesenchyme and Promote the Proliferation of Embryonic Pancreatic Epithelial Cells," Diabetologia, 2005, vol. 48, pp. 277-281.
Yin H., et al., "Non-viral Vectors for Gene-based Therapy," Nature Reviews Genetics, 2014, vol. 15(8), pp. 541-555.
Yokobori, T., et al., "Intestinal epithelial culture under an air-liquid interface: a tool for studying human and mouse esophagi," Dis. Esophagus, 2016, vol. 29, pp. 843-847.
Younossi, Z.M., et al., "Economic and Clinical Burden of Nonalcoholic Steatohepatitis in Patients With Type 2 Diabetes in the U.S.," Diabetes Care, 2020, vol. 43, pp. 283-289.
Yu J., et al., "Induced Pluripotent Stem Cell Lines Derived from Human Somatic Cells," Science, 2007, vol. 318, pp. 1917-1920.
Yu X. et al., "Lentiviral vectors with two independent internal promoters transfer highlevel expression of multiple transgenes to human hematopoietic stem-progenitor cells," Mol Ther, 2003, 7, 827-838.
Yu Y., "Chinese Studies on Disease Signaling Pathway and Targeted Therapy," Anhui Science and Technology Press, May 31, 2013, p. 363.
Yu, Y., Chinese Studies on Disease Signaling Pathway and Targeted Therapy, Anhui Science and Technology Press, May 31, 2013, p. 363 [Reference unavailable, citing referencing Search Report, 3 pgs.].
Yu, Y., et al., "A comparative analysis of liver transcriptome suggests divergent liver function among human, mouse and rat," Genomics, 2010, vol. 96, pp. 281-289.
Yusta B. et al., "Enteroendocrine localization of GLP-2 receptor expression in humans and rodents," Gastroenterology, 2000, 119, 744-755.
Zanini F., et al., "Developmental Diversity and Unique Sensitivity to Injury of Lung Endothelial Subtypes During Postnatal Growth," iScience, Mar. 2023, vol. 26, No. 3, doi: 10.1016/j.isci.2023.106097.

(56) References Cited

OTHER PUBLICATIONS

Zanini F., et al., "Phenotypic Diversity and Sensitivity to Injury of the Pulmonary Endothelium During a Period of Rapid Postnatal Growth," bioRxiv, Apr. 2021, doi: 10.1101/2021.04.27.441649.

Zeng, Q., et al., "O-Linked GlcNAcylation Elevated by HPV E6 Mediates Viral Oncogenesis." Proceedings of the National Academy of Sciences, vol. 113, No. 33, Aug. 16, 2016, pp. 9333-9338.

Zhang, D., et al., "Highly efficient differentiation of human ES cells and iPS cells into mature pancreatic insulin-producing cells," Cell Res., 2009, vol. 19, pp. 429-438.

Rossi J.M. et al., "Distinct mesodermal signals, including BMPs from the septum transversum mesenchyme, arc required in combination for hepatogenesis from the endoderm," Genes Dev, 2001, 15, 1998-2009.

Rubio-Cabezas O., et al., "Permanent Neonatal Diabetes and Enteric Anendocrinosis Associated with Biallelic Mutations in NEUROG3," Diabetes, 2011, vol. 60, pp. 1349-1353.

Sahdeo S., et al., "High-Throughput Screening of FDA-Approved Drugs Using Oxygen Biosensor Plates Reveals Secondary Mitofunctional Effects," Mitochondrion, 2014, vol. 17, pp. 116-125.

Saili K. S., et al., "Blood-Brain Barrier Development: Systems Modeling and Predictive Toxicology," Birth Defects Research, 2017, vol. 109, pp. 1680-1710.

Sajiki T., et al., "Transmission Electron Microscopic Study of Hepatocytes in Bioartificial Liver," Tissue Engineering, 2000, vol. 6, No. 6, pp. 627-640.

Samson A. et al., "Effect of somatostatin on electrogenic ion transport in the duodenum and colon of the mouse, *Mus domesticus*," Comparative Biochemistry and Physiology Part A: Molecular & Integrative Physiology, 2000, 125, 459-468.

Samuel, V.T., et al., "Nonalcoholic Fatty Liver Disease, Insulin Resistance, and Ceramides," New England Journal of Medicine, 2019, vol. 381, pp. 1866-1869.

Sankoda N., et al., "Epithelial Expression of Gata4 and Sox2 Regulates Specification of the Squamous-columnar Junction via MAPK/ERK Signaling in Mice," Nature Communications, 2021, vol. 12, pp. 1-15.

Santoro N., et al., "Variant in the Glucokinase Regulatory Protein (GCKR) Gene Is Associated with Fatty Liver in Obese Children and Adolescents," Hepatology, 2012, vol. 55, pp. 781-789.

Sarkar A., et al., "Sox2 Suppresses Gastric Tumorigenesis in Mice," Cell Reports, 2016, 16(7), pp. 1929-1941.

Sato T., et al., "Growing Self-Organizing Mini-Guts from a Single Intestinal Stem Cell: Mechanism and Applications," Science, 2013, vol. 340, pp. 1190-1194. DOI: 10.1126/science.1234852.

Saunders N. R., et al., "Barrier Mechanisms in the Developing Brain," Frontiers in Pharmacology, 2012, vol. 3, Article 46, 18 pages.

Sayar E., et al., "Chromogranin-A Staining Reveals Enteric Anendocrinosis in Unexplained Congenital Diarrhea," Journal of Pediatric Gastroenterology and Nutrition, 2013, vol. 57, No. 4, pp. e21.

Sayar E., et al., "Extremely Rare Cause of Congenital Diarrhea: Enteric Anendocrinosis," Pediatrics International, 2013, vol. 55, pp. 661-663.

Scheidecker, B., et al., "Induction of in vitro Metabolic Zonation in Primary Hepatocytes Requires Both Near-Physiological Oxygen Concentration and Flux," Frontiers in Bioengineering and Biotechnology, 2020, vol. 8.

Schreiber R., et al., "Inherited Renal Tubular Dysgenesis May Not Be Universally Fatal," Pediatric Nephrology, 2010, vol. 25, pp. 2531-2534.

Schreiber R., et al., "Renal Tubular Dysgenesis Secondary to Mutations in Genes Encoding the Renin-Angiotensin System," Harefuah, 2021, vol. 160, pp. 822-826.

Schuldiner et al. "Induced Neuronal Differentiation of Human Embryonic Stem Cells," Brain Research 2001, Sep. 21, 2001, vol. 913(2):201-205.

Schupp J.C., et al., "Integrated Single-Cell Atlas of Endothelial Cells of the Human Lung," Circulation, May 2021, vol. 144, No. 4, 286-302. doi: 10.1161/CIRCULATIONAHA.120.052318.

Sekar R. and Chow B. K. C., "Secrelin Receptor-Knockout Mice Are Resistant to High-Fat Diet-Induced Obesity and Exhibit Impaired Intestinal Lipid Absorption," The FASEB Journal, 2014, vol. 28, pp. 3494-3505.

Self M. et al., "Six2 activity is required for the formation of the mammalian pyloric sphincter," Dev Biol, 2009, 334, 409-417.

Shaham O. et al., "Pax6 is essential for lens fiber cell differentiation," Development (Cambridge, England), 2009, 136(15), 2567-2578.

Shankar A.S., et al., "Human Kidney Organoids Produce Functional Renin," Kidney International, 2021, vol. 99, pp. 134-147.

Shao Z. et al., "MAnorm: a robust model for quantitative comparison of ChIP-Seq data sets," Genome Biol, 2012, 13, R16, 17 pages.

Shapiro E., et al., "Single-cell Sequencing-based Technologies will Revolutionize Whole Organism Science," Nature Reviews Genetics, 2013, vol. 14(9), pp. 618-630.

Shen H., et al., "Glucokinase Regulatory Protein Gene Polymorphism Affects Postprandial Lipemic Response in a Dietary Intervention Study," Human Genetics, 2009, vol. 126, pp. 567-574.

Shoyaib A.A., et al., "Intraperitoneal Route of Drug Administration: Should it Be Used in Experimental Animal Studies?," Pharm Res, Dec. 2, 20193, vol. 37(1):12.

Simon, M., et al., "Expression of Vascular Endothelial Growth Factor and Its Receptors in Human Renal Ontogenesis and in Adult Kidney." American Journal of Physiology, vol. 268, No. 2, Feb. 1995, pp. F240-F250.

Simon T.G., et al., "Mortality in Biopsy-Confirmed Nonalcoholic Fatty Liver Disease: Results from a Nationwide Cohort," Gut, 2021, vol. 70, pp. 1375-1382. doi: 10.1136/gutjnl-2020-322786.

Sinagoga K. L., et al., "Distinct Roles for the mTOR Pathway in Postnatal Morphogenesis, Maturation and Function of Pancreatic Islets," Development, 2017, vol. 144, pp. 2402-2414.

Sinagoga K.L., et al., "Deriving Functional Human Enteroendocrine Cells from Pluripotent Stem Cells," Development, 2018, vol. 145.

Singh A., et al., "Transplanted Human Intestinal Organoids: A Resource for Modeling Human Intestinal Development," Development, 2023, vol. 150, dev201416. doi: 10.1242/dev.201416.

Singh S. K., et al., "Glucose-Dependent Insulinotropic Polypeptide (GIP) Stimulates Transepithelial Glucose Transport," Obesity, 2008, vol. 16, pp. 2412-2416.

Sinner D. et al. "Sox17 and Sox4 differentially regulate beta-catenin/T-cell factor activity and proliferation of colon carcinoma cells," Molecular and Cellular Biology, 27(22), 2007, 7802-7815.

Sloan S. A., et al., "Human Astrocyte Maturation Captured in 3D Cerebral Cortical Spheroids Derived from Pluripotent Stem Cells," Neuron, 2017, vol. 95, pp. 779-790.e1-e6.

Sloth B. et al., "Effect of subcutaneous injections of PYY1-36 and PYY3-36 on appetite, ad libitum energy intake, and plasma free fatty acid concentration in obese males," American Journal of Physiology Endocrinology and Metabolism, 2007, 293, E604-E609.

Sluch V.M., et al., "Highly Efficient Scarless Knock-in of Reporter Genes into Human and Mouse Pluripotent Stem Cells via Transient Antibiotic Selection", PLOS ONE, vol. 13, No. 11, Nov. 29, 2018. Retrieved from the Internet: URL :https://www.ncbi.nlm.nih.gov/pmc/articles/PMC6264506/pdf/ pone.0201683.pdf.

Smith, S.M., et al., "Obeticholic Acid: A Farnesoid X Receptor Agonist for Primary Biliary Cholangitis," Journal of Pharmacy Technology, 2017, vol. 33 (2), pp. 66-71.

Snellings D.A., et al., "Cerebral Cavernous Malformation: From Mechanism to Therapy," Circulation Research, 2021, vol. 129, pp. 195-215. doi: 10.1161/CIRCRESAHA.121.318174.

Snowball J. et al., "Endodermal Wnt signaling is required for tracheal cartilage formation," Dev Biol 405, 56-70 (2015).

Soneson C., et al., "Differential Analyses for RNA-Seq: Transcript-Level Estimates Improve Gene-Level Inferences," F1000Research, 2015, vol. 4, p. 1521.

Song H.W., et al., "Transcriptomic Comparison of Human and Mouse Brain Microvessels," Scientific Reports, 2020, vol. 10, 12358. doi: 10.1038/s41598-020-69096-7.

(56) References Cited

OTHER PUBLICATIONS

Spangle, J. M., et al., "The Human Papillomavirus Type 16 E6 Oncoprotein Activates mTORC1 Signaling and Increases Protein Synthesis," Journal of Virology, vol. 84, No. 18, Sep. 2010, pp. 9398-9407.

Sparrow D. B., et al., "A Mechanism for Gene-Environment Interaction in the Etiology of Congenital Scoliosis," Cell, 2012, vol. 149, pp. 295-306.

Speliotes E. K., et al., "Genome-Wide Association Analysis Identifies Variants Associated with Nonalcoholic Fatty Liver Disease That Have Distinct Effects on Metabolic Traits," PLoS Genetics, 2011, vol. 7, e1001324.

Spencer-Dene B. et al.," Stomach development is dependent on fibroblast growth factor 10/fibroblast growth factor receptor 2b-mediated signaling," Gastroenterology, 2006, 130, 1233-1244.

Sreter K.B., et al., "Plasma Brain-Derived Neurotrophic Factor (BDNF) Concentration and BDNF/TrkB Gene Polymorphisms in Croatian Adults with Asthma," Journal of Personalized Medicine, Oct. 2020, vol. 10, No. 4, doi: 10.3390/jpm10040189.

Stoeckius M., et al., "Cell Hashing with Barcoded antibodies enables Multiplexing and Doublet Detection for Single Cell Genomics," Genome Biology, 2018, vol. 19(1), pp. 1-12.

Stoffers D. A., et al., "Pancreatic Agenesis Attributable to a Single Nucleotide Deletion in the Human IPF1 Gene Coding Sequence," Nature Genetics, 1997, vol. 15, pp. 106-110.

Stoll B. J., et al., "Neonatal Outcomes of Extremely Preterm Infants from the NICHD Neonatal Research Network," Pediatrics, 2010, vol. 126, pp. 443-456.

Onaga T., et al., "Multiple Regulation of Peptide YY Secretion in the Digestive Tract," Peptides, 2002, vol. 23, pp. 279-290.

Onlilsoy Aksu A., et al., "Mutant Neurogenin-3 in a Turkish Boy with Congenital Malabsorptive Diarrhea," Pediatrics International, 2016, vol. 58, pp. 379-382.

Orho-Melander M., et al., "Common Missense Variant in the Glucokinase Regulatory Protein Gene Is Associated with Increased Plasma Triglyceride and C-Reactive Protein but Lower Fasting Glucose Concentrations," Diabetes, 2008, vol. 57, pp. 3112-3121.

Orskov C et al., "GLP-2 stimulates colonic growth via KGF, released by subepithelial myofibroblasts with GLP-2 receptors," Regulatory peptides, 2005, 124, 105-112.

Ortiz-Meoz, R. F., et al., "A Small Molecule that Inhibits OGT Activity in Cells." ACS Chemical Biology, vol. 10, No. 6, Jun. 19, 2015, pp. 1392-1397.

Pan S., "Physiology," Science and Technology of China Press, Chapter 6, "Digestion within Large Intestine," 149-150, Jan. 2014.

Pankevich D.E. et al., "Improving and accelerating drug development for nervous system disorders," Neuron, 2014, 84, 546-553.

Paris, J., et al., "Liver zonation, revisited," Hepatology, 2022, vol. 76.

Park E.J. et al., "System for tamoxifen-inducible expression of Cre-recombinase from the Foxa2 locus in mice," Developmental Dynamics, 2008, 237(2), 447-453.

Patel Y. C., "Somatostatin and Its Receptor Family," Frontiers in Neuroendocrinology, 1999, 20, 157-198.

Patro R., et al., "Salmon Provides Fast and Bias-Aware Quantification of Transcript Expression using Dual-Phase Inference," Nature Methods, 2017, vol. 14, pp. 417-419.

Pedersen J et al., "The glucagon-like peptide 2 receptor is expressed in enteric neurons and not in the epithelium of the intestine," Peptides, 2015, 67, 20-28.

Peng K., et al., "Regulation of O-Linked N-Acetyl Glucosamine Transferase (OGT) Through E6 Stimulation of the Ubiquitin Ligase Activity of E6AP." Journal of Molecular Sciences, 22, 2021, 10286. https://doi.org/10.3390/ijms221910286.

Perdomo J., et al., "Megakaryocyte differentiation and platelet formation from human cord blood derived CD34+ cells," Journal of Visualized Experiments. Dec. 27, 2017; 130:e56420 in 8 pages.

Petta S., et al., "Glucokinase Regulatory Protein Gene Polymorphism Affects Liver Fibrosis in Non-Alcoholic Fatty Liver Disease," PLoS One, 2014, vol. 9, e87523.

Pham D., et al., "stLearn: Integrating Spatial Location, Tissue Morphology and Gene Expression to Find Cell Types, Cell-Cell Interactions and Spatial Trajectories Within Undissociated Tissues," bioRxiv, May 2020, doi: 10.1101/2020.05.31.125658.

Picelli S., et al., "Smart-seq2 for Sensitive Full-length Transcriptome Profiling in Single Cells," Nature Methods, Nov. 2013, vol. 10(11), pp. 1096-1098.

Pierre C., et al., "Can We Live Without a Functional Renin-Angiotensin System?" Clinical and Experimental Pharmacology and Physiology, 2008, vol. 35, pp. 431-433.

Pinney S. E. et al., "Neonatal diabetes and congenital malabsorptive diarrhea attributable to a novel mutation in the human neurogenin-3 gene coding sequence," The Journal of clinical endocrinology and metabolism, 2011, 96, 1960-1965.

Pirola, C.J., et al., "A Rare Nonsense Mutation in the Glucokinase Regulator Gene Is Associated with a Rapidly Progressive Clinical Form of Nonalcoholic Steatohepatitis," Hepatology Communications, 2018, vol. 2, pp. 1030-1036.

Pless G., "Artificial and Bioartificial Liver Support," Organogenesis, Jan. 2007, vol. 3(1), pp. 20-24.

Podolsky D. K., "Healing the Epithelium: Solving the Problem from Two Sides," Journal of Gastroenterology, 1997, vol. 32, pp. 122-126. DOI: 10.1007/BF01213309.

Pollin T. I., et al., "Triglyceride Response to an Intensive Lifestyle Intervention Is Enhanced in Carriers of the GCKR Pro446Leu Polymorphism," Journal of Clinical Endocrinology Metabolism, 2011, vol. 96, pp. E1142-E1147.

Powell D. W., et al., "Myofibroblasts. II. Intestinal Subepithelial Myofibroblasts," American Journal of Physiology, 1999, vol. 277, pp. C183-C201. DOI: 10.1152/ajpcell.1999.277.2.C183.

Prakash Y., et al., "Neurotrophins in Lung Health and Disease," Expert Review of Respiratory Medicine, 2010, vol. 4, pp. 395-411.

Prakash Y. S., et al., "Brain-Derived Neurotrophic Factor in the Airways," Pharmacology & Therapeutics, 2014, vol. 143, pp. 74-86.

Pupilli C., et al., "Angiotensin II Stimulates the Synthesis and Secretion of Vascular Permeability Factor/Vascular Endothelial Growth Factor in Human Mesangial Cells," Journal of the American Society of Nephrology, 1999, vol. 10, pp. 245-255.

Pyke C., et al., "GLP-1 Receptor Localization in Monkey and Human Tissue: Novel Distribution Revealed With Extensively Validated Monoclonal Antibody," Endocrinology, 2014, 155, 1280-1290.

Qian T., et al., "Directed Differentiation of Human Pluripotent Stem Cells to Blood-Brain Barrier Endothelial Cells," Science Advances, 2017, vol. 3, e1701679.

Qiu X., et al., "Single-Cell mRNA Quantification and Differential Analysis with Census," Nature Methods, 2017, vol. 14, pp. 309-315.

Qiu X., et al., "Reversed Graph Embedding Resolves Complex Single-Cell Trajectories," Nature Methods, 2017, vol. 14, pp. 979-982.

Que J. et al., "Multiple dose-dependent roles for Sox2 in the patterning and differentiation of anterior foregut endoderm," Development (Cambridge, England), 2007,134(13), 2521-31.

Que J. et al., "Multiple roles for Sox2 in the developing and adult mouse trachea," Development (Cambridge, England), 2009,136(11), 1899-1907.

Que J., "The initial establishment and epithelial morphogenesis of the esophagus: a new model of tracheal-esophageal separation and transition of simple columnar into stratified squamous epithelium in the developing esophagus," Wiley Interdiscip. Rev. Dev. Biol., 2015, 4(4), 419-430.

Raisner, R., et al., "Enhancer Activity Requires CBP/P300 Bromodomain-Dependent Histone H3K27 Acetylation," Cell Reports, 2018, vol. 24, pp. 1722-1729.

Ramilowski J. A., et al., "A Draft Network of Ligand-Receptor-Mediated Multicellular Signalling in Human," Nature Communications, 2015, vol. 6, Article 7866, 11 pages.

Raredon M.S.B., et al., "Computation and Visualization of Cell-Cell Signaling Topologies in Single-Cell Systems Data Using Connectome," Scientific Reports, 2022, vol. 12, 4187. doi: 10.1038/s41598-022-07959-x.

(56) References Cited

OTHER PUBLICATIONS

Ren, X., et al., "Postnatal Alveologenesis Depends on FOXF1 Signaling in c-KIT+ Endothelial Progenitor Cells." American Journal of Respiratory and Critical Care Medicine, vol. 200, No. 9, 2019, pp. 1164-1176.
Revencu N. et al. "Cerebral cavernous malformation: new molecular and clinical insights," J Med Genet, 2006, 43, 716-721.
Reyes-Palomares A., et al., "Remodeling of Active Endothelial Enhancers is Associated with Aberrant Gene Regulatory Networks in Pulmonary Arterial Hypertension," Nature Communications, Apr. 2020, vol. 11, No. 1, 1673. doi: 10.1038/s41467-020-15463-x.
Reza H.A., et al., "Organoid Transplant Approaches for the Liver," Transplant International, Nov. 2021, vol. 34, No. 11, pp. 2031-2045.
Reza, H.A., et al., "Synthetic augmentation of bilirubin metabolism in human pluripotent stem cell-derived liver organoids," Stem Cell Reports, 2023.
Rhoads, K., et al., "A Role for Hox A5 in Regulating Angiogenesis and Vascular Patterning." Lymphatic Research and Biology, vol. 3, No. 4, 2005, pp. 240-252.
Rich, N.E., et al., "Racial and Ethnic Disparities in Nonalcoholic Fatty Liver Disease Prevalence, Severity, and Outcomes in the United States: A Systematic Review and Meta-Analysis," Clinical Gastroenterology and Hepatology, 2018, vol. 16, pp. 198-210 e192.
Robbins D. J. et al., "The Hedgehog Signal Transduction Network," Science Signaling 2012, 5(246), re6-re6, 28 pages.
Robinson B.D., et al., "Measurement of Microvascular Endothelial Barrier Dysfunction and Hyperpermeability In Vitro," Methods in Molecular Biology, Feb. 2018, vol. 1717, pp. 237-242.
Rochman M., et al., "Profound Loss of Esophageal Tissue Differentiation in Patients with Eosinophilic Esophagitis," Journal of Allergy and Clinical Immunology, 2017, 140(3), pp. 738-749.e3.
Roitbak T., et al., "Neural Stem/Progenitor Cells Promote Endothelial Cell Morphogenesis and Protect Endothelial Cells against Ischemia via HIF-1a-Regulated VEGF Signaling," Journal of Cerebral Blood Flow & Metabolism, 2008, vol. 28, pp. 1530-1542.
Rosekrans S. L. et al., "Esophageal development and epithelial homeostasis," American Journal of Physiology—Gastrointestinal and Liver Physiology, 2015, 309(4), G216-228.
Ross M.G. et al., "Development of ingestive behavior.," Am J Physiol, 1998, 274, R879-893.
Fang M., et al., "Ulinastatin Ameliorates Pulmonary Capillary Endothelial Permeability Induced by Sepsis Through Protection of Tight Junctions via Inhibition of TNFalpha and Related Pathways," Frontiers in Pharmacology, Sep. 2018, vol. 9, doi: 10.3389/fphar.2018.00823.
Fantes J. et al., "Mutations in SOX2 cause anophthalmia," Nature Genetics, 2003, 33(4), 461-463.
Fausett S. R. et al., "Compartmentalization of the foregut tube: developmental origins of the trachea and esophagus," Wiley Interdisciplinary eviews. Developmental Biology, 2012, (2), 184-202.
Fausett S.R., et al., "BMP antagonism by Noggin is required in presumptive notochord cells for mammalian foregut morphogenesis," Developmental Biology, 2014, 391(1), 111-24.
Feliers D., et al., "Mechanism of VEGF Expression by High Glucose in Proximal Tubule Epithelial Cells," Molecular and Cellular Endocrinology, 2010, vol. 314, pp. 136-142.
Ferguson, D., et al., "Emerging Therapeutic Approaches for the Treatment of NAFLD and Type 2 Diabetes Mellitus," Nature Reviews Endocrinology, 2021, vol. 17, pp. 484-495.
Fermini, B., et al., "Clinical Trials in a Dish: A Perspective on the Coming Revolution in Drug Development," SLAS Discovery, 2018, vol. 23, pp. 765-776.
Fischer B., et al., "Oxygen Tension in the Oviduct and Uterus of Rhesus Monkeys, Hamsters and Rabbits," Journal of Reproduction and Fertility, 1993, vol. 99, pp. 673-679.
Freedman B.S., "Physiology Assays in Human Kidney Organoids," American Journal of Physiology—Renal Physiology, 2022, vol. 322, pp. F625-F638.
Freund J.B. et al., "Fluid flows and forces in development: functions, features and biophysical principles," Development, 2012, 139(7), 1229-1245.
Fujita Y. et al., "Pax6 and Pdx1 are required for production of glucose-dependent insulinotropic polypeptide in proglucagon-expressing L cells," Am J Physiol Endocrinol Metab, 2008, 295, E648-657.
Funakoshi, K., et al., "Highly Sensitive and Specific Alu-Based Quantification of Human Cells Among Rodent Cells," Scientific Reports, 2017, vol. 7, Article 13202. DOI: 10.1038/s41598-017-13402-3.
Furuta G. T. et al., "Eosinophilic Esophagitis," New England Journal of Medicine, 2015, 373(17), 1640-1648.
Gang, X., et al., "P300 Acetyltransferase Regulates Fatty Acid Synthase Expression, Lipid Metabolism and Prostate Cancer Growth," Oncotarget, 2016, vol. 7, No. 11, pp. 15135-15149.
Gao C., et al., "RBFox1-Mediated RNA Splicing Regulates Cardiac Hypertrophy and Heart Failure," Journal of Clinical Investigation, 2016, vol. 126, pp. 195-206.
Gao et al., "Highly Branched Poly (β-amino esters) for Non-Viral Gene Delivery: High Transfection Efficiency and Low Toxicity Achieved by Increasing Molecular Weight",Biomacromolecules, 2016, vol. 17(11), pp. 3640-3647.
Gao, H., et al., "Association of GCKR Gene Polymorphisms with the Risk of Nonalcoholic Fatty Liver Disease and Coronary Artery Disease in a Chinese Northern Han Population," Journal of Clinical and Translational Hepatology, 2019, vol. 7, pp. 297-303.
García-Suárez, O., et al., "TrkB is Necessary for the Normal Development of the Lung." Respiratory Physiology & Neurobiology, vol. 167, No. 3, Jul. 31, 2009, pp. 281-291.
Garcia-Martinez, S., et al., "Mimicking physiological O2 tension in the female reproductive tract improves assisted reproduction outcomes in pig," Molecular Human Reproduction, 2018, vol. 24, pp. 260-270.
Garlanda C. et al., "Heterogeneity of endothelial cells. Specific markers" Arterioscler Thromb Vasc Biol, 1997, 17, 1193-1202.
Gazzin, S., et al., "Bilirubin Accumulation and Cyp mRNA Expression in Selected Brain Regions of Jaundiced Gunn Rat Pups," Pediatric Research, 2012, vol. 71, No. 6, pp. 653-660.
German-Diaz, M., et al., "A New Case of Congenital Malabsorptive Diarrhea and Diabetes Secondary to Mutant Neurogenin," Pediatrics, 2017, vol. 140, No. 2, 8 pages.
Ghatak S. et al., "Bile acid at low pH reduces squamous differentiation and activates EGFR signaling in esophageal squamous cells in 3-D culture," Journal of Gastrointestinal Surgery: Official Journal of the Society for Surgery of the Alimentary Tract, 2013, 17(10), 1723-31.
Ginestet C., "ggplot2: Elegant Graphics for Data Analysis," J R Stat Soc a Stat, 2011 174, 245,245.
Glass, L. L., et al., "Single-cell RNA-sequencing reveals a distinct population of proglucagon-expressing cells specific to the mouse upper small intestine," Molecular Metabolism, 2017, vol. 6, pp. 1296-1303.
Gololow N., et al., "Epitheliomesenchymal Interaction in Pancreatic Morphogenesis," Developmental Biology, 1962, vol. 4, pp. 242-255.
Gordillo M., et al., "Orchestrating liver development," Development, Jun. 2015, vol. 142(12), pp. 2094-2108.
Goss A.M., "Wnt2/2b and beta-catenin signaling are necessary and sufficient to specify lung progenitors in the foregut," Developmental Cell, 2009, 17(2), 290-8.
Gotoh S. et al. "Generation of Alveolar Epithelial Spheroids via Isolated Progenitor Cells from Human Pluripotent Stem cells" Stem Cell Reports (2014) 3(3):394-403.
Greene, A. S., et al., "Microvascular Angiogenesis and the Renin-Angiotensin System." Current Hypertension Reports, vol. 4, No. 1, Feb. 2002, pp. 56-62.
Greene Y. J., et al., "Ascorbic Acid Regulation of 3-Hydroxy-3-Methylglutaryl Coenzyme A Reductase Activity and Cholesterol Synthesis in Guinea Pig Liver." Biochimica et Biophysica Acta, 834(1), 1985, pp. 134-138.

(56) References Cited

OTHER PUBLICATIONS

Greggio C., et al., "Artificial Three-Dimensional Niches Deconstruct Pancreas Development In Vitro," Development, 2013, vol. 140, pp. 4452-4462.

Gribble, F. M., et al., "Enteroendocrine Cells: Chemosensors in the Intestinal Epithelium," Annu Rev Physiol, 2016, vol. 78, pp. 277-299.

Gribouval O., et al., "Mutations in Genes in the Renin-Angiotensin System Are Associated with Autosomal Recessive Renal Tubular Dysgenesis," Nature Genetics, 2005, vol. 37, pp. 964-968.

Gribouval, O., et al., "Spectrum of Mutations in the Renin-Angiotensin System Genes in Autosomal Recessive Renal Tubular Dysgenesis." Human Mutation, vol. 33, No. 2, Feb. 2012, pp. 316-326.

Gu G., et al., "Global expression analysis of gene regulatory pathways during endocrine pancreatic development," Development, 2004, 131, 165-179.

Gu M., et al., "iPSC-Endothelial Cell Phenotypic Drug Screening and In Silico Analyses Identify Tyrphostin-AG1296 for Pulmonary Arterial Hypertension," Science Translational Medicine, 2021, vol. 13, No. 592. doi: 10.1126/scitranslmed.aba6480.

Gu M., et al., "Microfluidic Single-Cell Analysis Shows That Porcine Induced Pluripotent Stem Cell-Derived Endothelial Cells Improve Myocardial Function by Paracrine Activation," Circulation Research, 2012, vol. 111, pp. 882-893.

Gu M., et al., "Patient-Specific iPSC-Derived Endothelial Cells Uncover Pathways that Protect Against Pulmonary Hypertension in BMPR2 Mutation Carriers," Cell Stem Cell, 2017, vol. 20, pp. 490-504.

Gualdi R. et al., "Hepatic specification of the gut endoderm in vitro: cell signaling and transcriptional control," Genes Dev, 1996, 10, 1670-1682.

Guan X. et al., "GLP-2 receptor localizes to enteric neurons and endocrine cells expressing vasoactive peptides and mediates increased blood flow," Gastroenterology, 2006, 130, 150-164.

Guarino, M., et al., "Nicotinamide and NAFLD: Is There Nothing New Under the Sun?" Metabolites, 2019, vol. 9.

Gubler M. C., et al., "Renin-Angiotensin System in Kidney Development: Renal Tubular Dysgenesis," Kidney International, 2010, vol. 77, pp. 400-406.

Gubler M. C., "Renal Tubular Dysgenesis," Pediatric Nephrology, 2014, vol. 29, pp. 51-59.

Guo L., et al., "The Adrenal Stress Response is an Essential Host Response Against Therapy-Induced Lethal Immune Activation," Science Signaling, 2023, vol. 16, eadd4900. doi: 10.1126/scisignal.add4900.

Guo M., et al., "Guided Construction of Single Cell Reference for Human and Mouse Lung," Nature Communications, Jul. 29, 2023, 14:4566, 20 pages.

Gupta A. et al., "The great divide: septation and malformation of the cloaca, and its implications for surgeons," Pediatr Surg Int, 2014, 30, 1089-1095.

Ha, T. Y., et al., "Ascorbate Indirectly Stimulates Fatty Acid Utilization in Primary Cultured Guinea Pig Hepatocytes by Enhancing Carnitine Synthesis," The Journal of Nutrition, 1994, vol. 124, pp. 732-737.

Haasdijk R. A., et al., "Cerebral Cavernous Malformations: From Molecular Pathogenesis to Genetic Counselling and Clinical Management," European Journal of Human Genetics, 2012, vol. 20, pp. 134-140.

Habib A. M. et al., "Overlap of endocrine hormone expression in the mouse intestine revealed by transcriptional profiling and flow cytometry," Endocrinology, 2012, 153, 3054-3065.

Zhang H., et al., "Generation of Quiescent Cardiac Fibroblasts From Human Induced Pluripotent Stem Cells for In Vitro Modeling of Cardiac Fibrosis," Circulation Research, Sep. 2019, vol. 125, No. 5, pp. 552-566.

Zhang S. L., et al., "Angiotensin II Stimulates Pax-2 in Rat Kidney Proximal Tubular Cells: Impact on Proliferation and Apoptosis," Kidney International, 2004, vol. 66, pp. 2181-2192.

Zhao Z., et al., "Establishment and Dysfunction of the Blood-Brain Barrier," Cell, 2015, vol. 163(5), pp. 1064-1078.

Zheng G.X.Y., et al., "Massively Parallel Digital Transcriptional Profiling of Single Cells," Nature Communications, 2017, vol. 8(1), pp. 1-12.

Zheng, Y., et al., pH- and Temperature-Senstive PCL-Grafted Poly (R-amino ester)-Poly (ethylene glycol)-Poly (R-amino ester) Copolymer Hydrogels, Macromolecular Research, 2010, vol. 18, No. 11, pp. 1096-1102.

Zhou C., et al., "Comprehensive Profiling Reveals Mechanisms of SOX2-Mediated Cell Fate Specification in Human ESCs and NPCs," Cell Research, 2016, 26(2), pp. 171-189. DOI: 10.1038/cr.2016.15.

Zhou H. J., et al., "Endothelial Exocytosis of Angiopoietin-2 Resulting from CCM3 Deficiency Contributes to Cerebral Cavernous Malformation," Nature Medicine, 2016, vol. 22, pp. 1033-1042.

Zhou Y., et al., "A Subtype of Oral, Laryngeal, Esophageal, and Lung Squamous Cell Carcinoma with High Levels of TrkB-T1 Neurotrophin Receptor mRNA," BMC Cancer, Jun. 2019, vol. 19, No. 1, doi: 10.1186/s12885-019-5789-8.

Zhou Z., et al., "Cerebral Cavernous Malformations Arise from Endothelial Gain of MEKK3-KLF2/4 Signaling," Nature, 2016, vol. 532, pp. 122-126.

Zhu, S., et al., "Liver Endothelial Heg Regulates Vascular/Biliary Network Patterning and Metabolic Zonation via Wnt Signaling," Cell Molecular Gastroenterology and Hepatology, 2022, vol. 13, pp. 1757-1783.

Zhu Z. et al., "Human pluripotent stem cells: an emerging model in developmental biology," Development 140, 705-717 (2013).

Zhuo J. L., et al., "Proximal Nephron," Comprehensive Physiology, 2013, vol. 3, No. 3, pp. 1079-1123.

Ziegler B. L., et al., "KDR Receptor: A Key Marker Defining Hematopoietic Stem Cells," Science, 1999, vol. 285, No. 5433, Sep. 3, 1999, pp. 1553-1558.

Zwerschke, W., et al., "Modulation of Type M2 Pyruvate Kinase Activity by the Human Papillomavirus Type 16 E7 Oncoprotein." Proceedings of the National Academy of Sciences USA, vol. 96, Feb. 1999, pp. 1291-1296.

Haeussler M., et al., "Evaluation of Off-Target and On-Target Scoring Algorithms and Integration into the Guide RNA Selection Tool CRISPOR," Genome Biology, 2016, vol. 17, No. 148, 12 pages.

Hagan D.M et al., "Mutation analysis and embryonic expression of the HLXB9 Currarino syndrome gene," Am. J. Hum. Genet., 2000, 66, 1504-1515.

Haigh J. J., et al., "Cortical and Retinal Defects Caused by Dosage-Dependent Reductions in VEGF-A Paracrine Signaling," Developmental Biology, 2003, vol. 262, pp. 225-241.

Hajal C., et al., "Biology and Models of the Blood-Brain Barrier," Annual Review of Biomedical Engineering, 2021, vol. 23, pp. 359-384.

Hale, C., et al., "Molecular Targeting of the GK-GKRP Pathway in Diabetes." Expert Opinion on Therapeutic Targets, vol. 19, No. 1, 2015, pp. 129-139.

Han L., et al., "Osr1 Functions Downstream of Hedgehog Pathway to Regulate Foregut Development," Developmental Biology, 2017, 427, pp. 72-83.

Hansmann G., et al., "Pulmonary Hypertension in Bronchopulmonary Dysplasia," Pediatric Research, Jun. 2020, No. 10.1038/s41390-020-0993-4.

Harris-Johnson K.S. et al., "l3-Catenin promotes respiratory progenitor identity in mouse foregut," Proc. Natl. Acad. Sci. U. S. A., 2009, 106, 16287-16292.

Harrison S.A., et al., "Selonsertib for Patients with Bridging Fibrosis or Compensated Cirrhosis Due to NASH: Results from Randomized Phase III STELLAR Trials," Journal of Hepatology, 2020, vol. 73, pp. 26-39.

Haussinger, D., "Nitrogen metabolism in liver: structural and functional organization and physiological relevance," Biochem J, 1990, vol. 267, pp. 281-290.

He, L., et al., "Proliferation tracing reveals regional hepatocyte generation in liver homeostasis and repair," Science, 2021, vol. 371, eabc4346.

(56) References Cited

OTHER PUBLICATIONS

Heinz S. et al., "Simple combinations of lineage-determining transcription factors prime cis-regulatory elements required for macrophage and B cell identities," Mol Cell, 2010, 38, 576-589.
Hernaez R., et al., "Association Between Variants in or near PNPLA3, GCKR, and PPP1R3B with Ultrasound-Defined Steatosis Based on Data from the Third National Health and Nutrition Examination Survey," Clinical Gastroenterology and Hepatology, 2013, vol. 11, pp. 1183-1190.e1182.
Hilgers K. F., et al., "Aberrant Renal Vascular Morphology and Renin Expression in Mutant Mice Lacking Angiotensin-Converting Enzyme," Hypertension, 1997, vol. 29, pp. 216-221.
Hill, D. R., et al., "Gastrointestinal Organoids: Understanding the Molecular Basis of the Host-Microbe Interface," Cell Mol Gastroenterol Hepatol, 2017, vol. 3, pp. 138-149.
Hirschhorn, J. N., et al., "Genome-Wide Association Studies for Common Diseases and Complex Traits." Nature Reviews Genetics, vol. 6, 2005, pp. 95-108.
Hirsh A. J., et al., "Effect of Cholecystokinin and Related Peptides on Jejunal Transepithelial Hexose Transport in the Sprague-Dawley Rat," American Journal of Physiology—Gastrointestinal and Liver Physiology, 1996, vol. 271, No. G755-G761.
Hoffmeister K.M., "Desialylated Platelets: A Missing Link in Hepatic Thrombopoietin Regulation," The Hematologist 2015; 12(3), 7 pages.
Hoffmeister K.M., "The role of lectins and glycans in platelet clearance," Journal of Thrombosis and Haemostasis. Jul. 2011;9 (suppl), pp. 35-43.
Hohwieler H., et al., "Human Pluripotent Stem Cell-Derived Acinar/Ductal Organoids Generate Human Pancreas upon Orthotopic Transplantation and Allow Disease Modelling," Gut, 2017, vol. 66, pp. 473-486.
Holt L.M., et al., "Astrocyte Morphogenesis is Dependent on BDNF Signaling via Astrocytic TrkB.T1," eLife, Aug. 2019, vol. 8, No. e44667. doi: 10.7554/eLife.44667.
Homayun B., et al., "Challenges and Recent Progress in Oral Drug Delivery Systems for Biopharmaceuticals," Pharmaceutics, Mar. 1, 20199, vol. 11(3):129.
Hoskins E. E., et al., Fanconi anemia deficiency stimulates HPV-associated hyperplastic growth in organotypic epithelial raft culture. Oncogene, 2009, 28(5), 674-685.
Hotta K., et al., "Association of the rs738409 Polymorphism in PNPLA3 with Liver Damage and the Development of Nonalcoholic Fatty Liver Disease," BMC Medical Genetics, 2010, vol. 11, p. 172.
Hu H., et al., "AnimalTFDB 3.0: A Comprehensive Resource for Annotation and Prediction of Animal Transcription Factors," Nucleic Acids Research, 2019, 47(D1), pp. D33-D38.
Hu Y. et al., "Targeted disruption of peptide transporter Pept1 gene in mice significantly reduces dipeptide absorption in intestine," Molecular pharmaceutics, 2008, 5(6), 1122-1130.
Hu Z. et al., "Generation of Naivetropic Induced Pluripotent Stem Cells from Parkinson's Desease Patients for High-Efficiency Genetic Manipulation oand Disease Modeling," Stem Cells and Development, 2015, vol. 24, No. 21, 2591-2604.
Huang H., et al., "p300-Mediated Lysine 2-Hydroxyisobutyrylation Regulates Glycolysis," Molecular Cell, 2018, vol. 70, pp. 663-678. e666. doi: 10.1016/j.molcel.2018.04.011.
Huang J., et al., "Activation of Wnt/β-Catenin Signalling via GSK3 Inhibitors Direct Differentiation of Human Adipose Stem Cells into Functional Hepatocytes," Nature Scientific Reports, 2017, 7, Article No. 40716, 12 pages.
Huang, S. X. L., et al., "Efficient generation of lung and airway epithelial cells from human pluripotent stem cells," Nat. Biotechnol., 2014, vol. 32, No. 1, pp. 84-91.
Hudert, C. A., et al., "Genetic Determinants of Steatosis and Fibrosis Progression in Paediatric Non-Alcoholic Fatty Liver Disease." Liver International, vol. 39, 2019, pp. 540-556.
Huo X. et al., "Acid and Bile Salt-Induced CDX2 Expression Differs in Esophageal Squamous Cells From Patients With and Without Barrett's Esophagus," Gastroenterology, 2010, 139(1), 194-203.e1.
Hurr, C., et al., "Liver Sympathetic Denervation Reverses Obesity-Induced Hepatic Steatosis." The Journal of Physiology, vol. 597, No. 17, Sep. 2019, pp. 4565-4580.
Hurskainen M., et al., "Single Cell Transcriptomic Analysis of Murine Lung Development on Hyperoxia-Induced Damage," Nature Communications, Mar. 2021, vol. 12, No. 1565. doi: 10.1038/s41467-021-21865-2.
Husson, A., et al., "Argininosuccinate synthetase from the urea cycle to the citrulline-NO cycle," European Journal of Biochemistry, 2003, vol. 270, pp. 1887-1899.
Huynh N., et al., "Feasibility and Scalability of Spring Parameters in Distraction Enterogenesis in a Murine Model," Journal of Surgical Research, 2017, vol. 215, pp. 219-224.
Iansante, V., et al., "Human hepatocyte transplantation for liver disease: current status and future perspectives," Pediatric Research, 2018, vol. 83, pp. 232-240.
Ikeda, Y., et al., "Bilirubin exerts pro-angiogenic property through Akt-eNOS787 dependent pathway," Hypertension Research, 2015, vol. 38, pp. 733-740.
Illig R. et al., "Spatio-temporal expression of HOX genes in human hindgut development," Developmental dynamics: an official publication of the American Association of Anatomists, 2013, 242, 53-66.
Isosaari L., et al., "Simultaneous Induction of Vasculature and Neuronal Network Formation on a Chip Reveals a Dynamic Interrelationship Between Cell Types," Cell Communication and Signaling, 2023, vol. 21, 132. doi: 10.1186/s12964-023-01159-4.
Iwafuchi-Doi, M. et al., "Pioneer transcription factors in cell reprogramming," Genes Dev 2014, 28, 2679-2692.
Iwasawa K., et al., "Organogenesis In Vitro," Current Opinion in Cell Biology, 2021, 73, pp. 84-91.
Jackerott M. et al., "Immunocytochemical localization of the NPY/PYY Y1 receptor in enteric neurons, endothelial cells, and endocrine-like cells of the rat intestinal tract," J Histochem Cytochem, 1997, 45(12), 1643-1650.
Jang S. W., et al., "A Selective TrkB Agonist with Potent Neurotrophic Activities by 7,8-Dihydroxyflavone," Proceedings of the National Academy of Sciences of the United States of America, 2010, vol. 107, pp. 2687-2692.
Jaramillo M., et al., "Endothelial Cells Mediate Islet-Specific Maturation of Human Embryonic Stem Cell-Derived Pancreatic Progenitor Cells," Tissue Engineering Part A, 2015, vol. 21, pp. 14-25.
Jarmas, A.E., et al., "Progenitor translatome changes coordinated by Tsc1 increase perception of Wnt signals to end nephrogenesis," Nature Communications, 2021, vol. 12.Low, J.H., et al., "Generation of Human PSC-Derived Kidney Organoids with Patterned Nephron Segments and a De Novo Vascular Network," Cell Stem Cell, 2019, vol. 25, pp. 373-387.
Jennings R. E., et al., "Development of the Human Pancreas from Foregut to Endocrine Commitment," Diabetes, 2013, vol. 62, pp. 3514-3522.
Jennings R. E., et al., "Human Pancreas Development," Development, 2015, vol. 142, pp. 3126-3137.
Jensen E. A., et al., "Epidemiology of Bronchopulmonary Dysplasia," Birth Defects Research Part A: Clinical and Molecular Teratology, 2014, vol. 100, pp. 145-157.
Jensen K. J., et al., "Hepatic Nervous System and Neurobiology of the Liver," Comprehensive Physiology, 2013, vol. 3, pp. 655-665.
Jeong, Y., et al., "Identification and genetic manipulation of human and mouse oesophageal stem cells," Gut, 2015, pp. 1-10.
Jho E. et al., "Wnt/beta-catenin/Tcf signaling induces the transcription of Axin2, a negative regulator of the signaling pathway," Molecular and Cellular Biology, 2002, 22(4), 1172-83.
Jiang C., et al., "Comparative Transcriptomics Analyses in Livers of Mice, Humans, and Humanized Mice Define Human-Specific Gene Networks," Cells, Nov. 2020, vol. 9, No. 2566.
Jiang H., et al., "Tyrosine Kinase Receptor B Protects Against Coronary Artery Disease and Promotes Adult Vasculature Integrity

(56) References Cited

OTHER PUBLICATIONS by Regulating Ets1-Mediated VE-Cadherin Expression," Arteriosclerosis, Thrombosis, and Vascular Biology, 2015, vol. 35, pp. 580-588.

Jiang M. et al., "BMP-driven NRF2 activation in esophageal basal cell differentiation and eosinophilic esophagitis," The Journal of Clinical Investigation, 2015, 125(14), 1-12.

Jiang M., et al., "Transitional Basal Cells at the Squamous-Columnar Junction Generate Barrett's Oesophagus," Nature, 2017, 550(7677), pp. 529-533.

Jin W., et al., "Regulation of BDNF-TrkB Signaling and Potential Therapeutic Strategies for Parkinson's Disease," Journal of Clinical Medicine, Jan. 2020, vol. 9, No. 1, doi: 10.3390/jcm9010257.

Jonatan D., et al., "Sox17 regulates insulin secretion in the normal and pathologic mouse beta cell," PloS one, 2014, 9, e104675, 16 pages.

Kaczmarek J. C., et al., "Polymer-Lipid Nanoparticles for Systemic Delivery of mRNA to the Lungs," Angewandte Chemie International Edition, 2016, vol. 55, pp. 13808-13812.

Kaczmarek J.C., et al., "Optimization of a Degradable Polymer-Lipid Nanoparticle for Potent Systemic Delivery of mRNA to the Lung Endothelium and Immune Cells," Nano Letters, 2018, vol. 18, No. 10, 6449-6454. doi: 10.1021/acs.nanolett.8b02917.

Kaiser J., Virus used in gene therapies may pose cancer risk, dog study hints, Science—Jan. 6, 2020 doi:10.1126/science.aba7696 in 3 pages.

Kajiwara, K., et al., "Molecular Mechanisms Underlying Twin-to-Twin Transfusion Syndrome," Cells, 2022, vol. 11, 18 pages.

Kalabis J. et al., "A subpopulation of mouse esophageal basal cells has properties of stem cells with the capacity for self-renewal and lineage specification," Journal of Clinical Investigation, 2008, (118), 3860-3869.

Kalabis J. et al., "Isolation and characterization of mouse and human esophageal epithelial cells in 3D organotypic culture," Nature Protocols, 2012, 7(2), 235-246.

Kang, J., et al., "Simultaneous deletion of the methylcytosine oxidases Tet1 and Tet3 increases transcriptome variability in early embryogenesis," Proceedings of the National Academy of Sciences, 2015, vol. 112, pp. E4236-E4245.

Kang, S. D., et al., "Effect of Productive Human Papillomavirus 16 Infection on Global Gene Expression in Cervical Epithelium." Journal of Virology, vol. 92, No. 20, Oct. 15, 2018, e01261-18.

Kapadia, B., et al., "PIMT regulates Hepatic Gluconeogenesis in Mice," iScience, 2023, 106120.

Kawaguchi T., et al., "Genetic Polymorphisms of the Human PNPLA3 Gene Are Strongly Associated with Severity of Non-Alcoholic Fatty Liver Disease in Japanese," PLoS One, 2012, vol. 7, e38322.

Kazumori H. et al., "Bile acids directly augment caudal related homeobox gene Cdx2 expression in oesophageal keratinocytes in Barrett's epithelium," Gut, 2006, 55(1), 16-25.

Kazumori H. et al., "Roles of caudal-related homeobox gene Cdx1 in oesophageal epithelial cells in Barrett's epithelium development," Gut, 2009, 58(5), 620-628.

KC K., et al., "In vitro model for studying esophageal epithelial differentiation and allergic inflammatory responses identifies keratin involvement in eosinophilic esophagitis," PloS One, 2015, 10(6), e0127755.

Kearns N. A. et al., "Generation of organized anterior foregut epithelia from pluripotent stem cells using small molecules," Stem Cell Res., 2013, 11, 1003-1012.

Kebschull et al., "High-throughput mapping of single-neuron projections by sequencing of barcoded RNA", Neuron, 2016, vol. 91(5), pp. 975-987.

Keebler M. E., et al., "Fine-Mapping in African Americans of 8 Recently Discovered Genetic Loci for Plasma Lipids: The Jackson Heart Study," Circulation: Cardiovascular Genetics, 2010, vol. 3, pp. 358-364.

Keeley, T.P., et al., "Defining Physiological Normoxia for Improved Translation of Cell Physiology to Animal Models and Humans," Physiological Reviews, 2019, vol. 99, pp. 161-234.

Kennedy D., et al., "Optimal Absorptive Transport of the Dipeptide Glycylsarcosine Is Dependent on Functional Na?/H? Exchange Activity," Pflugers Archiv, 2002, vol. 445, pp. 139-146.

Kermani P., et al., "Neurotrophins Promote Revascularization by Local Recruitment of TrkB+ Endothelial Cells and Systemic Mobilization of Hematopoietic Progenitors," Journal of Clinical Investigation, 2005, vol. 115, pp. 653-663.

Kietzmann, T., et al., "Metabolic zonation of the liver: The oxygen gradient revisited," Redox Biol, 2017, vol. 11, pp. 622-630.

Kim et al., "Recent progress in development of siRNA delivery vehicles for cancer therapy", Advanced Drug Delivery Reviews, 2016, vol. 104, pp. 61-77.

Kim M., et al., "O-Linked N-Acetylglucosamine Transferase Promotes Cervical Cancer Tumorigenesis through Human Papillomavirus E6 and E7 Oncogenes." Oncotarget, 7(28), 2016, 44596-44607.

Kim, S. G., et al., "Bilirubin Activates Transcription of HIF-1a in Human Proximal Tubular Cells Cultured in the Physiologic Oxygen Content," J Korean Med Sci, 2014, vol. 29, pp. S146-S154.

Kim Y. K., et al., "Gene-Edited Human Kidney Organoids Reveal Mechanisms of Disease in Podocyte Development," Stem Cells, 2017, vol. 35, pp. 2366-2378.

Kimura M., et al., "En Masse Organoid Phenotyping Informs Metabolic-Associated Genetic Susceptibility to NASH," Cell, Jun. 2022, vol. 185, No. 12, pp. 4216-4232.e4216.

Kitamoto A., et al., "Association of Polymorphisms in GCKR and TRIB1 with Nonalcoholic Fatty Liver Disease and Metabolic Syndrome Traits," Endocrine Journal, 2014, vol. 61, pp. 683-689.

Kleshchevnikov V., et al., "Comprehensive Mapping of Tissue Cell Architecture via Integrated Single Cell and Spatial Transcriptomics," bioRxiv, Nov. 2020, doi: 10.1101/2020.11.15.378125.

Kligerman S. J., et al., "From the Radiologic Pathology Archives: Organization and Fibrosis as a Response to Lung Injury in Diffuse Alveolar Damage, Organizing Pneumonia, and Acute Fibrinous and Organizing Pneumonia," Radiographics, 2013, 33, doi:10.1148/rg.337130057. PMID—24224590.

Kolbe E., et al., "Mutual Zonated Interactions of Wnt and Hh Signaling Are Orchestrating the Metabolism of the Adult Liver in Mice and Human," Cell Reports, Nov. 2019, vol. 29, No. 11, pp. 4553-4567.e4557.

Kong J. et al., "Ectopic Cdx2 expression in murine esophagus models an intermediate stage in the emergence of Barrett's esophagus," PLoS ONE, 2011, 6(4), 1-12.

Kong J. et al., "Induction of intestinalization in human esophageal keratinocytes is a multistep process," Carcinogenesis, 2009, 30(1), 122-130.

Kormish J.D. et al, "Interactions between SOX factors and Wnt/beta-catenin signaling in development and disease," Developmental Dynamics: An Official Publication of the American Association of Anatomists, 2010, 239, 56-68.

Koui Y., et al., "An In Vitro Human Liver Model by iPSC-Derived Parenchymal and Non-Parenchymal Cells," Stem Cell Reports, 2017, 9, pp. 490-498.

Kouznetsova I. et al., Self-renewal of the human gastric epithelium: new insights from expression profiling using laser microdissection. Mol Biosyst, 2011, 7, 1105-1112.

Kowalski P.S., et al., "Delivering the messenger: Advances in Technologies for Therapeutic mRNA delivery," Molecular Therapy . Apr. 10, 2019;27(4):710-728.

Kozyra M., et al., "Human Hepatic D Spheroids as a Model for Steatosis and Insulin Resistance", Scientific Reports, vol. 8, No. 1, Sep. 24, 2018, Retrieved from the Internet: URL: https://www.nature.com/articles/s41598-018-32722-6.

Krishnan, U., et al., "Evaluation and Management of Pulmonary Hypertension in Children with Bronchopulmonary Dysplasia." The Journal of Pediatrics, vol. 188, Sep. 2017, pp. 24-34.e1.

Kuhnert F. et al., "Essential regulation of CNS angiogenesis by the orphan G protein-coupled receptor GPR124," Science, 2010, 330, 985-989. 10.1126/science.1196554.

(56) References Cited

OTHER PUBLICATIONS

Kumagai et al., "A bilirubin-inducible fluorescent protein from eel muscle," Cell (2013) 153(7):1602-11.
Kumar A., et al., "Specification and Diversification of Pericytes and Smooth Muscle Cells from Mesenchymoangioblasts," Cell Reports, 2017, vol. 19, pp. 1902-1916.
Kumari, D., "States of Pluripotency: Naïve and Primed Pluripotent Stem Cells," InTech Open, vol. 1, Chapter 3, 2016, pp. 31-45.
Kurz H., "Cell Lineages and Early Patterns of Embryonic CNS Vascularization," Cell Adhesion & Migration, 2009, vol. 3, pp. 205-210.
Subramanian, A. et al., "Gene set enrichment analysis: A knowledge-based approach for interpreting genome-wide expression profiles," Proceedings of the National Academy of Sciences, 2005, 102(43), 15545-15550.
Sunshine J.C., "Effects of Base Polymer Hydrophobicity and End-Group Modification on Polymeric Gene Delivery," Biomacromolecules 2011, 12, pp. 3592-3600.
Suprynowicz, F. A., et al., "HPV-16 E5 Oncoprotein Upregulates Lipid Raft Components Caveolin-1 and Ganglioside GM1 at the Plasma Membrane of Cervical Cells." Oncogene, vol. 27, 2008, pp. 1071-1078.
Suzuki, et al., "Directed differentiation of human induced pluripotent stem cells into mature stratified bladder urothelium," Scientific Reports, 2019, vol. 9, 10506.
Takasato M., et al., "Kidney Organoids from Human iPS Cells Contain Multiple Lineages and Model Human Nephrogenesis," Nature, 2016, vol. 536, p. 238.
Tam P. P., and Loebel D. A., "Gene Function in Mouse Embryogenesis: Get Set for Gastrulation," Nature Reviews Genetics, 2007, 8, pp. 368-381.
Tanaka K., et al., "Structure and Functional Expression of the Cloned Rat Neurotensin Receptor," Neuron, 1990, vol. 4, pp. 847-854.
Tanii, H., et al., "Induction of Cytochrome P450 2A6 by Bilirubin in Human Hepatocytes," Pharmacology & Pharmacy, 2013, vol. 04, pp. 182-190.
Tannenbaum, S.E. et al., "Derivation of Xeno-Free and GMP-Grade Human Embryonic Stem Cells—Platforms for Future Clinical Applications," PLoS ONE, Jun. 2012, vol. 7, No. 6, 16 pages.
Tanwar S. et al., "Validation of terminal peptide of procollagen III for the detection and assessment of nonalcoholic steatohepatitis in patients with nonalcoholic fatty liver disease," Hepatology, 2013, 57, 103-111.
Tarlungeanu D. C., et al., "Impaired Amino Acid Transport at the Blood Brain Barrier Is a Cause of Autism Spectrum Disorder," Cell, 2016, vol. 167, pp. 1481-1494.e1418.
Terry, N. A. et al., "Lipid Malabsorption from Altered Hormonal Signaling Changes Early Gut Microbial Responses". Am J Physiol—Gastrointest Liver Physiol, 2018, 315(6), pp. G990-G1000.
Terry N.A. et al., "Dysgenesis of enteroendocrine cells in Aristaless-Related Homeobox polyalanine expansion mutationsm," J Pediatr Gastroenterol Nutr, 2015, 60, 2, 192-199.
Tessarollo L., et al., "TrkB Truncated Isoform Receptors as Transducers and Determinants of BDNF Functions," Frontiers in Neuroscience, Mar. 2022, vol. 16, doi: 10.3389/fnins.2022.847572.
Thakur, A., et al., "Hepatocyte Nuclear Factor 4-Alpha Is Essential for the Active Epigenetic State at Enhancers in Mouse Liver," Hepatology, 2019, vol. 70, pp. 1360-1376.
The Lancet Gastroenterology, "Headway and hurdles in nonalcoholic fatty liver disease," Lancet Gastroenterology & Hepatology, 2020, vol. 5, 93.
Thebaud B., et al., "Vascular Endothelial Growth Factor Gene Therapy Increases Survival, Promotes Lung Angiogenesis, and Prevents Alveolar Damage in Hyperoxia-Induced Lung Injury: Evidence that Angiogenesis Participates in Alveolarization," Circulation, 2005, vol. 112, pp. 2477-2486.
Thommensen L. et al., "Molecular mechanisms involved in gastrin-mediated regulation of cAMP-responsive promoter elements," Am J Physiol Endocrinol Metab, 2001, 281, E1316-1325.
Thompson F.M., et al., "Epithelial Growth of the Small Intestine Occurs by Both Crypt Fission and Crypt Hyperplasia During Infancy and Childhood in Humans," Journal of Gastroenterology and Hepatology, 2001, 2 Pages.
Tomassoni-Ardori F., et al., "Rbfox1 Up-Regulation Impairs BDNF-Dependent Hippocampal LTP by Dysregulating TrkB Isoform Expression Levels," eLife, Aug. 2019, vol. 8, e49673. doi: 10.7554/eLife.49673.
Totoson P., et al., "Activation of endothelial TrkB receptors induces relaxation of resistance arteries." Vascular Pharmacology, 106, 2018, pp. 46-53.
Touboul T. et al., "Generation of functional hepatocytes from human embryonic stem cells under chemically defined conditions that recapitulate liver development," Hepatology, 2010, 51, 1754-1765.
Traag V.A., et al., "From Louvain to Leiden: Guaranteeing Well-Connected Communities," Scientific Reports, 2019, vol. 9, 5233. doi: 10.1038/s41598-019-41695-z.
Tran M., et al., "Spatial Analysis of Ligand-Receptor Interaction in Skin Cancer at Genome-Wide and Single-Cell Resolution," bioRxiv, Sep. 2021, doi: 10.1101/2020.09.10.290833.
Trapnell C. et al., "The dynamics and regulators of cell fate decisions are revealed by pseudotemporal ordering of single cells," Nat Biotechnol, 2014, 32, 381-386.
Tsakmaki A., et al., "Diabetes Through a 3D Lens: Organoid Models," Diabetologia, Springer Berlin Heidelberg, Berlin/heidelberg, vol. 63, No. 6, Mar. 27, 2020, pp. 1093-1102.
Tsankov A. M. et al., "Transcription factor binding dynamics during human ES cell differentiation," Nature, 2015, 518(7539), 344-9.
Tufro-Mcreddie, A., et al., "Angiotensin II Regulates Nephrogenesis and Renal Vascular Development." American Journal of Physiology, vol. 269, No. 1, 1995, pp. F110-F115.
Uchida H., et al., "A Xenogeneic-free System Generating Functional Human Gut Organoids from Pluripotent Stem Cells," JCI Insight, Jan. 12, 2017, vol. 2, No. 1, 13 pages.
Uchimura, K., et al., "Human Pluripotent Stem Cell-Derived Kidney Organoids with Improved Collecting Duct Maturation and Injury Modeling," Cell Reports, 2020, vol. 33, 108514.
Vales, S., et al., "In Vivo Human PSC-Derived Intestinal Organoids to Study Stem Cell Maintenance." In Methods in Molecular Biology, vol. 2171, Chapter 12, 2020, pp. 201-214.
Van Den Berg C.W., et al., "Renal Subcapsular Transplantation of PSC-Derived Kidney Organoids Induces Neo-vasculogenesis and Significant Glomerular and Tubular Maturation In Vivo," Stem Cell Reports, 2018, vol. 10, pp. 751-765. doi: 10.1016/j.stemcr.2018.01.041.
Van Dop W. A., et al., "Hedgehog Signalling Stimulates Precursor Cell Accumulation and Impairs Epithelial Maturation in the Murine Oesophagus," Gut, 2012, 62(3), pp. 348-357.
Van Hoecke et al., "How mRNA therapeutics are entering the monoclonal antibody field," Journal of Translational Medicine . Feb. 22, 2019;17(1):54 in 14 pages.
Van Raay T. J. et al., "Frizzled 5 signaling governs the neural potential of progenitors in the developing Xenopus retina," Neuron, 2005, 46(1), 23-36.
Van Straten, G., et al., "Aberrant Expression and Distribution of Enzymes of the Urea Cycle and Other Ammonia Metabolizing Pathways in Dogs with Congenital Portosystemic Shunts," PLOS ONE, 2014, vol. 9, e100077, 11 pages.
Vatine G. D., et al., "Modeling Psychomotor Retardation Using iPSCs from MCT8-Deficient Patients Indicates a Prominent Role for the Blood-Brain Barrier," Cell Stem Cell, 2017, vol. 20, pp. 831-843.e835.
Vatine G.D., et al., "Human iPSC-Derived Blood-Brain Barrier Chips Enable Disease Modeling and Personalized Medicine Applications," Cell Stem Cell, 2019, vol. 24, pp. 995-1005.
Vega M. E. et al., "Inhibition of notch signaling enhances transdifferentiation of the esophageal squamous epithelium towards a Barrett's-like metaplasia via KLF4," Cell Cycle, 2014, 13(24), 3857-3866.
Veldman, T., et al., "Human Papillomavirus E6 and Myc Proteins Associate In Vivo and Bind to and Cooperatively Activate the

(56) References Cited

OTHER PUBLICATIONS

Telomerase Reverse Transcriptase Promoter." Proceedings of the National Academy of Sciences, vol. 100, No. 14, Jul. 8, 2003, pp. 8211-8216.

Verdera H,C., et al., AAV vector immunogenicity in humans: A long journey to successful gene transfer, Mol Thera. Mar. 4, 2020;28(3):723-746.

Verma S.K., et al., "RBFOX2 is Required for Establishing RNA Regulatory Networks Essential for Heart Development," Nucleic Acids Research, 2022, vol. 50, No. 4, 2270-2286. doi: 10.1093/nar/gkac055.

Verscheijden L.F.M., et al., "Differences in P-Glycoprotein Activity in Human and Rodent Blood-Brain Barrier Assessed by Mechanistic Modelling," Archives of Toxicology, 2021, vol. 95, pp. 3015-3029.

Vincent K.M., et al., "Expanding the Clinical Spectrum of Autosomal-Recessive Renal Tubular Dysgenesis: Two Siblings with Neonatal Survival and Review of the Literature," Molecular Genetics and Genomic Medicine, 2022, vol. 10, e1920.

Vohwinkel C.U., et al., "Bronchopulmonary Dysplasia: Endothelial Cells in the Driver's Seat," American Journal of Respiratory Cell and Molecular Biology, Apr. 2021, vol. 65, No. 1, pp. 6-7. doi: 10.1165/rcmb.2021-0145ED.

Wagner N., et al., "Coronary Vessel Development Requires Activation of the TrkB Neurotrophin Receptor by the Wilms' Tumor Transcription Factor Wt1," Genes & Development, 2005, vol. 19, pp. 2631-2642.

Wahlestedt C. et al., "Neuropeptide Y Receptor Subtypes, Y1 and Y2," Annals of the New York Academy of Sciences, 1990, 611, 7-26.

Wahlicht, T., et al., "Controlled Functional Zonation of Hepatocytes In Vitro by Engineering of Wnt Signaling." ACS Synthetic Biology, vol. 9, 2020, pp. 1638-1649.

Walker E.M. et al., "Characterization of the developing small intestine in the absence of either GATA4 or GATA6," BMC Res Notes, 2014, 7, 902, 12 pages.

Wang D. H., et al., "Regulation of Angiotensin Type 1 Receptor and Its Gene Expression: Role in Renal Growth," Journal of the American Society of Nephrology, 1997, vol. 8, pp. 193-198.

Kuzmichev A. N et al., "Sox2 acts through Sox21 to regulate transcription in pluripotent and differentiated cells," Cuurrent Biology, 22(18), 2012, 1705-1710.

Kwapiszewska G., et al., "BDNF/TrkB Signaling Augments Smooth Muscle Cell Proliferation in Pulmonary Hypertension," American Journal of Pathology, 2012, vol. 181, pp. 2018-2029.

L. Landsman, et al., "Pancreatic Mesenchyme Regulates Epithelial Organogenesis Throughout Development," PLoS Biology, 2011, vol. 9, Article e1001143, 14 pages.

Lammert E., "Induction of Pancreatic Differentiation by Signals from Blood Vessels," Science, 2001, vol. 294, pp. 564-567.

Lancaster M. A., et al., "Cerebral Organoids Model Human Brain Development and Microcephaly," Nature, 2013, vol. 501(7467), pp. 373-379.

Landin, B. H., et al., "Labeled Lectin Studies of Renal Tubular Dysgenesis and Renal Tubular Atrophy of Postnatal Renal Ischemia and End-Stage Kidney Disease." Pediatric Pathology, vol. 14, No. 1, 1994, pp. 87-99.

Langen U.H., et al., "Development and Cell Biology of the Blood-Brain Barrier," Annual Review of Cell and Developmental Biology, 2019, vol. 35, pp. 591-613.

Langer R., "Tissue Engineering," Science, 1990, vol. 249, pp. 1527-1533.

Lau J. Y., et al., "Systematic Review of the Epidemiology of Complicated Peptic Ulcer Disease: Incidence, Recurrence, Risk Factors and Mortality," Digestion, 2011, vol. 84, pp. 102-113. DOI: 10.1159/000323958.

Leblanc G. G., et al., "Biology of Vascular Malformations of the Brain," Stroke, 2009, vol. 40, pp. e694-e702.

Leedham S. J. et al., "Individual crypt genetic heterogeneity and the origin of metaplastic glandular epithelium in human Barrett's oesophagus," Gut, 2008, 57(8), 1041-1048.

Lehner, R. et al., "A Comparison of Plasmid DNA Delivery Efficiency and Cytotoxicity of Two Cationic Diblock Polyoxazoline Copolymers", Nanotechnology, 28, 2017, pp. 111.

Li B., et al., "Benchmarking Spatial and Single-Cell Transcriptomics Integration Methods for Transcript Distribution Prediction and Cell Type Deconvolution," Nature Methods, Jun. 2022, vol. 19, No. 6, pp. 662-670.

Li H., et al., "Directed Differentiation of Human Embryonic Stem Cells into Keratinocyte Progenitors In Vitro: An Attempt with Promise of Clinical Use," In Vitro Cellular Developmental Biology—Animal, 2016, 52(8), pp. 885-893.

Li H. et al., "Fast and accurate short read alignment with Burrows-Wheeler transform," Bioinformatics, 2009, 25(14), 1754-1760.

Li H.J. et al., Basic helix-loop-helix transcription factors and enteroendocrine cell differentiation. Diabetes Obes Metab, 2011, 13(01), Suppl 1, 5-12, 16 pages.

Li J., et al., "An Obligatory Role for Neurotensin in High Fat Diet-Induced Obesity," Nature, 2016, vol. 533, No. 7603, pp. 411-415.

Li, Y., et al., "The Renin-Angiotensin-Aldosterone System (RAAS) Is One of the Effectors by Which Vascular Endothelial Growth Factor (VEGF)/Anti-VEGF Controls the Endothelial Cell Barrier," American Journal of Pathology, 2020, vol. 190, pp. 1971-1981.

Li Y., et al., "Synthesis and Characterization of an Amphiphilic Graft Polymer and its Potential as a pH-Sensitive Drug Carrier", Polymer, vol. 58, No. 15, Jul. 2011, pp. 3304-3310.

Lin Y. C., et al., "Genetic Variants in GCKR and PNPLA3 Confer Susceptibility to Nonalcoholic Fatty Liver Disease in Obese Individuals," American Journal of Clinical Nutrition, 2014, vol. 99, pp. 869-874.

Lindström N. O., et al., "Integrated β-catenin, BMP, PTEN, and Notch signalling patterns the nephron." eLife, 4, e04000. 2015, 29 pages. https://doi.org/10.7554/eLife.04000.

Lindström N. O., et al., "Spatial Transcriptional Mapping of the Human Nephrogenic Program." Developmental Cell, 56(16), 2021, pp. 2381-2398.e6. https://doi.org/10.1016/j.devcel.2021.07.017.

Lindstrom N.O., et al., "Integrated Beta-Catenin, BMP, PTEN, and Notch Signalling Patterns the Nephron," eLife, 2015, vol. 3, e04000.

Liu D., Chinese Encyclopedia of Medicine—Pathophysiology, "China Signal Pathway and Targeted Therapeutics", edited by Yu Yuanxun, Anhui Science and Technology Press, May 2013, 1st edition.

Liu K., et al., "Sox2 Cooperates with Inflammation-Mediated Stat3 Activation in the Malignant Transformation of Foregut Basal Progenitor Cells," Cell Stem Cell, 2013, 12(3), 304-315.

Liu T., et al., "Regulation of Cdx2 expression by promoter methylation, and effects of Cdx2 transfection on morphology and gene expression of human esophageal epithelial cells," Carcinogenesis, 2007, 28(2), 488-496.

Lloyd D. J., et al., "Antidiabetic Effects of Glucokinase Regulatory Protein Small-Molecule Disruptors." Nature, 504, 2013, 16 pages.

Lois C. et al., "Germline transmission and tissue-specific expression of transgenes delivered by lentiviral vectors," Science, 2002, 295, 868-872.

Loomba, R., et al., "Combination Therapies Including Cilofexor and Firsocostat for Bridging Fibrosis and Cirrhosis Attributable to NASH." Hepatology, vol. 73, No. 2, Feb. 2021, pp. 625-643.

Loomba R., et al., "Heritability of Hepatic Fibrosis and Steatosis Based on a Prospective Twin Study," Gastroenterology, 2015, vol. 149, pp. 1784-1793.

Loquet PH., et al., "Influence of Raising Maternal Blood Pressure With Angiotensin II on Utero-Placental and Feto-Placental Blood Velocity Indices in the Human," Clinical Science, 1990, vol. 78, pp. 95-100.

Low, J.H., et al., "Generation of Human PSC-Derived Kidney Organoids with Patterned Nephron Segments and a De Novo Vascular Network," Cell Stem Cell, 2019, vol. 25, pp. 373-387 e379.

Lu T.M., et al., "Pluripotent Stem Cell-Derived Epithelium Misidentified as Brain Microvascular Endothelium Requires ETS Factors to Acquire Vascular Fate," Proceedings of the National Academy of Sciences of the United States of America, 2021, vol. 118.

(56) References Cited

OTHER PUBLICATIONS

Lubinsky M. Sonic Hedgehog, VACTERL, and Fanconi anemia: Pathogenetic connections and therapeutic implications. American Journal of Medical Genetics, Part A, 2015, 167(11), 2594-2598.
Lucía Selfa, I., et al., "Directed Differentiation of Human Pluripotent Stem Cells for the Generation of High-Order Kidney Organoids." Methods in Molecular Biology, vol. 2258, 2021, pp. 171-189.
Lustig B. et al., "Negative feedback loop of Wnt signaling through upregulation of conductin/axin2 in colorectal and liver tumors," Molecular and Cellular Biology, 2002, 22(4), 1184-93.
Luzio J.P. et al., "Lysosomes: fusion and function", Nature reviews Molecular cell biology, 2007, vol. 8, No. 8, pp. 622-632.
Ma, R., et al., "Metabolic and non-metabolic liver zonation is established non-synchronously and requires sinusoidal Wnts," eLife, 2020, vol. 9, e46206.
Mace O. J. et al., "Pharmacology and physiology of gastrointestinal enteroendocrine cells," Pharmacol Res Perspect, 2015 3(4), e00155, 26 pages.
Maddaluno L., et al., "EndMT Contributes to the Onset and Progression of Cerebral Cavernous Malformations." Nature, vol. 498, 2013, 7 pages.
Madisen L. et al., "A robust and high-throughput Cre reporting and characterization system for the whole mouse brain," Nat Neurosci, 2020, 13, 133-140.
Madsen K., et al., "Angiotensin II Promotes Development of the Renal Microcirculation through AT1 Receptors," Journal of the American Society of Nephrology, 2010, vol. 21, pp. 448-459.
Mahieu-Caputo D., et al., "Twin-to-Twin Transfusion Syndrome: Role of the Fetal Renin-Angiotensin System," American Journal of Pathology, 2000, vol. 156, pp. 629-636.
Mammen J. M., et al., "Mucosal Repair in the Gastrointestinal Tract," Critical Care Medicine, 2003, vol. 31, pp. S532-S537. DOI: 10.1097/01.CCM.0000081429.89277.AF.
Mammoto A., et al., "Vascular Niche in Lung Alveolar Development, Homeostasis, and Regeneration," Frontiers in Bioengineering and Biotechnology, Nov. 2019, vol. 7, No. 318. doi: 10.3389/fbioe.2019.00318.
Mammoto, T., et al., "Mechanical control of tissue and organ development," Development, 2010, vol. 137, No. 9, pp. 1407-1420.
Mandegar M. A., et al., "CRISPR Interference Efficiently Induces Specific and Reversible Gene Silencing in Human iPSCs," Cell Stem Cell, 2016, 18(4), pp. 541-553.
Marable, S.S., et al., "Hnf4a deletion in the mouse kidney phenocopies Fanconi renotubular syndrome," JCI Insight, 2018, vol. 3, 12 Pages.
Mari L. et al., "A pSMAD/CDX2 complex is essential for the intestinalization of epithelial metaplasia," Cell Reports, 2014, 7(4), 1197-1210.
Marino G. et al., "Self-consumption: the interplay of autophagy and apoptosis", Nature reviews Molecular cell biology, 2014, vol. 15, No. 2, pp. 81-94.
Coskun T. et al., "Activation of Prostaglandin E Receptor 4 Triggers Secretion of Gut Hormone Peptides GLP-1, GLP-2, and PYY," Endocrinology, 2013, 154, 45-53.
Cox H. M., "Endogenous PYY and NPY mediate tonic Y(1)- and Y(2)-mediated absorption in human and mouse colon," Nutrition, 2008, 24, 900-906.
Creane M., et al., "Biodistribution and Retention of Locally Administered Human Mesenchymal Stromal Cells: Quantitative Polymerase Chain Reaction-Based Detection of Human DNA in Murine Organs," Cytotherapy, 2017, vol. 19, pp. 384-394. DOI: 10.1016/j.jcyt.2016.12.003.
Crisera C. A., et al., "Expression and Role of Laminin-1 in Mouse Pancreatic Organogenesis," Diabetes, 2000, vol. 49, pp. 936-944.
Cruz, N. M., et al., "Differentiation of Human Kidney Organoids from Pluripotent Stem Cells." In Methods in Cell Biology, vol. 153, Chapter 7, 2019, pp. 133-150.
Cucullo L., et al., "The role of shear stress in Blood-Brain Barrier endothelial physiology," BMC Neurosci, 2011, 40, 15 pages.
Cuevas I., et al., "Sustained Endothelial Expression of HoxA5 In Vivo Impairs Pathological Angiogenesis and Tumor Progression," PLoS One, 2015, vol. 10, e0121720.
Cui, J., et al., "Progressive Pseudogenization: Vitamin C Synthesis and Its Loss in Bats," Molecular Biology and Evolution, 2011, vol. 28, No. 4, pp. 1025-1031.
Cunningham, R.P., et al., "Liver Zonation—Revisiting Old Questions With New Technologies," Frontiers in Physiology, 2021, vol. 12, 732929.
Dahlman et al., "Barcoded Nanoparticles for High Throughput in Vivo Discovery of Targeted Therapeutics", PNAS, U.S.A., 2017, vol. 114(8), pp. 2060-2065.
Daneman R., et al., "The Blood-Brain Barrier," Cold Spring Harbor Perspectives in Biology, 2015, vol. 7, a020412.
Daniely Y. et al., "Critical role of p63 in the development of a normal esophageal and tracheobronchial epithelium," American Journal of Physiology, Cell Physiology, 2004, 287(1), C171-C181.
Dathan N. et al., "Distribution of the titf2/foxe1 gene product is consistent with an important role in the development of foregut endoderm, palate, and hair," Dev. Dyn., 2002, 224, 450-456.
Davidson L. M., et al., "Bronchopulmonary Dysplasia: Chronic Lung Disease of Infancy and Long-Term Pulmonary Outcomes," Journal of Clinical Medicine, 2017, vol. 6, p. 20.
Davis B. P., et al., "Eosinophilic Esophagitis-Linked Calpain 14 is an IL-13-Induced Protease that Mediates Esophageal Epithelial Barrier Impairment," JCI Insight, 2016, 1(4), 11 pages.
Dawkins H.J.S., et al., "Progress in rare diseases research 2010-2016: An IRDiRC Perspective," Clinical and Translational Science. Jan. 2018;11(1):11-20.
De Felice, M. et al., "A mouse model for hereditary thyroid dysgenesis and cleft palate," Nat. Genet., 1998, 19, 395-398.
De Jong E. M. et al., Etiology of esophageal atresia and tracheoesophageal fistula: 'Mind the gap', Current Gastroenterology Reports, 2010, 12(3), 215-222.
De Paepe M. E., et al., "Growth of Pulmonary Microvasculature in Ventilated Preterm Infants," American Journal of Respiratory and Critical Care Medicine, 2006, vol. 173, pp. 204-211.
De Santa Barbara P., et al., "Molecular Etiology of Gut Malformations and Diseases," American Journal of Medical Genetics, Dec. 3, 20020; vol. 115(4), pp. 221-230.
De Santa Barbara, P., et al., "Tail gut endoderm and gut/genitourinary/tail development: a new tissue-specific role for Hoxa13," Development, 2002, vol. 129, pp. 551-561.
Demirgan E.B., et al., "AGTR1-related Renal Tubular Dysgeneses May Not Be Fatal," Kidney International Reports, 2021, vol. 6, pp. 846-852.
Distefano P.V. et al., "KRIT1 protein depletion modifies endothelial cell behavior via increased vascular endothelial growth factor (VEGF)signaling," J Biol Chem, 2014, 289, 33054-33065.
D'mello R. J., et al., "LRRC31 is Induced by IL-13 and Regulates Kallikrein Expression and Barrier Function in the Esophageal Epithelium," Mucosal Immunology, 2016, 9(3), pp. 744-756.
Dolinay T., et al., "Integrated Stress Response Mediates Epithelial Injury in Mechanical Ventilation," American Journal of Respiratory Cell and Molecular Biology, 2017, 57, pp. 193-203.
Dollard S. C., et al., "Production of Human Papillomavirus and Modulation of the Infectious Program in Epithelial Raft Cultures." Genes & Development, 6, 1992, pp. 1131-1142.
Domyan E.T. et al., "Signaling through BMP receptors promotes respiratory identity in the foregut via repression of Sox2," Development (Cambridge, England), 2011, 138(5), 971-981.
Donati, B., et al., "The rs2294918 E434K Variant Modulates Patatin-Like Phospholipase Domain-Containing 3 Expression and Liver Damage." Hepatology, vol. 63, No. 3, Mar. 2016, pp. 787-798.
Dong R., et al., "SpatialDWLS: Accurate Deconvolution of Spatial Transcriptomic Data." Genome Biology, 22, 145, 2021, 10 pages. https://doi.org/10.1186/s13059-021-02362-7.
Dorison A., et al., "What Can We Learn from Kidney Organoids?" Kidney International, 102, 2022, pp. 1013-1029. https://doi.org/10.1016/j.kint.2022.06.032.
Dougherty, E., "Tackling the common denominator in liver disease," Novartis, Jun. 16, 2016, https://www.novartis.com/stories/tackling-common-denominator-liver-disease.

(56) References Cited

OTHER PUBLICATIONS

Doupe D. P. et al., "A Single Progenitor Population Switches Behavior to Maintain and Repair Esophageal Epithelium," Science, 2012, 337(6098), 1091-1093.
Draheim K. M., et al., "Cerebral Cavernous Malformation Proteins at a Glance," Journal of Cell Science, 2014, vol. 127(4), pp. 701-707.
Drukcer, D. J., "Evolving Concepts and Translational Relevance of Enteroendocrine Cell Biology," J Clin Endocrinol Metab, 2016, vol. 101, No. 3, pp. 778-786.
Du A. et al., "Arx is required for normal enteroendocrine cell development in mice and humans," Developmental biology, 2012, 365, 175-188.
Du Y., et al., "Lung Gene Expression Analysis (LGEA): An Integrative Web Portal for Comprehensive Gene Expression Data Analysis in Lung Development," Thorax, 2017, 72, pp. 481-484.
Du Y. et al., "'LungGENS': a web-based tool for mapping single-cell gene expression in the developing lung," Thorax, 2015, 70, 1092-1094.
Dubrovskyi O., et al., "Measurement of Local Permeability at Subcellular Level in Cell Models of Agonist- and Ventilator-Induced Lung Injury," Laboratory Investigation, 2013, vol. 93, pp. 254-263.
Duluc I., et al., "Changing Intestinal Connective Tissue Interactions Alters Homeobox Gene Expression in Epithelial Cells," Journal of Cell Science, 1997, vol. 110, pp. 1317-1324.
Dunn A., et al., "POLY seq: A poly(J3-amino ester)-based Vector for Multifunctional Cellular Barcoding," Stem Cell Reports. Sep. 2021, vol. 14(2), pp. 2149-2158.
Dunn A., et al., "Polymeric Vectors for Strategic Delivery of Nucleic Acids," Nano Life, 2017, vol. 7, No. 02, 1730003, 12 pages.
Dunn et al., "Highly Efficient In Vivo Targeting of the Pulmonary Endothelium Using Novel Modifications of Polyethylenimine: An Importance of Charge", Advan Health Mater. 2018, vol. 7(23): 1800876, 25 pages.
Duval, K., et al., "Revisiting the role of Notch in nephron segmentation confirms a role for proximal fate selection during mouse and human nephrogenesis," Development, 2022, vol. 149.
Dye B. R., et al., "A Bioengineered Niche Promotes In Vivo Engraftment and Maturation of Pluripotent Stem Cell Derived Human Lung Organoids," eLife 5, 2016, 18 pages.
Dye B.R. et al., "In vitro generation of human pluripotent stem cell derived lung organoids," Elife 4:e05098 (2015), 25 pages.
Efremova I., et al., "CellPhoneDB: Inferring Cell-Cell Communication from Combined Expression of Multi-Subunit Receptor-Ligand Complexes," Nature Protocols, 2020, vol. 15, pp. 1484-1506.
Eicher A.K., et al., "Functional Human Gastrointestinal Organoids Can Be Engineered from Three Primary Germ Layers Derived Separately from Pluripotent Stem Cells," Cell Stem Cell, 2022, vol. 29, pp. 36-51.e6. doi: 10.1016/j.stem.2021.10.010.
Engelstoft, M. S. et al., "Enteroendocrine Cell Types Revisited". Current Opinion in Pharmacology, 2013, vol. 13, pp. 912-921.
Everhart J. E., et al., "Fatty Liver: Think Globally," Hepatology, 2010, vol. 51, pp. 1491-1493.
Fan Y., et al., "Bioengineering Thymus Organoids to Restore Thymic Function and Induce Donor-Specific Immune Tolerance to Allografts", The American Society of Gene & Cell Therapy, vol. 23, No. 7, Jul. 2015, pp. 1262-1277.
Aakerlund, L., et al., "Y1 receptors for neuropeptide Y are coupled to mobilization of intracellular calcium and inhibition of adenylate cyclase," FEBS Letters, 1990, vol. 260, pp. 73-78.
Abbott N.J., "Astrocyte-Endothelial Interactions and Blood-Brain Barrier Permeability," Journal of Anatomy, 2002, vol. 200, pp. 629-638.
Adams S. H. et al., "Effects of peptide YY [3-36] on short-term food intake in mice are not affected by prevailing plasma ghrelin levels," Endocrinology, 2004, 145, 4967-4975.
Aday S., et al., "Stem Cell-Based Human Blood-Brain Barrier Models for Drug Discovery and Delivery," Trends in Biotechnology, 2016, vol. 34, pp. 382-393.
Afgan E., et al., "The Galaxy Platform for Accessible, Reproducible and Collaborative Biomedical Analyses: 2016 Update," Nucleic Acids Research, 2016, vol. 44, pp. W3-W10.
Ager E. I., et al., "The Renin-Angiotensin System and Malignancy," Carcinogenesis, 2008, vol. 29, pp. 1675-1684.
Aird W.C. et al., "Endothelial cell heterogeneity," Cold Spring Harb Perspect Med, 2012, 2, a006429, 14 pages.
Aizarani N., et al., "A Human Liver Cell Atlas Reveals Heterogeneity and Epithelial Progenitors," Nature, Aug. 2019, vol. 572, No. 7770, pp. 199-204.
Akbari S., et al., "Next-Generation Liver Medicine Using Organoid Models", Frontiers in Cell and Developmental Biology, vol. 7, Dec. 20, 2019.
Akers A., et al., "Synopsis of Guidelines for the Clinical Management of Cerebral Cavernous Malformations: Consensus Recommendations Based on Systematic Literature Review by the Angioma Alliance Scientific Advisory Board Clinical Experts Panel," Neurosurgery, 2017, vol. 80, pp. 665-680.
Al Alam D., et al., "Contrasting expression of canonical Wnt signaling reporters TOPGAL, BATGAL and Axin2(LacZ) during murine lung development and repair," PLoS One, 2011, 6, 8, e23139, 11 pages.
Alber A.B., et al., "Directed Differentiation of Mouse Pluripotent Stem Cells into Functional Lung-Specific Mesenchyme," bioRxiv, Aug. 2022, doi: 10.1101/2022.08.12.502651.
Alber A.B., et al., "Directed Differentiation of Mouse Pluripotent Stem Cells into Functional Lung-specific Mesenchyme," Nature Communications, Jun. 13, 2023 , vol. 14:3488. 18 pages.
Allanson J.E., et al., "Possible New Autosomal Recessive Syndrome With Unusual Renal Histopathological Changes," American Journal of Medical Genetics, 1983, vol. 16, pp. 57-60.
Almeida, L. F., et al., "Role of the Renin-Angiotensin System in Kidney Development and Programming of Adult Blood Pressure." Clinical Science, vol. 134, No. 6, Mar. 27, 2020, pp. 641-656.
Alvira C. M., "Aberrant Pulmonary Vascular Growth and Remodeling in Bronchopulmonary Dysplasia," Frontiers in Medicine (Lausanne), 2016, vol. 3, p. 21.
Alvira C. M., "Nuclear Factor-Kappa-B Signaling in Lung Development and Disease: One Pathway, Numerous Functions," Birth Defects Research Part A: Clinical and Molecular Teratology, 2014, vol. 100, pp. 202-216.
Amir et al., "Comparing the Cellular Phenotype of Naïve and Primed Human Embryonic Stem Cells," Fertility and Sterility, Sep. 2018 110(4):e36 Abstract.
Amir M., et al., "Hepatic Autonomic Nervous System and Neurotrophic Factors Regulate the Pathogenesis and Progression of Non-Alcoholic Fatty Liver Disease," Frontiers in Medicine (Lausanne), 2020, vol. 7, Article 62. doi: 10.3389/fmed.2020.00062.
Amireddy N., et al., "The Unintended Mitochondrial Uncoupling Effects of the FDA-Approved Anti-Helminth Drug Nitazoxanide Mitigates Experimental Parkinsonism in Mice," Journal of Biological Chemistry, 2017, vol. 292, pp. 15731-15743.
Andl C.D. et al., "Epidermal growth factor receptor mediates increased cell proliferation, migration, and aggregation in esophageal keratinocytes in vitro and in vivo," Journal of Biological Chemistry, 2003, 278(3), 1824-1830.
Andrews T.S., et al., "Single-Cell, Single-Nucleus, and Spatial RNA Sequencing of the Human Liver Identifies Cholangiocyte and Mesenchymal Heterogeneity," Hepatology Communications, Nov. 2022, vol. 6, No. 11, pp. 821-840.
Anstee, Q.M., et al., "Genome-wide association study of non-alcoholic fatty liver and steatohepatitis in a histologically characterised cohort," Journal of Hepatology, 2020, vol. 73, pp. 505-515.
Appuhn S.V., et al., "Capillary Changes Precede Disordered Alveolarization in a Mouse Model of Bronchopulmonary Dysplasia," American Journal of Respiratory Cell and Molecular Biology, Mar. 2021, vol. 65, No. 1, pp. 81-91. doi: 10.1165/rcmb.2021-0004OC.
Arnold K. et al., "Sox2+ Adult Stem and Progenitor Cells Are Important for Tissue Regeneration and Survival of Mice," Cell Stem Cell, 2011, 9(4), 317-329.

(56) References Cited

OTHER PUBLICATIONS

Artegiani B., et al., "Fast and Efficient Generation of Knock-in Human Organoids Using Homology-independent CRISPR-Cas9 Precision Genome Editing", Nature Cell Biology, 2020, vol. 22, No. 3, pp. 321-331.
Auerbach A. D., "Fanconi anemia and its diagnosis," Mutation Research—Fundamental and Molecular Mechanisms of Mutagenesis, 2009, 668(1-2), 4-10.
Aven L., et al., "An NT4/TrkB Dependent Increase in Innervation Links Early-Life Allergen Exposure to Persistent Airway Hyperreactivity," FASEB Journal, 2014, vol. 28, pp. 897-907.
Bagnat M. et al., "Genetic control of single lumen formation in the zebrafish gut," Nat Cell Biol, 2007, 9, 954-960.
Bakker S. T. et al., "Learning from a paradox: recent insights into Fanconi anaemia through studying mouse models," Disease Models & Mechanisms, 2013, 6(1), 40-47.
Baldelli, S., et al., "Glutathione and Nitric Oxide: Key Team Players in Use and Disuse of Skeletal Muscle," Nutrients, 2019, vol. 11.
Ballermann B. J., "Dependence of Renal Microvessel Density on Angiotensin II: Only in the Fetus?" Journal of the American Society of Nephrology, 2010, vol. 21, pp. 386-388.
Bamberger C. et al., "Retinoic acid inhibits downregulation of DeltaNp63alpha expression during terminal differentiation of human primary keratinocytes," The Journal of Investigative Dermatology, 2002, 118(1), 133-8.
Bandara, N., et al., "Molecular Control of Nitric Oxide Synthesis through eNOS and Caveolin-1 Interaction Regulates Osteogenic Differentiation of Adipose-Derived Stem Cells by Modulation of Wnt/β-Catenin Signaling," Stem Cell Research Therapy, 2016, vol. 7, No. 182, pp. 1-15.
Barbera M. et al., "The human squamous oesophagus has widespread capacity for clonal expansion from cells at diverse stages of differentiation," Gut, 2015, 64, 11-19.
Bartl, M., et al., "Optimality in the Zonation of Ammonia Detoxification in Rodent Liver." Archives of Toxicology, vol. 89, 2015, pp. 2069-2078.
Basu-Roy U. et al., "Sox2 maintains self renewal of tumor-initiating cells in osteosarcomas," Oncogene, 2012, 31(18), 2270-2282.
Batra S., et al., "Cavernous Malformations: Natural History, Diagnosis and Treatment." Nature Reviews Neurology, 2009, vol. 5, pp. 659-670.
Beer N. L., et al., "The P446L Variant in GCKR Associated with Fasting Plasma Glucose and Triglyceride Levels Exerts Its Effect through Increased Glucokinase Activity in Liver," Human Molecular Genetics, 2009, vol. 18, pp. 4081-4088.
Belalcazar L. M., et al., "Lifestyle Intervention for Weight Loss and Cardiometabolic Changes in the Setting of Glucokinase Regulatory Protein Inhibition: Glucokinase Regulatory Protein-Leu446Pro Variant in Look AHEAD," Circulation: Cardiovascular Genetics, 2016, vol. 9, pp. 71-78.
Bellentani, S., et al., "Epidemiology of Non-Alcoholic Fatty Liver Disease." Digestive Diseases, vol. 28, 2010, pp. 155-161.
Bergers G. et al., "The role of pericytes in blood-vessel formation and maintenance," Neuro Oncol, 2005, 7, 452-464.
Besserer-Offroy, E., et al., "The signaling signature of the neurotensin type 1 receptor with endogenous ligands," Eur J Pharmacol, 2017, vol. 805, pp. 1-13.
Beucher A., et al., "The homeodomain-containing transcription factors Arx and Pax4 control enteroendocrine subtype specification in mice," PLoS One, 2012, 7(5), e36449, 11 pages.
Bhatt A. J., et al., "Disrupted Pulmonary Vasculature and Decreased Vascular Endothelial Growth Factor, Flt-1, and TIE-2 in Human Infants Dying with Bronchopulmonary Dysplasia," American Journal of Respiratory and Critical Care Medicine, 2001, vol. 164, pp. 1971-1980.
Biancalani T., et al., "Deep Learning and Alignment of Spatially Resolved Single-Cell Transcriptomes with Tangram," Nature Methods, Nov. 2021, vol. 18, No. 11, pp. 1352-1362.
Bilchik A. J., et al., "Peptide YY Augments Postprandial Small Intestinal Absorption in the Conscious Dog," The American Journal of Surgery, 1994, vol. 167, pp. 570-574.
Biology Stack Exchange., "Are there situations where in vivo results work better than in vitro results would have shown?", Forum post , reply on Sep. 28, 2018; Retrieved Jul. 25, 2024 from https://biology.stackexchange.com/questions/77736/are-there-situations-where-in-vivo-results-work-better-th (Year: 2018).
Blair T.A., et al., "Mass cytometry reveals distinct platelet subtypes in healthy subjects and novel alterations in surface glycoproteins in Glanzmann thrombasthenia," Scientific Reports. Jul. 9, 2018; 8(1):10300 in 13 pages.
Blakenberg D. et al., "Manipulation of FASTQ data with Galaxy," Bioinformatics, 2010, 26(14), 1783-1785.
Tian A., et al., "Studying Human Neurodevelopment and Diseases Using 3D Brain Organoids," The Journal of Neuroscience, Feb. 5, 2020, vol. 40, No. 6, pp. 1186-1193, Retrieved from the Internet URL: https://www.ncbi.nlm.nih.gov/pmc/articles/PMC7002141/.
Trujillo, C.A. et al., "Complex Oscillatory Waves Emerging from Cortical Organoids Model Early Human Brain Network Development," Cell Stem Cell, 2019, 25, pp. 558-569 e557.
Uzquiano, A. et al., "Proper acquisition of cell class identity in organoids allows definition of fate specification programs of the human cerebral cortex," Cell, 2022, 185, pp. 3770-3788.e3727.
Valdoz, J.C. et al., "Soluble extracellular matrix promotes organotypic formation in lung alveolar model," Biomaterials, 2022, 283, pp. 121464.
Van Der Meijden, P.E.J. et al., "Platelet biology and functions: new concepts and clinical perspectives," Nature Reviews Cardiology, 2018, 14, pp. 14 pages.
Vazquez-Armendariz, A.I. et al., "From Clones to Buds and Branches: The Use of Lung Organoids to Model Branching Morphogenesis Ex Vivo," Frontiers in Cell and Developmental Biology, 2021, 9, pp. 631579.
Velasco, S. et al., "Individual brain organoids reproducibly form cell diversity of the human cerebral cortex," Nature, 2019, 1317, 570, pp. 523-527.
Venema, W.T.C.U. et al., "Gut mucosa dissociation protocols influence cell type proportions and single-cell gene expression levels," Scientific Reports, 2022, 12, pp. 9897.
Vincent C. C., et al., "Scalable GMP Compliant Suspension Culture System for Human ES cells," Stem Cell Research, May 1, 2012, vol. 8, No. 3, DOI: 10.1016/j.scr.2012.02.001, pp. 388-402.
Wang, C. et al., "A critical role of RUNX1 in governing megakaryocyte-primed hematopoietic stem cell differentiation," Blood Advances, 2023, 7, pp. 2590-2605.
Wang, X. et al., "Genome-wide analysis of PDX1 target genes in human pancreatic progenitors," Molecular Metabolism, 2018, 9, pp. 57-68.
Watanabe, S. et al., "Transplantation of intestinal organoids into a mouse model of colitis," Nature Protocols, 2022, 17, pp. 649-671.
Weijts, B. et al., "Blood flow-induced Notch activation and endothelial migration enable vascular remodeling in zebrafish embryos," Nature Communications, 2018, 9, 5314, 11 Pages.
Wiedenmann, S. et al., "Single-cell-resolved differentiation of human induced pluripotent stem cells into pancreatic duct-like organoids on a microwell chip," Nature Biomedical Engineering, 2021, 5, pp. 897-913.
Worsdorfer, P. et al., "Generation of complex human organoid models including vascular networks by incorporation of mesodermal progenitor cells," Scientific Reports, 2019, 9, pp. 15663.
Wu, H. et al., "Progressive Pulmonary Fibrosis Is Caused by Elevated Mechanical Tension on Alveolar Stem Cells," Cell, 2020, 180, pp. 107-121.e117.
Wu, L. et al., "Filaggrin and tight junction proteins are crucial for IL-13-mediated esophageal barrier dysfunction," American Journal of Physiology—Gastrointestinal and Liver Physiology, 2018, ajpgi.00404.2017, pp. 39 pages.
Wynne, K. et al., "Diabetes of the exocrine pancreas," Journal of Gastroenterology and Hepatology, 2019, 34, pp. 346-354.
Xu T.Y., et al., "HiFi-Slide Spatial RNA Sequencing," Protocol.io, 2023, pp. 12 pages.

(56) References Cited

OTHER PUBLICATIONS

Yu I., et al., "A Novel 96-Well Plate Cell Culture Assay for Lineage-Specific Hematopoietic Cell Toxicity Screening," Stemcell Technologies, Retreived from: https://www.stemcell.com/media/files/poster/SP00174-A_Novel_96-well_Plate_Cell_Culture_Assay_for_Lineage-Specific_Hematopoietic_Cell_Toxicity_Screening.pdf.
Yu, Y. et al., "Research progress of Hedgehog signaling pathway in liver fibrosis," Chinese Journal of Anatomy, 2019, 42, No. 6, pp. Machine Translated Abstract.
Zepp, J.A. et al., "Genomic, epigenomic, and biophysical cues controlling the emergence of the lung alveolus," Science, 2021, 371, pp. doi:10.1126/science.abc3172.
Zhang T., et al., "The Role of Glycosphingolipids in Immune Cell Functions," Frontiers in Immunology, Jan. 29, 2019, vol. 10, 22 pages.
Kendig K.I., et al., "Sentieon DNASeq Variant Calling Workflow Demonstrates Strong Computational Performance and Accuracy," Frontiers in Genetics, 2019, vol. 10, pp. 736.
Kishimoto K., et al., "Bidirectional Wnt Signaling Between Endoderm and Mesoderm Confers Tracheal Identity in Mouse and Human Cells," Nature Communications, 2020, vol. 11.
Kishimoto K., et al., "Directed Differentiation of Human Pluripotent Stem Cells into Diverse Organ-Specific Mesenchyme of the Digestive and Respiratory Systems," Nature Protocols, 2022, vol. 17, pp. 2699-2719.
Kishimoto. K., et al., "Mammalian tracheal development and reconstruction: insights from in vivo and in vitro studies," Development, 2021, vol. 148, No. 13, 43 pages.
Kitazawa T., et al., "Regulation of Gastrointestinal Motility by Motilin and Ghrelin in Vertebrates," Frontiers in Endocrinology (Lausanne), 2019, vol. 10, 17 Pages.
Krefft O., et al., "Generation of Standardized and Reproducible Forebrain-type Cerebral Organoids from Human Induced Pluripotent Stem Cells," Journal of Visualized Experiments, Jan. 2018, vol. 131, 8 pages, doi:10.3791/56768, Retrieved from the Internet URL: https://www.ncbi.nlm.nih.gov/pmc/articles/PMC5908685/.
Leeman K.T., et al., "Mesenchymal Stem Cells Increase Alveolar Differentiation in Lung Progenitor Organoid Cultures," Scientific reports, Apr. 23, 2019, vol. 9(1), 10 pages.
Li R., et al., "Myofibroblast Contraction is Essential for Generating and Regenerating the Gas-Exchange Surface," Journal of Clinical Investigation, 2020, vol. 130, pp. 2859-2871.
Llurfrio E.M., et al., "Sorting Cells Alters Their Redox State and Cellular Metabolome," Redox Biology, 2018, vol. 16, pp. 381-387.
Loomans N., et al., "Expansion of Adult Human Pancreatic Tissue Yields Organoids Harboring Progenitor Cells with Endocrine Differentiation Potential," Stem Cell Reports, 2018, vol. 10, pp. 712-724.
Lopez-Ramirez. M.A., et al., "Astrocytes Propel Neurovascular Dysfunction During Cerebral Cavernous Malformation Lesion Formation," Journal of Clinical Investigation, 2021, vol. 131, 15 pages.
Lyu H., et al., "The Role of Bone-Derived Exosomes in Regulating Skeletal Metabolism and Extraosseous Diseases," Frontiers in Cell and Developmental Biology, 2020, vol. 8, pp. 1-17.
Matthisa.L., et al., "Deficient Active Transport Activity in Healing Mucosa After Mild Gastric Epithelial Damage," Digestive Diseases and Sciences, 2020, vol. 65, No. 1, pp. 119-131.
Maxwell K.G., et al., "Gene-edited Human Stem Cell-Derived Cells from a Patient with Monogenic Diabetes Reverse Preexisting Diabetes in Mice," Science Translational Medicine, 2020, vol. 12, No. 540, 23 pages.
Mayran A., et al., "Pioneer Transcription Factors Shape the Epigenetic Landscape," Journal of Biological Chemistry, 2018, vol. 293, pp. 13795-13804.
Mead B.E., et al., "All Models are Wrong, but Some Organoids May be Useful," Genome Biology, 2019, vol. 20, 3 pages.
Meng G., et al., "Optimizing Human Induced Pluripotent Stem Cell Expansion in Stirred-Suspension Culture," Stem Cells and Development, Dec. 15, 2017, vol. 26, No. 24, pp. 1804-1817, DOI: 10.1089/scd.2017.0090, Retrieved from the Internet URL: https://www.liebertpub.com/doi/pdf/10.1089 scd.2017.0090casatoken=4jmtP MYfDEcAAAAA:3nd20wOrb6Kyltkq641ZOmaNdxD4fHqdAl8it 6DjaU7EuxXp4q009t16ps7WJfgbo9HkQEJU.
Mitchell M.J., et al., "Engineering Precision Nanoparticles for Drug Delivery," Nature Reviews Drug Discovery, 2021, vol. 20, pp. 101-124.
Mulvihill E.E., "Regulation of Intestinal Lipid and Lipoprotein Metabolism by the Proglucagon-Derived Peptides Glucagon Like Peptide 1 and Glucagon like Peptide 2," Current Opinion in Lipidology, 2018, vol. 29, No. 2, pp. 95-103.
Munera. J.O., "Development of functional resident macrophages in human pluripotent stem cell-derived colonic organoids and human fetal colon," Cell Stem Cell, 2023, vol. 30(11), pp. 1434-1451.e9.
Neuschulz A., et al., "A Single-Cell RNA Labeling Strategy for Measuring Stress Response Upon Tissue Dissociation," Molecular Systems Biology, 2023, vol. 19, 13 pages.
Ng W.H., et al., "Recapitulate Human Cardio-pulmonary Co-development Using Simultaneous Multilineage Differentiation of Pluripotent Stem Cells," bioRxiv, Mar. 3, 2021., 24 pages.
Oberg H-H., et al., "Differential Expression of CD126 and CD130 Mediates Different STAT-3 Phosphorylation in CD4+ CD25- and CD25high Regulatory T Cells," International Immunology, 2006, vol. 18, No. 4, pp. 555-563.
Ouelette J., et al., "Vascular Contributions to 16p11.2 Deletion Autism Syndrome Modeled in Mice," Nature Neuroscience, 2020, vol. 23, pp. 1090-1101.
Oz-Levi D., et al., "Noncoding Deletions Reveal a Gene that is Critical for Intestinal Function," Nature, 2019, vol. 571, pp. 107-111.
Pera M. F., et al., The Exploration of Pluripotency Space: Charting Cell State Transitions in Peri-Implantation Development, Cell Stem Cell, Nov. 4, 2021, vol. 28, No. 11, pp. 1896-1906.
Pfister G., et al., "An Evaluation of Sorter Induced Cell Stress (SICS) on Peripheral Blood Mononuclear Cells (PBMCs) After Different Sort Conditions—Are your sorted cells getting SICS?" Journal of Immunological Methods, 2020, vol. 487, 7 pages.
Pode-Shakked N., et al., "RAAS-Deficient Organoids Indicate Delayed Angiogenesis as a Possible Cause for Autosomal Recessive Renal Tubular Dysgenesis," Nature Communications, 2023, vol. 14.
Pradhan. S., et al., "Tissue Responses to Shiga Toxin in Human Intestinal Organoids," Cellular and Molecular Gastroenterology & Hepatology, 2020, vol. 10, pp. 171-190.
Protze. S.I., et al., "Human Pluripotent Stem Cell-Derived Cardiovascular Cells: From Developmental Biology to Therapeutic Applications," Cell Stem Cell, 2019, vol. 25, pp. 311-327.
Ramaiahgari S. C., et al., "A 3D in Vitro Model of Differentiated HepG2 Cell Spheroids with Improved Liver-Like Properties for Repeated Dose High-Throughput Toxicity Studies," Archives of Toxicology, Mar. 6, 2014, pp. 1083-1095, DOI: 10.1007/s00204-014-1215-9.
Raouf Z., et al., "Colitis-Induced Small Intestinal Hypomotility Is Dependent on Enteroendocrine Cell Loss in Mice," Cellular and Molecular Gastroenterology and Hepatology, 2024, vol. 18, No. 1, pp. 53-70, DOI: 10.1016/j.jcmgh.2024.02.017.
Ren. H., et al., "Identifying multicellular spatiotemporal organization of cells with SpaceFlow," Nature Communications, 2022, vol. 13, Article 4076, 14 pages.
Romayor I., et al., "A Comparative Study of Cell Culture Conditions During Conversion from Primed to Naive Human Pluripotent Stem Cells," Biomedicines, Jun. 9, 2022, vol. 10, 19 pages.
Rutherford. D., et al., "Therapeutic Potential of Human Intestinal Organoids in Tissue Repair Approaches in Inflammatory Bowel Diseases," Inflammatory Bowel Diseases, 2023, vol. 29, pp. 1488-1498.
Ryu. S., et al., "Enhancing the Fitness of Embryoid Bodies and Organoids by Chemical Cytoprotection," bioRxiv preprint, Mar. 23, 2022, 40 pages.
Selvaggi. G., et al., "Overview of intestinal and multivisceral transplantation," UpToDate, Jul. 3, 2024, https://www.uptodate.com/contents/overview-of-intestinal-and-multivisceral-transplantation/print, accessed Sep. 11, 2024, 3 pages.
Shafa M., et al., "Expansion and Long-Term Maintenance of Induced Pluripotent Stem Cells in Stirred Suspension Bioreactors",

(56) References Cited

OTHER PUBLICATIONS

Journal of Tissue Engineering and Regenerative Medicine, Jun. 1, 2012, vol. 6, No. 6, pp. 462-472, DOI: 10.1002/term.450.
Shi M., et al., "Directed differentiation of ureteric bud and collecting duct organoids from human pluripotent stem cells," Nature Protocols, 2023, vol. 18, pp. 2485-2508.
Shi. M., et al., "Human ureteric bud organoids recapitulate branching morphogenesis and differentiate into functional collecting duct cell types," Nature Biotechnology, 2023, vol. 41, pp. 252-261.
Simunovic M., et al., "Embryoids, Organoids and Gastruloids: New Approaches to Understanding Embryogenesis," Development, 2017, vol. 144, pp. 976-985, doi: 10.1242/dev.143529.
Song L., "Modelling 3-D Brain-like Tissues Using Human Stem Cell-Derived Vascular Spheroids, Cortical Spheroids and Microglia-like Cells," Florida State University Libraries, 2018, 208 pages, Retrieved from Internet URL: https://www.proquest.com/docview/2124413137?pq-origsite=gscholar&fromopenview=true.
Stirparo. G.G., et al., "Integrated analysis of single-cell embryo data yields a unified transcriptome signature for the human pre-implantation epiblast," Development, 2018, vol. 145(3), 26 pages.
Stresser. D., et al., "Validation of Pooled Cryopreserved Human Hepatocytes as a Model for Metabolism Studies," ResearchGate, Jan. 1, 2004, Retrieved from: https://www.researchgate.net/publication/268359224, accessed Jun. 28, 2024.
Sweeney. M., et al., "It Takes Two: Endothelial-Perivascular Cell Cross-Talk in Vascular Development and Disease," Cell Reports, 2018, vol. 24, pp. 2705-2715.
Sweeney, M.D. et al., "Blood-brain barrier breakdown in Alzheimer disease and other neurodegenerative disorders," Nature Reviews Neurology, 2018, 14, pp. 133-150.
Takahashi J., et al., Suspension Culture in a Rotating Bioreactor for Efficient Generation of Human Intestinal Organoids, Cell Reports Methods, Nov. 1, 2022, vol. 2, No. 11, 15 pages, DOI: 101-110 10.1016/j.crmeth.2022.100337, Retrieved from the Internet URL: https://www.ncbi.nlm.nih.gov/pmc/articles/PMC9701612/pdf/main.pdf.
Takahashi, Y. et al., "Organoid-derived intestinal epithelial cells are a suitable model for preclinical toxicology and pharmacokinetic studies," iScience, 2022, 25, pp. 104542.
Takebe, T. et al., "Organoids by design," Science, 2019, vol. 364, pp. 956-959.
The Tabula Muris Consortium, "Single-cell transcriptomics of 20 mouse organs creates a Tabula Muris," Nature, 2018, 562, pp. 367-372.
Ahn Y., et al., "Human Blood Vessel Organoids Penetrate Human Cerebral Organoids and Form a Vessel-Like System," Cells, Aug. 9, 2021, vol. 10, No. 2036, 12 pages, Retrieved from the Internet URL: https://doi.org/10.3390/cells10082036.
Andang M. et al., "Optimized Mouse ES Cell Culture System by Suspension Growth in a Fully Defined Medium", Nature Protocols, May 1, 2008, vol. 3, No. 6, pp. 1013-1017, DOI: 10.1038/nprot.2008.65.
Asano H., et al., "Astrocyte Differentiation of Neural Precursor Cells is Enhanced by Retinoic Acid Through a Change in Epigenetic Modification," Stem Cells, 2009, vol. 27, pp. 2744-2752, Retrieved from the Internet URL: https://academic.oup.com/stmcls/article/27/11/2744/6401847.
Bakhti. M., et al., "Modelling the Endocrine Pancreas in Health and Disease," Nat Rev Endocrinol, 2019, vol. 15, pp. 155-171.
Balboa. D., et al., "Functional, Metabolic and Transcriptional Maturation of Human Pancreatic Islets Derived from Stem Cells," Nat Biotechnol, 2022, vol. 40, pp. 1042-1055.
Bar-Nur O., et al., "Small Molecules Facilitate Rapid and Synchronous iPSC Generation" Nature Methods, Nov. 2024, vol. 11, No. 11, pp. 1170-1179.
Binek. A., et al., "Flow Cytometry Has a Significant Impact on the Cellular Metabolome," Journal of Proteome Research, 2019, vol. 18, pp. 169-181.
Bipat. R., et al., "Drinking Water with Consumption of a Jelly Filled Doughnut Has a Time Dependent Effect on the Postprandial Blood Glucose Level in Healthy Young Individuals," Clinical Nutrition ESPEN, 2018, vol. 27, pp. 20-23.
Box. A., et al., "Evaluating the Effects of Cell Sorting on Gene Expression," Journal of Biomolecular Techniques, 2020, vol. 31, pp. 100-111.
Brafman D.A., et al., "Analysis of SOX2-Expressing Cell Populations Derived from Human Pluripotent Stem Cells," Stem Cell Reports, Nov. 19, 2013, vol. 1, pp. 464-478.
Campinho. P., et al., "Blood Flow Forces in Shaping the Vascular System: A Focus on Endothelial Cell Behavior," Frontiers in Physiology, 2020, vol. 11, pp. 552.
Cervantes D. C., et al., "Peering Into Tunneling Nanotubes—The Path Forward," The EMBO Journal, 2021, vol. 40, 22 pages.
Coll. M., et al., "Generation of Hepatic Stellate Cells from Human Pluripotent Stem Cells Enables In Vitro Modeling of Liver Fibrosis," Cell Stem Cell, 2018, vol. 23, pp. 101-113.
Cormier J.T., et al., "Expansion of Undifferentiated Murine Embryonic Stem Cells as Aggregates in Suspension Culture Bioreactors," Tissue Engineering, Nov. 1, 2006, vol. 12, No. 11, pp. 3233-3245, Retrieved from the Internet URL: https://www.liebertpub.com/doi/epdf/10.1089/ten.2006.12.3233.
Crouch. E.E., et al., "Ensembles of Endothelial and Mural Cells Promote Angiogenesis in Prenatal Human Brain," Cell, 2022, vol. 185, pp. 3753-3769.
Dao. L., etal., "Modeling Blood-Brain Barrier Formation and Cerebral Cavernous Malformations in Human PSC-Derived Organoids," Cell Stem Cell, Jun. 6, 2024, vol. 31, pp. 818-833.
Darrigrand. J. F., et al., "Acinar-Ductal Cell Rearrangement Drives Branching Morphogenesis of the Murine Pancreas in an IGF/PI3K-Dependent Manner," Developmental Cell, 2024, vol. 59, pp. 326-338.
Duester G., "Retinoic Acid Synthesis and Signaling During Early Organogenesis," Cell, Sep. 19, 2008, vol. 134, No. 6, pp. 921-931.
Duggal G., et al., "Alternative Routes to Induce Naive Pluripotency in Human Embryonic Stem Cells," Stem Cells, 2015, vol. 33, pp. 2686-2698.
Edwards. N.A., et al., "Developmental Basis of Trachea-Esophageal Birth Defects," Developmental Biology, 2021, vol. 477, pp. 85-97.
Eicher. A.K., et al., "Engineering Functional Human Gastrointestinal Organoid Tissues Using the Three Primary Germ Layers Separately Derived from Pluripotent Stem Cells," Biorxiv, 2021, 41 pages.
Elmentaite. R., et al., "Single-Cell Sequencing of Developing Human Gut Reveals Transcriptional Links to Childhood Crohn's Disease," Developmental Cell, 2020, vol. 55, pp. 771-783.
Eubelen. M., et al., "A Molecular Mechanism for Wnt Ligand-Specific Signaling," Science, Jul. 19, 2018, vol. 361, 14 pages.
Eze. U.C., et al., "Single-cell atlas of early human brain development highlights heterogeneity of human neuroepithelial cells and early radial glia," Nature Neuroscience, 2021, vol. 24, pp. 584-594.
Fan. X., et al., "Single-Cell Transcriptome Analysis Reveals Cell Lineage Specification in Temporal-Spatial Patterns in Human Cortical Development," Science Advances, 2020, vol. 6, 15 pages.
Feng. Y., et al., "Identification of Rare Heterozygous Missense Mutations in FANCA in Esophageal Atresia Patients Using Next Generation Sequencing," Gene, 2018, vol. 661, pp. 182-188.
Gehart. H., et al., "Identification of Enteroendocrine Regulators by Real-Time Single-Cell Differentiation Mapping," Cell, 2019, vol. 176, pp. 1158-1173.
Geudens. I., et al., "Artery-Vein Specification in the Zebrafish Trunk is Pre-Patterned by Heterogeneous Notch Activity and Balanced by Flow-Mediated Fine-Tuning," Development, 2019, vol. 146, No. 16, 26 pages.
Gieseck R. L., et al., "Maturation of Induced Pluripotent Stem Cell Derived Hepatocytes by 3D-Culture," PLoS ONE, vol. 9, No. 1, Jan. 22, 2014, vol. 9, No. 1, 7 pages, DOI: 10.1371/journal.pone.0086372.
Goodwin. K., et al., "Branching Morphogenesis," Development, 2020, vol. 147, 6 Pages.
Grenier K., et al., "Three-Dimensional Modeling of Human Neurodegeneration: Brain Organoids Coming of Age," Molecular Psychiatry, 2020, vol. 25, pp. 254-274, DOI: 10.1038/S41380-019-0500-7.

(56) References Cited

OTHER PUBLICATIONS

Guo, Z., et al., "Human Vascularized Brain Organoids with Blood-Brain-Barrier Formation for Study of Brain Vascular Disorders," Center for Stem Cell & Organoid Medicine (CUSTOM), Division of Developmental Biology Cincinnati Children's Hospital Medical Center, Frontiers in Stem Cell & Organoid Medicine Symposium, Mar. 24, 2022.

Gupta A. K., et al., "An Efficient Method to Generate Kidney Organoids at the Air-Liquid Interface," Journal of Biological Methods, 2021, vol. 8, No. 2, 11 pages.

Hagey. D. W., et al., "SOX2 Regulates Common and Specific Stem Cell Features in the CNS and Endoderm-Derived Organs," PLOS Genetics, 2018, vol. 14, No. 2, 20 pages.

Han. X., et al., "Construction of a Human Cell Landscape at Single-Cell Level," Nature, 2020, vol. 581, pp. 303-309.

Hancili S., et al., "A Novel NEUROG3 Mutation in Neonatal Diabetes Associated with a Neuro-Intestinal Syndrome," Pediatric Diabetes, 2018, vol. 19, pp. 381-387.

Hao Y., et al., "Dictionary Learning for Integrative, Multimodal and Scalable Single-Cell Analysis," Nature Biotechnology, 2024, vol. 42, pp. 293-304.

Harley J. B., et al., "Transcription Factors Operate Across Disease Loci, with EBNA2 Implicated in Autoimmunity," Nature Genetics, 2018, vol. 50, No. 5, pp. 699-707.

He S. et al., "Single-Cell Transcriptome Profiling of an Adult Human Cell Atlas of 15 Major Organs," Genome Biology, 2020, vol. 21, No. 294, 34 pages.

Herring C. A., et al., "Human Prefrontal Cortex Gene Regulatory Dynamics from Gestation to Adulthood at SingleCell Resolution," Cell, 2020, vol. 185, pp. 4428-4447.

Honda A., et al., "Discrimination of Stem Cell Status After Subjecting Cynomolgus Monkey Pluripotent Stem Cells to Naive Conversion," Scientific Reports, Mar. 28, 2017, vol. 7, 14 pages, DOI: 10.1038/srep45285.

Huang L., et al., "Commitment and Oncogene-Induced Plasticity of Human Stem Cell-Derived Pancreatic Acinar and Ductal Organoids," Cell Stem Cell, 2021, vol. 28, pp. 1090-1104.

Huang L., et al., "Revealing the Structure and Organization of Intercellular Tunneling Nanotubes (TNTs) by STORM Imaging", Nanoscale Advances, 2022, vol. 4, pp. 4258-4262.

Jaeseo L., et al., "A 3D Alcoholic Liver Disease Model on a Chip", Integrative Biology, Jan. 1, 2016, vol. 8, No. 3, pp. 302-308.

Kamada T., et al., "Evidence-Based Clinical Practice Guidelines for Peptic Ulcer Disease 2020," Journal of Gastroenterology, 2021, vol. 56, pp. 303-322.

Kamal K., et al., "Bioengineering an Artificial Human Blood-Brain Barrier in Rodents," Bioengineering, Apr. 30, 2019, vol. 6, 14 pages, doi:10.3390/bioengineering6020038.

Kasagi Y., et al., "The Esophageal Organoid System Reveals Functional Interplay Between Notch and Cytokines in Reactive Epithelial Changes," Cellular and Molecular Gastroenterology and Hepatology, 2018, vol. 5(3), pp. 333-352.

Katsura H., et al., "Human Lung Stem Cell-Based Alveolospheres Provide Insights into SARS-CoV-2 Mediated Interferon Responses and Pneumocyte Dysfunction," Cell Stem Cell, 2020, doi:10.1016/j.stem.2020.10.005.

Kechele D.O., et al., "Recent Advances in Deriving Human Endodermal Tissues from Pluripotent Stem Cells," Current Opinion in Cell Biology, 2019, vol. 61, pp. 92-100.

Kehoe D. E et al., "Scalable Stirred-Suspension Bioreactor Culture of Human Pluripotent Stem Cells," Tissue Engineering, Jan. 1, 2010, vol. 16, No. 2, pp. 405-421, DOI: 10.1089/ten.tea.2009.0454.

Basak O., et al., "Induced Quiescence of Lgr5+ Stem Cells in Intestinal Organoids Enables Differentiation of Hormone-Producing Enteroendocrine Cells", Cell Stem Cell, Feb. 2, 2017, vol. 20, No. 2, pp. 177-190.

Dana-Farber Cancer Institute, "Clinical Trials for Relapsed Cancer," 2025, [retrieved on Mar. 28, 2025], 4 pages, Retrieved from the Internet URL: https://www.danafarberbostonchildrens.org/our-services/innovative-approaches/clinical-trials-relapsed-cancer.

Guerra V. A., et al., "Venetoclax-based Therapies for Acute Myeloid Leukemia," Best Practice and Research Clinical Haematology, 2019, vol. 32, pp. 145-153.

International Search Report and Written Opinion for Application No. PCT/US2023/067716, mailed Nov. 29, 2023, 12pages.

Macea M.M.I., et al., "Quantitative Study of Brunner's Galnds in the Human Duodenal Submucosa," Int. J. Morphol, Jan. 1, 2006, vol. 24, No. 1, pp. 7-12, Retrieved from the Internet: URL: https://www.scielo.cl/pdf/ijmorphol/v24n1/art02.pdf.

Ni X., et al., "A Region-Resolved Mucosa Proteome of the Human Stomach," Nature Communications, 2019, vol. 10, pp. 1-11.

Schmidt S., et al., "A Blood Vessel Organoid Model Recapitulating Aspects of Vasculogenesis, Angiogenesis and Vessel Wall Maturation" Organoids, Apr. 28, 2022, vol. 1, No. 1, pp. 41-53, DOI: 10.3390/organoids1010005.

Willenbring H., et al., "Transplantable Liver Organoids Made From Only Three Ingredients," Cell Stem Cell, Aug. 1, 2013, vol. 13, No. 2, 4 pages, DOI:10.1016/j.stem.2013.07.014.

Wong H. R., et al., "Biomarkers for Estimating Risk of Hospital Mortality and Long-Term Quality of Life Morbidity after Surviving Pediatric Septic Shock: A Secondary Analysis of the LAPSE Investigation" Pediatric Critical Care Medicine, Jan. 1, 2021, vol. 22, No. 1, pp. 8-15.

World Health Organization, "Preventing Cancer" 2025, [retrieved on Mar. 28, 2025], 11 pages, Retrieved from the Internet URL: "https://www.who.int/activities/preventing-cancer".

Xinaris C., et al., "In Vivo Maturation of Functional Renal Organoids Formed from Embryonic Cell Suspensions," Journal of the American Society of Nephrology, Nov. 1, 2012, vol. 23, No. 11, pp. 1857-1868.

\* cited by examiner

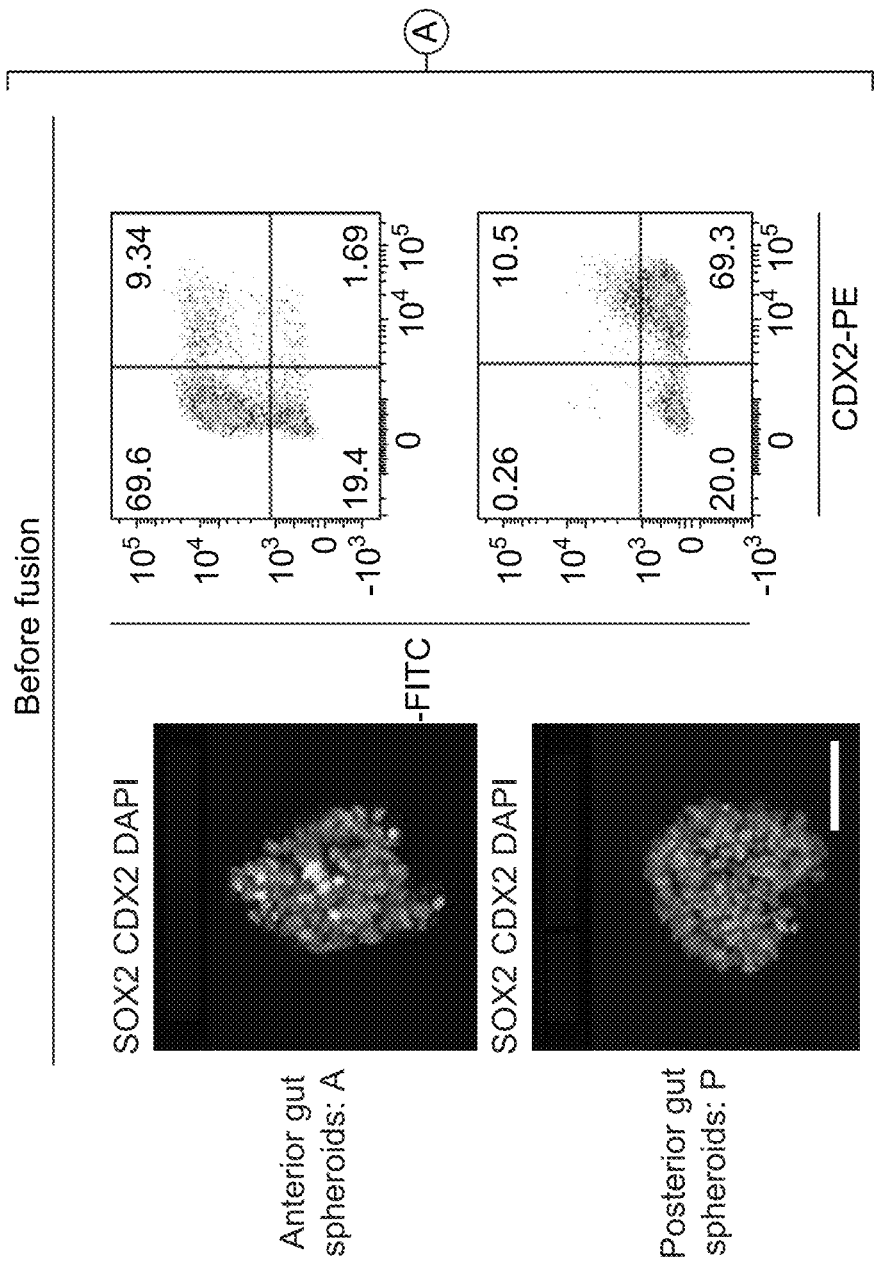
FIG. 1B-A

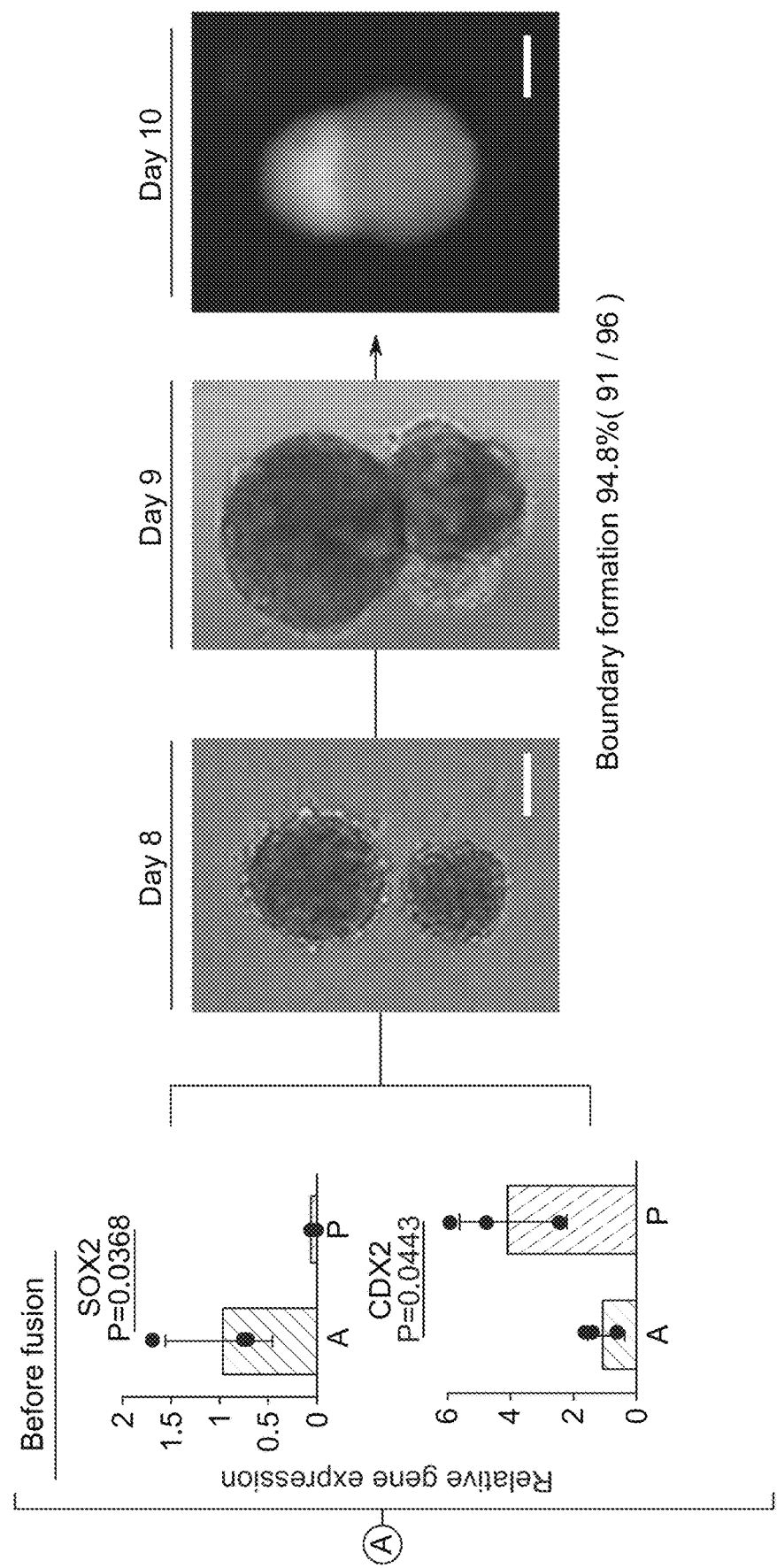
FIG. 1B-B

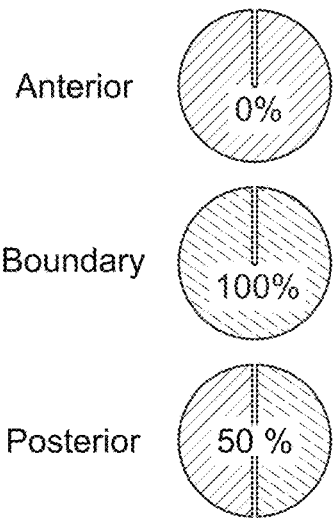
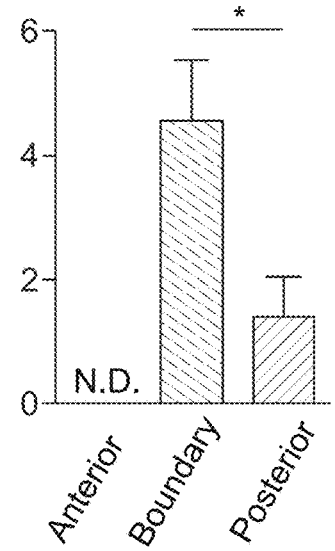
FIG. 1D
FIG. 1E
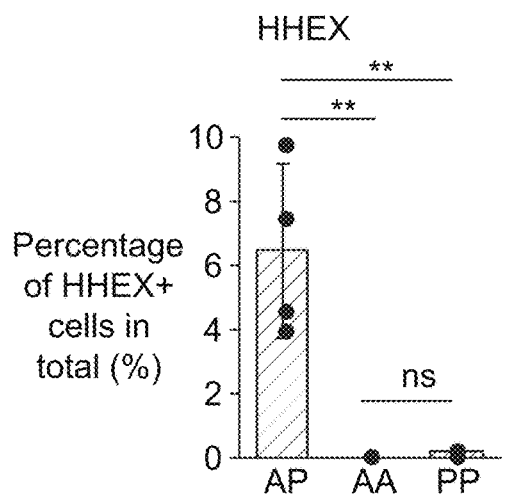
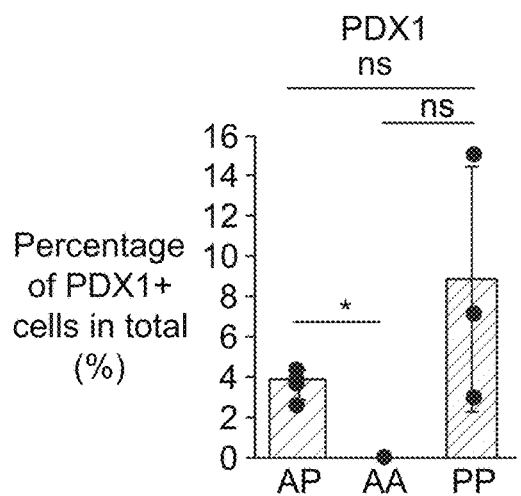
FIG. 1F

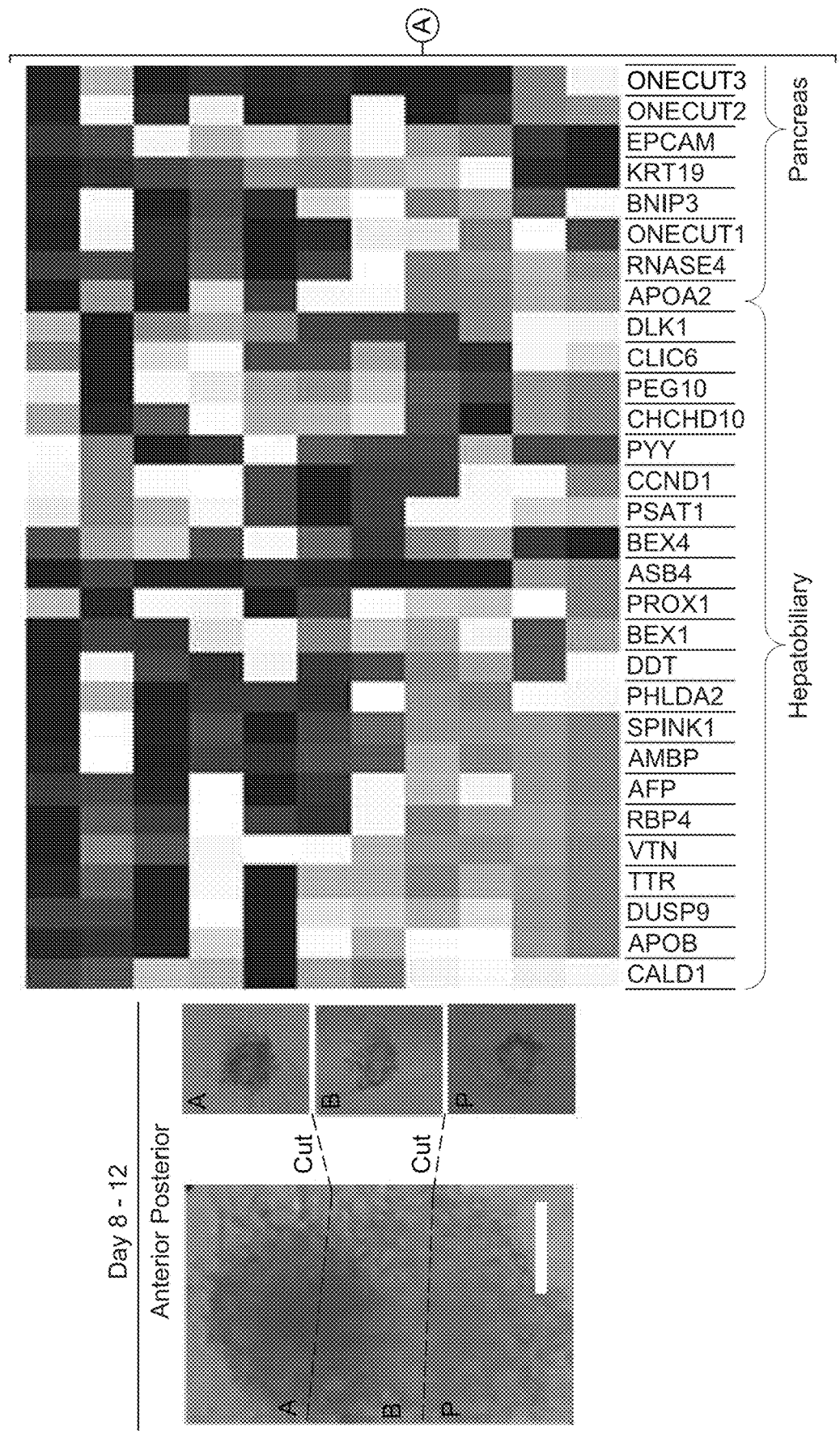
FIG. 1G-A

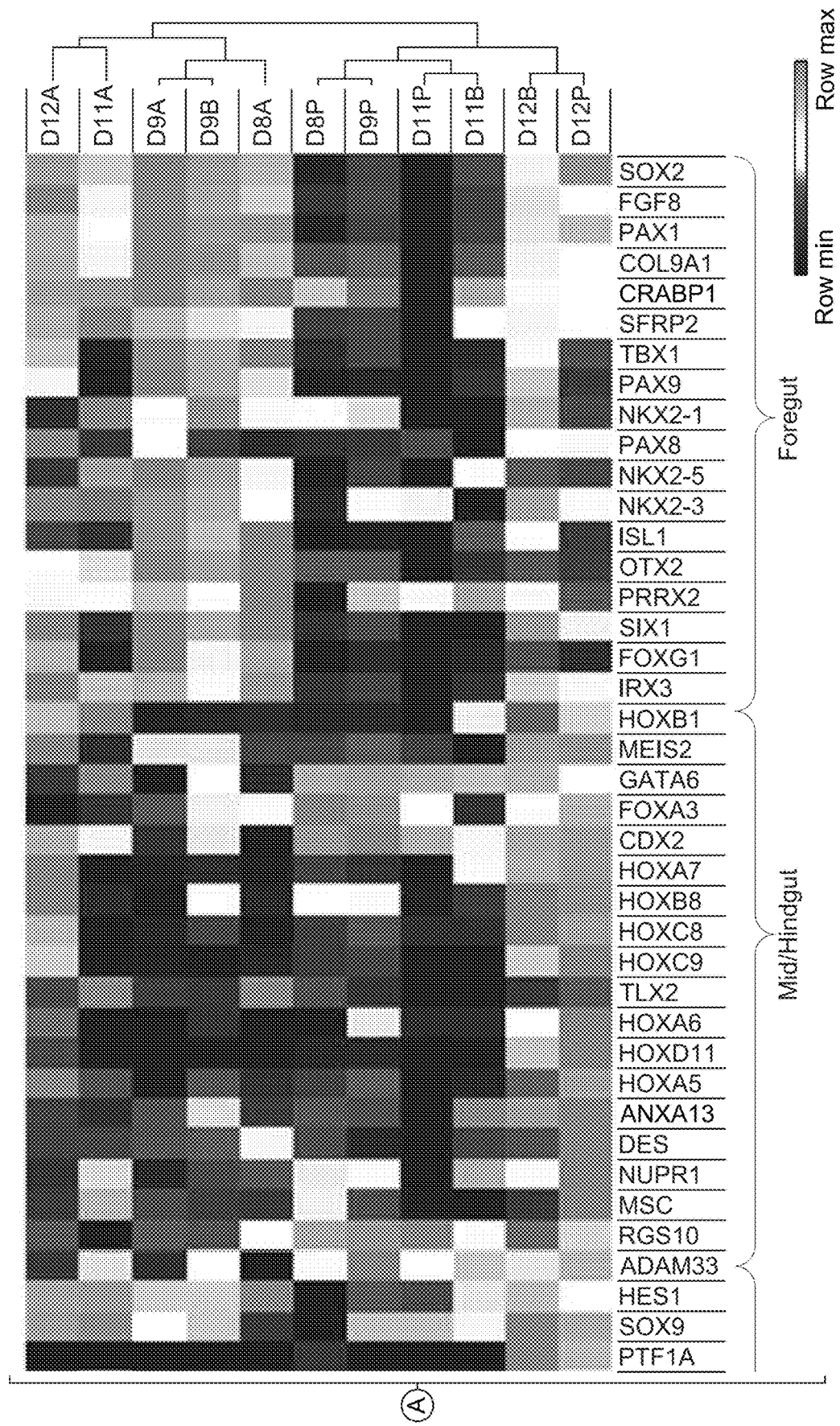
FIG. 1G-B

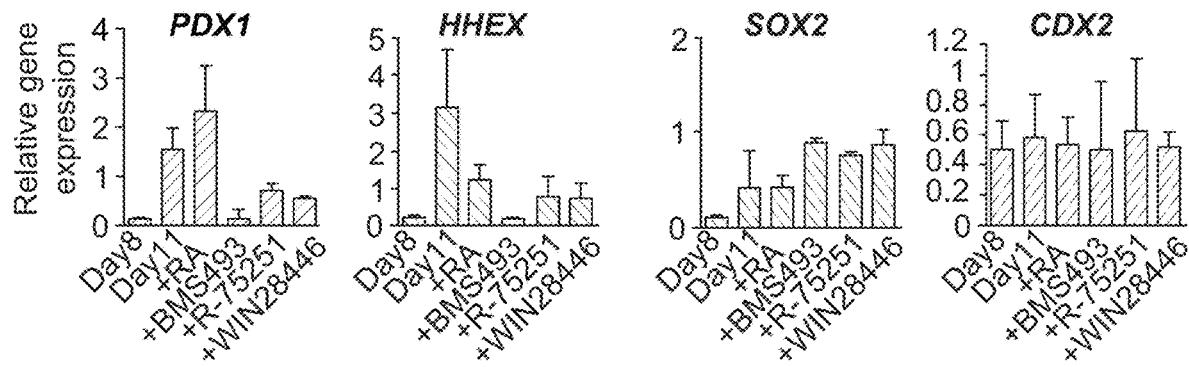
FIG. 2G
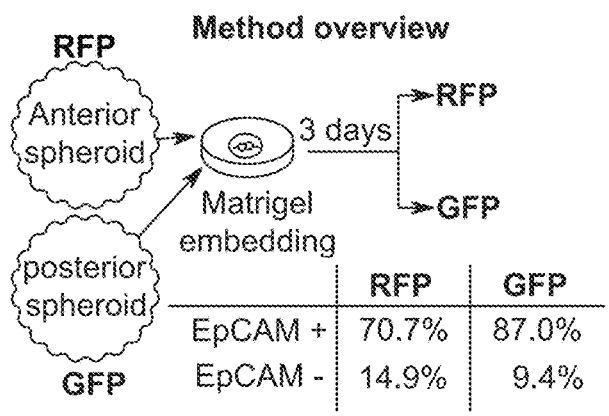
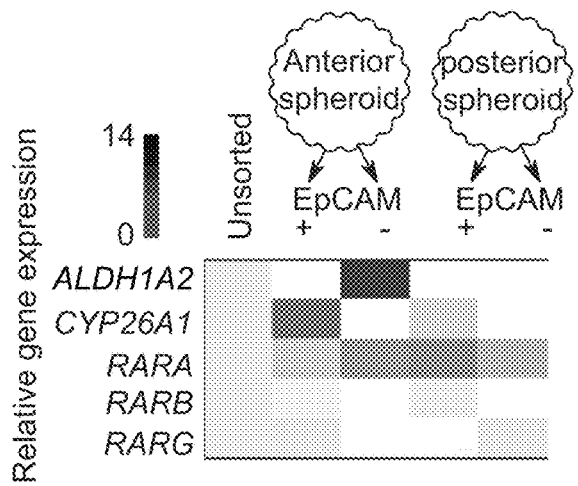
FIG. 2H

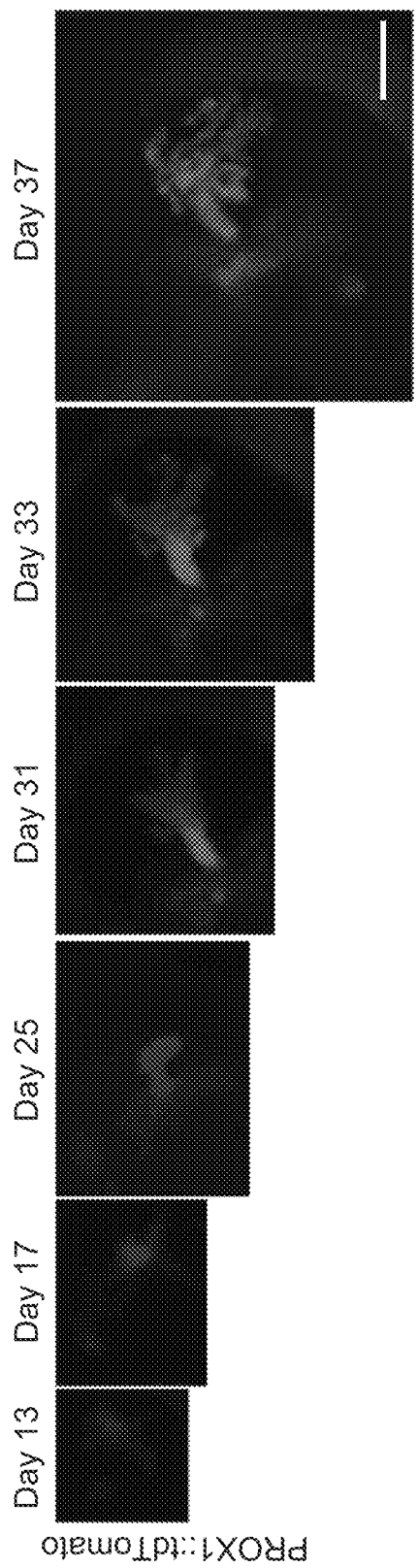
FIG. 3D
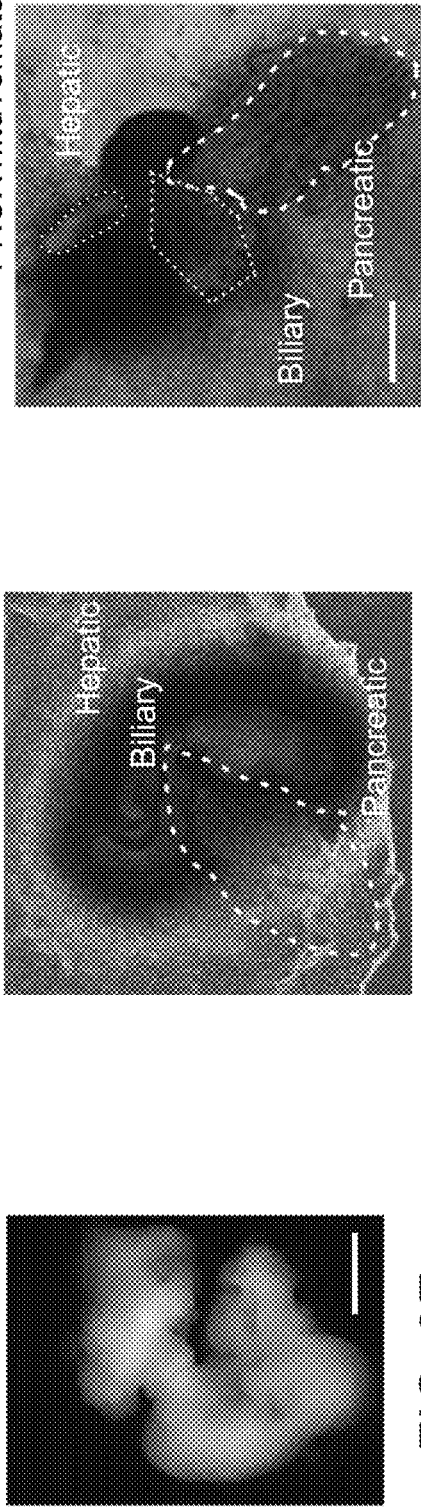
FIG. 3F
FIG. 3E

SEQ ID NO: 50 — AAAAAAAAAGGAAAATGCCAGCTGATATAATGGAGAAAATTCCTCGTC
SEQ ID NO: 51 — AAAAA
SEQ ID NO: 52 — CCCGGTGCTACCCCAGCCAGTGTCAACACGACACCGGATAA WT
SEQ ID NO: 53 — CACGACACCGGATAA Del #11

FIG. 4B

Fused at D9
D9 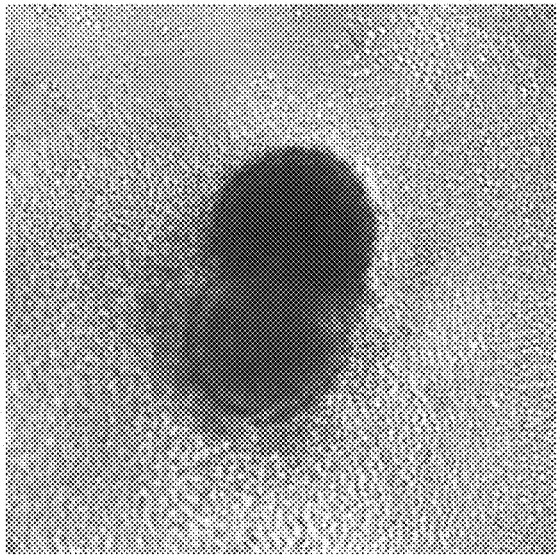 D12 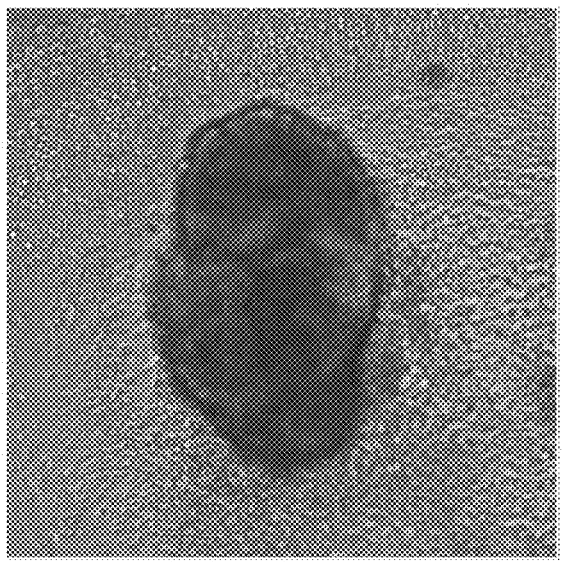
Non-fused
D9 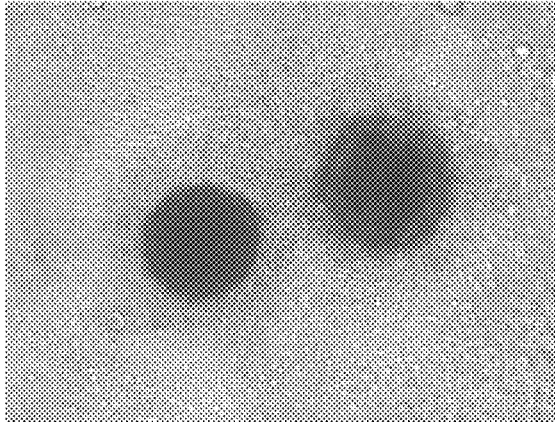 D12 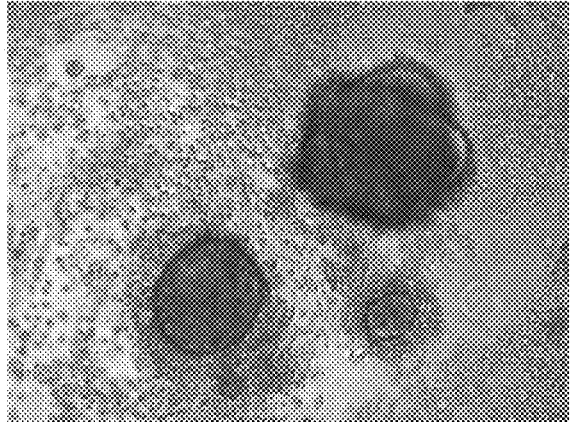
FIG. 7A

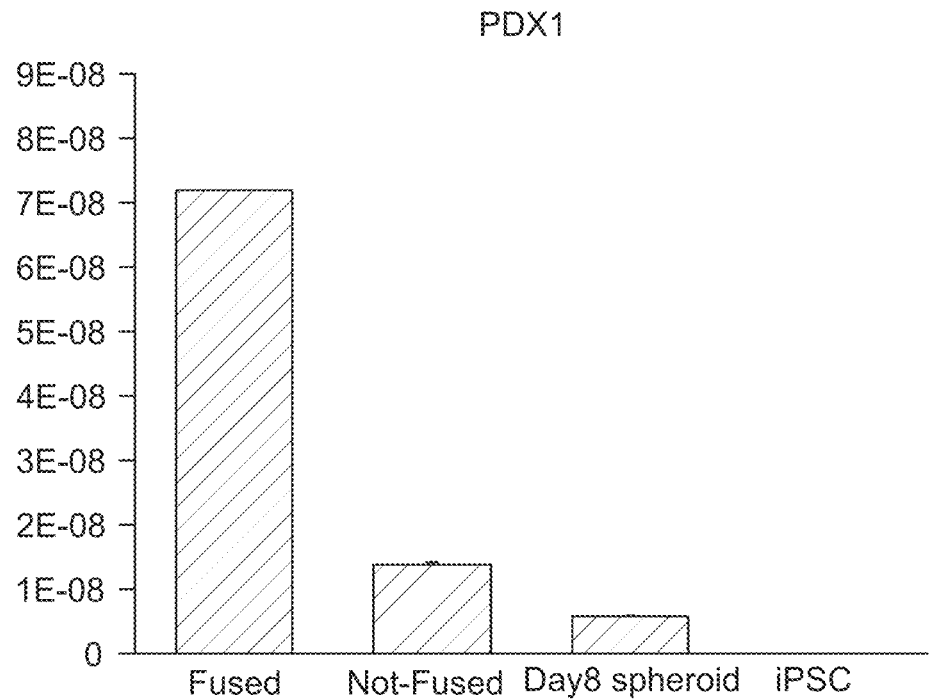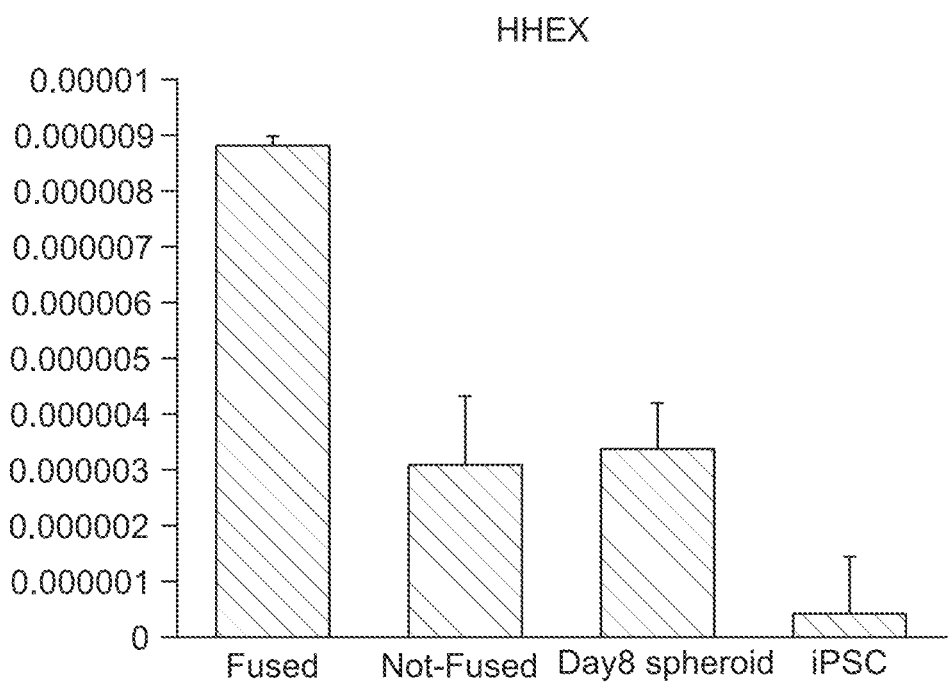
FIG. 7B

HEPATO-BILIARY-PANCREATIC TISSUES AND METHODS OF MAKING SAME

CROSS-REFERENCE TO RELATED APPLICATIONS

This application is a National Phase entry of International Application No. PCT/US2019/041985, filed Jul. 16, 2019, designating the United States and published in the English language, which claims priority to and benefit of U.S. Application No. 62/703,559, entitled "Modeling hepato-biliary-pancreatic organogenesis from the foregut-midgut boundary in humans," filed Jul. 26, 2018, the contents of each of which are expressly incorporated herein by reference in their entirety for all purposes.

REFERENCE TO SEQUENCE LISTING

The present application is being filed with a Sequence Listing in electronic format. The Sequence Listing is provided as a file entitled CHMC63_016SeqListing. TXT, which was created and last modified on Jan. 25, 2021 and is 10,282 bytes in size. The information in the electronic Sequence Listing is hereby expressly incorporated by reference in its entirety.

BACKGROUND

Organogenesis is a complex and inter-connected process, orchestrated by multiple boundary tissue interactions[1-7]. However, to date, it has been unclear how individual, neighboring components coordinate to establish an integral multi-organ structure. Thus, multi-organ integration in stem cell culture has been a critical unmet challenge. Specifically, obtaining structurally and functionally integrated organoids having more than one tissue type is an unmet need in the art. More particularly, the patterning and balanced organogenesis of the hepato-biliary-pancreatic (HBP) system has not been successfully modelled in tissue culture due to technical complexities, hindering detailed mechanistic studies[16,17]. The instant disclosure seeks to address one or more of the aforementioned needs in the art.

BRIEF SUMMARY

Disclosed herein are hepato-biliary-pancreatic organoid ("HBPO" or "HBP organoid") compositions, and methods of making and using hepato-biliary-pancreatic organoid compositions. The disclosed compositions may have two or more functions selected from hepatic tissue function, biliary tissue function, exocrine pancreatic function, and endocrine pancreatic tissue function. Methods of treating individuals using the hepato-biliary-pancreatic organoid compositions is also disclosed.

BRIEF DESCRIPTION OF THE DRAWINGS

Those of skill in the art will understand that the drawings, described below, are for illustrative purposes only. The drawings are not intended to limit the scope of the present teachings in any way.

FIG. 1A-1G. Boundary organoid generates multi-endoderm domains. 1A. Schematic overview for establishing the hepato-biliary-pancreatic (HBP) organoid ("HBPO") from iPSC. Human PSCs were differentiated into anterior or posterior gut cells. The cells were dissociated into single cells and reaggregated to form anterior/posterior gut spheroids, and anterior-posterior boundary organoids were generated in Matrigel™ Matrigel™ embedding initiated multi-organ specification and invagination from boundary organoids. 1B. Generation of boundary organoid via fusion of SOX2+ anterior and CDX2+ posterior gut spheroids. SOX2 and CDX2 expressions were confirmed by wholemount immunostaining for SOX2, CDX2, and DAPI in White, flowcytometry for percentage of each population showed as inlet numbers, and by qPCR. Data is mean±s.d.; n=3 independent experiments. Unpaired, two-tailed Student's t-test. 1C. Tracing of human iPSC derived anterior and posterior organoids mix from Day 8 to Day 11. Upper row: Brightfield. Middle row: whole mount immunostaining for SOX2 in Red, PDX1, CDX2 and DAPI in White. Lower row: whole mount immunostaining for CDX2, HHEX, PDX1 and DAPI in White. Arrow: PDX1 and HHEX positive region. 1D. Frequency of detected PDX1 positive cell in each area of boundary organoid immunofluorescent stained for PDX1. 1E. Position of PDX1 positive cells in each boundary organoid. Y axis showed percentages of PDX1 positive cells in each area compared to DAPI stained total cell numbers. f. Percentage of HHEX and PDX1 positive cells for fused organoid in various combination, anterior-posterior (AP) (n=4), anterior-anterior (AA) (n=3) and posterior-posterior (PP) (n=3) at Day 11. Y axis showed percentages of positive cells compared to DAPI stained total cell numbers. Data are mean±s.d. *P<0.05, **P<0.01; one-way ANOVA.g. Transcriptomic characterization of boundary organoids with time course, from Day 8 (D8) to Day 12 (D12). Anterior (A), boundary (B), and posterior (P) domains were dissected, separated, and applied for RNA sequencing as indicated in left representative image (anterior gut spheroid was labeled by GFP and posterior gut spheroid was labeled by RFP). Anterior, boundary, and posterior domains showed the enrichment of the gene-sets of anterior foregut, liver/biliary/pancreas primordium and mid/hindgut markers reported[31,32], respectively. Scale bars, 50 μm (1B), 100 μm (1C), 50 μm (1G).

FIG. 2A-2I. Self-emergence of hepato-biliary-pancreatic progenitors from boundary organoid without inductive factors. 2A. Generating PROX1-tdTomato reporter line by CRISPR-Cas9 gene editing system. 2B. PROX1-tdTomato expression in established PROX1 reporter iPSCs from Day 9 to Day 11. 2C. PROX1-tdTomato positive area in each organoid. AP, AA and PP combinations were evaluated. The tdTomato expression was confirmed in the cell membrane of boundary organoids in AP combination. 2D. Hepatic invagination in mouse liver primordium explant (Prox1::GFP) and human iPSC-derived boundary organoids (PROX1::m-tdTomato). 2E. The immunostaining of PROX1 in E8.75 mice embryo and boundary organoids at Day 13. 2F. Transcriptomic characterization of boundary organoids. Anterior, boundary, and posterior domains were dissected, separated, and applied for RNA sequencing. Heatmap shows downstream gene expression related to FGF, BMP, Hedgehog, NOTCH and RA signal pathway selected from GO term category and KEGG pathway category. Heatmap was separated into 8 detailed groups (C1-C8) by unbiased hierarchical clustering. C6 which showed unique expression pattern of highly expressed genes in B indicated an enrichment of RA down-stream gene-sets compared to others. 2G. Gene expression of HHEX, PDX1, SOX2, and CDX2 at Day 11 with three days culture of retinoic acid, BMS493, R-75251, or WIN18446. 2H. Gene expression analysis for RA signal pathway related genes in epithelial or mesenchymal cells from original anterior or posterior gut spheroids. Each gut spheroids were differentiated using RFP or GFP labeled iPSCs and dissociated into single cells after boundary formation. Anterior/Posterior separation was performed by RFP or GFP expression, whereas epithelial/mesenchymal separation was by EpCAM expression. 2I. Default developmental potential of transplanted boundary organoid. Middle panels show H&E staining and immunohistochemistry analysis, whereas right panels show immunofluorescent analysis. Scale bars, 50 μm (2B), 200 μm (2D), 100 μm (2E), 100 μm (2I).

FIG. 4A-4J. Modeling HES1-mediated organ segregation error in HBP organoids. 4A. Gene targeting strategy for HES1 knock out (KO) line by CRISPR-Cas9 system. 4B. Confirmation of modified gene sequence of WT and HES1KO (Del #11) 4C. Photo of HES1-/-iPSC culture 4D. Gene expression of HES1 in HES1 KO iPSC-derived boundary organoid at Day 20. 4E. Confirmation of boundary organoid formation from HES1-/-iPS line by wholemount immunostaining of SOX2, CDX2, PDX1 and HHES. Hepato-biliary-pancreatic precursor specification was preserved even in the presence of HES1 mutation. 4F. PROX1-tdTomato expression in anterior and posterior boundary spheroids generated from HES1+/+ and HES1-/- at D11. 4G. RNAseq of pancreas associated markers at Day 22 of HES1+/+ and HES1-/-HBP organoids. 4H. Gene expression of GCG, NEUROG3, INS, and NKX2-2 in HES1+/+, HES1-/-organoids, and human adult pancreatic tissue. 4I. Macroscopic observation of boundary tissue of HES1+/+ and HES1-/-. 4J. Wholemount immunostaining for DBA and PDX1 shows enhanced PDX1 expression and diminished DBA stained area in HES1 KO organoids. Scale bars, 500 μm (4C), 200 μm (4E), 100 μm (4F), 500 μm (4I), 500 μm (4J).

FIG. 7A-7B Cell-cell contact dependent HBP gene induction. 7A. Anterior and posterior gut spheroids were mixed at D8, fused the following day at D9, cultured and collected at D12 for quantitative RT-PCR. The spheroids that not fused were also collected at D12 for comparison. 7B. PDX1 and HHEX gene expressions in the condition of fused, not-fused, posterior gut spheroid (day 8), and iPS cells.

In FIG. 3A-3C, various culture formats were compared to enhance morphological change, such as invagination and branching morphogenesis, of PROX1 positive HBP precursor region. At D7, anterior and posterior gut spheroids were mixed and connected after 24 hour-culture. Connected spheroids were transferred into Matrigel™ drop or low binding culture plate to compare between non-floating and floating conditions during HBP precursor emergence. The organoid in Matrigel™ embedded group was started to express tdTomato at D11. The tdTomato positive region was manually dissected under microscope according to the fluorescence expression and transferred into Matrigel™ drop again or Transwell™ to compare the effect from various agonist and antagonist in medium.

DETAILED DESCRIPTION

Definitions

Figure 1A:
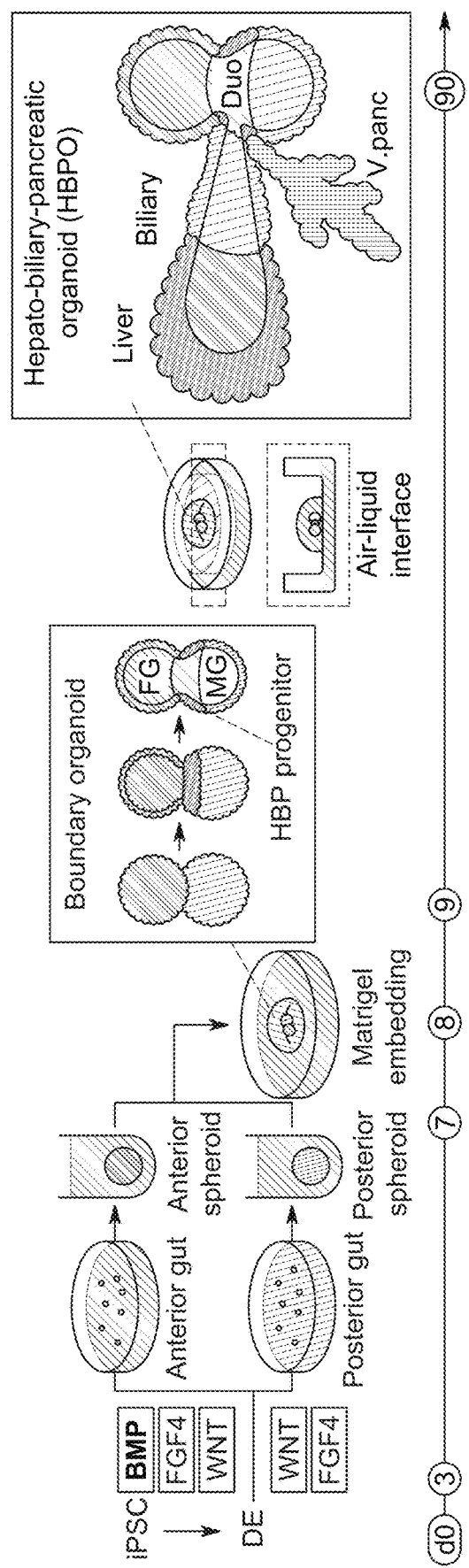

Unless otherwise noted, terms are to be understood according to conventional usage by those of ordinary skill in the relevant art. In case of conflict, the present document, including definitions, will control. Preferred methods and materials are described below, although methods and materials similar or equivalent to those described herein may be used in practice or testing of the present invention. All publications, patent applications, patents and other references mentioned herein are incorporated by reference in their entirety. The materials, methods, and examples disclosed herein are illustrative only and not intended to be limiting.

As used herein and in the appended claims, the singular forms "a," "and," and "the" include plural referents unless the context clearly dictates otherwise. Thus, for example, reference to "a method" includes a plurality of such methods and reference to "a dose" includes reference to one or more doses and equivalents thereof known to those skilled in the art, and so forth.

The term "about" or "approximately" means within an acceptable error range for the particular value as determined by one of ordinary skill in the art, which will depend in part on how the value is measured or determined, e.g., the limitations of the measurement system. For example, "about" may mean within 1 or more than 1 standard deviation, per the practice in the art. Alternatively, "about" may mean a range of up to 20%, or up to 10%, or up to 5%, or up to 1% of a given value. Alternatively, particularly with respect to biological systems or processes, the term may mean within an order of magnitude, preferably within 5-fold, and more preferably within 2-fold, of a value. Where particular values are described in the application and claims, unless otherwise stated the term "about" meaning within an acceptable error range for the particular value should be assumed.

As used herein, the term "definitive endoderm (DE) cell" means one of the three primary germ layers produced by the process of gastrulation.

As used herein the term "wnt signalling pathway" means the wnt/beta-catenin pathway and is a signal transduction pathway that is mediated by Wnt ligands and frizzled cell surface receptors that acts through the beta-catenin protein.

As used herein the term "activator" with respect to a pathway, such as a "wnt pathway" means a substance that activates the Wnt/beta-catenin pathway such that Wnt/beta-catenin targets are increased.

As used herein, the term "FGF signaling pathway activator" means a substance that activates the FGF pathway such that FGF targets are increased.

As used herein, the term "BMP signaling pathway inhibitor" a substance that interferes with the BMP pathway and causes BMP targets to be decreased.

As used herein, the term "growth factor" means a substance capable of stimulating cellular processes including but not limited to growth, proliferation, morphogenesis or differentiation.

As used herein, the term "stable expression" of a marker means expression that does not change upon modification of the growth environment.

As used herein, the term "totipotent stem cells" (also known as omnipotent stem cells) are stem cells that can differentiate into embryonic and extra-embryonic cell types. Such cells can construct a complete, viable, organism. These cells are produced from the fusion of an egg and sperm cell. Cells produced by the first few divisions of the fertilized egg are also totipotent.

As used herein, the term "pluripotent stem cells (PSCs)," also commonly known as PS cells, encompasses any cells that can differentiate into nearly all cells, i.e., cells derived from any of the three germ layers (germinal epithelium), including endoderm (interior stomach lining, gastrointestinal tract, the lungs), mesoderm (muscle, bone, blood, urogenital), and ectoderm (epidermal tissues and nervous system). PSCs can be the descendants of totipotent cells, derived from embryos (including embryonic germ cells) or obtained through induction of a non-pluripotent cell, such as an adult somatic cell, by forcing the expression of certain genes.

As used herein, the term "induced pluripotent stem cells (iPSCs)," also commonly abbreviated as iPS cells, refers to a type of pluripotent stem cells artificially derived from a normally non-pluripotent cell, such as an adult somatic cell, by inducing a "forced" expression of certain genes.

As used herein, the term "precursor cell" encompasses any cells that can be used in methods described herein, through which one or more precursor cells acquire the ability to renew itself or differentiate into one or more specialized cell types. In some aspects, a precursor cell is pluripotent or has the capacity to becoming pluripotent. In some aspects, the precursor cells are subjected to the treatment of external factors (e.g., growth factors) to acquire pluripotency. In some aspects, a precursor cell can be a totipotent stem cell; a pluripotent stem cell (induced or non-induced); a multipotent stem cell; and a unipotent stem cell. In some aspects, a precursor cell can be from an embryo, an infant, a child, or an adult. In some aspects, a precursor cell can be a somatic cell subject to treatment such that pluripotency is conferred via genetic manipulation or protein/peptide treatment.

In developmental biology, cellular differentiation is the process by which a less specialized cell becomes a more specialized cell type. As used herein, the term "directed differentiation" describes a process through which a less specialized cell becomes a particular specialized target cell type. The particularity of the specialized target cell type can be determined by any applicable methods that can be used to define or alter the destiny of the initial cell. Exemplary methods include but are not limited to genetic manipulation, chemical treatment, protein treatment, and nucleic acid treatment.

Disclosed herein are hepato-biliary-pancreatic organoid ("HBPO" or "HBP organoid") compositions. The disclosed HBPO compositions may have, in some aspects, two or more functions selected from hepatic tissue function, biliary tissue function, exocrine pancreatic function, and endocrine pancreatic tissue function. In one aspect, the HBPO disclosed herein may be referred to interchangeably as a "multi-organ three-dimensional organoid" and may comprise an anterior region, a posterior region and a boundary region. In one aspect, the boundary region may express Pancreatic and Duodenal Homeobox 1 (PDX1) and Hematopoietically-Expressed Homeobox Protein (HHEX). In one aspect, the HBPO may comprise bile duct tissue and pancreatic tissue. In one aspect, the bile duct tissue and pancreatic tissue may be connected in the HBPO. In one aspect, the HBPO may comprise liver cells, pancreas cells, bile duct cells, and intestinal cells.

In one aspect, the HBPO may comprise endothelial cells, mesenchymal cells, or both endothelial cells and mesenchymal cells. The HBPO may comprise, in certain aspects, endoderm and mesoderm.

The disclosed HBPOs may be characterized by a branched structure, as shown, for example, in the corresponding figures herein.

In one aspect, the HBPOs disclosed herein may be characterized by expression of a functional exocrine marker. In one aspect, the marker may be amylase. In one aspect, the marker may be an endocrine marker, for example, insulin.

In certain aspects, the HBPOs disclosed herein may be characterized by a functional response to an exogenously administered agent. For example, in one aspect, the HBPO may secrete amylase in response to contact with cholecystokinin (CCK).

In certain aspects, the disclosed HBPOs may be characterized in that the HBPO may be substantially free of one or more of submucosal glands, transition zones, vasculature, immune cells, or submucosal layers. Such features distinguish the three-dimensional organoid structure from that of native tissue found endogenously in a human, or other mammal.

In one aspect, the HBPO is obtained by expansion of one or more precursor cells as defined above, for example, an iPSC obtained from an individual.

Figure 12:
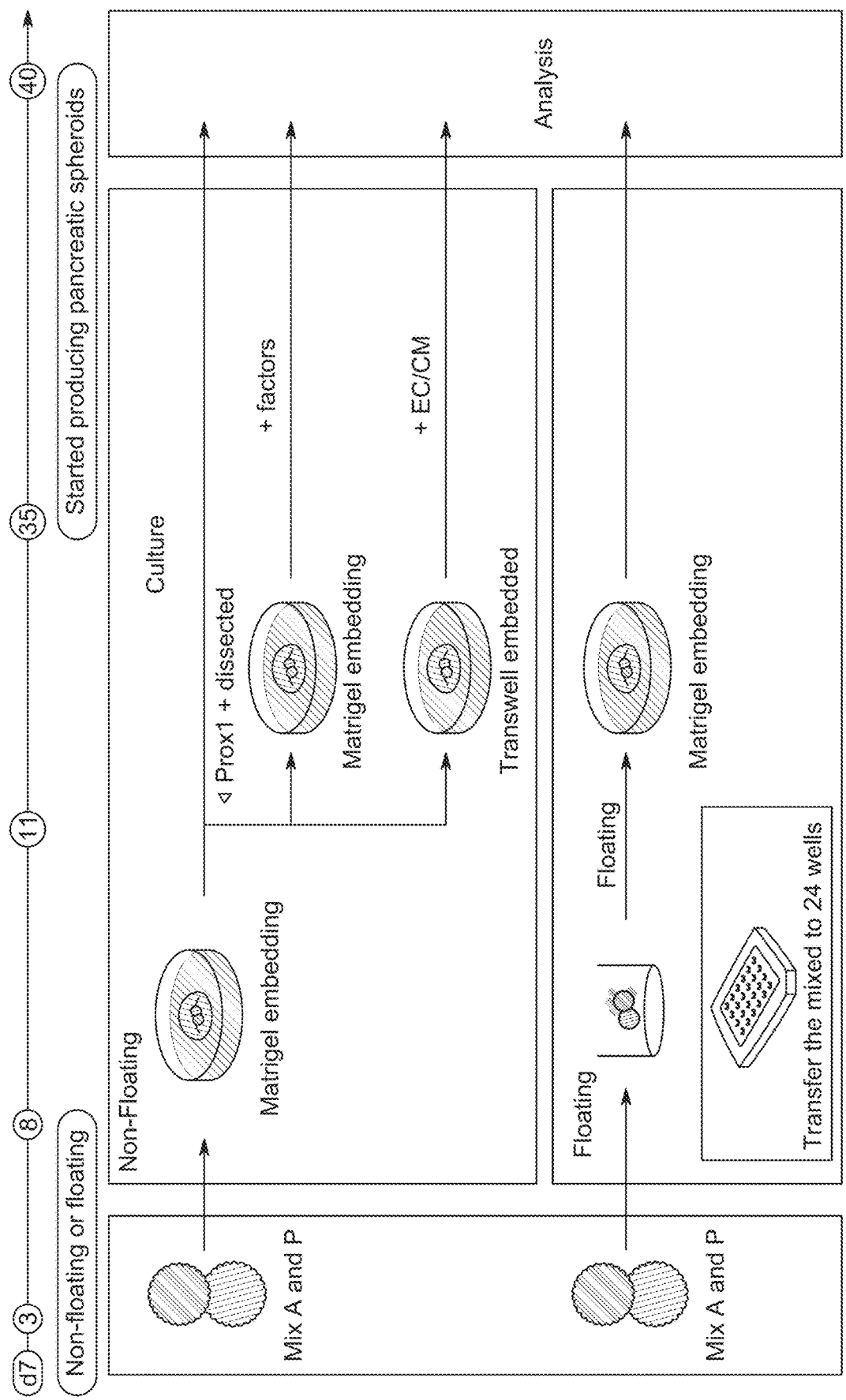

Also disclosed herein are methods of making a hepato-biliary-pancreatic organoid ("HBPO" or "HBP organoid"). In this aspect, the method may comprise contacting a first definitive endoderm with a Wnt signaling pathway activator, an FGF signaling pathway activator, and a BMP signaling pathway inhibitor to form an anterior gut spheroid; contacting a second definitive endoderm with a Wnt signaling pathway activator and an FGF signaling pathway activator to form a posterior gut spheroid; contacting the anterior gut spheroid with the posterior gut spheroid until the anterior gut spheroid and the posterior gut spheroid are fused to form a boundary organoid having a foregut-midgut boundary; and culturing the boundary organoid having the foregut-midgut boundary to form the HBPO; wherein the HBPO comprises biliary tissue and pancreatic tissue. (See, for example, FIG. 12) In one aspect, the disclosed methods may allow for the production of an HBPO that may comprise liver tissue, pancreatic tissue, bile duct tissue, and intestinal tissue.

As used herein, the term hepato-biliary-pancreatic organoid ("HBPO" or "HBP organoid") generally refers to the organoid at the stage in which multi-organ domains (hepatic, biliary and pancreatic organ domains) are segregated, which usually occurs around D30. With regard to the term "boundary organoid," this may include an organoid after D7, which includes organoid compositions that do not yet have tissue specification.

In one aspect, the anterior gut spheroids may comprise cells expressing SRY-box 2 (SOX2). In one aspect, the anterior gut spheroid may be characterized by SRY-box 2 (SOX2) expression. In one aspect, the anterior gut spheroids may be substantially free of Pancreatic and Duodenal Homeobox 1 (PDX1) expressing cells. In one aspect, the posterior gut spheroids comprise cells expressing Pancreatic and Duodenal Homeobox 1 (PDX1). In one aspect, the posterior gut spheroids may express CDX2. In one aspect, the posterior gut spheroid may be characterized by Caudal Type Homeobox 2 (CDX2) expression. In one aspect, the posterior gut spheroids may comprise cells expressing Caudal type homeobox 2 (CDX2). In one aspect, the HBPO may comprise cells expressing Pancreatic and Duodenal Homeobox 1 (PDX1), cells expressing Hematopoietically-expressed homeobox protein (HHEX), and cells expressing Prospero-Related Homeobox 1 (PROX1). In one aspect, the fused anterior gut spheroid and posterior gut spheroid may comprise a biliary-pancreatic primordium characterized by expression of SOX2, CDX2, HHEX, and PDX1, wherein PDX1 expression is localized to the boundary region of the fused anterior gut spheroid and the posterior gut spheroid.

In one aspect, the HBPO may be embedded into a morphogenic factor, preferably a basement membrane matrix, such as, for example, Matrigel™. The method may further comprise excising PROX1 positive regions from the HBPO and culturing the excised HBPO to form invaginating epithelium and a branching structure.

In one aspect, the HBPO may be cultured with rotation, for example, using the methods disclosed herein.

In one aspect, the disclosed methods may be used to obtain an HBPO as described herein, in particular, an HBPO comprising endoderm and mesoderm.

In one aspect, the definitive endoderm may be derived from a precursor cell selected from an embryonic stem cell, an embryonic germ cell, an induced pluripotent stem cell, a mesoderm cell, a definitive endoderm cell, a posterior endoderm cell, a posterior endoderm cell, and a hindgut cell, preferably a definitive endoderm derived from a pluripotent stem cell, more preferably a definitive endoderm derived from a pluripotent stem cell selected from an embryonic stem cell, an adult stem cell, or an induced pluripotent stem cell.

In one aspect, the definitive endoderm may be derived from contacting a pluripotent stem cell with one or more molecules selected from Activin, the BMP subgroups of the TGF-beta superfamily of growth factors; Nodal, Activin A, Activin B, BMP4, Wnt3a, and combinations thereof.

In one aspect, the WNT signaling pathway activator may be selected from one or more molecules selected from the group consisting of Wnt1, Wnt2, Wnt2b, Wnt3, Wnt3a, Wnt4, Wnt5a, Wnt5b, Wnt6, Wnt7a, Wnt7b, Wnt8a, Wnt8b, Wnt9a, Wnt9b, Wnt10a, Wnt10b, Wnt11, Wnt16, a GSKβ inhibitor (e.g., CHIR99021, i.e. "CHIRON"), BIO, LY2090314, SB-216763, lithium, porcupine inhibitors IWP, LGK974, C59, SFRP inhibitor WAY-316606, beta-catenin activator DCA.

In one aspect, the FGF signaling pathway activator may be selected from one or more molecules selected from the group consisting of FGF1, FGF2, FGF3, FGF4, FGF10, FGF11, FGF12, FGF13, FGF14, FGF15, FGF16, FGF17, FGF18, FGF19, FGF20, FGF21, FGF22, FGF23, and combinations thereof, preferably FGF4 or FGF10, or a combination thereof.

In one aspect, the BMP signaling pathway inhibitor may be selected from Noggin, Dorsomorphin, LDN189, DMH-1, and combinations thereof, preferably wherein the BMP signaling pathway inhibitor is Noggin.

In one aspect, the disclosed methods may be conducted in vitro. In certain aspect, at least one step of the method may be carried out on a solid support. For example, the solid support may be selected from collagen, basement membrane matrix (Matrigel™), or a combination thereof.

In one aspect, a method for making an HBPO having an endothelium is disclosed. In this aspect, the method may comprise the step of culturing an HBPO according to the methods disclosed herein, with endothelial cells derived from induced pluripotent stem cells. The endothelial cells may be formed into an endothelial cell (EC) spheroid prior to culturing with an HBPO. For example, for endothelial cell (EC) differentiation, human iPSCs may be dissociated using Accutase (Thermo Fisher Scientific Inc., Waltham, MA, USA) and plated on Laminin 511 E8 fragment (iMatrix-511™, provided by Nippi, Inc.) at varying optimal density (depending on the cell line) in StemFit® (Ajinomoto Co., Inc.) with Rho-associated kinase inhibitor (Y-27632). From the next day, they may first be differentiated into mesoderm using the Priming Medium having B27 medium (1:1 mixture of DMEM:F12 (1:1) with 1% Glutamax and 1% B27 (all Life Technologies) with Wnt activator and bone morphogenetic protein 4 (BMP4) for three days. The priming medium may then be replaced with EC induction medium, StemPro-34 SFM medium (Life Technologies) supplemented with VEGF and forskolin. The induction medium may be renewed daily. On day seven of differentiation, ECs are dissociated and subjected to FACS analysis. iPSC derived ECs should display typical endothelial morphology with junctional localization of CD144 and CD31. ECs may be re-plated on Fibronectin coated dishes at a density of 50,000 cells cm-2 in EC Expansion Medium consisting of StemPro-34 SFM supplemented with VEGF-A. EC Expansion Medium may be replaced every other day. The differentiated EC may be dissociated to single cells and formed into spheroids using the spheroid formation protocol of the anterior gut spheroids and posterior gut spheroids as described herein. The ECs may then be mixed with the fused anterior gut spheroid and the posterior gut spheroid on 96 well round bottom ultra-low attachment plate in gut growth medium for 24 hours to form fused EC spheroid, the anterior gut spheroid and the posterior gut spheroid.

In one aspect, a method for making an HBPO having a mesenchyme is disclosed. In this aspect, the method may comprise the step of culturing an HBPO according to a method as disclosed herein with mesenchymal cells derived from induced pluripotent stem cells. The mesenchyme cells may be formed into a mesenchyme cell (MC) spheroid prior to culturing with the HBPO. The disclosed multi-organ, three-dimensional organoid and mesenchymal cells or a mesenchymal spheroid may be cultured together to improve the growth and maturation of the multi-organ, three-dimensional organoid. For example, for mesenchyme (MSC) differentiation, human iPSCs may be differentiated to mesoderm. The mesoderm cells may then be exposed to 3 days of additional Activin A and PDGFBB. Differentiated MSC may then be dissociated to single cells and formed into spheroids using the spheroid formation protocol of the anterior gut spheroid and posterior gut spheroid. The MSC spheroid may then be mixed with the fused anterior gut spheroid and posterior gut spheroid on 96 well round bottom ultra-low attachment plate in gut growth medium for 24 hours to form a fused MSC spheroid, anterior gut spheroid and posterior gut spheroid.

In one aspect, a method of making a hepato-biliary-pancreatic organoid ("HBPO") is disclosed, wherein the method may comprise deriving an anterior gut spheroid from anterior gut cells and a deriving a posterior gut spheroid from posterior gut cells to make a boundary organoid; and culturing the boundary organoid in gut growth medium to make the HBPO. In one aspect, a method of making a hepato-biliary-pancreatic organoid ("HBPO"), may comprise deriving an anterior gut spheroid and deriving a posterior gut spheroid from anterior gut cells and posterior gut cells to make the HBPO in the absence of inducing factors; and culturing the boundary organoids in a gut growth medium to make HBPO.

By "inducing factors," it is meant a factor used to direct differentiation, for example, retinoic acid (RA; Sigma, MO, USA), hepatocyte growth factor (HGF; PeproTech, NJ, USA), 0.1 µM Dexamethasone (Dex; Sigma) and 20 ng/mL Oncostatin M (OSM; R&D Systems) for hepatocyte differentiation. Many other inducing factors are known for pancreas and biliary also, and would be readily understood by one of skill in the art.

In one aspect, a of method of making a hepato-biliary-pancreatic organoid ("HBPO") is disclosed, wherein the method may comprise culturing a definitive endoderm (DE) differentiated from a pluripotent stem cell (PSC) in gut growth medium to make anterior gut cells and posterior gut cells, making an anterior gut spheroid from anterior gut cells and a posterior gut spheroid from posterior gut cells to make a boundary organoid in the absence of inducing factors; and (iii) culturing boundary organoids in gut growth medium to make an HBPO. In one aspect, the gut growth medium may be a medium comprising a ROCK inhibitor. In one aspect, the ROCK inhibitor may be Y-27632. In one aspect, the growth medium is Advanced DMEM/F-12 (Dulbecco's Modified Eagle Medium/Ham's F-12), a widely used basal medium that allows the culture of mammalian cells with reduced Fetal Bovine Serum (FBS) supplementation, available at Thermo Fisher, with addition of Glutamine, HEPES, N2 and B27. In one aspect, the media may include addition of the following cytokines to Advanced DMEM: Noggin (BMP inhibitor), CHIR (WNT activator), FGF4 for anterior gut cells, CHIR and FGF4 (without Noggin) for posterior gut cells.

In one aspect, a machine for producing an HBPO is disclosed herein. The machine may comprise a gut growth medium containing a Wnt signaling pathway activator and an FGF signaling pathway activator, in the presence or absence of a BMP signaling pathway inhibitor; and a gut growth medium containing a ROCK inhibitor.

In one aspect, use of a plurality of culture mediums for the production of an HBPO, is disclosed, wherein the plurality of culture mediums comprise a gut growth medium containing a Wnt signaling pathway activator and an FGF signaling pathway activator, optionally comprising a BMP signaling pathway inhibitor; and an intestinal growth medium containing a ROCK inhibitor.

In one aspect, the HBPO may be transplanted into a mammal, such as a non-human mammal, for a period of time to increase growth and maturation of the HBPO. In one aspect, the HBPO may be transplanted to rescue organ dysfunction, for example, in an individual in need thereof. In one example, In vitro generated HBPOs may be collected and transplanted into the subscapular site of kidney or mesentery of the small intestine in non-obese diabetic/severe combined immunodeficient (NOD/SCID) mice. An increase in growth of the organoid may be observed at 8 weeks after the transplant. The viability and growth can be monitored based on blood tests such as human-Alb, human-C-peptide levels.

In one aspect, a method of treating an individual, comprising transplanting an HBPO as described herein is disclosed. In this aspect, an organoid produced according to any of the methods used herein, may be transplanted into an individual in need thereof, using standard surgical procedures as known in the art. In one aspect, the individual may have a disease state selected from hepatic disease, such as liver failure and congenital liver diseases, pancreatic disease, such as diabetes, or biliary disease.

In one aspect, methods of identifying a treatment for one or more disease states selected from a biliary inflammatory disease and/or a pancreatic inflammatory disease such as pancreatitis is disclosed. In this aspect, the disclosed organoid compositions may be contacted with a potential therapeutic agent of interest with an organoid composition as disclosed herein. A measure of organ activity may then be detected in the organoid. Based on the output of this detection, it may be determined whether the potential therapeutic agent of interest improves the measure of the disease state, and may thereby be used to identify therapeutic agents likely to be useful in treating a disease state which involves a malfunction of any of the tissues embodied in the HBPO.

Pluripotent Stem Cells Derived from Embryonic Cells

In some aspects, one step may include obtaining stem cells that are pluripotent or that can be induced to become pluripotent. In some aspects, pluripotent stem cells are derived from embryonic stem cells, which are in turn derived from totipotent cells of the early mammalian embryo and are capable of unlimited, undifferentiated proliferation in vitro. Embryonic stem cells are pluripotent stem cells derived from the inner cell mass of the blastocyst, an early-stage embryo. Methods for deriving embryonic stem cells from blastocytes are well known in the art. Human embryonic stem cells H9 (H9-hESCs) are used in the exemplary embodiments described in the present application, but it would be understood by one of skill in the art that the methods and systems described herein are applicable to any stem cells.

Additional stem cells that can be used in embodiments in accordance with the present invention include but are not limited to those provided by or described in the database hosted by the National Stem Cell Bank (NSCB), Human Embryonic Stem Cell Research Center at the University of California, San Francisco (UCSF); WISC cell Bank at the Wi Cell Research Institute; the University of Wisconsin Stem Cell and Regenerative Medicine Center (UW-SCRMC); Novocell, Inc. (San Diego, Calif.); Cellartis AB (Goteborg, Sweden); ES Cell International Pte Ltd (Singapore); Technion at the Israel Institute of Technology (Haifa, Israel); and the Stem Cell Database hosted by Princeton University and the University of Pennsylvania. Exemplary embryonic stem cells that can be used in embodiments in accordance with the present invention include but are not limited to SA01 (SA001); SA02 (SA002); ES01 (HES-1); ES02 (HES-2); ES03 (HES-3); ES04 (HES-4); ES05 (HES-5); ES06 (HES-6); BG01 (BGN-01); BG02 (BGN-02); BG03 (BGN-03); TE03 (13); TE04 (14); TE06 (16); UC01 (HSF1); UC06 (HSF6); WA01 (H1); WA07 (H7); WA09 (H9); WA13 (H13); WA14 (H14). More details on embryonic stem cells can be found in, for example, Thomson et al., 1998, "Embryonic Stem Cell Lines Derived from Human Blastocysts," Science 282 (5391): 1145-1147; Andrews et al., 2005, "Embryonic stem (ES) cells and embryonal carcinoma (EC) cells: opposite sides of the same coin," Biochem Soc Trans 33:1526-1530; Martin 1980, "Teratocarcinomas and mammalian embryogenesis,". Science 209 (4458): 768-776; Evans and Kaufman, 1981, "Establishment in culture of pluripotent cells from mouse embryos," Nature 292 (5819): 154-156; Klimanskaya et al., 2005, "Human embryonic stem cells derived without feeder cells," Lancet 365 (9471): 1636-1641; each of which is hereby incorporated herein in its entirety.

Induced Pluripotent Stem Cells (iPSCs)

In some aspects, iPSCs are derived by transfection of certain stem cell-associated genes into non-pluripotent cells, such as adult fibroblasts. Transfection may be achieved through viral vectors, such as retroviruses. Transfected genes include the master transcriptional regulators Oct-3/4 (Pouf51) and Sox2, although it is suggested that other genes enhance the efficiency of induction. After 3-4 weeks, small numbers of transfected cells begin to become morphologically and biochemically similar to pluripotent stem cells, and are typically isolated through morphological selection, doubling time, or through a reporter gene and antibiotic selection. As used herein, iPSCs include but are not limited to first generation iPSCs, second generation iPSCs in mice, and human induced pluripotent stem cells. In some aspects, a retroviral system is used to transform human fibroblasts into pluripotent stem cells using four pivotal genes: Oct3/4, Sox2, Klf4, and c-Myc. In alternative aspects, a lentiviral system is used to transform somatic cells with OCT4, SOX2, NANOG, and LIN28. Genes whose expression are induced in iPSCs include but are not limited to Oct-3/4 (e.g., Pou5fl); certain members of the Sox gene family (e.g., Sox1, Sox2, Sox3, and Sox15); certain members of the Klf family (e.g., Klf1, Klf2, Klf4, and Klf5), certain members of the Myc family (e.g., C-myc, L-myc, and N-myc), Nanog, and LIN28.

In some aspects, non-viral based technologies are employed to generate iPSCs. In some aspects, an adenovirus can be used to transport the requisite four genes into the DNA of skin and liver cells of mice, resulting in cells identical to embryonic stem cells. Since the adenovirus does not combine any of its own genes with the targeted host, the danger of creating tumors is eliminated. In some aspects, reprogramming can be accomplished via plasmid without any virus transfection system at all, although at very low efficiencies. In other aspects, direct delivery of proteins is used to generate iPSCs, thus eliminating the need for viruses or genetic modification. In some embodiment, generation of mouse iPSCs is possible using a similar methodology: a repeated treatment of the cells with certain proteins channeled into the cells via poly-arginine anchors was sufficient to induce pluripotency. In some aspects, the expression of pluripotency induction genes can also be increased by treating somatic cells with FGF2 under low oxygen conditions.

More details on embryonic stem cells can be found in, for example, Kaji et al., 2009, "Virus free induction of pluripotency and subsequent excision of reprogramming factors," Nature 458:771-775; Woltjen et al., 2009, "piggyBac transposition reprograms fibroblasts to induced pluripotent stem cells," Nature 458:766-770; Okita et al., 2008, "Generation of Mouse Induced Pluripotent Stem Cells Without Viral Vectors," Science 322(5903):949-953; Stadtfeld et al., 2008, "Induced Pluripotent Stem Cells Generated without Viral Integration," Science 322(5903):945-949; and Zhou et al., 2009, "Generation of Induced Pluripotent Stem Cells Using Recombinant Proteins," Cell Stem Cell 4(5):381-384; each of which is hereby incorporated herein in its entirety.

In some aspects, exemplary iPS cell lines include but not limited to iPS-DF19-9; iPS-DF19-9; iPS-DF4-3; iPS-DF6-9; iPS (Foreskin); iPS (IMR90); and iPS (IMR90).

More details on the functions of signaling pathways relating to DE development can be found in, for example, Zorn and Wells, 2009, "Vertebrate endoderm development and organ formation," Annu Rev Cell Dev Biol 25:221-251; Dessimoz et al., 2006, "FGF signaling is necessary for establishing gut tube domains along the anterior-posterior axis in vivo," Mech Dev 123:42-55; McLin et al., 2007, "Repression of Wnt/β-catenin signaling in the anterior endoderm is essential for liver and pancreas development. Development," 134:2207-2217; Wells and Melton, 2000, Development 127:1563-1572; de Santa Barbara et al., 2003, "Development and differentiation of the intestinal epithelium," Cell Mol Life Sci 60(7): 1322-1332; each of which is hereby incorporated herein in its entirety.

Any methods for producing definitive endoderm from pluripotent cells (e.g., iPSCs or ESCs) are applicable to the methods described herein. In some aspects, pluripotent cells are derived from a morula. In some aspects, pluripotent stem cells are stem cells. Stem cells used in these methods can include, but are not limited to, embryonic stem cells. Embryonic stem cells can be derived from the embryonic inner cell mass or from the embryonic gonadal ridges. Embryonic stem cells or germ cells can originate from a variety of animal species including, but not limited to, various mammalian species including humans. In some aspects, human embryonic stem cells are used to produce definitive endoderm. In some aspects, human embryonic germ cells are used to produce definitive endoderm. In some aspects, iPSCs are used to produce definitive endoderm.

In one aspect, the definitive endoderm may be derived from a precursor cell selected from an embryonic stem cell, an embryonic germ cell, an induced pluripotent stem cell, a mesoderm cell, a definitive endoderm cell, a posterior endoderm cell, a posterior endoderm cell, and a hindgut cell. In one aspect, the definitive endoderm may be derived from a pluripotent stem cell. In one aspect, the definitive endoderm may be derived from a pluripotent stem cell selected from an embryonic stem cell, an adult stem cell, or an induced pluripotent stem cell. In one aspect, the DE may be a DE monolayer, wherein greater than 90% of the cells in the DE monolayer co-express FOXA2 and SOX17.

In one aspect, the definitive endoderm may be derived from contacting a pluripotent stem cell with one or more molecules selected from Activin, the BMP subgroups of the TGF-beta superfamily of growth factors; Nodal, Activin A, Activin B, BMP4, Wnt3a, and combinations thereof.

In one aspect, the BMP signaling pathway inhibitor may be selected from Noggin, Dorsomorphin, LDN193189, DMH-1, and combinations thereof. In one aspect, the BMP signaling pathway inhibitor is Noggin. The BMP inhibitor may be present at a concentration of between from about 50 to about 1500 ng/ml.

In one aspect, the WNT signaling pathway activator may be selected from one or more molecules selected from the group consisting of Wnt1, Wnt2, Wnt2b, Wnt3, Wnt3a, Wnt4, Wnt5a, Wnt5b, Wnt6, Wnt7a, Wnt7b, Wnt8a, Wnt8b, Wnt9a, Wnt9b, Wnt10a, Wnt10b, Wnt11, Wnt16, a GSKβ inhibitor (e.g., CHIR99021, i.e. "CHIRON"), BIO, LY2090314, SB-216763, lithium, SFRP inhibitor WAY-316606, beta-catenin activator DCA. The concentration of the Wnt pathway activator may be, for example, used at a concentration between about 50 to about 1500 ng/ml. There are many ways to activate the Wnt/beta-catenin pathway (see Stanford University's Nussel Lab's web site). Suitable Some existing wnt signaling pathway activators include but are not limited to protein-based activators, which may include Wnt ligands including but not limited to Wnt1, Wnt2, Wnt2b, Wnt3, Wnt3a, Wnt8, et al; modifiers of Wnt ligand activity including but not limited to activated Wnt frizzled receptors, (LRP) co-receptors, R-spondin proteins, Dkk proteins, regulators of Wnt ligand secretion and trafficking (Wntless, Porcupine), inhibiting beta-catenin degredation APC and GSK3beta inhibition, activated beta-catenin, constitutively active TCF/Lef proteins and chemical activators, which may include over 28 known chemicals that either activate or inhibit Wnt/beta-catenin signaling. Some activators include but are not limited to GSK3-beta inhibitors CHIR99021 (CHIRON), BIO, LY2090314, SB-216763, lithium, SFRP inhibitor WAY-316606, beta-catenin activator DCA.

In one aspect, the FGF signaling pathway activator may be one or more molecules selected from the group consisting of FGF1, FGF2, FGF3, FGF4, FGF10, FGF11, FGF12, FGF13, FGF14, FGF15, FGF16, FGF17, FGF18, FGF19, FGF20, FGF21, FGF22, FGF23, and combinations thereof, preferably FGF4 or FGF10, or a combination thereof. In one aspect, the concentration of the FGF pathway activator may be used at a concentration between about 50 to about 1500 ng/ml, though it will be understood by one of ordinary skill in the art that various concentrations may be used. Proteins and chemicals that stimulate the FGF receptor and signaling components downstream of the receptors including MAPK, MEK, ERK proteins and chemicals that modulate their activity. FGF signaling can be activated by inhibiting inhibitors of FGF signaling pathways including but not limited to Sprouty protein family members.

EXAMPLES

The following non-limiting examples are provided to further illustrate embodiments of the invention disclosed herein. It should be appreciated by those of skill in the art that the techniques disclosed in the examples that follow represent approaches that have been found to function well in the practice of the invention, and thus may be considered to constitute examples of modes for its practice. However, those of skill in the art should, in light of the present disclosure, appreciate that many changes may be made in the specific embodiments that are disclosed and still obtain a like or similar result without departing from the spirit and scope of the invention.

Organogenesis is a complex and inter-connected process, orchestrated by multiple boundary tissue interactions[1-7]. However, it is currently unclear how individual, neighboring components coordinate to establish an integral multi-organ structure. Disclosed herein is the continuous patterning and dynamic morphogenesis of hepatic, biliary and pancreatic structures, invaginating from a three-dimensional culture of human pluripotent stem cell (PSC).

Applicant has found that the boundary interactions between anterior and posterior gut spheroids differentiated from human PSCs enables autonomous emergence of hepato-biliary-pancreatic (HBP) organ domains specified at the foregut-midgut boundary organoids in the absence of extrinsic factor supply. Whereas transplant-derived tissues were dominated by midgut derivatives, long-term culture of micro dissected HBP organoids develop into a segregated hepato-pancreato-biliary anlage, followed by the recapitulation of early morphogenetic events including the invagination and branching of three different and inter-connected organ structures, reminiscent of tissues derived from mouse explanted foregut-midgut culture. Mis-segregation of multi-organ domains incurred by a genetic mutation in HES1 abolishes the biliary specification potential in culture, as seen in vivo[8,9]. Applicant has demonstrated that the experimental multi-organ integrated model can be established by the juxta-positioning of foregut and midgut tissues, and which may serve as a tractable, manipulatable and easily accessible model for the study of complicated endoderm organogenesis in human.

The hepato-biliary-pancreatic (HBP) anlage, which is demarcated by HHEX (Hematopoietically-expressed homeobox protein) and PDX1 (Pancreatic and duodenal homeobox 1) expression is first specified at the boundary between the foregut-midgut[10], and forms an epithelial vesicle invaginating ventrally from the primitive gut[11-13]. The disruption of boundary-defining genes around this area such as BMPR1A (Bone morphogenetic protein receptor, type 1A)[1], HLX (H2.0-like homeobox)[2], CDX2 (Caudal type homeobox 2)[3], NKX3-2 (NK3 Homeobox 2)[4], HHEX[5], PDX1 and SOX9 (SRY-box 9)[6] significantly alters balanced organogenesis along the stomach-HBP-intestine in vivo[1-7]. Subsequent diversification of HBP lineages is likely mediated by adjacent mesenchymal BMP at their boundary by indirectly repressing SOX9 in the posterior liver bud cells[14]. Thus, contiguous, dynamic organogenesis occurs in a complex environment and is likely driven by successive neighboring tissue interactions[5,6,15]. However, the patterning and balanced organogenesis of the HBP system has not been successfully modelled in tissue culture due to technical complexities, hindering detailed mechanistic studies[16,17].

Here, Applicant used a three-dimensional differentiation approach using human pluripotent stem cells (PSCs) to specify gut spheroids with distinct regional identities comprised of both endoderm and mesoderm. Applicant demonstrated that antero-posterior interactions recapitulate the foregut (marked by SOX2, SRY-Box 2) and the midgut (marked by CDX2) boundary in vitro, modeling the inter-coordinated specification and invagination of the human hepato-biliary-pancreatic system.

Figure 1C:
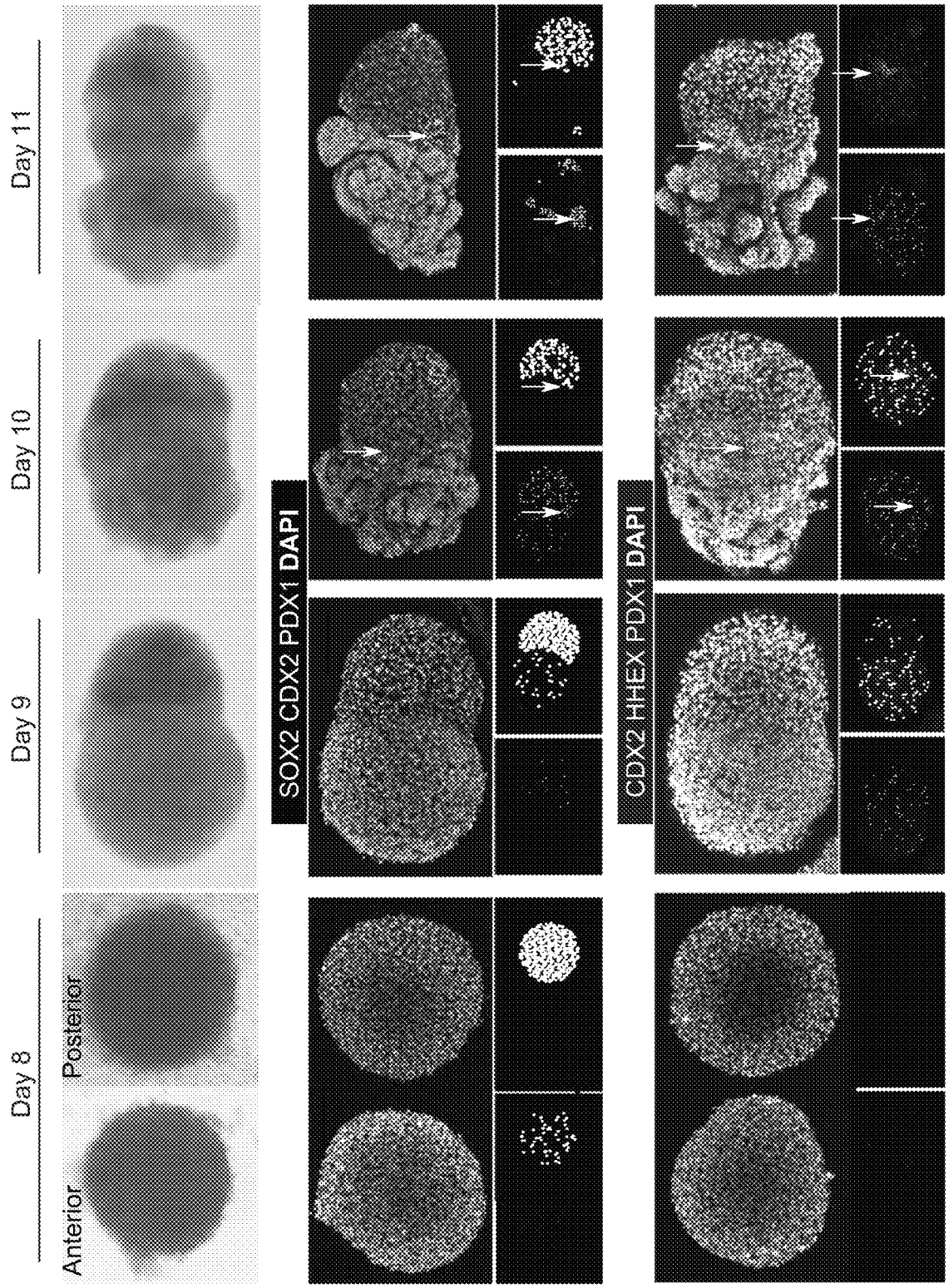
Figure 3A:
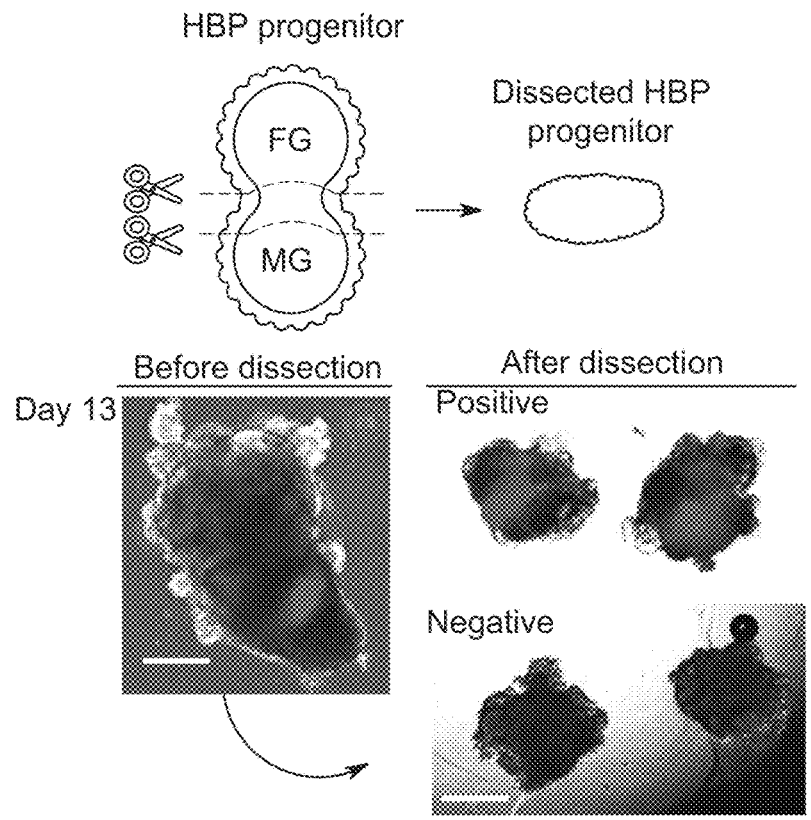
FIG. 3A-3O. Modeling human hepato-biliary-pancreatic organogenesis. 3A. Illustration of dissection of PROX1 positive region from HBP organoids and image of before/after dissection. 3B. Optimization of cultured system with 1) Floating, 2) Embedded into Matrigel™, 3) Embedded into Matrigel™ and cultured with Transwell™ from D13, 4). Dissected, embedded into Matrigel™, and cultured with Transwell™ from D13. Left panel shows the classification of invaginating or branching organoid. 3C. Morphogenesis of boundary organoids through 2 days from Day 13. 3D. Morphogenetical change of PROX1 dissected tissue from boundary organoids through 30 days of air-liquid interface cultured system. 3E. Stereomicroscopic image of Day 37 organoids. 3F. Boundary organoid has tdTomato expressing hepatobiliary tissues branched out for putative pancreatic domains, similar to cultured mouse E10.5 derived hepato-biliary-pancreas. Left: cultured mouse embryonic tissue during 4 days, Right: PROX1-tdTomato reporter iPSCs at Day 90. 3G. Right: Illustration of invagination liver, bile duct and pancreas connected with intestine. Left: H&E in D90 boundary tissue. 3H-3I. Immunostaining for combination of CK19, PDX1, PROX1, SOX9 and NGN3, and alpha-SMA and SOX17 (3H) and AFP, EpCAM, and alpha-SMA (3I). 3J, 3K. Whole mount staining of PDX1, NKX6.1 and GATA4, and DBA, PDX1, and PROX1 (3K). 3L-3N. Immunostaining of NKX6.1 and HNF1B (3L), Amylase and GATA4 (3M) and Amylase and CCKAR (3N). 3O. CCK treatment response in putative biliary structure. 3P. Hormone induced secretory function of exocrine pancreatic domain. Enzyme-linked immunosorbent assay of amylase in boundary tissue before and after 3 days-CCK. Scale bars, 100 μm (a), 100 μm (3B), 100 μm (3C), 200 μm (3D), 1 mm (3E), 200 μm (3F), 200 μm (3G), 200 μm (3H), 200 μm (3I), 200 μm (3J), 100 μm (3K'), 200 μm (3L), 100 μm (3M), 500 μm (3N), 50 μm (3O).
Figure 3B:
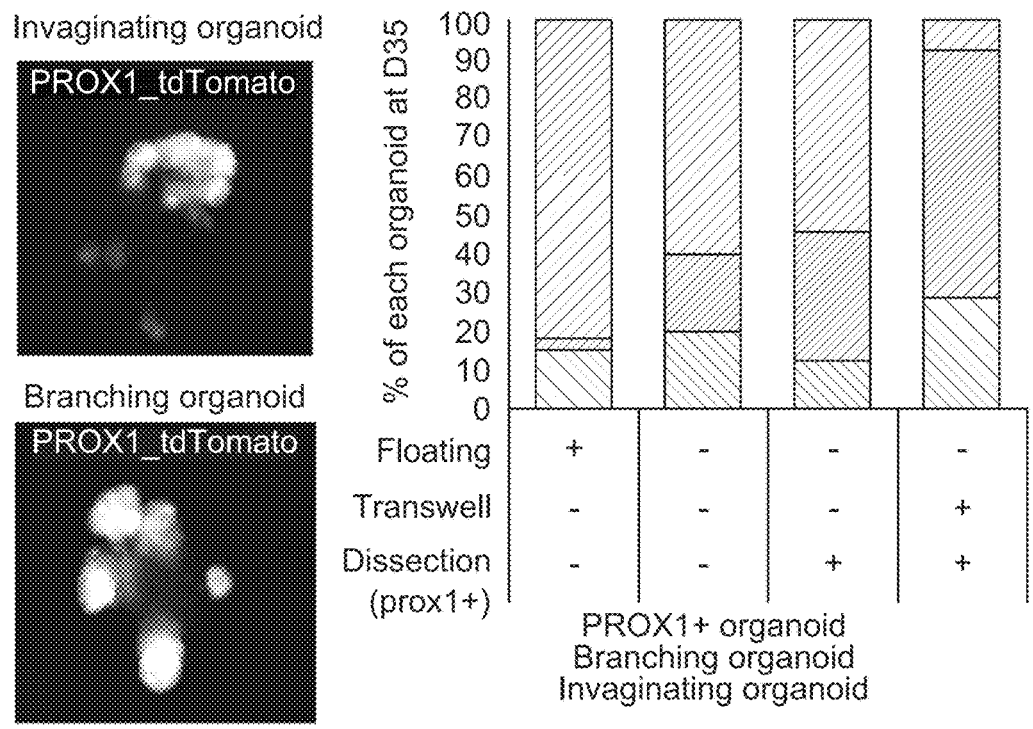
Figure 5:
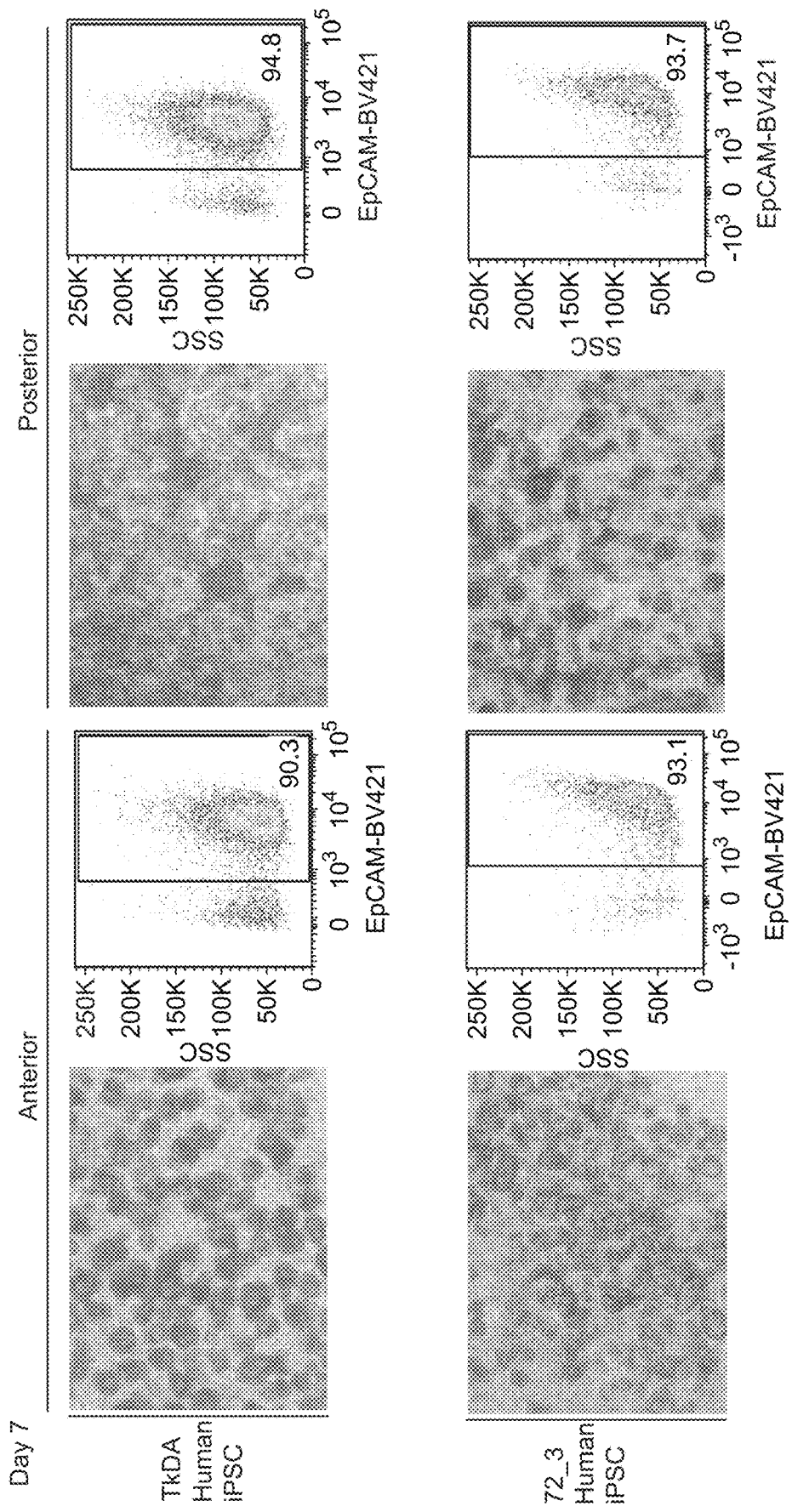
FIG. 5. Anterior and posterior gut cell characterization. Flow cytometry of EpCAM in Day 7 anterior and posterior gut cells using TkDA human iPSCs and 72_3 human iPSCs.
Figure 6A:
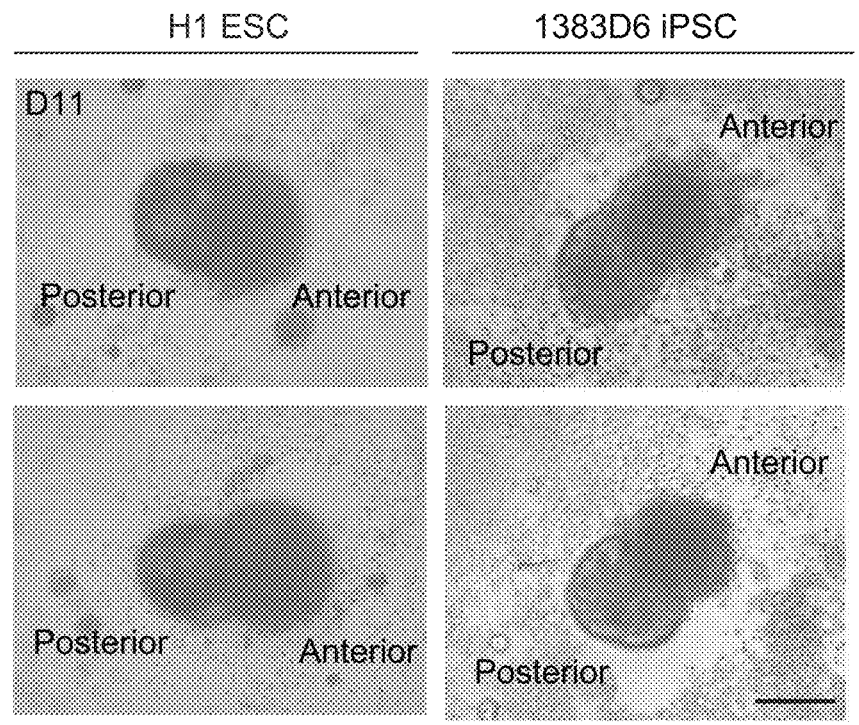
FIG. 6A-6B Reproducibility of boundary organoid formation. 6A. The image of D11 boundary organoids. Anterior and posterior gut spheroids were differentiated from H1 ESCs or 1383D6 iPSCs, mixed and transferred into Matrigel™. Scale bar is 200 μm. 6B. Immunofluorescent staining of CDX2, epithelial marker ECAD, and HHEX in boundary spheroids derived from HIESC. 6C. Immunofluorescent staining of PDX1, CDX2, FOXF1, and HHEX in boundary spheroids derived from 72_3 iPS.
Figure 6B:
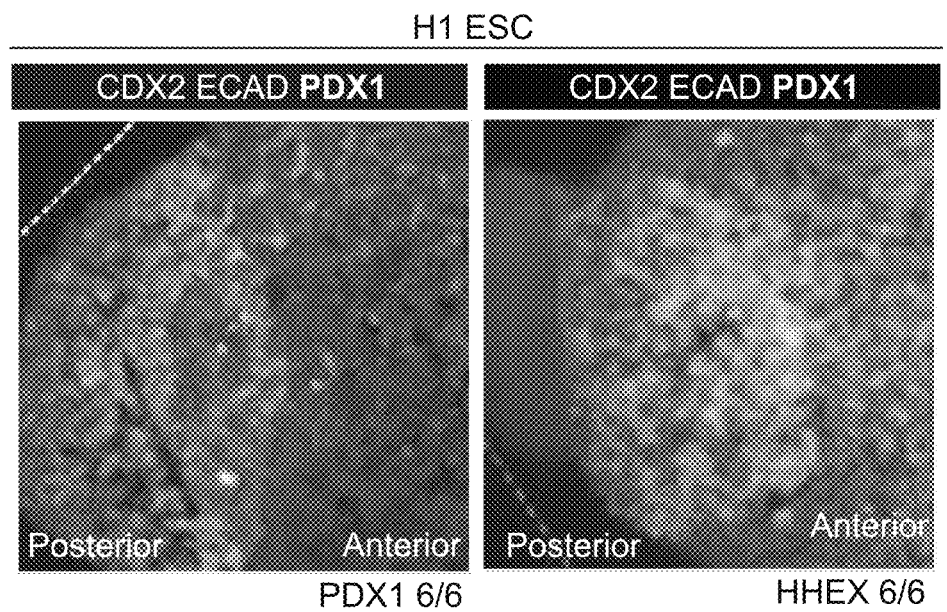
Figure 6C:
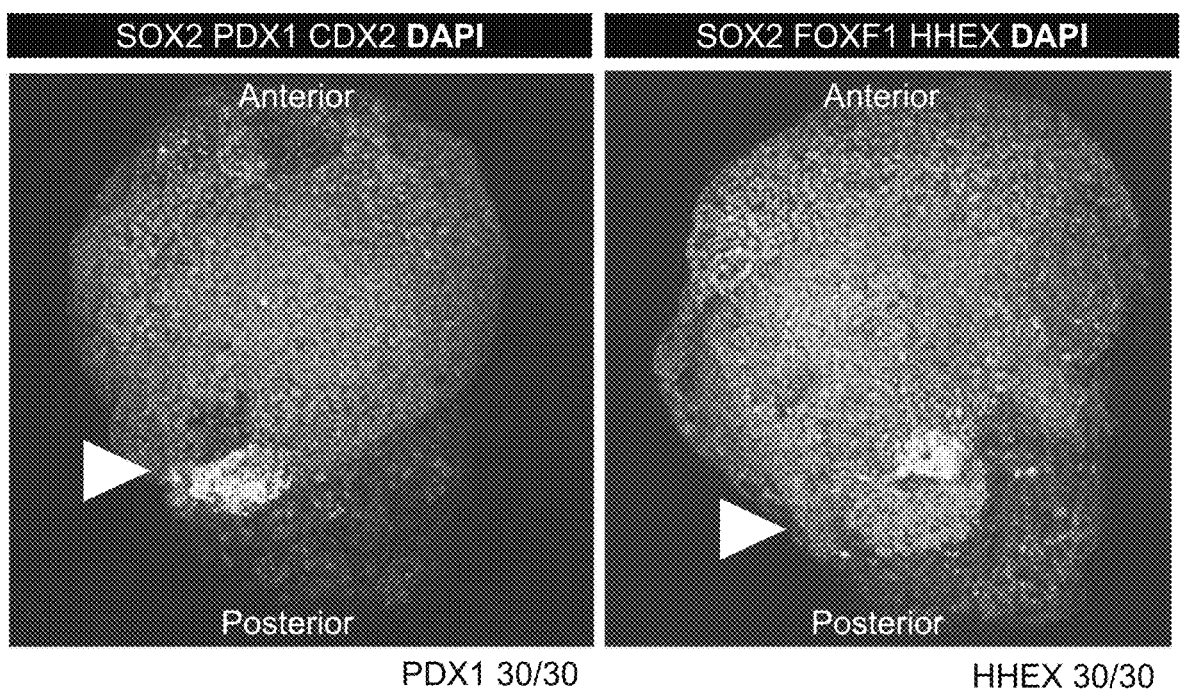
Figure 8:
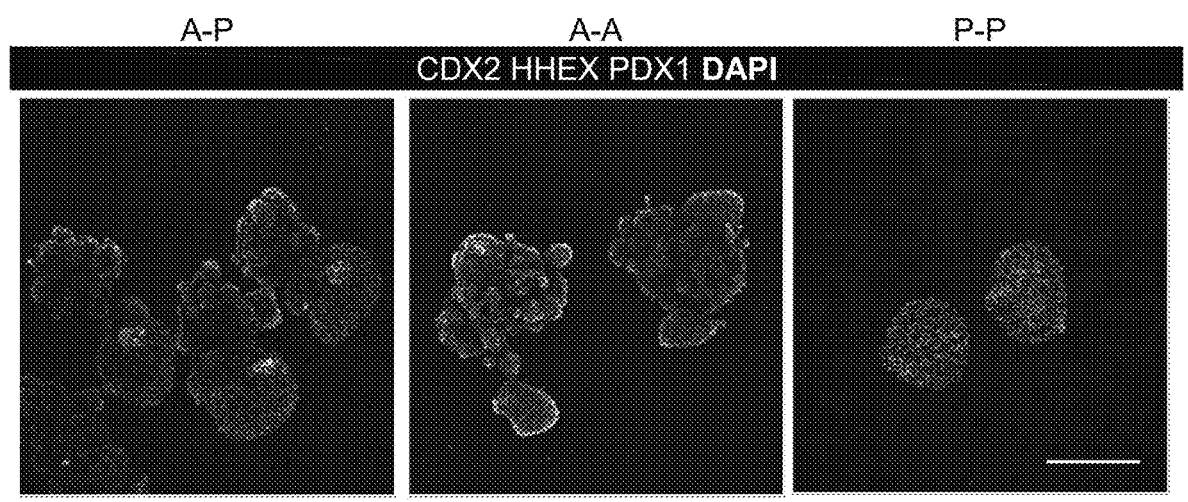
FIG. 8 Comparison of different anterior and posterior gut combinations. Immunofluorescent staining of CDX2, HHEX, and PDX1 in the combination of AP, AA, and PP spheroids at D12. Scale bar is 200 μm.

To develop a foregut-midgut boundary model, Applicant first exposed definitive endoderm cells, which were patterned as previously described[18,19], to the recombinant protein FGF4, and the small molecule CHIR99021 (that modulates the WNT pathway) in the presence of a BMP antagonist Noggin for anterior gut and in the absence of Noggin for posterior gut identity (FIG. 1A and FIG. 5). At Day 7 (D7), anterior or posterior gut cells were individually aggregated to form spheroids with a preferential expression of the foregut and mid/hindgut transcription factors SOX2 and CDX2, respectively (FIG. 1B). Applicant then transferred a posterior gut spheroid adjacent to an anterior gut spheroid. At D9, the two spheroids were fused in 94.8% of the wells, and fused spheroids were embedded into a morphogenetic factor, namely Matrigel™ (FIGS. 1A and B). Surprisingly, without adding any exogenous factors, the HBP primordium emerged at the interface of the anterior and posterior gut spheroids, as evidenced by whole mount staining of the spheroids over D9, D10 and D11, using the markers SOX2, CDX2, the immature liver marker HHEX, and the antrum, duodenum and pancreas progenitor marker PDX1 (FIG. 1C). At D9, the anterior and posterior gut spheroids did not exhibit any expression of HHEX and PDX1. At D10, HHEX and PDX1 expressions were emerged, and HHEX was only detectable at the boundary of the anterior and posterior (bAP) organoids. Both PDX1 and HHEX positive cells were distinctively increased in the boundary region at D11 (FIG. 1C). The use of three additional induced pluripotent stem cells (iPSCs) and embryonic stem cells (ESCs) lines confirmed the reproducibility in developing HHEX and PDX1 expressing cells at the boundary of bAP organoids (FIG. 6A-6C). HBP progenitor induction requires cell-to-cell contact between the anterior and posterior gut spheroids (FIG. 3A and FIG. 3B). Of all the detected PDX1 positive cells at the boundary site (30 out of 30 stained organoids) (FIG. 1D), the percentage of PDX1 positive cells per total cell number was 5% in the boundary region while 0 and 1% in the anterior and the posterior region, respectively (FIG. 1E). PDX1 expressing cells were observed in A-P organoids and posterior-posterior (P-P) gut spheroid combinations. In contrast, HHEX positive cells were only detected in A-P organoids, but not in anterior-anterior (A-A) nor P-P combinations (FIG. 1F and FIG. 8), indicating the balanced induction of the HBP progenitors involves A-P fusion.

Figure 9A:
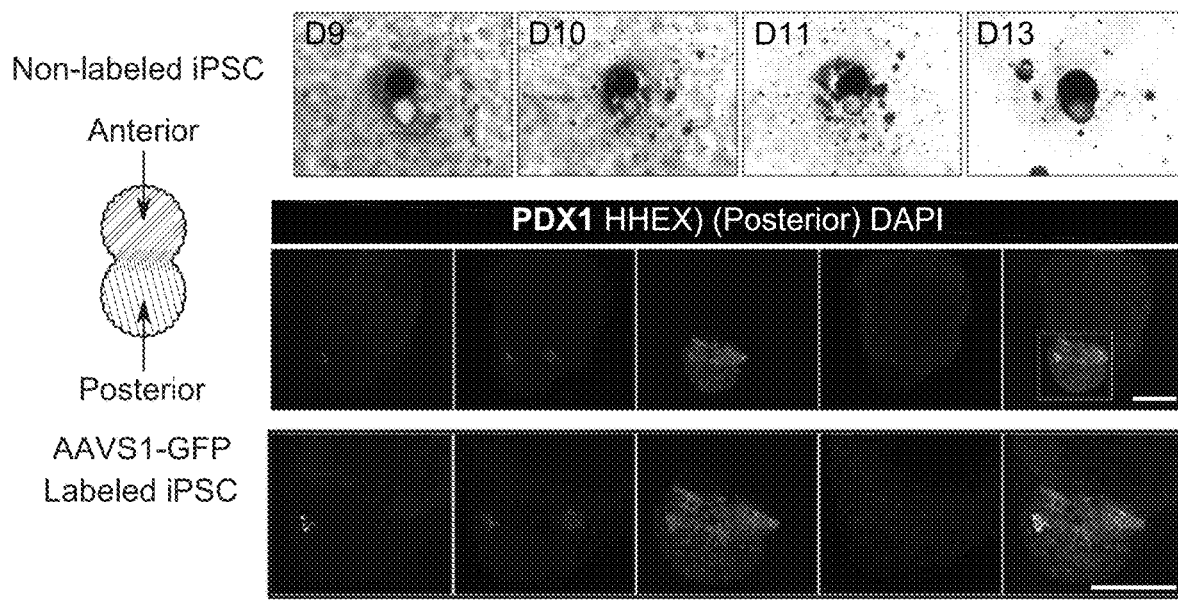
FIG. 9A-9C. HBP progenitors develop from posterior gut cells. 9A. Non labeled iPS cells were differentiated into anterior gut spheroid while AAVS1-GFP labeled iPS cells were differentiated into posterior gut spheroid. Top column showed bright field and GFP fluorescent image during boundary organoid formation. Bottom column showed whole mount immunostaining for HHEX and PDX1 at Day 13. The HHEX expression was overlapped with GFP expression. Scale bar is 200 μm. 9B. H2B-GFP labeled and unlabeled PROX1-tdTomato reporter iPSCs were differentiated into anterior and posterior gut spheroid, respectively. tdTomato expression was only detected in unlabeled original posterior gut spheroid. Scale bar is 200 μm. 9C. Using unlabeled iPSCs and PROX1-tdTomato reporter iPSCs, anterior and posterior gut spheroids were differentiated. Two combinations, reporter cell derived anterior and unlabeled cell posterior (left column), or unlabeled cell derived anterior and reporter cell derived posterior gut spheroid (right column) were examined by tdTomato expression. Top row: bright field image, bottom row: tdTomato fluorescence image. Scale bar is 200 μm FIG. 10. Abolishment of HHEX and PDX1 induction in posterior gut specific BMS493. BMS493 pretreated anterior or posterior gut spheroids were fused to induce HBP anlage formation. Compared to untreated control group, the group of BMS493 pretreated posterior gut spheroid was inhibited HHEX and PDX1 expression at boundary, suggesting retinoic acid receptor function in posterior side was important to establish HBP boundary organoid. Scale bar: 200 μm FIGS. 11A and 11B. PROX1 inhibition by BMS493 exposure with E9.0 PROX1::GFP reporter mouse embryo explant culture. Embryonic Day 9.0 Prox1-GFP whole embryo was cultured in the rotator-type bottle culture system for 24 hrs. Retinoic acid receptors antagonist BMS493 treated group was compared with control (adding DMSO) group. 11A. Bright field image and GFP fluorescent image for embryo after culture. 11B. The area of GFP expressing parts was quantified from GFP image in (a). Scale bar: 1 mm FIG. 12 Optimization of in vitro culture system.

To trace the source of HHEX and PDX1 expressing cells, the bAP organoids were established using non-labeled anterior and GFP-labeled posterior gut spheroids. Applicant found that both HHEX and PDX1 expression overlapped with GFP, suggesting that the HBP progenitors originate from the posterior gut (FIG. 9A). RNA-sequencing of D8, D9, D11 and D12 micro-dissected anterior, boundary and posterior regions showed that the boundary tissues at D11 and D12 progressively expressed the arrays of HBP specification markers, whereas anterior or posterior regions gained foregut or mid/hindgut identity, respectively (FIG. 1G). Of note, in agreement with A-P recombination experiments, posterior tissues possess a closer identity to boundary regions (FIG. 1G). Taken together, the AP boundary strategy orchestrates autonomous patterning of HHEX and PDX1 positive HBP progenitors in the absence of exogenous inductive factors.

Figure 2A:
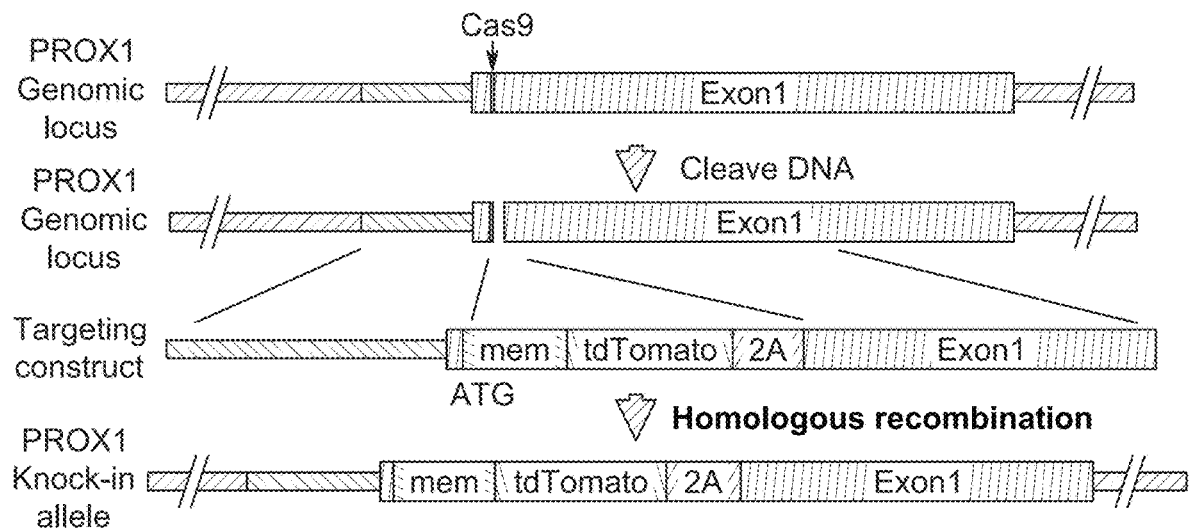
Figure 2B:
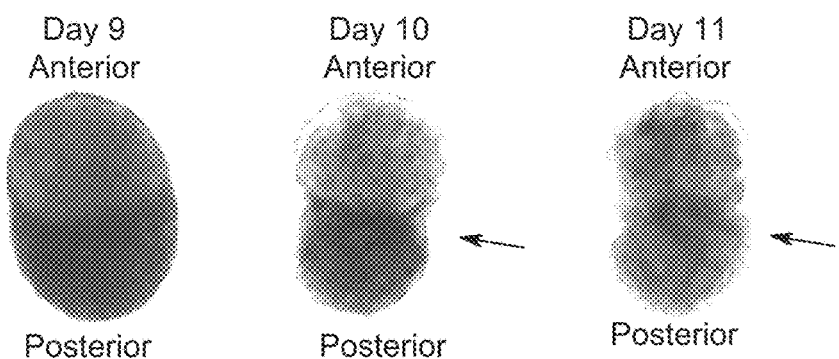
Figure 2C:
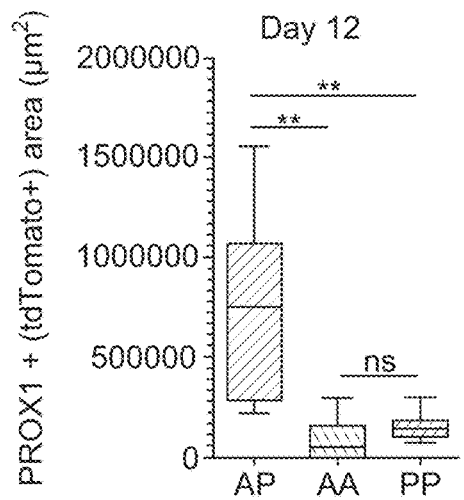
Figure 2D:
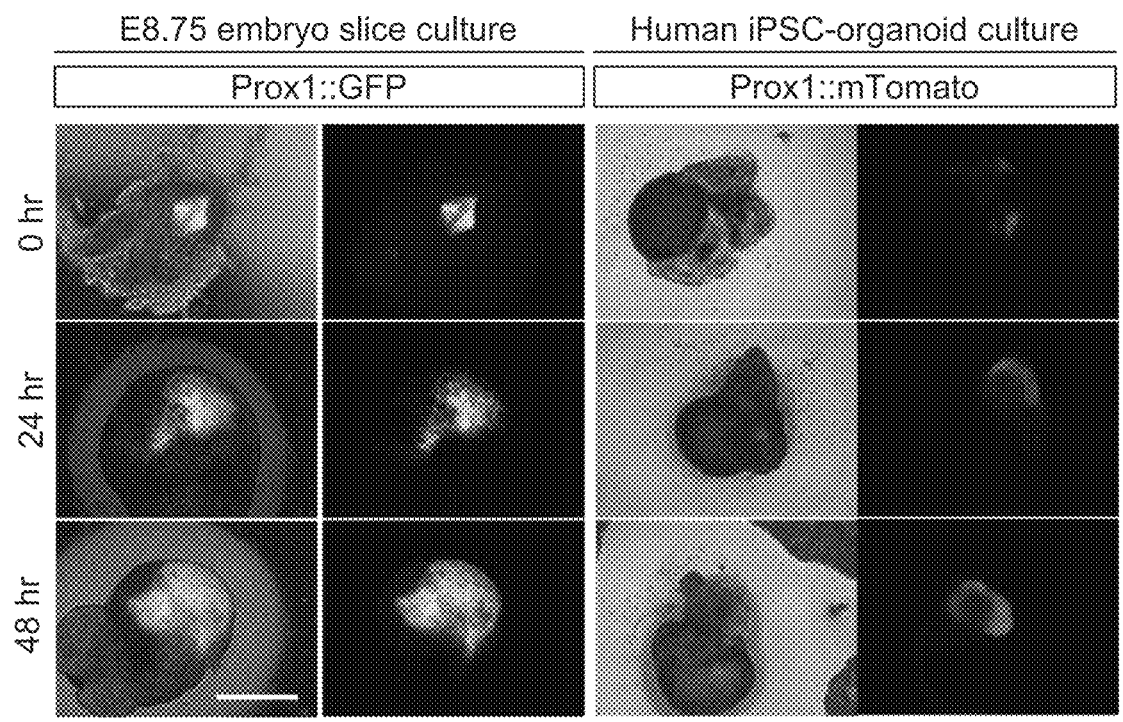
Figure 9B:
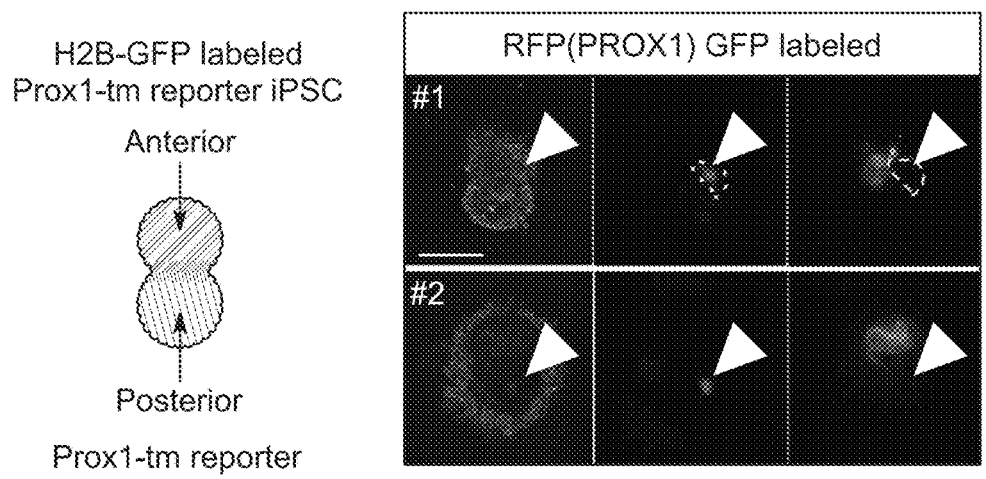
Figure 9C:
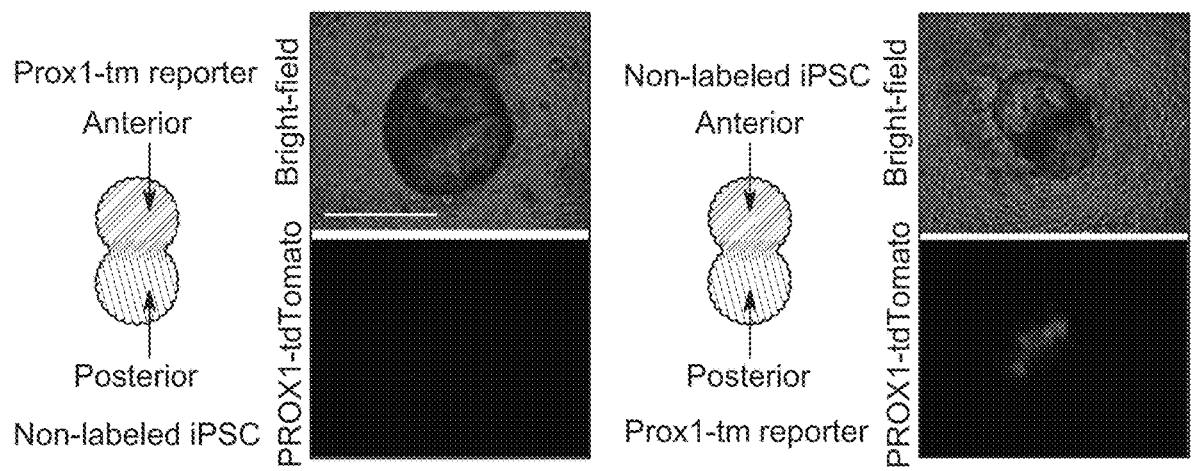

Applicant further established a reporter human iPSC to track their fate by visualizing tdTomato under the common progenitor marker of the liver, bile duct, and pancreas, a prospero-related homeobox 1 (PROX1) using CRISPR/Cas9 genome editing (FIG. 2A). Similar to HHEX and PDX1, PROX1 expression initiated at the boundary at D10 and increased afterwards (FIG. 2B). The PROX1 emergence was specific to the A-P organoids but not in A-A nor P-P combinations (FIG. 2C). A-P recombination assays indicated PROX1 positive cells also originated from the posterior gut cells (FIGS. 9B and 9C). Air-liquid interface culture induced additional growth of the PROX1 positive area, as seen in E8.75 Prox1::EGFP mouse embryonic liver tissue (FIG. 2D). PROX1 immunostaining confirmed that the morphologically invaginating tissue induced from bAP organoids was similar with the boundary region of mouse at E8.5-8.75 (FIG. 2E).

To delineate the HBP progenitor self-inductive mechanism, Applicant evaluated the boundary specific expression profiles of known inductive signaling pathways. Amongst FGF, BMP, HH (hedgehog), NOTCH and RA (retinoic acid) signals, RNAseq identified that the signal downstream of RA were activated prominently at the boundary region, but not in the anterior or posterior regions at D11 (FIG. 2F and Table1).

TABLE 1

Figure 2E:
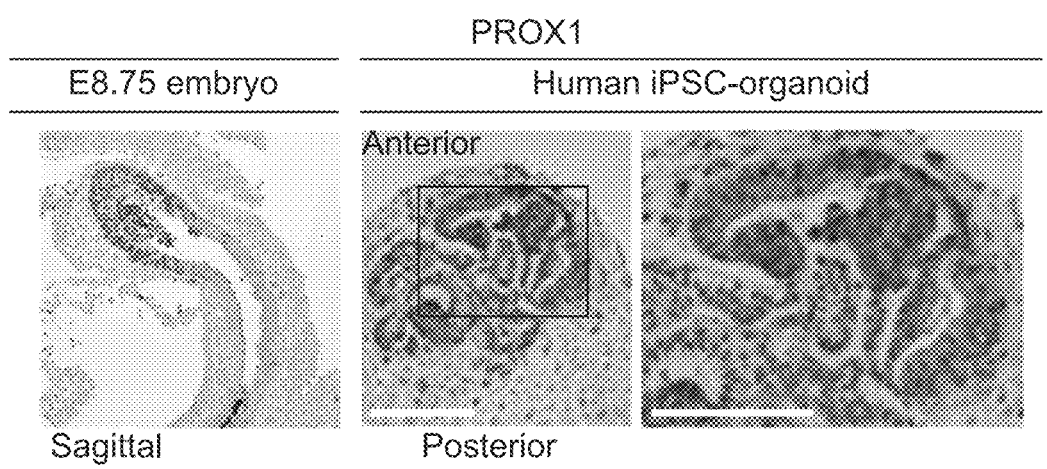
Figure 2F:
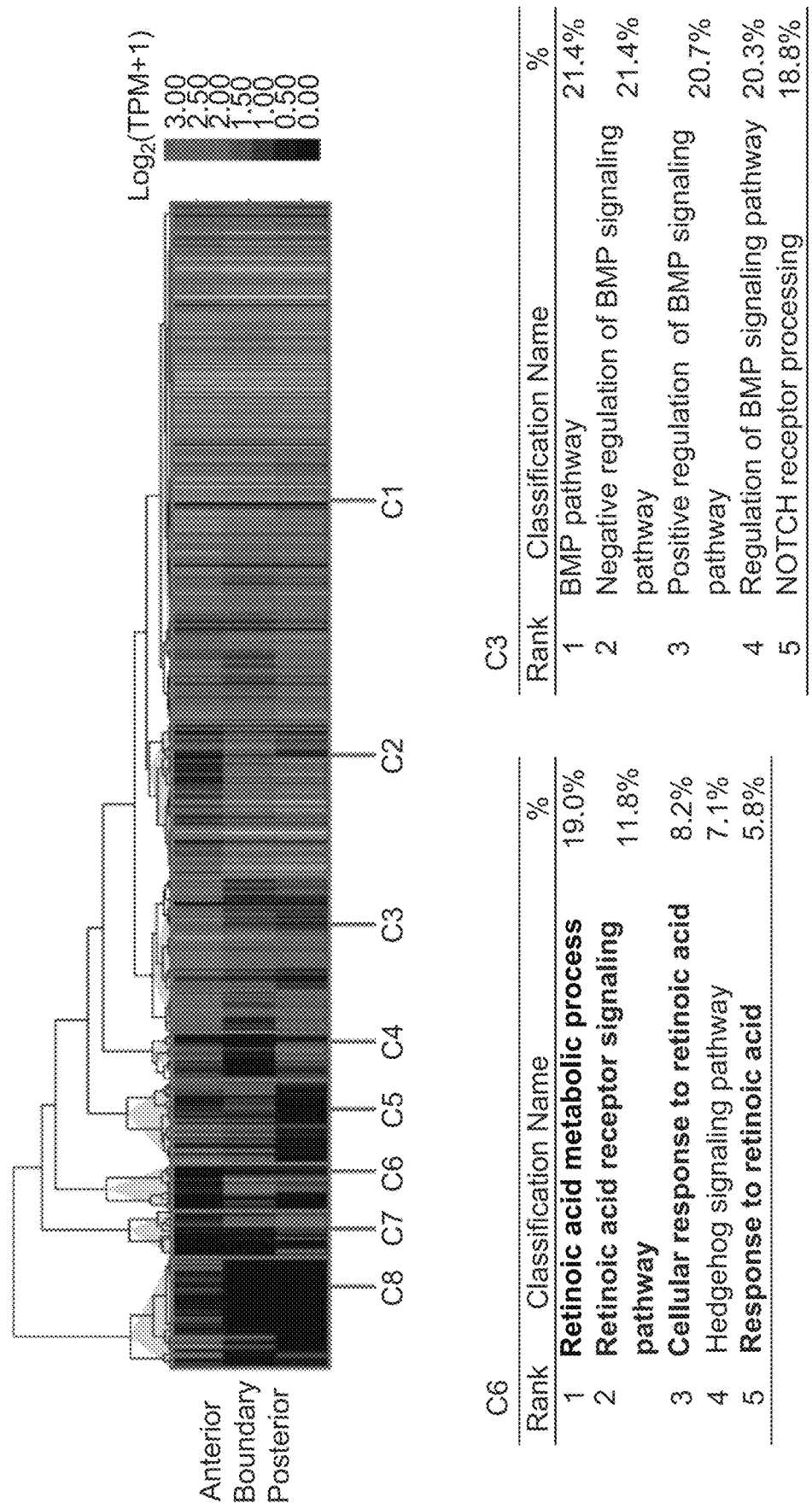
Figure 21:
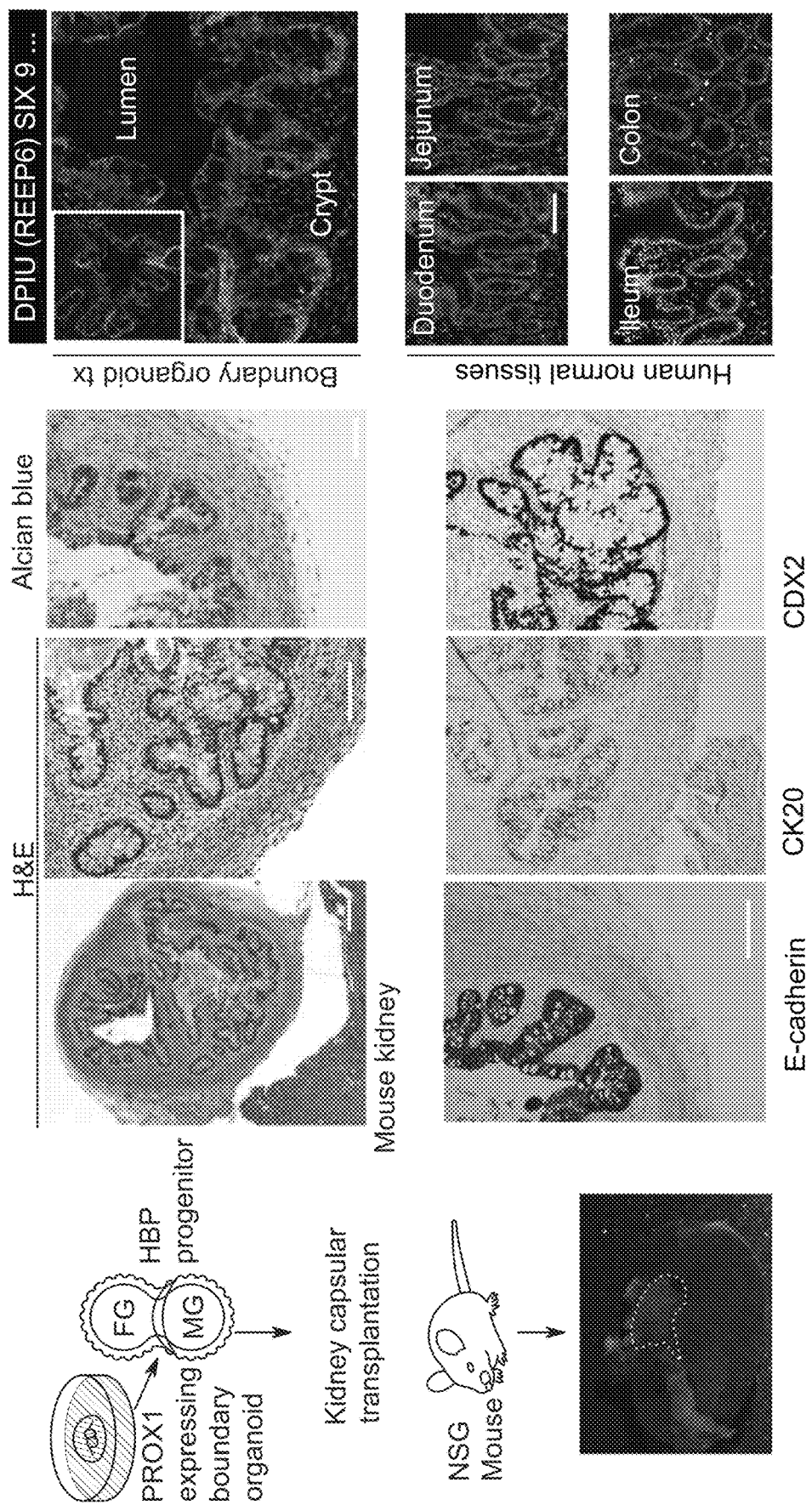

Gene ontology analysis for RNA sequencing (related to FIG. 2E)

| Term | Original size | After restricting to dataset | % |
|---|---|---|---|
| C1 | | | |
| BIOCARTA_TGFB_PATHWAY | 19 | 12 | 63.2% |
| PID_RETINOIC_ACID_PATHWAY | 30 | 17 | 56.7% |
| GO_NOTCH_RECEPTOR_PROCESSING | 16 | 9 | 56.3% |
| GO_POSITIVE_REGULATION_OF_NOTCH_SIGNALING_PATHWAY | 33 | 18 | 54.5% |
| PID_FGF_PATHWAY | 55 | 29 | 52.7% |
| GO_POSITIVE_REGULATION_OF_BMP_SIGNALING_PATHWAY | 29 | 15 | 51.7% |
| GO_REGULATION_OF_NOTCH_SIGNALING_PATHWAY | 63 | 32 | 50.8% |
| GO_NOTCH_SIGNALING_PATHWAY | 111 | 50 | 45.0% |
| HALLMARK_HEDGEHOG_SIGNALING | 35 | 15 | 42.9% |
| PID_BMP_PATHWAY | 42 | 18 | 42.9% |
| GO_REGULATION_OF_BMP_SIGNALING_PATHWAY | 74 | 27 | 36.5% |
| GO_NEGATIVE_REGULATION_OF_NOTCH_SIGNALING_PATHWAY | 25 | 9 | 36.0% |
| KEGG_HEDGEHOG_SIGNALING_PATHWAY | 56 | 19 | 33.9% |
| GO_RESPONSE_TO_RETINOIC_ACID | 103 | 33 | 32.0% |
| GO_NOTCH_BINDING | 17 | 5 | 29.4% |
| GO_REGULATION_OF_RETINOIC_ACID_RECEPTOR_SIGNALING_PATHWAY | 29 | 8 | 27.6% |
| GO_CELLULAR_RESPONSE_TO_RETINOIC_ACID | 61 | 15 | 24.6% |
| GO_RETINOIC_ACID_METABOLIC_PROCESS | 21 | 5 | 23.8% |
| GO_NEGATIVE_REGULATION_OF_BMP_SIGNALING_PATHWAY | 42 | 10 | 23.8% |
| GO_RETINOIC_ACID_RECEPTOR_SIGNALING_PATHWAY | 17 | 4 | 23.5% |
| GO_NEGATIVE_REGULATION_OF_RETINOIC_ACID_RECEPTOR_SIGNALING_PATHWAY | 23 | 3 | 13.0% |
| C2 | | | |
| GO_NEGATIVE_REGULATION_OF_NOTCH_SIGNALING_PATHWAY | 25 | 5 | 20.0% |
| GO_NEGATIVE_REGULATION_OF_BMP_SIGNALIN_PATHWAY | 42 | 8 | 19.0% |
| BIOCARTA_TGFB_PATHWAY | 19 | 3 | 15.8% |
| GO_RESPONSE_TO_RETINOIC_ACID | 103 | 16 | 15.5% |
| GO_REGULATION_OF_BMP_SIGNALING_PATHWAY | 74 | 11 | 14.9% |
| PID_FGF_PATHWAY | 55 | 8 | 14.5% |
| GO_RETINOIC_ACID_METABOLIC_PROCESS | 21 | 3 | 14.3% |
| GO_NOTCH_SIGNALING_PATHWAY | 111 | 15 | 13.5% |
| GO_NOTCH_RECEPTOR_PROCESSING | 16 | 2 | 12.5% |
| PID_BMP_PATHWAY | 42 | 5 | 11.9% |
| GO_RETINOIC_ACID_RECEPTOR_SIGNALING_PATHWAY | 17 | 2 | 11.8% |
| GO_CELLULAR_RESPONSE_TO_RETINOIC_ACID | 61 | 7 | 11.5% |
| HALLMARK_HEDGEHOG_SIGNALING | 35 | 4 | 11.4% |
| KEGG_HEDGEHOG_SIGNALING_PATHWAY | 56 | 6 | 10.7% |
| GO_POSITIVE_REGULATION_OF_BMP_SIGNALING_PATHWAY | 29 | 3 | 10.3% |
| GO_REGULATION_OF_NOTCH_SIGNALING_PATHWAY | 63 | 6 | 9.5% |
| PID_RETINOIC_ACID_PATHWAY | 30 | 2 | 6.7% |
| GO_NOTCH_BINDING | 17 | 1 | 5.9% |
| GO_REGULATION_OF_RETINOIC_ACID_RECEPTOR_SIGNALING_PATHWAY | 29 | 1 | 3.4% |
| GO_POSITIVE_REGULATION_OF_NOTCH_SIGNALING_PATHWAY | 33 | 1 | 3.0% |
| GO_NEGATIVE_REGULATION_OF_RETINOIC_ACID_RECEPTOR_SIGNALING_PATHWAY | 23 | | 0.0% |
| C3 | | | |
| PID_BMP_PATHWAY | 42 | 9 | 21.4% |
| GO_NEGATIVE_REGULATION_OF_BMP_SIGNALING_PATHWAY | 42 | 9 | 21.4% |
| GO_POSITIVE_REGULATION_OF_BMP_SIGNALING_PATHWAY | 29 | 6 | 20.7% |
| GO_REGULATION_OF_BMP_SIGNALING_PATHWAY | 74 | 15 | 20.3% |
| GO_NOTCH_RECEPTOR_PROCESSING | 16 | 3 | 18.8% |
| GO_NOTCH_BINDING | 17 | 3 | 17.6% |

TABLE 1-continued

Gene ontology analysis for RNA sequencing (related to FIG. 2E)

| Term | Original size | After restricting to dataset | % |
|---|---|---|---|
| PID_RETINOIC_ACID_PATHWAY | 30 | 5 | 16.7% |
| BIOCARTA_TGFB_PATHWAY | 19 | 3 | 15.8% |
| GO_CELLULAR_RESPONSE_TO_RETINOIC_ACID | 61 | 9 | 14.8% |
| GO_RETINOIC_ACID_METABOLIC_PROCESS | 21 | 3 | 14.3% |
| KEGG_HEDGEHOG_SIGNALING_PATHWAY | 56 | 8 | 14.3% |
| GO_RESPONSE_TO_RETINOIC_ACID | 103 | 14 | 13.6% |
| GO_NEGATIVE_REGULATION_OF_RETINOIC_ACID_RECEPTOR_SIGNALING_PATHWAY | 23 | 3 | 13.0% |
| GO_POSITIVE_REGULATION_OF_NOTCH_SIGNALING_PATHWAY | 33 | 4 | 12.1% |
| GO_NOTCH_SIGNALING_PATHWAY | 111 | 12 | 10.8% |
| GO_REGULATION_OF_RETINOIC_ACID_RECEPTOR_SIGNALING_PATHWAY | 29 | 3 | 10.3% |
| HALLMARK_HEDGEHOG_SIGNALING | 35 | 3 | 8.6% |
| GO_REGULATION_OF_NOTCH_SIGNALING_PATHWAY | 63 | 5 | 7.9% |
| PID_FGF_PATHWAY | 55 | 4 | 7.3% |
| GO_RETINOIC_ACID_RECEPTOR_SIGNALING_PATHWAY | 17 | 1 | 5.9% |
| GO_NEGATIVE_REGULATION_OF_NOTCH_SIGNALING_PATHWAY | 25 | 1 | 4.0% |
| C4 | | | |
| GO_NEGATIVE_REGULATION_OF_NOTCH_SIGNALING_PATHWAY | 25 | 3 | 12.0% |
| PID_RETINOIC_ACID_PATHWAY | 30 | 2 | 6.7% |
| GO_NOTCH_SIGNALING_PATHWAY | 111 | 7 | 6.3% |
| GO_NOTCH_BINDING | 17 | 1 | 5.9% |
| GO_RETINOIC_ACID_RECEPTOR_SIGNALING_PATHWAY | 17 | 1 | 5.9% |
| GO_REGULATION_OF_NOTCH_SIGNALING_PATHWAY | 63 | 3 | 4.8% |
| PID_FGF_PATHWAY | 55 | 2 | 3.6% |
| KEGG_HEDGEHOG_SIGNALING_PATHWAY | 56 | 2 | 3.6% |
| GO_CELLULAR_RESPONSE_TO_RETINOIC_ACID | 61 | 2 | 3.3% |
| GO_POSITIVE_REGULATION_OF_NOTCH_SIGNALING_PATHWAY | 33 | 1 | 3.0% |
| GO_RESPONSE_TO_RETINOIC_ACID | 103 | 3 | 2.9% |
| PID_BMP_PATHWAY | 42 | 1 | 2.4% |
| GO_NEGATIVE_REGULATION_OF_BMP_SIGNALING_PATHWAY | 42 | 1 | 2.4% |
| GO_REGULATION_OF_BMP_SIGNALING_PATHWAY | 74 | 1 | 1.4% |
| GO_NOTCH_RECEPTOR_PROCESSING | 16 | | 0.0% |
| GO_RETINOIC_ACID_METABOLIC_PROCESS | 21 | | 0.0% |
| BIOCARTA_TGFB_PATHWAY | 19 | | 0.0% |
| HALLMARK_HEDGEHOG_SIGNALING | 35 | | 0.0% |
| GO_POSITIVE_REGULATION_OF_BMP_SIGNALING_PATHWAY | 29 | | 0.0% |
| GO_REGULATION_OF_RETINOIC_ACID_RECEPTOR_SIGNALING_PATHWAY | 29 | | 0.0% |
| GO_NEGATIVE_REGULATION_OF_RETINOIC_ACID_RECEPTOR_SIGNALING_PATHWAY | 23 | | 0.0% |
| C5 | | | |
| HALLMARK_HEDGEHOG_SIGNALING | 35 | 6 | 17.1% |
| PID_BMP_PATHWAY | 42 | 5 | 11.9% |
| GO_NOTCH_BINDING | 17 | 2 | 11.8% |
| GO_RETINOIC_ACID_RECEPTOR_SIGNALING_PATHWAY | 17 | 2 | 11.8% |
| GO_CELLULAR_RESPONSE_TO_RETINOIC_ACID | 61 | 6 | 9.8% |
| GO_RETINOIC_ACID_METABOLIC_PROCESS | 21 | 2 | 9.5% |
| GO_NEGATIVE_REGULATION_OF_BMP_SIGNALING_PATHWAY | 42 | 4 | 9.5% |
| KEGG_HEDGEHOG_SIGNALING_PATHWAY | 56 | 5 | 8.9% |
| GO_RESPONSE_TO_RETINOIC_ACID | 103 | 8 | 7.8% |
| GO_REGULATION_OF_BMP_SIGNALING_PATHWAY | 74 | 5 | 6.8% |
| GO_NOTCH_SIGNALING_PATHWAY | 111 | 7 | 6.3% |
| PID_FGF_PATHWAY | 55 | 3 | 5.5% |
| BIOCARTA_TGFB_PATHWAY | 19 | 1 | 5.3% |
| GO_NEGATIVE_REGULATION_OF_RETINOIC_ACID_RECEPTOR_SIGNALING_PATHWAY | 23 | 1 | 4.3% |

TABLE 1-continued

Gene ontology analysis for RNA sequencing (related to FIG. 2E)

| Term | Original size | After restricting to dataset | % |
|---|---|---|---|
| GO_NEGATIVE_REGULATION_OF_NOTCH_SIGNALING_PATHWAY | 25 | 1 | 4.0% |
| GO_POSITIVE_REGULATION_OF_BMP_SIGNALING_PATHWAY | 29 | 1 | 3.4% |
| GO_REGULATION_OF_RETINOIC_ACID_RECEPTOR_SIGNALING_PATHWAY | 29 | 1 | 3.4% |
| PID_RETINOIC_ACID_PATHWAY | 30 | 1 | 3.3% |
| GO_REGULATION_OF_NOTCH_SIGNALING_PATHWAY | 63 | 2 | 3.2% |
| GO_NOTCH_RECEPTOR_PROCESSING | 16 |  | 0.0% |
| GO_POSITIVE_REGULATION_OF_NOTCH_SIGNALING_PATHWAY | 33 |  | 0.0% |
| C6 | | | |
| GO_RETINOIC_ACID_METABOLIC_PROCESS | 21 | 4 | 19.0% |
| GO_RETINOIC_ACID_RECEPTOR_SIGNALING_PATHWAY | 17 | 2 | 11.8% |
| GO_CELLULAR_RESPONSE_TO_RETINOIC_ACID | 61 | 5 | 8.2% |
| KEGG_HEDGEHOG_SIGNALING_PATHWAY | 56 | 4 | 7.1% |
| GO_RESPONSE_TO_RETINOIC_ACID | 103 | 6 | 5.8% |
| HALLMARK_HEDGEHOG_SIGNALING | 35 | 2 | 5.7% |
| GO_NEGATIVE_REGULATION_OF_RETINOIC_ACID_RECEPTOR_SIGNALING_PATHWAY | 23 | 1 | 4.3% |
| GO_NEGATIVE_REGULATION_OF_NOTCH_SIGNALING_PATHWAY | 25 | 1 | 4.0% |
| GO_REGULATION_OF_RETINOIC_ACID_RECEPTOR_SIGNALING_PATHWAY | 29 | 1 | 3.4% |
| PID_RETINOIC_ACID_PATHWAY | 30 | 1 | 3.3% |
| GO_NOTCH_SIGNALING_PATHWAY | 111 | 3 | 2.7% |
| GO_REGULATION_OF_NOTCH_SIGNALING_PATHWAY | 63 | 1 | 1.6% |
| GO_NOTCH_RECEPTOR_PROCESSING | 16 |  | 0.0% |
| GO_NOTCH_BINDING | 17 |  | 0.0% |
| BIOCARTA_TGFB_PATHWAY | 19 |  | 0.0% |
| GO_POSITIVE_REGULATION_OF_NOTCH_SIGNALING_PATHWAY | 33 |  | 0.0% |
| PID_BMP_PATHWAY | 42 |  | 0.0% |
| PID_FGF_PATHWAY | 55 |  | 0.0% |
| GO_POSITIVE_REGULATION_OF_BMP_SIGNALING_PATHWAY | 29 |  | 0.0% |
| GO_NEGATIVE_REGULATION_OF_BMP_SIGNALING_PATHWAY | 42 |  | 0.0% |
| GO_REGULATION_OF_BMP_SIGNALING_PATHWAY | 74 |  | 0.0% |
| C7 | | | |
| GO_CELLULAR_RESPONSE_TO_RETINOIC_ACID | 61 | 5 | 8.2% |
| GO_NOTCH_RECEPTOR_PROCESSING | 16 | 1 | 6.3% |
| GO_POSITIVE_REGULATION_OF_NOTCH_SIGNALING_PATHWAY | 33 | 2 | 6.1% |
| GO_NOTCH_BINDING | 17 | 1 | 5.9% |
| GO_RESPONSE_TO_RETINOIC_ACID | 103 | 6 | 5.8% |
| GO_REGULATION_OF_BMP_SIGNALING_PATHWAY | 74 | 4 | 5.4% |
| KEGG_HEDGEHOG_SIGNALING_PATHWAY | 56 | 3 | 5.4% |
| GO_RETINOIC_ACID_METABOLIC_PROCESS | 21 | 1 | 4.8% |
| GO_REGULATION_OF_NOTCH_SIGNALING_PATHWAY | 63 | 3 | 4.8% |
| GO_NEGATIVE_REGULATION_OF_BMP_SIGNALING_PATHWAY | 42 | 2 | 4.8% |
| GO_NEGATIVE_REGULATION_OF_NOTCH_SIGNALING_PATHWAY | 25 | 1 | 4.0% |
| GO_NOTCH_SIGNALING_PATHWAY | 111 | 4 | 3.6% |
| GO_POSITIVE_REGULATION_OF_BMP_SIGNALING_PATHWAY | 29 | 1 | 3.4% |
| PID_BMP_PATHWAY | 42 | 1 | 2.4% |
| PID_FGF_PATHWAY | 55 | 1 | 1.8% |
| GO_RETINOIC_ACID_RECEPTOR_SIGNALING_PATHWAY | 17 |  | 0.0% |
| BIOCARTA_TGFB_PATHWAY | 19 |  | 0.0% |
| HALLMARK_HEDGEHOG_SIGNALING | 35 |  | 0.0% |
| PID_RETINOIC_ACID_PATHWAY | 30 |  | 0.0% |
| GO_REGULATION_OF_RETINOIC_ACID_RECEPTOR_SIGNALING_PATHWAY | 29 |  | 0.0% |

TABLE 1-continued

Gene ontology analysis for RNA sequencing (related to FIG. 2E)

| Term | Original size | After restricting to dataset | % |
|---|---|---|---|
| GO_NEGATIVE_REGULATION_OF_RETINOIC_ACID_RECEPTOR_SIGNALING_PATHWAY | 23 | | 0.0% |
| C8 | | | |
| GO_NOTCH_BINDING | 17 | 3 | 17.6% |
| GO_CELLULAR_RESPONSE_TO_RETINOIC_ACID | 61 | 10 | 16.4% |
| GO_POSITIVE_REGULATION_OF_NOTCH_SIGNALING_PATHWAY | 33 | 5 | 15.2% |
| KEGG_HEDGEHOG_SIGNALING_PATHWAY | 56 | 8 | 14.3% |
| GO_RESPONSE_TO_RETINOIC_ACID | 103 | 14 | 13.6% |
| GO_REGULATION_OF_NOTCH_SIGNALING_PATHWAY | 63 | 8 | 12.7% |
| GO_NEGATIVE_REGULATION_OF_NOTCH_SIGNALING_PATHWAY | 25 | 3 | 12.0% |
| HALLMARK_HEDGEHOG_SIGNALING | 35 | 4 | 11.4% |
| PID_FGF_PATHWAY | 55 | 6 | 10.9% |
| PID_RETINOIC_ACID_PATHWAY | 30 | 2 | 6.7% |
| GO_NOTCH_SIGNALING_PATHWAY | 111 | 7 | 6.3% |
| GO_NOTCH_RECEPTOR_PROCESSING | 16 | 1 | 6.3% |
| GO_RETINOIC_ACID_METABOLIC_PROCESS | 21 | 1 | 4.8% |
| PID_BMP_PATHWAY | 42 | 2 | 4.8% |
| GO_NEGATIVE_REGULATION_OF_BMP_SIGNALING_PATHWAY | 42 | 2 | 4.8% |
| GO_NEGATIVE_REGULATION_OF_RETINOIC_ACID_RECEPTOR_SIGNALING_PATHWAY | 23 | 1 | 4.3% |
| GO_POSITIVE_REGULATION_OF_BMP_SIGNALING_PATHWAY | 29 | 1 | 3.4% |
| GO_REGULATION_OF_RETINOIC_ACID_RECEPTOR_SIGNALING_PATHWAY | 29 | 1 | 3.4% |
| GO_REGULATION_OF_BMP_SIGNALING_PATHWAY | 74 | 2 | 2.7% |
| GO_RETINOIC_ACID_RECEPTOR_SIGNALING_PATHWAY | 17 | | 0.0% |
| BIOCARTA_TGFB_PATHWAY | 19 | | 0.0% |

Figure 10:
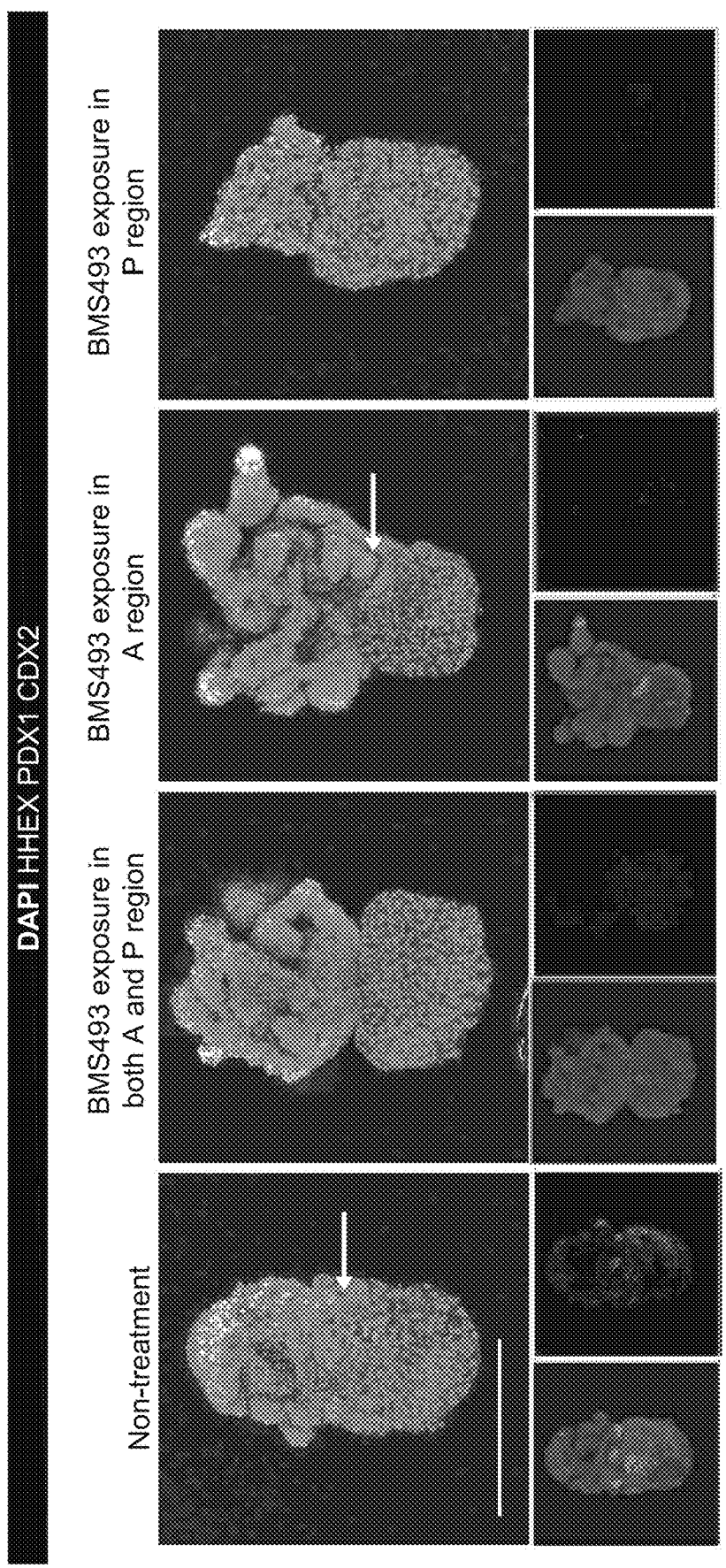
Figure 11A:
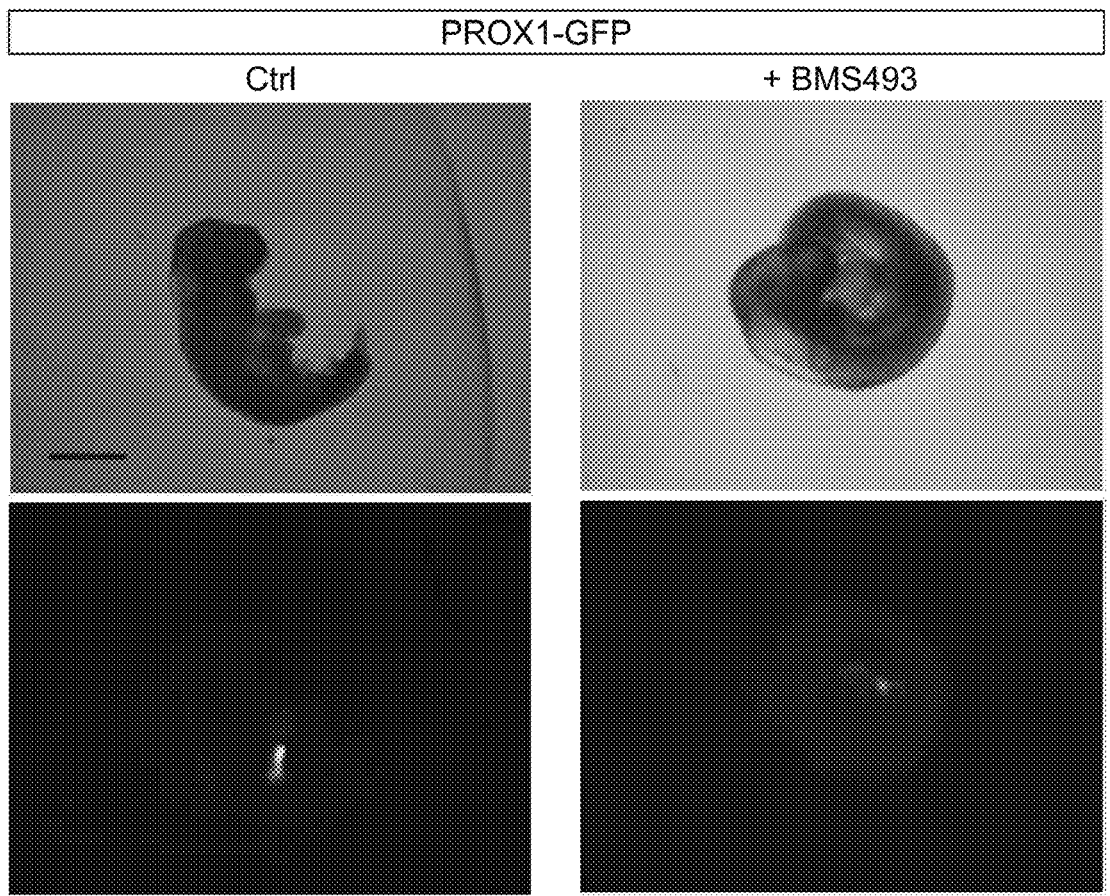
Figure 11B:
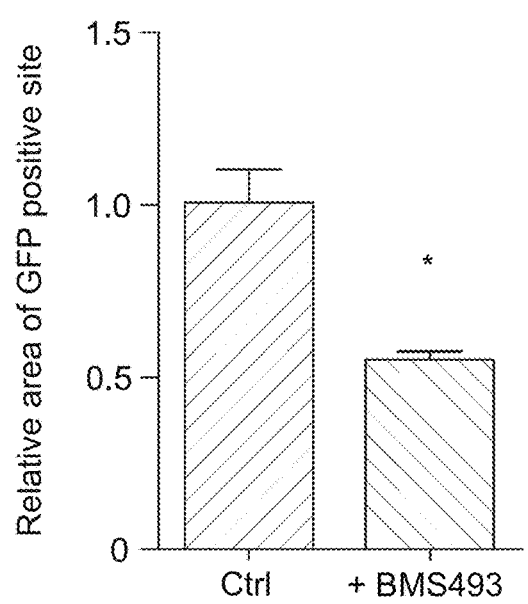

In support, Applicant exposed the bAP organoids at D9 to various RA signaling agonists or antagonists. The RA receptor antagonist BMS493 strongly suppressed the gene expression of both HHEX and PDX1 (FIG. 2G). Animal studies suggested that RA signaling has an important role in the lineage specification into the hepato-biliary-pancreatic systems[20,21]. Lateral plate mesoderm population acts as an activator for RA signaling during the specification in vivo[22-24]. To implicate the cellular source for RA in the model system, RA signaling related genes were assessed in the isolated epithelial and non-epithelial cell populations. FACS analysis showed that there were 90.3% Epithelial Cell Adhesion Molecule (EpCAM) positive epithelial cells in the anterior gut cells, whereas 94.8% EpCAM positive in the posterior gut cells (FIG. 5). Interestingly, the anterior non-epithelial cells, but not in other populations, highly expressed the RA synthesis gene Aldehyde Dehydrogenase 1 Family Member A2 (ALDH1A2) similar to previous in vivo animal model studies (FIG. 2H). Complementing this, exposing only the posterior gut spheroid, and not the anterior gut spheroid to BMS493 prior to fusion suppressed the protein-level induction of HHEX and PDX1 (FIG. 10). An E9.0 PROX1::GFP reporter mouse embryo, cultured in a whole embryo culture system with BMS493, also displayed significant inhibition of PROX1 expressing cells after 2 days (FIGS. 11A and 11B). Taken together, HBP progenitor self-specification derived from posterior region in boundary organoid model system is regulated by RA signals, and may be supported by co-differentiating anterior non-epithelial, most likely mesenchymal, lineages.

It has been noted that stem cell-derived embryonic endodermal cells are highly plastic and usually generate intestinal tissues[18,25]. To examine whether there is an ability to form HBP tissues from progenitors in vivo, transplantations of human PROX1 expressing organoids into immunodeficient mice were performed. One month transplant derived tissues exhibited the small intestinal tissue markers Keratin 20 (CK20), CDX2, and EpCAM, but negligible expression of the other HBP markers (FIG. 2I). In addition, the duodenum maker Receptor Accessory Protein 6 (REEP6/DP1L1) and SOX9 expression pattern informed that these human tissues were most similar to duodenum tissue (FIG. 2I). These results indicated that despite the presence of HBP progenitors, ectopically transplanted organoids tend to develop intestinal tissues in vivo.

Figure 3C:
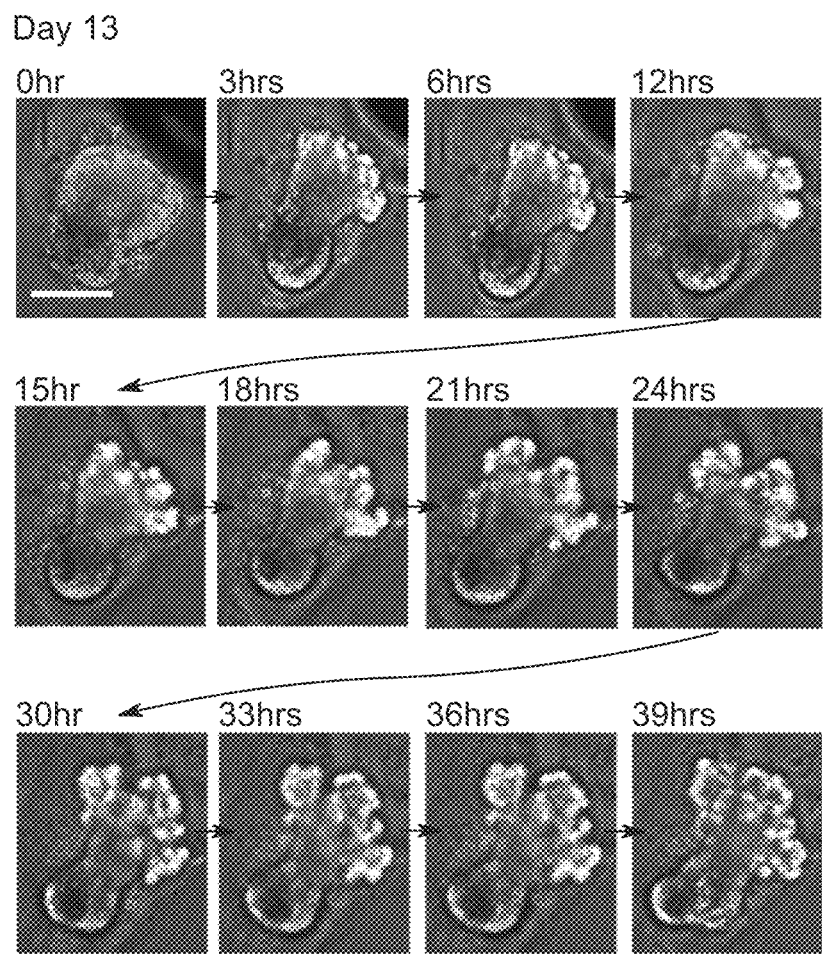
Figure 13:
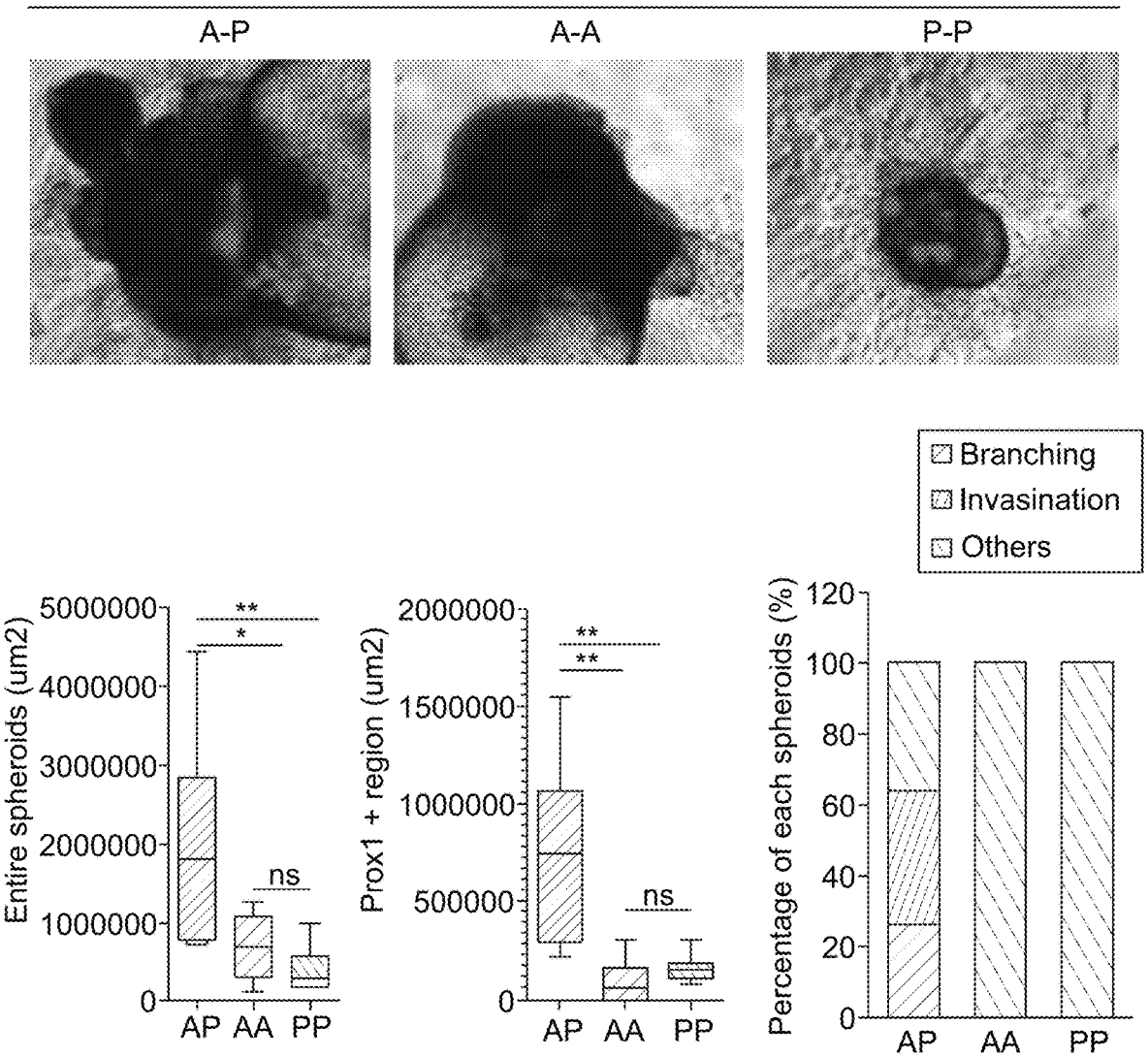
FIG. 13. Comparison of organoid size, PROX1 positive area, branching and invagination. Only AP combination increased the size of the organoids and PROX1 expressing region. Moreover, AP combination showed the spheroids with branching and invagination while other two combination did not. Scale bar: 500 µm FIG. 14. Failure to branch and invaginate from posterior region of HBP organoids. While HBP organoid formed Prox1 expressing branching structure, posterior region of HBP that contain PDX1 expression did not form its structure. Scale bar is 200 µm.
Figure 14:
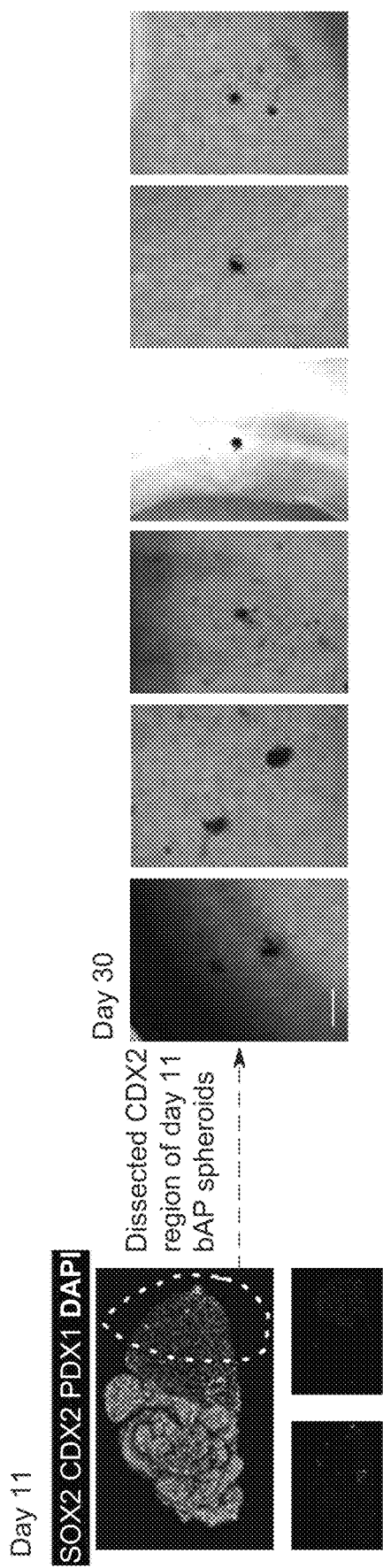

Because the HBP organoids generated predominantly duodenum tissue in vivo, Applicant next excised PROX1 positive regions from the D13 boundary organoids and cultured them in different formats to effectively model HBP organogenesis (FIGS. 3A and B). Strikingly, among the various tested culture conditions (FIG. 12), excised tissues were cultured for two weeks in Matrigel™ drop on Transwell™ without specific growth factors; most of the PROX1 tissues developed into spatially organized invaginating epithelium, and formed a branching structure (FIG. 3b). In contrast, only a small number of PROX1 positive epithelium cultured in floating conditions or non-dissected organoids were invaginated (FIG. 3B). Time course imaging showed the dissected PROX1 positive tissue changed from an epithelial morphology into a more convoluted structure during 2 days of culture (FIG. 3C). Around D25, the PROX1 epithelium portion of the organoid started to invaginate. The PROX1 positive region subsequently started to grow outward in multiple directions, forming a branching structure via progressive invagination (FIGS. 3D and D). The branching structures were not observed in A-A and P-P combination (FIG. 13). Furthermore, the posterior gut spheroids alone, which expressed PDX1 initially but dissected from the bAP organoids, were not capable of growing invaginating structures (FIG. 14).

Figure 3G:
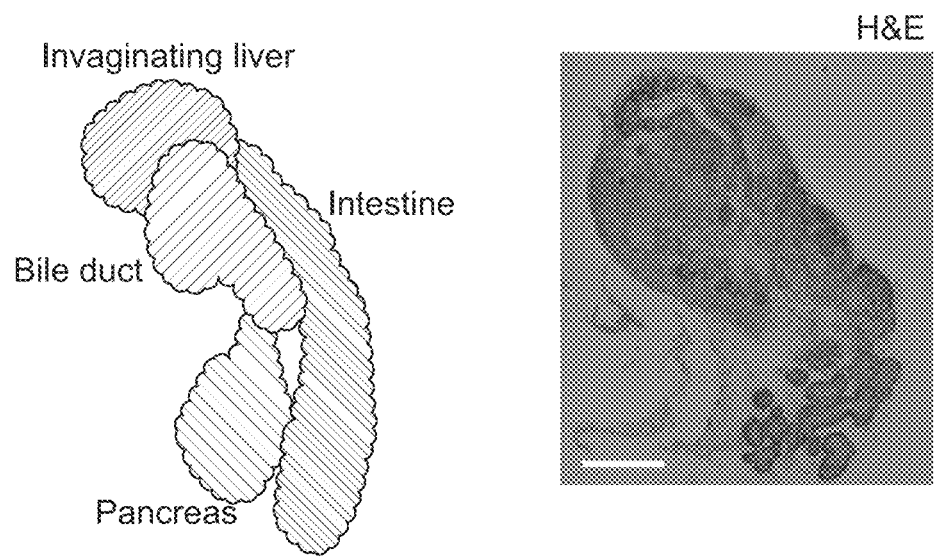
Figure 3H:
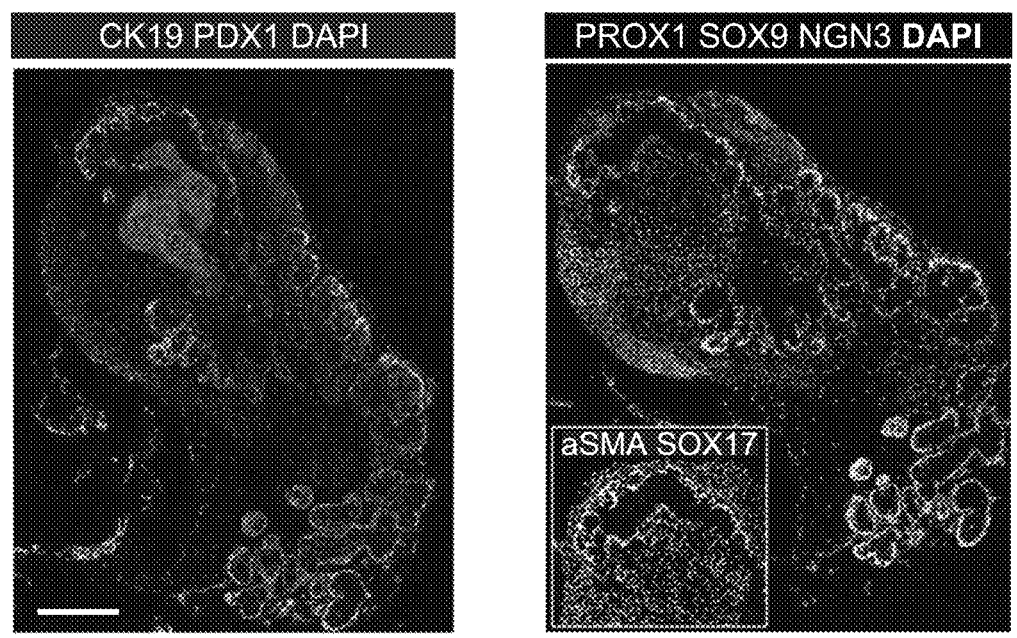
Figure 3I:
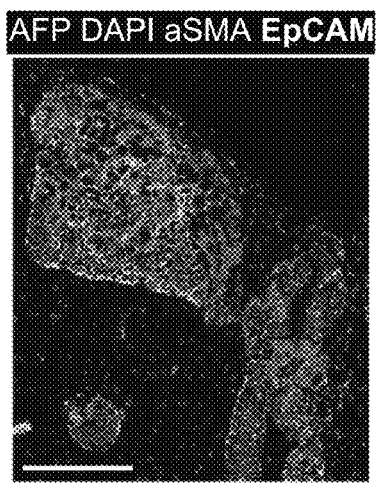
Figure 3J:
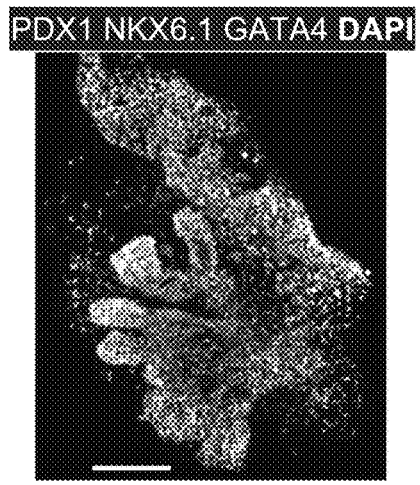
Figure 3K:
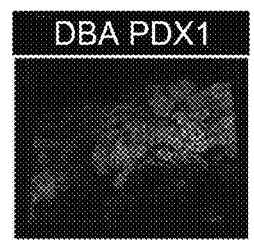
Figure 3K:
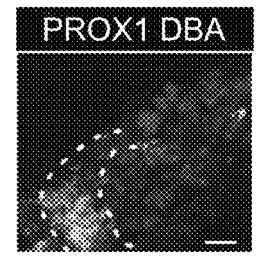
Figure 3L:
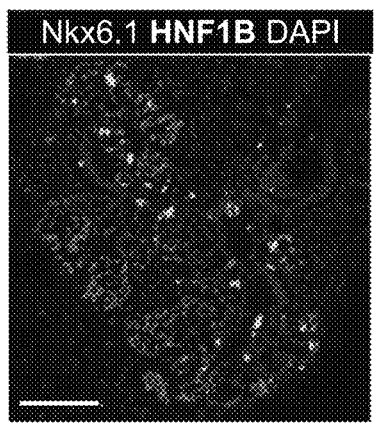
Figure 3M:
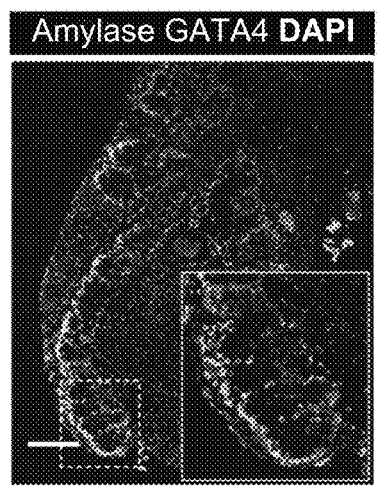
Figure 3O:
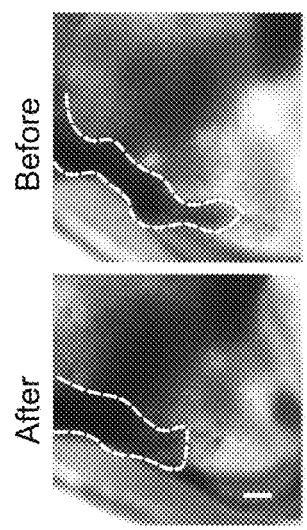
Figure 3M:
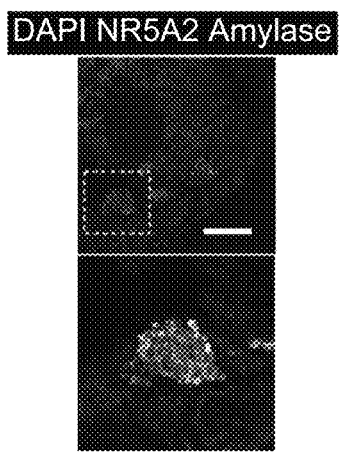
Figure 3N:
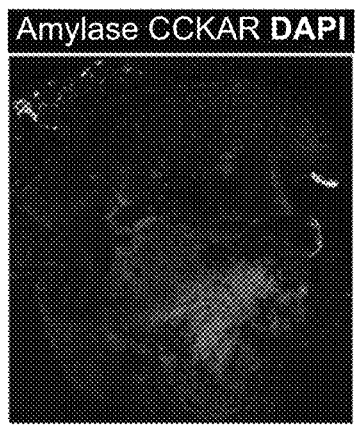
Figure 3P:
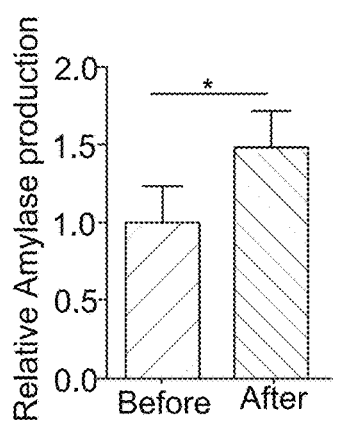
Figure 15A:
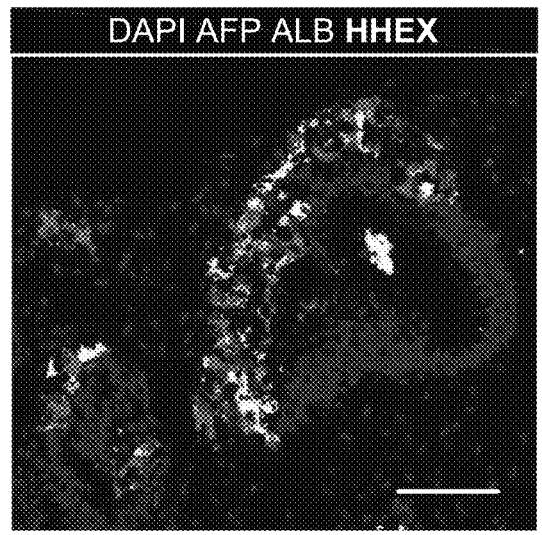
FIG. 15A-15C. Expression of organ domain-specific markers in HBP organoids. 15A. Immunofluorescent staining of AFP, Albumin, and HHEX at Day 30. AFP and Albumin expressed in the same region but not HHEX. HHEX were hepatocyte progenitor marker which result in disappearance of the expression at the later stage. 15B. Immunofluorescent staining of NKX6.1, NKX6.3 and PDX1. NKx6.3 were expressed in the area of pancreatic markers PDX1 and NKX6.1 expression. 15C. Immunofluorescent staining of EpCAM, PROX1, SOX9, and CLF. Scale bar: 100 µm FIG. 16. Pancreatic associated genes were upregulated in HES−/−organoids. RNAseq of pancreatic associated markers at Day 22 of HES1+/+ and HES1−/−HBP organoids. This is related to FIG. 4G.
Figure 15B:
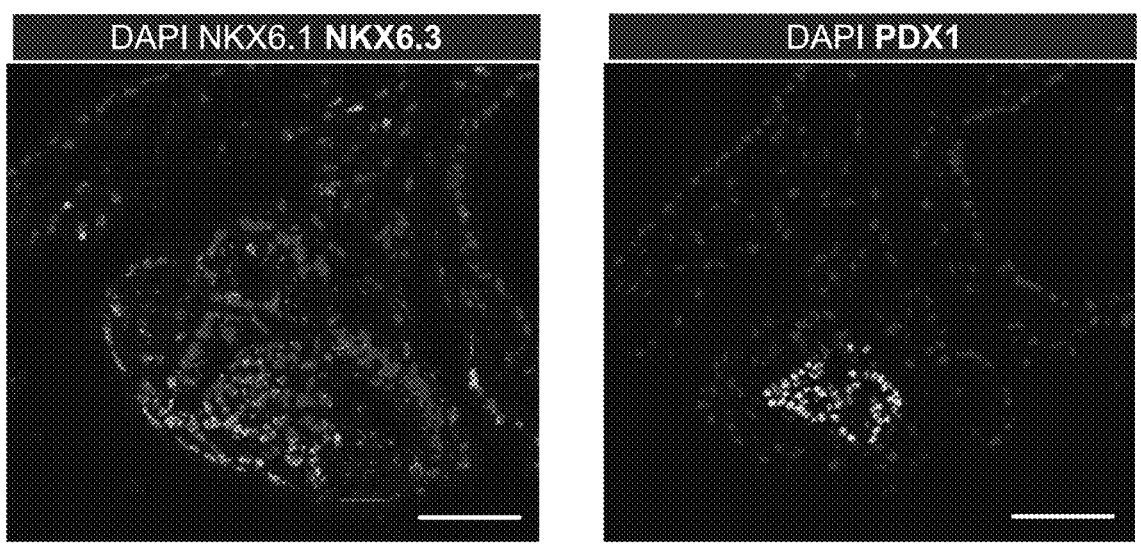
Figure 15C:
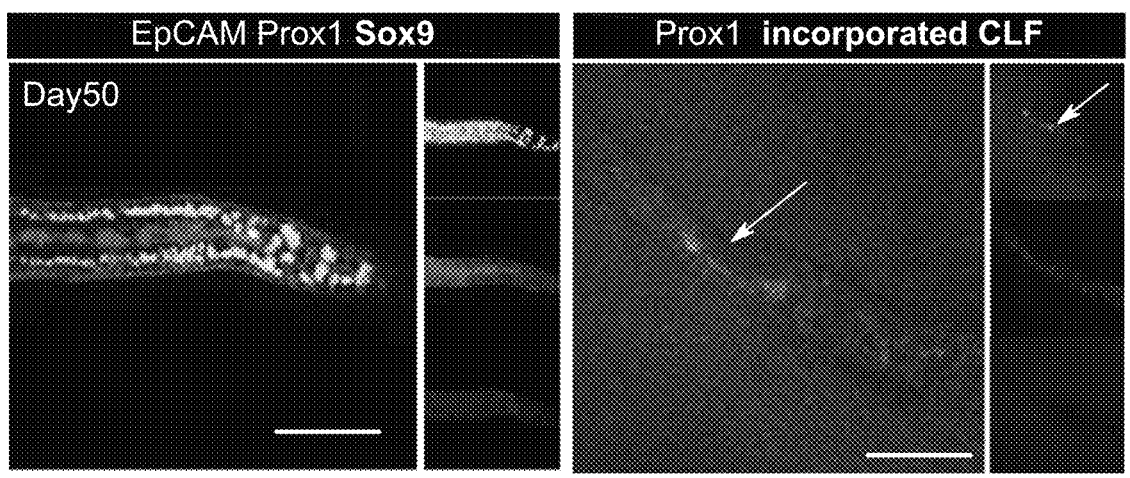

To determine whether longer-term culture can produce more mature tissue, organoids were cultured until D90. The D90 organoids were morphologically similar to mouse E14.5 explanted organ culture (FIG. 3F). H&E staining showed that the long-term cultured organoids morphologically contain liver, pancreas, bile duct and intestine tissues (FIG. 3G). Furthermore, the immunofluorescent staining detected the expression of the pancreas marker PDX1 and NGN3, the liver marker PROX1, and the bile duct markers CK19 and SOX9 in the organoids (FIG. 3H). Alpha-SMA expressing mesenchyme cells wrapped around bile duct SOX17+ cells similar to developing gallbladder tissue[26] (FIG. 3h). Immunofluorescent and whole mount staining with liver markers AFP and albumin, pancreatic markers PDX1, NKX6.1 and GATA4, and bile duct markers DBA and SOX9 confirmed that each lineage of tissues segregated from the same boundary organoids after more than 30 days of culture (FIG. 3I-L and FIG. 15A-15B). NKX6.1, HNF1B and GATA4 were differentially expressed on the PDX1 positive region, and pancreatic mesenchymal marker NKX6.3 expression was observed alongside the PDX1 expressing cells, as seen in in vivo developing pancreas (FIG. 3I-L and FIG. 15A-15C). Remarkably, the bile duct and pancreas tissue are directly connected in branching organoids, as evidenced by whole mount co-staining of DBA, SOX9, and PDX1 and by the capacity to incorporate fluorescein-labelled bile acid (CLF) (FIGS. 3K and 3K' and FIG. 15C). Moreover, at 90 days, a pancreatic region expressing the exocrine markers amylase and GATA4 was identified in the organoids (FIG. 3M). Given the Cholecystokinin A Receptor (CCKAR) expression in the organoids (FIG. 3N), organoids were exposed to CCK and the pancreatic secretory function was analyzed with an amylase Enzyme-linked immune sorbent assay (ELISA). The ductal structures constricted on the following day, and the CCK treated tissues increased amylase secretion in supernatants compared with untreated controls (FIGS. 3O and 3P). These results indicate that the boundary organoid strategy not merely generates multiple organ (HBP) tissues but also establishes a functional connection of the pancreas, especially exocrine lineage, and bile duct.

Figure 4A:
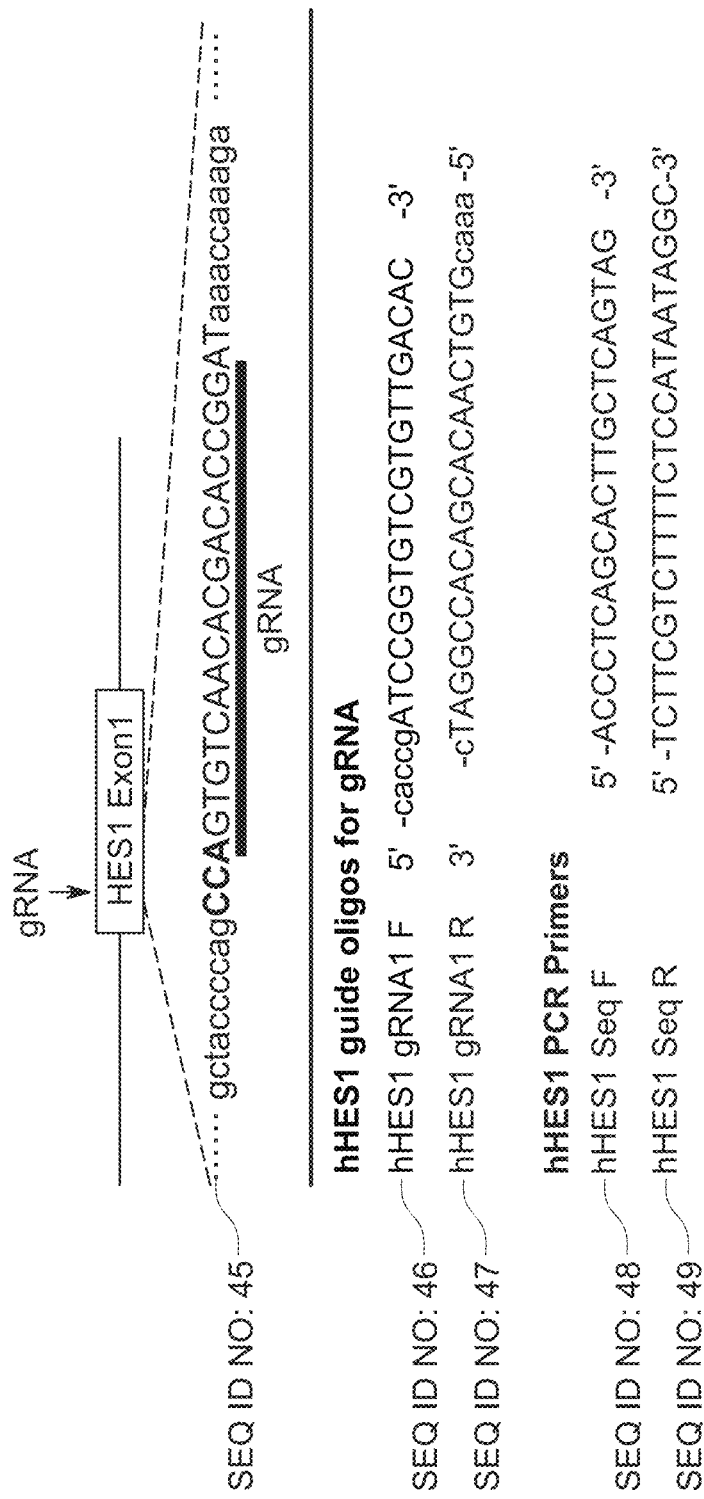
Figure 4C:
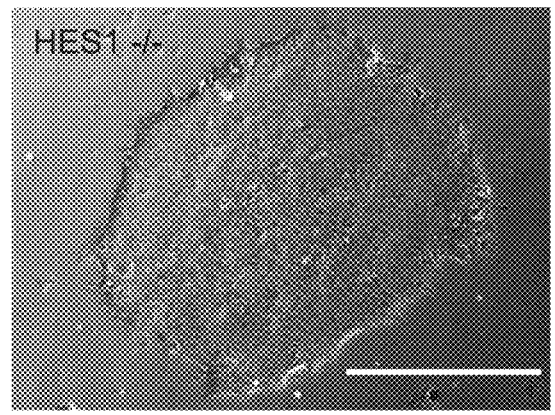
Figure 4D:
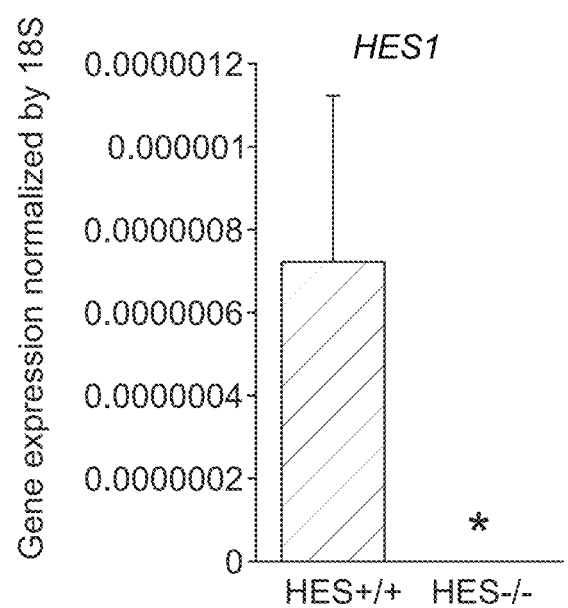
Figure 4E:
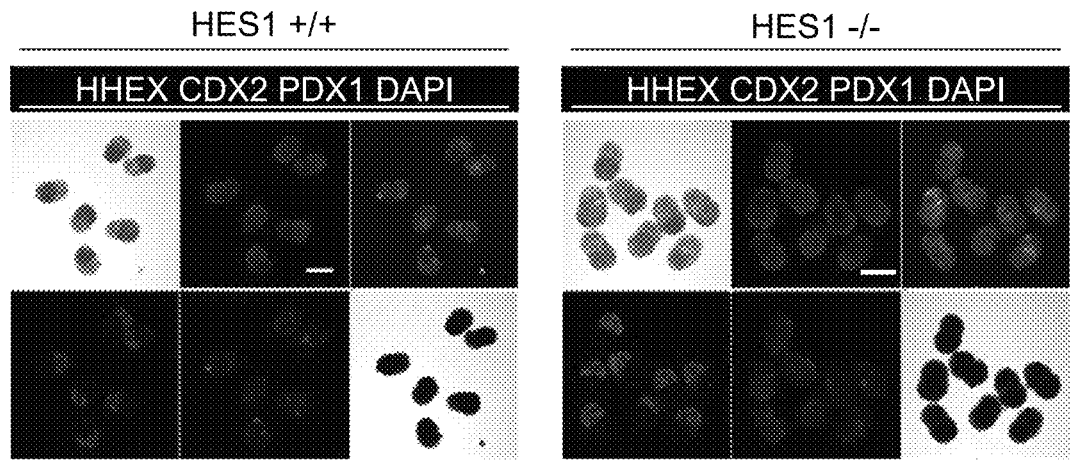
Figure 4F:
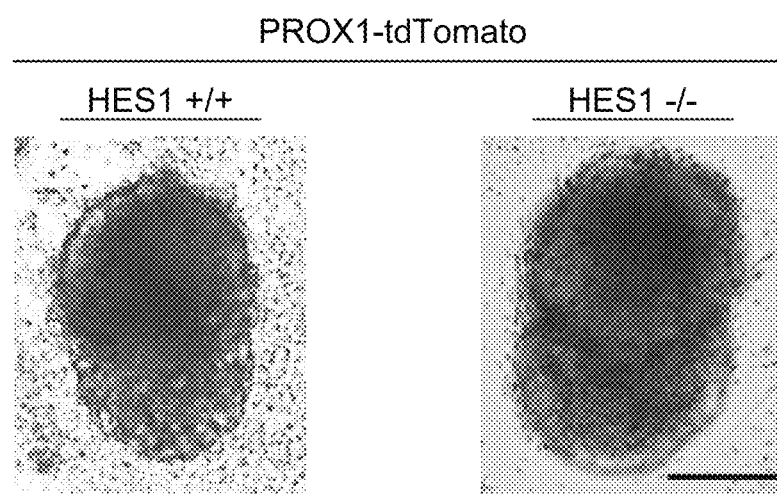
Figure 4G:
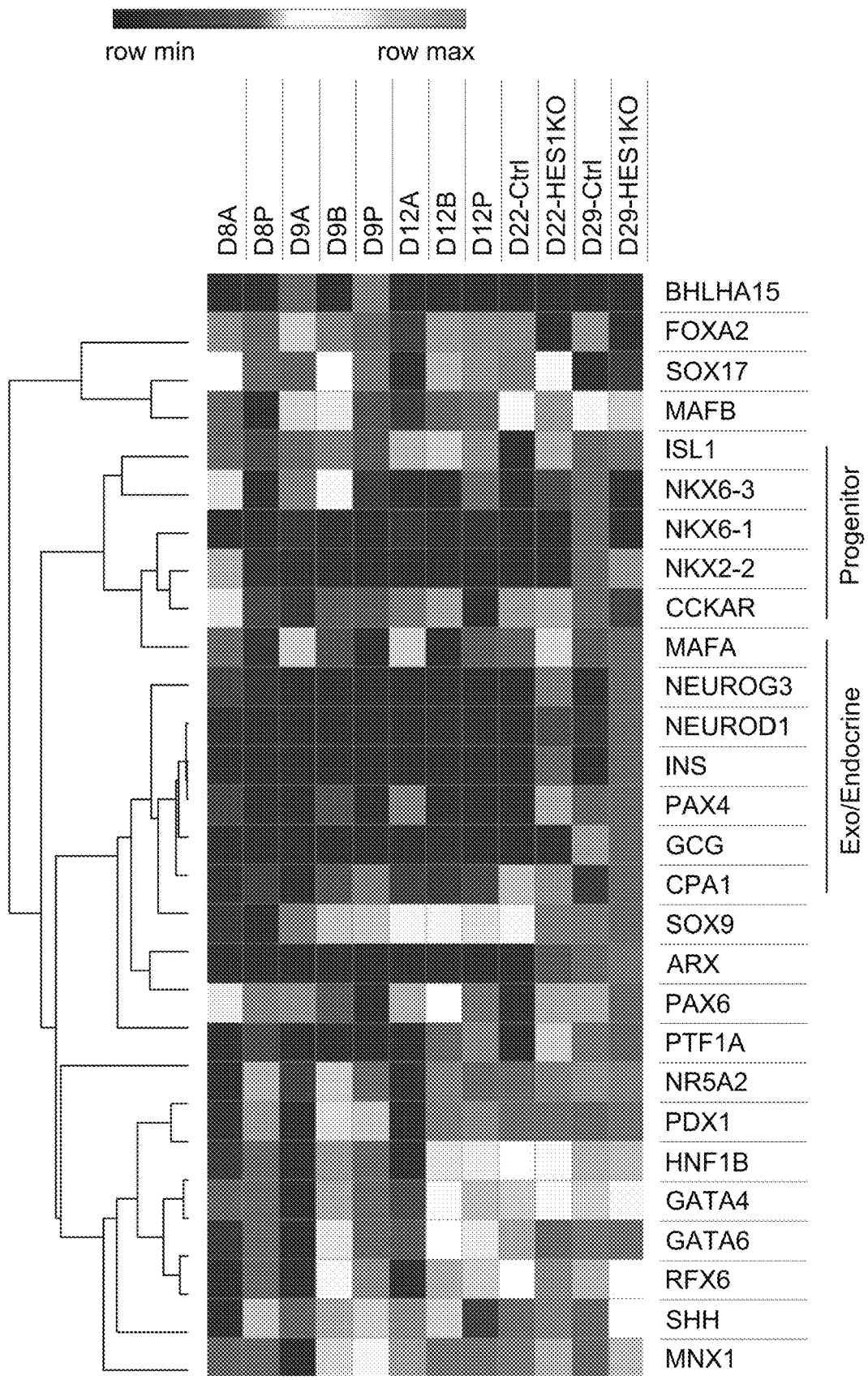
Figure 4H:
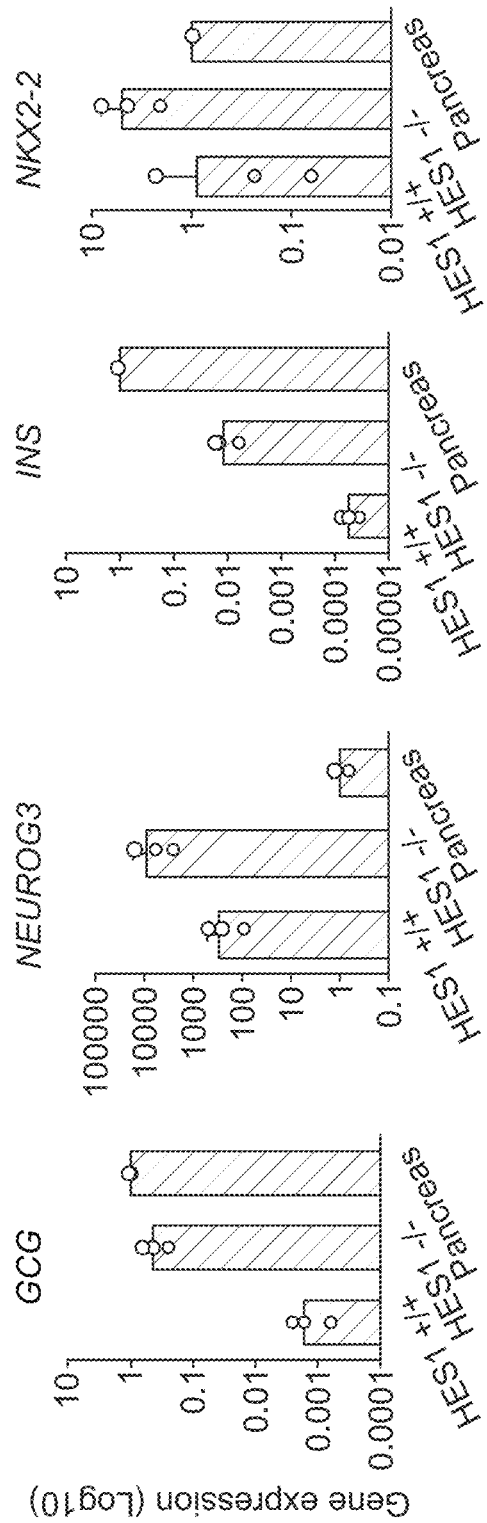
Figure 4I:
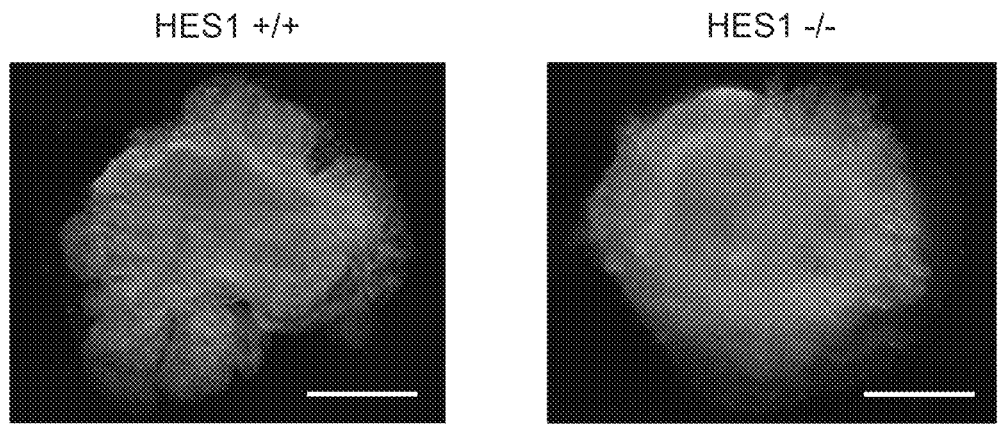
Figure 4J:
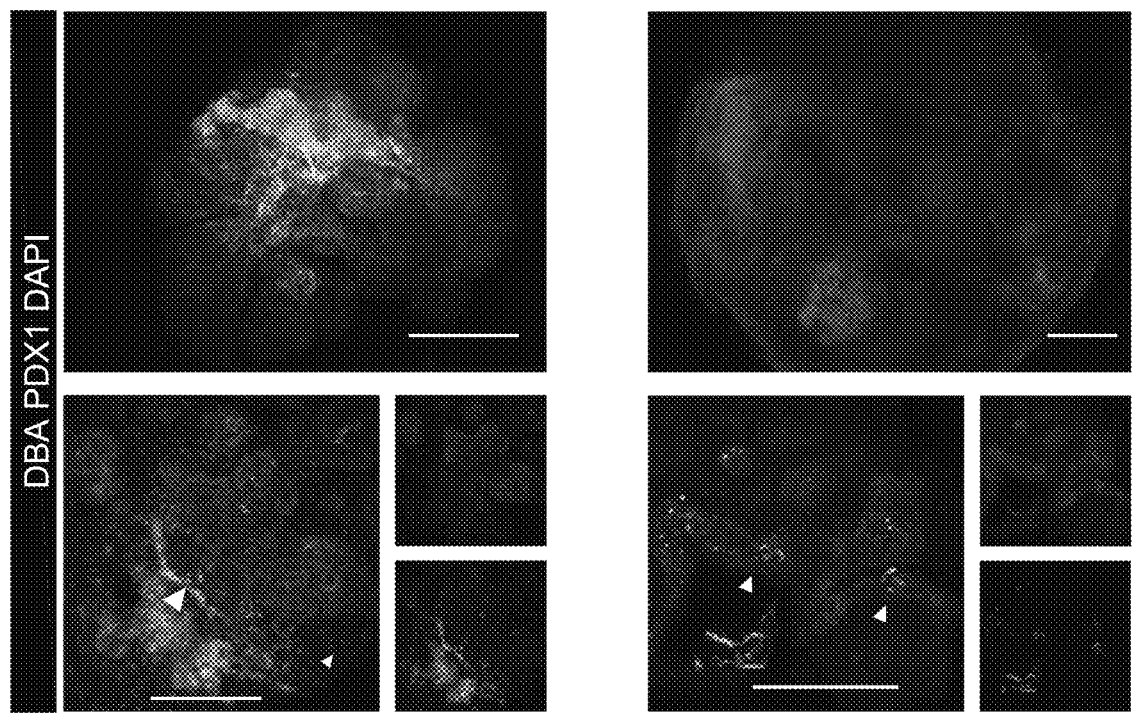
Figure 16:
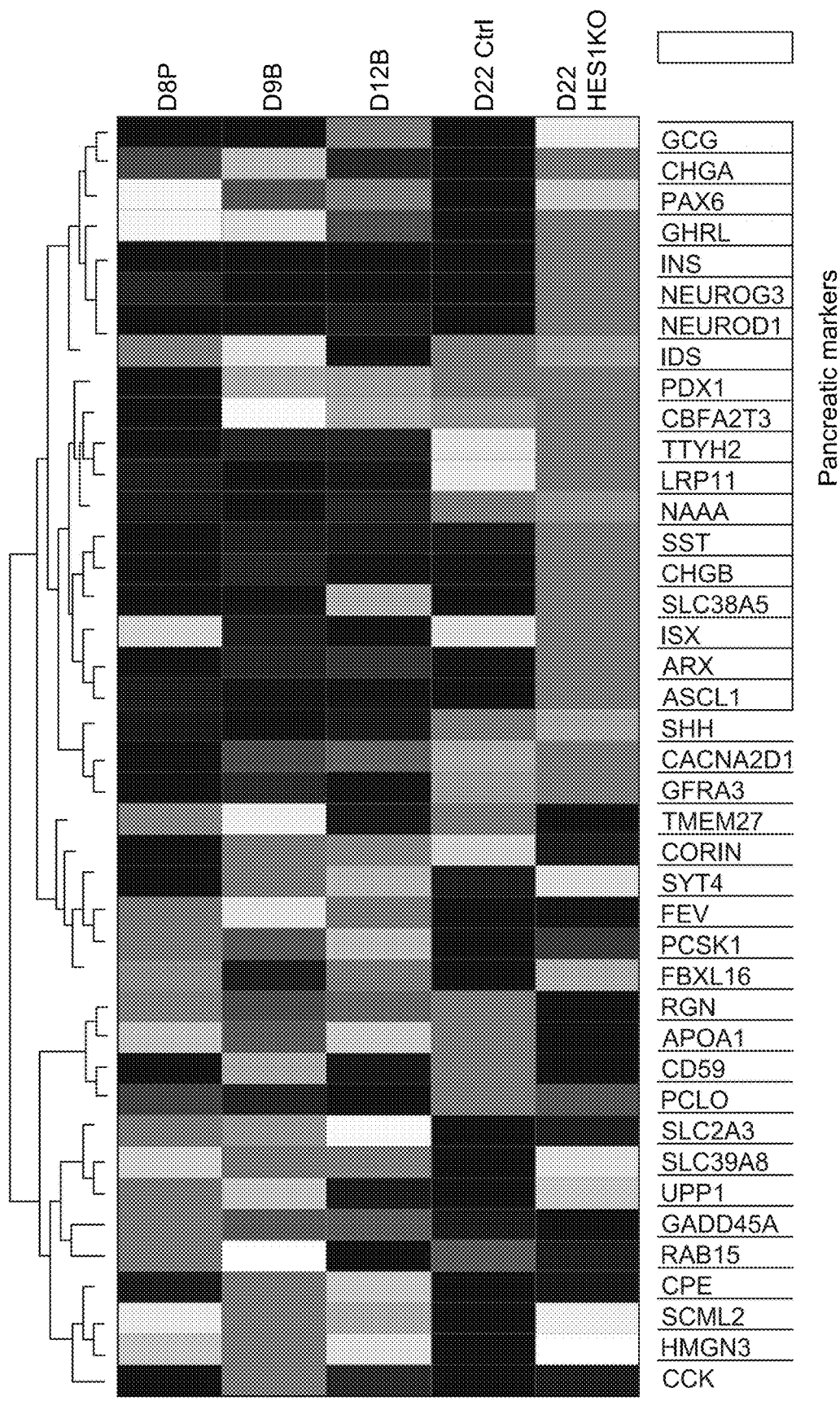
Figure 17:
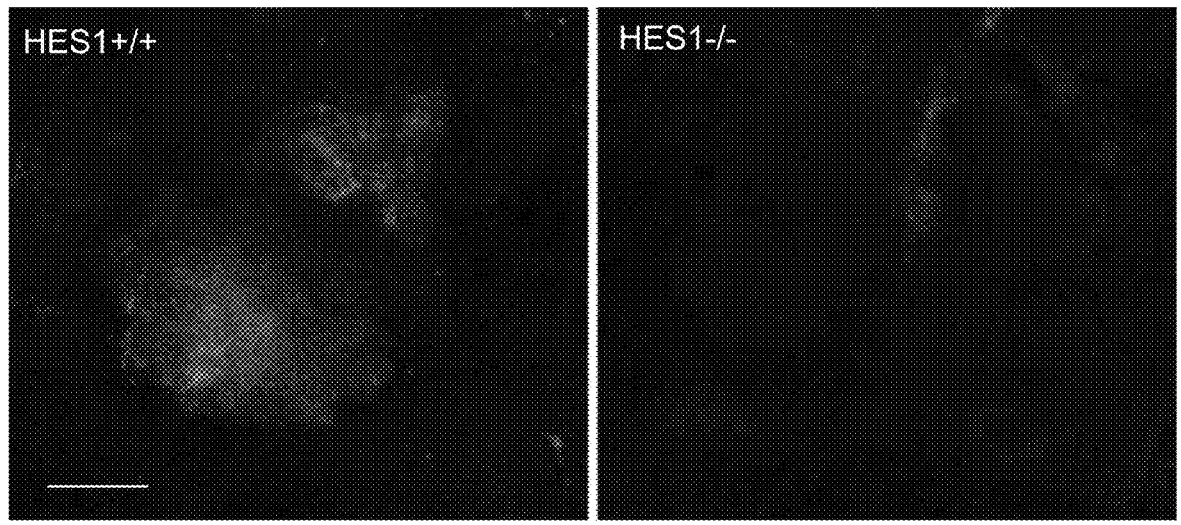
FIG. 17. Connected structure in long term cultured organoid. Whole mount staining of DBA and SOX9 in HES1−/− and HES1+/+organoids. DBA and SOX9 disappeared in HES1−/−organoids. Scale bar: 200 µm.

HES1 (Hes family bHLH transcription factor 1) is a transcription factor that regulates the posterior foregut lineage[15,27]. In Hes1 knock-out rodents, conversion of the biliary system to pancreatic tissue occurs due to failed pancreato-biliary organ segregation[8,9]. To elucidate whether the HBP organoid recapitulates HES1 mediated developmental process, Applicant established HES1 KO on PROX1 reporter iPSCs by CRISPR/Cas9 system (FIG. 4A-4C), and confirmed the absence of HES1 gene expression in HES1−/− iPSC derived organoids at D20 (FIG. 4D). HES1−/−organoids retained PROX1 reporter activity (FIG. 4E) and HHEX/PDX1 expression at the bAP at D11 (FIG. 4F). RNAseq of HES1−/− and HES1+/+ organoids at Day 22 showed that the significant upregulation of reported pancreatic associated murine genes, including endocrine markers, as HES1 targets[9,28], in HES1−/− organoids, compared with HES1+/+ organoids (FIG. 4G and FIG. 16). qRT-PCR showed that all the pancreatic gene expression levels of GCG, NEUROG3, INS, and NKX2-2 were upregulated in HES1−/−organoids, compared with HES1+/+organoids (GCG: 264 fold; NEUROG3: 29.8 fold; INS: 212 fold), however the expression level of GCG, INS were still lower than human pancreases tissue, in both of HES1+/+ and HES1−/−organoids (FIG. 4H). Moreover, consistent with in vivo rodent studies, HES1−/−human organoids produced less DBA and SOX9 positive ductal tissue and more PDX1 positive pancreatic structures compared with HES1+/+organoids (FIG. 4I and J and FIG. 17), highlighting the phenotypic relevance to animal model studies.

Multi-organ integration in stem cell culture is a critical unmet challenge. The instant disclosure demonstrates the generation of a human three-dimensional antero-posterior boundary system that leads to structurally and functionally integrated HBP organoids developed at foregut-midgut border.

Methods

Maintenance of PSCs

Human PSC lines were maintained as described previously. Undifferentiated hPSCs were maintained on feeder-free conditions in mTeSR™1 medium (StemCell technologies, Vancouver, Canada) or Stem Fit™ medium (Ajinomoto Co, Japan) on plates coated either with Matrigel™ Growth Factor Reduced (Corning Inc., New York, NY, USA) at 1/30 dilution or iMatrix™-511 (Nippi, Japan) at 0.25 ug/cm² in an incubator with 5% CO2/95% air at 37° C.

Differentiation of PSCs into Anterior and Posterior Gut Spheroid

Differentiation of hPSCs into definitive endoderm was induced using previously described methods[18,19] with modifications. In brief, colonies of hiPSCs were isolated in Accutase™ (Thermo Fisher Scientific Inc., Waltham, MA, USA) and 150,000 cells/mL were plated on Matrigel™ coated tissue culture plate (VWR Scientific Products, West Chester, PA). Medium was changed to RPMI 1640 medium (Life Technologies, Carlsbad, CA) containing 100 ng/ml Activin A (R&D Systems, Minneapolis, MN) and 50 ng/ml bone morphogenetic protein 4 (BMP4; R&D Systems) at Day 1, 100 ng/mL Activin A and 0.2% fetal calf serum (FCS; Thermo Fisher Scientific Inc.) at Day 2 and 100 ng/ml Activin A and 2% FCS at Day 3. For Day 4-7, cells were cultured in gut growth medium (Advanced DMEM/F12 (Thermo Fisher Scientific Inc.) with 15 mM HEPES, 2 mM L-glutamine, penicillin-streptomycin, B27 (Life Technologies) and N2 (Gibco, Rockville, MD)) supplemented with 200 ng/ml noggin (NOG; R&D Systems), 500 ng/ml fibroblast growth factor 4 (FGF4; R&D Systems) and 2 µM CHIR99021 (Stemgent, Cambridge, MA, USA) for anterior gut cell induction and supplemented with 500 ng/ml FGF 4 and 3 µM CHIR99021 for posterior gut cell induction. Cultures for cell differentiation were maintained at 37° C. in an atmosphere of 5% CO2/95% air and the medium was replaced every day.

Anterior-Posterior Boundary Spheroid Formation

On Day 7, anterior or posterior gut cells were dissociated to single cells by incubation with TrypLE™ Express (Life Technologies) at 37° C. Cells were centrifuged at 1000 rpm for 3 minutes and, after removing supernatant, the pellet was re-suspended in gut growth medium containing 10 µM of Y-27632 dihydrochloride (Tocris Bioscience, Bristol, United Kingdom). The anterior or posterior gut cell suspensions were plated on 96 well round bottom ultra-low attachment plate (Corning Inc) at density of 10,000 cells/well and incubated at 37° C. for 24 hours to form spheroid. On Day 8, generated single anterior gut spheroid and posterior gut spheroid were mixed on 96 well round bottom ultra-low attachment plate in gut growth medium for 24 hours to form fused boundary spheroids (A-P spheroids).

Hepato-Biliary-Pancreatic (HBP) Organoid Culture and Transplantation

On Day 9, A-P spheroids were embedded in Matrigel™ drop and were cultured in gut growth medium to generate multi-organ HBP organoids. For longer-term culture, HBP organoids were dissected and/or transferred to transwell Transwell™ for air-liquid interface culture at Day 13. Cultures for spheroid were maintained at 37° C. in an atmosphere of 5% CO2/95% air and the gut growth medium were replaced every 4 days. Single HBP organoid at Day 13 was transplanted into the subcapsule of the kidney in male immune deficient NSG (NOD.Cg-Prkdc$^{scid}$Il2$^{tg1Wjl}$/SzJ) mice, aged 12 weeks old. All experiments were performed under the approval of the Institutional Animal Care and Use Committee of CCHMC (protocols IACUC2018-0096).

H&E Staining and Immunohistochemistry

Spheroid and organoid were collected from Matrigel™, fixed in 4% paraformaldehyde (PFA) and embedded in paraffin. Sections were subjected to H&E and immunohistochemical staining. The primary antibodies were listed in Table 1. Immunohistochemical staining was performed by using ultra View Universal DAB Detection Kit (Roche Diagnostics, Basel, Switzerland). The specimens were observed under a microscope.

For whole mount immunohistochemical staining, spheroid and organoid were collected from Matrigel™ and removed remaining Matrigel™ by treating with Cell recovery solution at 4° C. for 30 min. The tissues were washed by PBS and were fixed in 4% PFA at 4° C. for overnight. The fixed samples were treated by 4% PFA with 0.5% Triton X100 at room temperature for 15 min and permeabilized with 0.1% Tween 20 (Sigma) at room temperature for 15 min. The samples were treated with blocking solution (1% BSA, 0.3% Triton X100) at room temperature for 1 hour and were incubated overnight at 4° C. with the primary antibodies diluted in blocking solution. After washing, fluorescent dye-conjugated secondary antibodies were applied to the samples at room temperature for 2 hours. The primary and secondary antibodies are listed in Table 1. After the secondary antibody reaction, the samples were washed three times. Nuclei were stained with DAPI mounting solution.

The stained section and whole mount samples were observed under a Nikon A1Rsi inverted confocal microscope.

RNA Isolation, RT-qPCR

RNA was isolated using the RNeasy™ mini kit (Qiagen, Hilden, Germany). Reverse transcription was carried out using the SuperScript IV First-Strand Synthesis System for RT-PCR (Invitrogen, CA, USA) according to manufacturer's protocol. qPCR was carried out using TaqMan™ gene expression master mix (Applied Biosystems) on a QuantStudio™ 3 Real-Time PCR System (Thermo). All primers and probe information for each target gene was obtained from the Universal ProbeLibrary Assay Design Center and listed in Table 2.

RNA Sequencing

Sample preparation for RNA sequencing was performed using SMART-seq v4 Ultra Low Input RNA Kit for Sequencing (Clontech Laboratories) according manufacture's user manual.

Briefly, First-strand cDNA synthesis was primed by the 3' SMART-seq™ CDS Primer II A and uses the SMART-Seq™ v4 Oligonucleotide for template switching at the 5' end of the transcript. PCR Primer II A amplified cDNA from the SMART sequences introduced by 3' SMART-Seq™ CDS Primer II A and the SMART-Seq™ v4 Oligonucleotide by PCR. PCR-amplified cDNA was purified by immobilization on AMPure XP beads. The beads were then washed with 80% ethanol and cDNA was eluted with Elution Buffer. Amplified cDNA was validated using the Agilent 2100 Bioanalyzer and Agilent's High Sensitivity DNA Kit (Agilent) according Kit User Manual. The full-length cDNA output of the SMART-Seq™ v4 Ultra Low Input RNA Kit for Sequencing was processed with the Nextera XT DNA Library Preparation Kit (Illumina).

The RNA profiles were compiled with Kallisto software and expressed as transcripts per million (TPM). The data sets filtered by the threshold requiring greater than 0 in at least 1 sample were first subjected to gene functional classification based on gene sets related to FGF, BMP, Hedgehog, NOTCH and RA signaling pathway. The lists of gene sets were acquired from Molecular Signatures Database (ver 6.2). Unbiased cluster analysis for filtered data sets performed by using Cluster 3.0 software. Detail of gene sets included in each cluster were listed in Table 3.

Flow Cytometry.

For flow cytometry, Anterior gut cells were differentiated from GFP-Labeled iPSCs and posterior gut cells were differentiated from mCherry-Labeled iPSCs. At day 13, A-P spheroid were dissociated to single cells by the treatment of TrypLE Express for 10 min at 37° C. After PBS wash, the single cells were incubated with BV421-conjugated EpCAM antibody (BioLegend) at room temperature for 30 min. After PBS wash, cell sorting was performed by BD FACS™ AriaII (BD Biosciences). Analysis was performed by BD FACS DIVA software and FlowJo™ (FlowJo, LLC).

CRISPR Editing

The plasmid encoding Cas9-2A-GFP was acquired from addgene (#44719, doi: 10.1016/j.stem.2013.03.006). Guide RNA targeting the N-terminus of PROX1 or HES1 was synthesized by Integrated DNA Technologies, cloned into the pGL3-U6-sgRNA-PGK-puromycin vector (addgene #51133, doi: 10.1038/nmeth.2857) and sequenced using the RV3 universal primer. To construct the HDR template, homology arms flanking the PROX1 start codon were independently amplified from genomic DNA and then fused to tdTomato via overlap extension PCR using the high-fidelity taq polymerase iProof (Bio-Rad). The resulting PCR product was then cloned into the pCR-Blunt II-TOPO cloning vector (Invitrogen) and confirmed by Sanger sequencing.

Human iPSCs were transfected with 2 ug of each plasmid using the Lipofectamine 3000 following the manufacturer's instructions. Twenty-four hours after transfection, cells were sorted by GFP expression to select for positively transfected cells. Clonal cells were expanded for 2 weeks and screened for inserted PROX1-tdTomato or depleted HES1 exon1 sequence and karyotyped.

Amylase ELISA.

To measure Amylase secretion level of organoids, 200 µL of culture supernatant was collected from organoid embedded in Matrigel™. The culture supernatants were collected at 48 hrs time points after the culture and stored at −80° C. until use. The supernatant was centrifuged at 1,500 rpm for 3 min and to pellet debris, and the resulting supernatant was assayed with Human Amylase ELISA Kit according to the manufacturer's instructions.

Statistics and Reproducibility.

Statistical analysis was performed using unpaired two-tailed Student's t-test, Dunn-Holland-Wolfe test, or Welch's t-test. Results were shown mean±s.d.; P values <0.05 were considered statistically significant. N-value refers to biologically independent replicates, unless noted otherwise. For comparisons between unpaired 2 groups, non-parametric Brunner-Munzel test was performed when 2 samples were independent, and the variances of the samples were unequal. For comparisons between more than 2 samples, non-parametric Kruskal-Wallis and post hoc Dunn-Holland-Wolf test were performed.

Mouse Whole Embryo Culture

The culturing of the multi-organ three-dimensional organoid may be carried out using a whole embryo culture system (Ikemoto Scientific Technology, Tokyo, Japan) with improved growth. The multi-organ three-dimensional organoid may be transferred into a sterile glass roller bottle containing culture media and the flask closed by silicon plug. The number of transferred organoids depends on how long they will be cultured. The culture bottles may be attached to a rotator drum and rotated at 20 rpm and 37° C. in the dark while being continuously supplied with a gas mixture (mainly 20% O2, 5% $CO_2$ and 75% N2, but the $O_2$ concentration can be modified with balanced with N2). The organoids can be cultured for a few weeks (with the longest trial being 10 weeks). The culture media is changed every 5-7 days and the viability and growth can be monitored based on the organoid length and media components such as Alb, Amy, C-peptide levels.

The Rotator-type Bottle Culture System (Ikemoto Scientific Technology Co., Ltd) was used for whole embryo culture. E9.0 Prox1-GFP mouse embryo was dissected and transfer to culture bottle with Advanced DMEM/F12 supplemented B27 and N2 supplements. The temperature inside the whole embryo culture system was kept at 37.0° C.

TABLE 2

Antibodies used in this study

| Target | Company | Catalog |
|---|---|---|
| SOX2 | Seven Hills | WRAB-1236 |
| CDX2 | Biogenex | MU392A-UC |
| PDX1 | Abcam | ab47308 |
| HHEX | R&D | MAB83771 |
| E-Cadherin | R&D | AF648 |
| E-Cadherin | BD Pharmingen | 610182 |
| RFP | Rockland | RL600-401-379S |
| REEP6 | Proteintech | 12088-1-AP |
| REEP6 | Novus | NBP2-37919 |
| SOX9 | R&D | AF3075 |
| Insulin | eBioscience | 14-9769 |
| Amylase | Sigma-Aldrich | HPA045394 |
| GATA4 | Santa cruz | sc-25310 |
| GATA4 | Abcam | ab134057 |
| Cytokeratin 19 | eBioscience | 14-9898 |
| Neurogenin 3 | R&D | MAB3444 |
| PROX1 | Abcam | ab38692 |
| PROX1 | Millipore | AB5475 |
| Alpha smooth muscle Actin | Abcam | ab5694 |
| SOX17 | R&D | AF1924 |
| SOX17 | R&D | MAB1924 |
| Alpha-Fetoprotein | eBioscience | 14-9499 |
| EpCAM | R&D | AF960 |
| NKX6.1 | Novus | NBP1-49672SS |
| Albumin | Sigma-Aldrich | A6684 |
| CD31 | eBioscience | 14-0318 |
| CD34 | Abcam | ab198395 |
| HNF1B | Santa cruz | sc-7411 |
| CCKAR | Novus | AF2680 |
| NKX6-3 | Sigma-Aldrich | HPA042790 |

TABLE 3

Primers for qPCR used in this study

| Gene | Probe | 5' primer | 3' primer |
|---|---|---|---|
| SOX2 | 65 | gggggaatggaccttgtatag (SEQ ID NO: 1) | gcaaagctcctaccgtacca (SEQ ID NO: 2) |
| CDX2 | 34 | atcaccatccggaggaaag (SEQ ID NO: 3) | tgcggttctgaaaccagatt (SEQ ID NO: 4) |
| PDX1 | 78 | aagctcacgcgtggaaag (SEQ ID NO: 5) | gccgtgagatgtacttgttgaa (SEQ ID NO: 6) |
| HHEX | 61 | cggacggtgaacgactaca (SEQ ID NO: 7) | agaaggggctccagagtagag (SEQ ID NO: 8) |
| ALDH1A2 | 63 | Ccacagtgattccaacgtc (SEQ ID NO: 9) | tcctgaacagggccaaag (SEQ ID NO: 10) |
| CYP26A1 | 28 | Cgagcactcgtgggagag (SEQ ID NO: 11) | ccaaagaggagttcggttga (SEQ ID NO: 12) |
| RARA | 67 | Gccatctgcctcatctgc (SEQ ID NO: 13) | tccgcacgtagacctttagc (SEQ ID NO: 14) |
| RARB | 53 | Ccgaaaagctcaccagga (SEQ ID NO: 15) | cgatggtcagcactggaat (SEQ ID NO: 16) |
| RARG | 24 | Cagccctacatgttcccaag (SEQ ID NO: 17) | ggcctggaatctccatcttc (SEQ ID NO: 18) |
| HES1 | 20 | tgccagctgatataatggagaa (SEQ ID NO: 19) | ctccataataggctttgatgactttt (SEQ ID NO: 20) |
| INS | 27 | aggcttcttctacacacccaag (SEQ ID NO: 21) | Cacaatgccacgcttctg (SEQ ID NO: 22) |
| GCG | 82 | gtacaaggcagctggcaac (SEQ ID NO: 23) | Tgggaagctgagaatgatctg (SEQ ID NO: 24) |

TABLE 3-continued

Primers for qPCR used in this study

| Gene | Probe | 5' primer | 3' primer |
|---|---|---|---|
| NKX2-2 | 71 | cgagggccttcagtactcc (SEQ ID NO: 25) | ggggacttggagcttgagt (SEQ ID NO: 26) |
| CPA1 | 37 | cagcatcatcaaggcaatttat (SEQ ID NO: 27) | ggagctcgaaggtgaagga (SEQ ID NO: 28) |
| CEL | 73 | caccttcaactaccgtgtcg (SEQ ID NO: 29) | gatcccgaaggccatagttac (SEQ ID NO: 30) |
| CFTR | 52 | gaagtagtgatggagaatgtaacagc (SEQ ID NO: 31) | gctttctcaaataattccccaaa (SEQ ID NO: 32) |
| CAPN6 | 4 | aggctgctataacaaccgtga (SEQ ID NO: 33) | catcctcaggcacagtgaag (SEQ ID NO: 34) |
| ALB | 7 | gtgaggttgctcatcggttt (SEQ ID NO: 35) | gagcaaaggcaatcaacacc (SEQ ID NO: 36) |
| CYP3A7 | 2 | caaacttggccgtggaaa (SEQ ID NO: 37) | agtccatgtgtacgggttcc (SEQ ID NO: 38) |
| HNF4A | 68 | gagatccatggtgttcaagga (SEQ ID NO: 39) | gtgccgagggacaatgtagt (SEQ ID NO: 39) |
| AFP | 61 | tgtactgcagagataagtttagctgac (SEQ ID NO: 41) | tccttgtaagtggcttcttgaac (SEQ ID NO: 42) |
| APOA2 | 68 | gagaaggtcaagagcccaga (SEQ ID NO: 43) | ccttcttgatcaggggtgtc (SEQ ID NO: 44) |

REFERENCES

1 Smith, D. M., Nielsen, C., Tabin, C. J. & Roberts, D. J. Roles of BMP signaling and Nkx2.5 in patterning at the chick midgut-foregut boundary. Development 127, 3671-3681 (2000).

2 Hentsch, B. et al. Hlx homeo box gene is essential for an inductive tissue interaction that drives expansion of embryonic liver and gut. Genes Dev 10, 70-79 (1996).

3 San Roman, A. K. & Shivdasani, R. A. Boundaries, junctions and transitions in the gastrointestinal tract. Exp Cell Res 317, 2711-2718, doi: 10.1016/j.yexcr.2011.07.011 (2011).

4 Nielsen, C., Murtaugh, L. C., Chyung, J. C., Lassar, A. & Roberts, D. J. Gizzard formation and the role of Bapx1. Dev Biol 231, 164-174, doi: 10.1006/dbio.2000.0151 (2001).

5 Bort, R., Martinez-Barbera, J. P., Beddington, R. S. & Zaret, K. S. Hex homeobox gene-dependent tissue positioning is required for organogenesis of the ventral pancreas. Development 131, 797-806, doi: 10.1242/dev.00965 (2004).

6 Shih, H. P. et al. A Gene Regulatory Network Cooperatively Controlled by Pdx1 and Sox9 Governs Lineage Allocation of Foregut Progenitor Cells. Cell Rep 13, 326-336, doi: 10.1016/j.celrep.2015.08.082 (2015).

7 Tepass, U. & Hartenstein, V. Epithelium formation in the Drosophila midgut depends on the interaction of endoderm and mesoderm. Development 120, 579-590 (1994).

8 Fukuda, A. et al. Ectopic pancreas formation in Hes1-knockout mice reveals plasticity of endodermal progenitors of the gut, bile duct, and pancreas. J Clin Invest 116, 1484-1493, doi: 10.1172/JCI27704 (2006).

9 Sumazaki, R. et al. Conversion of biliary system to pancreatic tissue in Hes1-deficient mice. Nat Genet 36, 83-87, doi: 10.1038/ng1273 (2004).

10 Udager, A., Prakash, A. & Gumucio, D. L. Dividing the tubular gut: generation of organ boundaries at the pylorus. Prog Mol Biol Transl Sci 96, 35-62, doi: 10.1016/B978-O-12-381280-3.00002-6 (2010).

11 Zhang, Z., Rankin, S. A. & Zorn, A. M. Syndecan4 coordinates Wnt/JNK and BMP signaling to regulate foregut progenitor development. Dev Biol 416, 187-199, doi: 10.1016/j.ydbio.2016.05.025 (2016).

12 McLin, V. A., Rankin, S. A. & Zorn, A. M. Repression of Wnt/beta-catenin signaling in the anterior endoderm is essential for liver and pancreas development. Development 134, 2207-2217, doi: 10.1242/dev.001230 (2007).

13 Nissim, S. et al. Iterative use of nuclear receptor Nr5a2 regulates multiple stages of liver and pancreas development. Dev Biol 418, 108-123, doi: 10.1016/j.ydbio.2016.07.019 (2016).

14 Palaria, A., Angelo, J. R., Guertin, T. M., Mager, J. & Tremblay, K. D. Patterning of the hepato-pancreatobiliary boundary by BMP reveals heterogeneity within the murine liver bud. Hepatology 68, 274-288, doi: 10.1002/hep.29769 (2018).

15 Spence, J. R. et al. Sox17 regulates organ lineage segregation of ventral foregut progenitor cells. Dev Cell 17, 62-74, doi: 10.1016/j.devcel.2009.05.012 (2009).

16 Ameri, J. et al. FGF2 specifies hESC-derived definitive endoderm into foregut/midgut cell lineages in a concentration-dependent manner. Stem Cells 28, 45-56, doi: 10.1002/stem.249 (2010).

17 Zhang, R. R. et al. Human iPSC-Derived Posterior Gut Progenitors Are Expandable and Capable of Forming Gut and Liver Organoids. Stem Cell Reports 10, 780-793, doi: 10.1016/j.stemcr.2018.01.006 (2018).

18 Spence, J. R. et al. Directed differentiation of human pluripotent stem cells into intestinal tissue in vitro. Nature 470, 105-109, doi: 10.1038/nature09691 (2011).

19 McCracken, K. W. et al. Modelling human development and disease in pluripotent stem-cell-derived gastric organoids. Nature 516, 400-404, doi: 10.1038/nature13863 (2014).
20 Wang, Z., Dollé, P., Cardoso, W. V. & Niederreither, K. Retinoic acid regulates morphogenesis and patterning of posterior foregut derivatives. Dev Biol 297, 433-445, doi: 10.1016/j.ydbio.2006.05.019 (2006).
21 Rankin, S. A. et al. Timing is everything: Reiterative Wnt, BMP and RA signaling regulate developmental competence during endoderm organogenesis. Dev Biol 434, 121-132, doi: 10.1016/j.ydbio.2017.11.018 (2018).
22 Cunningham, T. J. & Duester, G. Mechanisms of retinoic acid signalling and its roles in organ and limb development. Nat Rev Mol Cell Biol 16, 110-123, doi: 10.1038/nrm3932 (2015).
23 Rankin, S. A. et al. A Retinoic Acid-Hedgehog Cascade Coordinates Mesoderm-Inducing Signals and Endoderm Competence during Lung Specification. Cell Rep 16, 66-78, doi: 10.1016/j.celrep.2016.05.060 (2016).
24 Bayha, E., Jørgensen, M. C., Serup, P. & Grapin-Botton, A. Retinoic acid signaling organizes endodermal organ specification along the entire antero-posterior axis. PLOS One 4, e5845, doi: 10.1371/journal.pone.0005845 (2009).
25 Watson, C. L. et al. An in vivo model of human small intestine using pluripotent stem cells. Nat Med 20, 1310-1314, doi: 10.1038/nm.3737 (2014).
26 Higashiyama, H. et al. Embryonic cholecystitis and defective gallbladder contraction in the. Development 144, 1906-1917, doi: 10.1242/dev.147512 (2017).
27 Thamm, K. & Seaver, E. C. Notch signaling during larval and juvenile development in the polychaete annelid Capitella sp. I. Dev Biol 320, 304-318, doi: 10.1016/j.ydbio.2008.04.015 (2008).
28 Jørgensen, M. C. et al. Neurog3-dependent pancreas dysgenesis causes ectopic pancreas in. Development 145, doi: 10.1242/dev.163568 (2018).
29 Camp, J. G. et al. Multilineage communication regulates human liver bud development from pluripotency. Nature 546, 533-538, doi: 10.1038/nature22796 (2017).
30 Takebe, T. et al. Vascularized and functional human liver from an iPSC-derived organ bud transplant. Nature 499, 481-484, doi: 10.1038/nature12271 (2013).
31 Davenport, C., Diekmann, U., Budde, I., Detering, N. & Naujok, O. Anterior-Posterior Patterning of Definitive Endoderm Generated from Human Embryonic Stem Cells Depends on the Differential Signaling of Retinoic Acid, Wnt-, and BMP-Signaling. Stem Cells 34, 2635-2647, doi: 10.1002/stem.2428 (2016).
32 Green, M. D. et al. Generation of anterior foregut endoderm from human embryonic and induced pluripotent stem cells. Nat Biotechnol 29, 267-272, doi: 10.1038/nbt.1788 (2011).

All percentages and ratios are calculated by weight unless otherwise indicated.

All percentages and ratios are calculated based on the total composition unless otherwise indicated.

It should be understood that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "20 mm" is intended to mean "about 20 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications may be made without departing from the spirit and scope of the invention. It is therefore intended to cover in the appended claims all such changes and modifications that are within the scope of this invention.

What is claimed is:

1. A method of making a hepato-biliary-pancreatic organoid (HBPO), comprising:
   a) contacting an anterior gut spheroid with a posterior gut spheroid for a first period of time sufficient to form a fused spheroid, wherein the contacting is in a gut growth medium;
   b) culturing the fused spheroid for a second period of time sufficient to form a boundary organoid having a foregut-midgut boundary, wherein culturing the fused spheroid comprises embedding said fused spheroid into a basement membrane matrix; and
   c) culturing the boundary organoid of step b) in a second gut growth medium in an air-liquid interface to form the HBPO, wherein said HBPO comprises biliary tissue and pancreatic tissue.

2. The method of claim 1, wherein said gut growth medium and/or said second gut growth medium is a medium comprising a ROCK inhibitor.

3. The method of claim 2, wherein said ROCK inhibitor is Y-27632.

4. The method of claim 1, wherein the first period of time is about 1 day.

5. The method of claim 1, wherein the second period of time is about 1 day to about 3 days.

6. The method of claim 1, the method further comprising contacting a first definitive endoderm with a Wnt signaling pathway activator, an FGF signaling pathway activator, and a BMP signaling pathway inhibitor to form said anterior gut spheroid, and contacting a second definitive endoderm with a Wnt signaling pathway activator and an FGF signaling pathway activator to form said posterior gut spheroid.

7. The method of claim 1, further comprising the step of selecting the anterior gut spheroid cells for step a), wherein said selected anterior gut spheroid comprise cells expressing SRY-box 2 (SOX2) and is substantially free of Pancreatic and Duodenal Homeobox 1 (PDX1) expressing cells, and wherein said posterior gut spheroids comprise cells expressing PDX1 and Caudal type homeobox 2 (CDX2).

8. The method of claim 1, further comprising the step of selecting a boundary organoid comprising cells expressing Pancreatic and Duodenal Homeobox 1 (PDX1), cells expressing Hematopoietically-expressed homeobox protein (HHEX), and cells expressing Prospero-Related Homeobox 1 (PROX1).

9. The method of claim 1, further comprising excising PROX1 positive regions from said boundary organoid and culturing said excised boundary organoid to form invaginating epithelium and branching structure.

10. The method of claim 1, further comprising the step of selecting a boundary organoid of step b) comprising a biliary-pancreatic primordium characterized by expression of SOX2, CDX2, HHEX, and PDX1, and wherein PDX1 expression is localized to boundary regions of said boundary organoid.

11. The method of claim 1, further comprising the step of selecting a HBPO comprising liver tissue and intestinal tissue.

12. The method of claim 1, further comprising the step of selecting a HBPO comprising endoderm and mesoderm.

13. The method of claim 1, further comprising the step of culturing the HBPO with endothelial cells derived from induced pluripotent stem cells.

14. The method of claim 13, wherein said endothelial cells are formed into an endothelial cell (EC) spheroid prior to said culturing with said HBPO.

15. The method of claim 1, further comprising the step of culturing the HBPO with mesenchymal cells derived from induced pluripotent stem cells.

16. The method of claim 15, wherein said mesenchyme cells are formed into a mesenchyme cell (MC) spheroid prior to said culturing with said HBPO.

17. The method of claim 1, further comprising transplanting said HBPO into a mammal for a period of time to increase growth and maturation of said HBPO.

* * * * *

SEQUENCE LISTING

<160> NUMBER OF SEQ ID NOS: 53

<210> SEQ ID NO 1
<211> LENGTH: 21
<212> TYPE: DNA
<213> ORGANISM: Artificial Sequence
<220> FEATURE:
<223> OTHER INFORMATION: SOX2 5'Primer

<400> SEQUENCE: 1 ggggggaatgg accttgtata g                                    21

<210> SEQ ID NO 2
<211> LENGTH: 20
<212> TYPE: DNA
<213> ORGANISM: Artificial Sequence

```
<220> FEATURE:
<223> OTHER INFORMATION: SOX2 3'Primer

<400> SEQUENCE: 2
gcaaagctcc taccgtacca                                                   20

<210> SEQ ID NO 3
<211> LENGTH: 19
<212> TYPE: DNA
<213> ORGANISM: Artificial Sequence
<220> FEATURE:
<223> OTHER INFORMATION: CDX2 5'Primer

<400> SEQUENCE: 3
atcaccatcc ggaggaaag                                                    19

<210> SEQ ID NO 4
<211> LENGTH: 20
<212> TYPE: DNA
<213> ORGANISM: Artificial Sequence
<220> FEATURE:
<223> OTHER INFORMATION: CDX2 3'Primer

<400> SEQUENCE: 4
tgcggttctg aaaccagatt                                                   20

<210> SEQ ID NO 5
<211> LENGTH: 18
<212> TYPE: DNA
<213> ORGANISM: Artificial Sequence
<220> FEATURE:
<223> OTHER INFORMATION: PDX1 5'Primer

<400> SEQUENCE: 5
aagctcacgc gtggaaag                                                     18

<210> SEQ ID NO 6
<211> LENGTH: 22
<212> TYPE: DNA
<213> ORGANISM: Artificial Sequence
<220> FEATURE:
<223> OTHER INFORMATION: PDX1 3'Primer

<400> SEQUENCE: 6
gccgtgagat gtacttgttg aa                                                22

<210> SEQ ID NO 7
<211> LENGTH: 19
<212> TYPE: DNA
<213> ORGANISM: Artificial Sequence
<220> FEATURE:
<223> OTHER INFORMATION: HHEX 5'Primer

<400> SEQUENCE: 7
cggacggtga acgactaca                                                    19

<210> SEQ ID NO 8
<211> LENGTH: 21
<212> TYPE: DNA
<213> ORGANISM: Artificial Sequence
<220> FEATURE:
<223> OTHER INFORMATION: HHEX 3'Primer

<400> SEQUENCE: 8
agaaggggct ccagagtaga g                                                 21
```

```
<210> SEQ ID NO 9
<211> LENGTH: 20
<212> TYPE: DNA
<213> ORGANISM: Artificial Sequence
<220> FEATURE:
<223> OTHER INFORMATION: ALDH1A2 5'Primer

<400> SEQUENCE: 9
ccacagtgtt ttccaacgtc                                          20

<210> SEQ ID NO 10
<211> LENGTH: 18
<212> TYPE: DNA
<213> ORGANISM: Artificial Sequence
<220> FEATURE:
<223> OTHER INFORMATION: ALDH1A2 3'Primer

<400> SEQUENCE: 10
tcctgaacag ggccaaag                                            18

<210> SEQ ID NO 11
<211> LENGTH: 18
<212> TYPE: DNA
<213> ORGANISM: Artificial Sequence
<220> FEATURE:
<223> OTHER INFORMATION: CYP26A1 5'Primer

<400> SEQUENCE: 11
cgagcactcg tgggagag                                            18

<210> SEQ ID NO 12
<211> LENGTH: 20
<212> TYPE: DNA
<213> ORGANISM: Artificial Sequence
<220> FEATURE:
<223> OTHER INFORMATION: CYP26A1 3'Primer

<400> SEQUENCE: 12
ccaaagagga gttcggttga                                          20

<210> SEQ ID NO 13
<211> LENGTH: 18
<212> TYPE: DNA
<213> ORGANISM: Artificial Sequence
<220> FEATURE:
<223> OTHER INFORMATION: RARA 5'Primer

<400> SEQUENCE: 13
gccatctgcc tcatctgc                                            18

<210> SEQ ID NO 14
<211> LENGTH: 20
<212> TYPE: DNA
<213> ORGANISM: Artificial Sequence
<220> FEATURE:
<223> OTHER INFORMATION: RARA 3'Primer

<400> SEQUENCE: 14
tccgcacgta gacctttagc                                          20

<210> SEQ ID NO 15
<211> LENGTH: 18
<212> TYPE: DNA
<213> ORGANISM: Artificial Sequence
<220> FEATURE:
<223> OTHER INFORMATION: RARB 5'Primer
```

```
<400> SEQUENCE: 15
ccgaaaagct caccagga                                                 18

<210> SEQ ID NO 16
<211> LENGTH: 19
<212> TYPE: DNA
<213> ORGANISM: Artificial Sequence
<220> FEATURE:
<223> OTHER INFORMATION: RARB 3'Primer

<400> SEQUENCE: 16
cgatggtcag cactggaat                                                19

<210> SEQ ID NO 17
<211> LENGTH: 20
<212> TYPE: DNA
<213> ORGANISM: Artificial Sequence
<220> FEATURE:
<223> OTHER INFORMATION: RARG 5'Primer

<400> SEQUENCE: 17
cagccctaca tgttcccaag                                               20

<210> SEQ ID NO 18
<211> LENGTH: 20
<212> TYPE: DNA
<213> ORGANISM: Artificial Sequence
<220> FEATURE:
<223> OTHER INFORMATION: RARG 3'Primer

<400> SEQUENCE: 18
ggcctggaat ctccatcttc                                               20

<210> SEQ ID NO 19
<211> LENGTH: 22
<212> TYPE: DNA
<213> ORGANISM: Artificial Sequence
<220> FEATURE:
<223> OTHER INFORMATION: HES1 5'Primer

<400> SEQUENCE: 19
tgccagctga tataatggag aa                                            22

<210> SEQ ID NO 20
<211> LENGTH: 25
<212> TYPE: DNA
<213> ORGANISM: Artificial Sequence
<220> FEATURE:
<223> OTHER INFORMATION: HES1 3'Primer

<400> SEQUENCE: 20
ctccataata ggctttgatg acttt                                         25

<210> SEQ ID NO 21
<211> LENGTH: 22
<212> TYPE: DNA
<213> ORGANISM: Artificial Sequence
<220> FEATURE:
<223> OTHER INFORMATION: INS 5'Primer

<400> SEQUENCE: 21
aggcttcttc tacacaccca ag                                            22

<210> SEQ ID NO 22
```

```
<211> LENGTH: 18
<212> TYPE: DNA
<213> ORGANISM: Artificial Sequence
<220> FEATURE:
<223> OTHER INFORMATION: INS 3'Primer

<400> SEQUENCE: 22
cacaatgcca cgcttctg                                                 18

<210> SEQ ID NO 23
<211> LENGTH: 19
<212> TYPE: DNA
<213> ORGANISM: Artificial Sequence
<220> FEATURE:
<223> OTHER INFORMATION: GCG 5'Primer

<400> SEQUENCE: 23
gtacaaggca gctggcaac                                                19

<210> SEQ ID NO 24
<211> LENGTH: 21
<212> TYPE: DNA
<213> ORGANISM: Artificial Sequence
<220> FEATURE:
<223> OTHER INFORMATION: GCG 3'Primer

<400> SEQUENCE: 24
tgggaagctg agaatgatct g                                             21

<210> SEQ ID NO 25
<211> LENGTH: 19
<212> TYPE: DNA
<213> ORGANISM: Artificial Sequence
<220> FEATURE:
<223> OTHER INFORMATION: NKX2-2 5'Primer

<400> SEQUENCE: 25
cgagggcctt cagtactcc                                                19

<210> SEQ ID NO 26
<211> LENGTH: 19
<212> TYPE: DNA
<213> ORGANISM: Artificial Sequence
<220> FEATURE:
<223> OTHER INFORMATION: NKX2-2 3'Primer

<400> SEQUENCE: 26
ggggacttgg agcttgagt                                                19

<210> SEQ ID NO 27
<211> LENGTH: 22
<212> TYPE: DNA
<213> ORGANISM: Artificial Sequence
<220> FEATURE:
<223> OTHER INFORMATION: CPA1 5'Primer

<400> SEQUENCE: 27
cagcatcatc aaggcaattt at                                            22

<210> SEQ ID NO 28
<211> LENGTH: 19
<212> TYPE: DNA
<213> ORGANISM: Artificial Sequence
<220> FEATURE:
<223> OTHER INFORMATION: CPA1 3'Primer

<400> SEQUENCE: 28
```

```
ggagctcgaa ggtgaagga                                                    19

<210> SEQ ID NO 29
<211> LENGTH: 19
<212> TYPE: DNA
<213> ORGANISM: Artificial Sequence
<220> FEATURE:
<223> OTHER INFORMATION: CEL 5'Primer

<400> SEQUENCE: 29
ggagctcgaa ggtgaagga                                                    19

<210> SEQ ID NO 30
<211> LENGTH: 21
<212> TYPE: DNA
<213> ORGANISM: Artificial Sequence
<220> FEATURE:
<223> OTHER INFORMATION: CEL 3'Primer

<400> SEQUENCE: 30
gatcccgaag gccatagtta c                                                 21

<210> SEQ ID NO 31
<211> LENGTH: 26
<212> TYPE: DNA
<213> ORGANISM: Artificial Sequence
<220> FEATURE:
<223> OTHER INFORMATION: CFTR 5'Primer

<400> SEQUENCE: 31
gaagtagtga tggagaatgt aacagc                                            26

<210> SEQ ID NO 32
<211> LENGTH: 23
<212> TYPE: DNA
<213> ORGANISM: Artificial Sequence
<220> FEATURE:
<223> OTHER INFORMATION: CFTR 3'Primer

<400> SEQUENCE: 32
gctttctcaa ataattcccc aaa                                               23

<210> SEQ ID NO 33
<211> LENGTH: 21
<212> TYPE: DNA
<213> ORGANISM: Artificial Sequence
<220> FEATURE:
<223> OTHER INFORMATION: CAPN6 5'Primer

<400> SEQUENCE: 33
aggctgctat aacaaccgtg a                                                 21

<210> SEQ ID NO 34
<211> LENGTH: 20
<212> TYPE: DNA
<213> ORGANISM: Artificial Sequence
<220> FEATURE:
<223> OTHER INFORMATION: CAPN6 3'Primer

<400> SEQUENCE: 34
catcctcagg cacagtgaag                                                   20

<210> SEQ ID NO 35
<211> LENGTH: 20
<212> TYPE: DNA
```

```
<213> ORGANISM: Artificial Sequence
<220> FEATURE:
<223> OTHER INFORMATION: ALB 5'Primer

<400> SEQUENCE: 35
gtgaggttgc tcatcggttt                                              20

<210> SEQ ID NO 36
<211> LENGTH: 20
<212> TYPE: DNA
<213> ORGANISM: Artificial Sequence
<220> FEATURE:
<223> OTHER INFORMATION: ALB 3'Primer

<400> SEQUENCE: 36
gagcaaaggc aatcaacacc                                              20

<210> SEQ ID NO 37
<211> LENGTH: 18
<212> TYPE: DNA
<213> ORGANISM: Artificial Sequence
<220> FEATURE:
<223> OTHER INFORMATION: CYP3A7 5'Primer

<400> SEQUENCE: 37
caaacttggc cgtggaaa                                                18

<210> SEQ ID NO 38
<211> LENGTH: 20
<212> TYPE: DNA
<213> ORGANISM: Artificial Sequence
<220> FEATURE:
<223> OTHER INFORMATION: CYP3A7 3'Primer

<400> SEQUENCE: 38
agtccatgtg tacgggttcc                                              20

<210> SEQ ID NO 39
<211> LENGTH: 21
<212> TYPE: DNA
<213> ORGANISM: Artificial Sequence
<220> FEATURE:
<223> OTHER INFORMATION: HNF4A 5'Primer

<400> SEQUENCE: 39
gagatccatg gtgttcaagg a                                            21

<210> SEQ ID NO 40
<211> LENGTH: 20
<212> TYPE: DNA
<213> ORGANISM: Artificial Sequence
<220> FEATURE:
<223> OTHER INFORMATION: HNF4A 3'Primer

<400> SEQUENCE: 40
gtgccgaggg acaatgtagt                                              20

<210> SEQ ID NO 41
<211> LENGTH: 27
<212> TYPE: DNA
<213> ORGANISM: Artificial Sequence
<220> FEATURE:
<223> OTHER INFORMATION: AFP 5'Primer

<400> SEQUENCE: 41
tgtactgcag agataagttt agctgac                                      27
```

<210> SEQ ID NO 42
<211> LENGTH: 23
<212> TYPE: DNA
<213> ORGANISM: Artificial Sequence
<220> FEATURE:
<223> OTHER INFORMATION: AFP 3'Primer

<400> SEQUENCE: 42
tccttgtaag tggcttcttg aac                                    23

<210> SEQ ID NO 43
<211> LENGTH: 20
<212> TYPE: DNA
<213> ORGANISM: Artificial Sequence
<220> FEATURE:
<223> OTHER INFORMATION: APOA2 5'Primer

<400> SEQUENCE: 43
gagaaggtca agagcccaga                                        20

<210> SEQ ID NO 44
<211> LENGTH: 20
<212> TYPE: DNA
<213> ORGANISM: Artificial Sequence
<220> FEATURE:
<223> OTHER INFORMATION: APOA2 3'Primer

<400> SEQUENCE: 44
ccttcttgat cagggtgtc                                         20

<210> SEQ ID NO 45
<211> LENGTH: 43
<212> TYPE: DNA
<213> ORGANISM: Homo sapiens

<400> SEQUENCE: 45
gctaccccag ccagtgtcaa cacgacaccg gataaaccaa aga              43

<210> SEQ ID NO 46
<211> LENGTH: 25
<212> TYPE: DNA
<213> ORGANISM: Artificial Sequence
<220> FEATURE:
<223> OTHER INFORMATION: hHES1 gRNA1 F

<400> SEQUENCE: 46
caccgatccg gtgtcgtgtt gacac                                  25

<210> SEQ ID NO 47
<211> LENGTH: 25
<212> TYPE: DNA
<213> ORGANISM: Artificial Sequence
<220> FEATURE:
<223> OTHER INFORMATION: hHES1 gRNA1 R

<400> SEQUENCE: 47
ctaggccaca gcacaactgt gcaaa                                  25

<210> SEQ ID NO 48
<211> LENGTH: 22
<212> TYPE: DNA
<213> ORGANISM: Artificial Sequence
<220> FEATURE:
<223> OTHER INFORMATION: hHES1 Seq F

```
<400> SEQUENCE: 48
accctcagca cttgctcagt ag                                              22

<210> SEQ ID NO 49
<211> LENGTH: 25
<212> TYPE: DNA
<213> ORGANISM: Artificial Sequence
<220> FEATURE:
<223> OTHER INFORMATION: hHES1 Seq R

<400> SEQUENCE: 49
tcttcgtctt ttctccataa taggc                                           25

<210> SEQ ID NO 50
<211> LENGTH: 50
<212> TYPE: DNA
<213> ORGANISM: Artificial Sequence
<220> FEATURE:
<223> OTHER INFORMATION: Modified gene sequence of WT and HES1KO (Del
      #11)-A

<400> SEQUENCE: 50
aaaaaaaaaa ggaaaatgcc agctgatata atggagaaaa attcctcgtc                50

<210> SEQ ID NO 51
<211> LENGTH: 5
<212> TYPE: DNA
<213> ORGANISM: Artificial Sequence
<220> FEATURE:
<223> OTHER INFORMATION: Modified gene sequence of WT and HES1KO (Del
      #11)-B

<400> SEQUENCE: 51 aaaaa                                                                  5

<210> SEQ ID NO 52
<211> LENGTH: 41
<212> TYPE: DNA
<213> ORGANISM: Artificial Sequence
<220> FEATURE:
<223> OTHER INFORMATION: Modified gene sequence of WT and HES1KO (Del
      #11)-C

<400> SEQUENCE: 52
cccggtgcta ccccagccag tgtcaacacg acaccggata a                         41

<210> SEQ ID NO 53
<211> LENGTH: 15
<212> TYPE: DNA
<213> ORGANISM: Artificial Sequence
<220> FEATURE:
<223> OTHER INFORMATION: Modified gene sequence of WT and HES1KO (Del
      #11)-D

<400> SEQUENCE: 53
cacgacaccg gataa                                                      15
```